United States Patent
Abnousi

(10) Patent No.: US 11,939,371 B2
(45) Date of Patent: Mar. 26, 2024

(54) ANTIBODIES AGAINST MICROORGANISMS AND USES THEREOF

(71) Applicant: NOVOBIND LIVESTOCK THERAPEUTICS INC., Vancouver (CA)

(72) Inventor: Hamlet Abnousi, Vancouver (CA)

(73) Assignee: NOVOBIND LIVESTOCK THERAPEUTICS INC., Vancouver (CA)

(*) Notice: Subject to any disclaimer, the term of this patent is extended or adjusted under 35 U.S.C. 154(b) by 0 days.

(21) Appl. No.: 17/409,559

(22) Filed: Aug. 23, 2021

(65) Prior Publication Data

US 2022/0259293 A1    Aug. 18, 2022

Related U.S. Application Data

(62) Division of application No. 16/300,457, filed as application No. PCT/IB2017/000684 on May 19, 2017, now Pat. No. 11,130,800.

(60) Provisional application No. 62/339,732, filed on May 20, 2016, provisional application No. 62/339,735, filed on May 20, 2016.

(51) Int. Cl.
| | |
|---|---|
| *A61K 39/02* | (2006.01) |
| *A23K 20/147* | (2016.01) |
| *A23K 20/195* | (2016.01) |
| *A23K 50/75* | (2016.01) |
| *A23L 33/18* | (2016.01) |
| *A61K 9/00* | (2006.01) |
| *A61P 31/04* | (2006.01) |
| *C07K 16/12* | (2006.01) |
| *A61K 39/00* | (2006.01) |

(52) U.S. Cl.
CPC ........ *C07K 16/1235* (2013.01); *A23K 20/147* (2016.05); *A23K 20/195* (2016.05); *A23K 50/75* (2016.05); *A23L 33/18* (2016.08); *A61K 9/0053* (2013.01); *A61P 31/04* (2018.01); *A23V 2002/00* (2013.01); *A61K 2039/505* (2013.01); *A61K 2039/54* (2013.01); *A61K 2039/55* (2013.01); *A61K 2039/552* (2013.01); *C07K 2317/10* (2013.01); *C07K 2317/24* (2013.01); *C07K 2317/31* (2013.01); *C07K 2317/35* (2013.01); *C07K 2317/56* (2013.01); *C07K 2317/565* (2013.01); *C07K 2317/569* (2013.01); *C07K 2317/64* (2013.01); *C07K 2317/70* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,335,107 A | 6/1982 | Snoeyenbos et al. |
| 6,790,446 B2 | 9/2004 | Jacobs et al. |
| 8,637,025 B2 | 1/2014 | Robins-Browne et al. |
| 8,926,980 B2 | 1/2015 | Mitteness et al. |
| 11,130,800 B2 | 9/2021 | Abnousi |
| 2002/0106397 A1 | 8/2002 | Nash et al. |
| 2003/0003104 A1 | 1/2003 | Mottola et al. |
| 2007/0110758 A1 | 5/2007 | Campbell et al. |
| 2007/0280949 A1 | 12/2007 | Alfa |
| 2009/0191208 A1 | 7/2009 | Salzman et al. |
| 2009/0208506 A1 | 8/2009 | Rachamim et al. |
| 2014/0112938 A1 | 4/2014 | Robins-Browne et al. |
| 2015/0307597 A1 | 10/2015 | Arbabi Ghahroudi et al. |
| 2017/0183643 A1 | 6/2017 | Krogh et al. |
| 2017/0202242 A1 | 7/2017 | Blom et al. |
| 2017/0223986 A1 | 8/2017 | Schnorr |
| 2017/0240873 A1 | 8/2017 | Li et al. |
| 2021/0269512 A1 | 9/2021 | Abnousi et al. |
| 2022/0064224 A1 | 3/2022 | Abnousi et al. |
| 2022/0119506 A1 | 4/2022 | Abnousi et al. |

FOREIGN PATENT DOCUMENTS

| | | |
|---|---|---|
| CN | 103665152 A | 3/2014 |
| WO | WO-8600993 A1 | 2/1986 |
| WO | WO-8601805 A1 | 3/1986 |
| WO | WO-8604352 A1 | 7/1986 |
| WO | WO-0140280 A2 | 6/2001 |
| WO | WO-03070258 A1 | 8/2003 |
| WO | WO-2010079149 A1 | 7/2010 |
| WO | WO-2015145250 A2 | 10/2015 |
| WO | WO-2017199094 A1 | 11/2017 |
| WO | WO-2020035741 A2 | 2/2020 |
| WO | WO-2020099922 A1 | 5/2020 |
| WO | WO-2020163284 A1 | 8/2020 |
| WO | WO-2020234642 A1 | 11/2020 |

OTHER PUBLICATIONS

Arbabi-Ghahroudi, Camelid single-domain antibodies: historical perspective and future outlook. Frontiers in Immunology 8:1589 [1-8] (2017).
Da Costa et al., Variable protection against experimental broiler necrotic enteritis after immunization with the C-terminal fragment of Clostridium perfringens alpha-toxin and a non-toxic NetB variant. Avian Pathology 45(3):381-388 (2016).
Ebrahimizadeh et al., Isolation and characterization of protective anti-LPS nanobody against V. cholerae O1 recognizing Inaba and Ogawa serotypes. Appl Microbiol Biotechnol. 97(10):4457-66. doi: 10.1007/s00253-012-4518-x (2013; epub 2012).
International Application No. PCT/IB2017/000684 International Preliminary Report on Patentability dated Nov. 20, 2018.

(Continued)

Primary Examiner — Jennifer E Graser
(74) Attorney, Agent, or Firm — BCF LLP

(57) ABSTRACT

Described herein are methods and antibodies useful for reducing, eliminating, or preventing infection with a bacterial population in domestic animals or humans. Also described herein are antigens useful for targeting by heavy chain antibodies and $V_HH$ fragments for reducing a bacterial population in domestic animals or humans.

9 Claims, 24 Drawing Sheets

Specification includes a Sequence Listing.

(56) References Cited

OTHER PUBLICATIONS

International Application No. PCT/IB2017/000684 International Search Report and Written Opinion of the International Searching Authority dated Oct. 11, 2017.
Keyburn et al., Vaccination with recombinant NetB toxin partially protects broiler chickens from necrotic enteritis. Veterinary Research 44:54 [1-8] (2013).
McClain et al., Functional analysis of neutralizing antibodies against Clostridium perfringens epsilon-toxin. Infection and Immunity 75(4):1785-1793 (2007).
Muyldermans et al.: Sequence and structure of VH domain from naturally occurring camel heavy chain immunoglobulins lacking light chains. Protein Engineering. 7(9):1125-1135 (1994) Abstract Only.
Nowacka: Isolation of Salmonella serovar-Specific Single Domain Antibodies, A Thesis Presented to the University of Guelph, Ontario, Canada, https://atrium.lib.uoguelph.ca/xmlui/handle/10214/8503 (2014).
PCT/IB2019/000687 International Preliminary Report on Patentability dated Dec. 18, 2020.
PCT/IB2019/000687 International Search Report and Written Opinion dated Dec. 12, 2019.
PCT/IB2019/001196 International Preliminary Report on Patentability dated May 27, 2021.
PCT/IB2019/001196 International Search Report and Written Opinion dated Mar. 18, 2020.
PCT/IB2019/001198 International Invitation to Pay Additional Fees dated Jan. 17, 2020.
PCT/IB2019/001198 International Preliminary Report on Patentability dated Jan. 15, 2021.
PCT/IB2019/001198 International Search Report and Written Opinion dated Mar. 20, 2020.
PCT/IB2020/000380 International Search Report and Written Opinion dated Aug. 28, 2020.
Sato et al., Monoclonal antibodies against alpha toxin of Clostridium perfringens. FEMS Microbiol Lett. 50(1-2):173-176 (1989).
U.S. Appl. No. 16/300,457 Final Office Action dated Feb. 1, 2021.
U.S. Appl. No. 16/300,457 Office Action dated Jul. 30, 2020.
Wu et al., Panning anti-LPS nanobody as a capture target to enrich Vibrio fluvialis. Biochem Biophys Res Commun. 512(3):531-536. doi: 10.1016/j.bbrc.2019.03.104 (2019).
Yuan et al.: Comparison of two single-chain antibodies that neutralize canine parvovirus: analysis of an antibody-combining site and mechanisms of neutralization. Virology. 269(2):471-480 (2000).
Zeng et al., The generation and characterization of recombinant protein and antibodies of clostridium perfringens beta2 toxin. Journal of Immunological Research 2016:5708468 [1-12] (2016).
Abid et al.: Emerging threat of necrotic enteritis in poultry and its control without use of antibiotics: a review. The Journal of Animal and Plant Sciences. 26(6):1556-1567 (2016).
Boucher et al.: The apicomplexan glideosome and adhesins—structures and function. Journal of Structural Biology. 190(2):93-114 (2015).
Chapman: Milestones in avian coccidiosis research: a review. Poultry Science. 93(3):501-511 (2014).
EP19831311.6 Supplemental European Search Report dated Feb. 16, 2022.
EP19849450.2 Extended European Search Report dated Mar. 3, 2022.
Froelich et al., The interactions of Vibrio vulnificus and the oyster Crassostrea virginica. Microb Ecol. 65(4):807-816 (2013).
Garcia, E. Neutralizacion de la toxinas PirA y PirB de Vibrio parahaemolyticus asociado a AHPND con fragmentos de anticuerpos deplegados en fagos. Masters of Science Thesis, Centro de Investigaciones Biologicas del Noroeste S.C. Baja, Mexico (2016).
Keyburn et al.: NetB, a Pore-Forming Toxin from Necrotic Enteritis Strains of Clostridium perfringens. Toxins, Molecular Diversity Preservation International (MDPI) 2:1913-1927 (2010).
Lam et al., Nanobody-aided structure determination of the EpsI:EpsJ pseudopilin heterodimer from Vibrio vulnificus. J Struct Biol. 166(1):8-15 (2009).
Lee et al., The opportunistic marine pathogen Vibrio parahaemolyticus becomes virulent by acquiring a plasmid that expresses a deadly toxin. Proc Natl Acad Sci U S A 112(34):10798-10803 (2015).
Moore: Necrotic enteritis predisposing factors in broiler chickens. Avian Pathology. 45(3):275-281 (2016).
Unger et al.: Selection of Nanobodies that Block the Enzymatic and Cytotoxic Activities of the Binary Clostridium Difficile Toxin CDT. Scientific Reports. 5:7850 (2015).
Uzal et al.: Clostridium Perfringens Toxins Involved in Mammalian Veterinary Diseases. The Open Toxinology Journal. 3(1):24-42 (2013).
Van Meirhaeghe et al.: Coccidiosis a major threat to the chicken gut. Retrieved on May 25, 2018 from: https://www.poultryworld.net/Home/General/2014/9/Coccidiosis-a-major-threat-to-the-chicken-gut-1568808W/?dossier=35765&widgetid=1 (2014).
Wade et al.: The adherent abilities of Clostridium perfringensstrains are critical for the pathogenesis of avian necrotic enteritis. Veterinary Microbiology. Elsevier BV. 197:53-61 (2016).
Wade et al.: The true cost of necrotic enteritis. Retrieved on May 25, 2018 from: https://www.poultryworld.net/Meat/Articles/2015/10/The-true-cost-of-necrotic-enteritis-2699819W (2015).
Wangman et al., Development of monoclonal antibodies specific to ToxA and ToxB of Vibrio parahaemolyticus that cause acute hepatopancreatic necrosis disease (AHPND). Aquaculture 474:75-81 (2017).
Wesolowski et al.: 2009, "Single domain antibodies: promising experimental and therapeutic tools in infection and immunity," Med Microbiol Immunol. 198(3): 157-174.

SEQUENCE LISTING

```
<160> NUMBER OF SEQ ID NOS: 781

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Ile Phe Ser Ile Asn Ala Met
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ser Ile Phe Ser Ile Asn Ala Met
1               5

<210> SEQ ID NO 3
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 3

Gly Ile Ile Phe Ser Pro Asn Ala Met
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Asn Ile Phe Ser Ile Asn Ala Met
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Arg Ser Val Ser Ile Asn Pro Met
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ile Ser Val Asn Ile Asn Pro Met
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ser Thr Phe Ser Ile Asn Ala Met
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Ser Ile Asn Pro Met
1               5
```

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Arg Ile Phe Ser Ser Tyr Asp Met
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ser Ile Phe Ser Ile Pro Ser Met
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Arg Ile Phe Ser Ser Tyr Asp Met
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Arg Thr Phe Ser Asn Asn Ala Met
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Arg Thr Phe Ser Arg Leu Ala Met
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Arg Met Phe Ser Ser Tyr Asp Met
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ser Ile Phe Ser Ile Asn Ala Val
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Arg Ile Phe Ser Ser Tyr Asp Met
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Arg Ile Phe Ser Ile Asn Pro Met
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Arg Ile Phe Ser Ile Tyr Asp Met
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Phe Ser Ser Ala Trp Met
1               5

<210> SEQ ID NO 20
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ile Ile Phe Ser Pro Asn Ala Met
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ile Ile Phe Ser Pro Asn Ala Met
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ile Ile Phe Ser Pro Asn Ala Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Ile Ile Phe Ser Pro Asn Ala Met
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Arg Ser Val Ser Ile Asn Pro Met
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Phe Ile Leu Asn Ala Met
```

```
<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Gly Thr Phe Thr Thr Asp Ala Met
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Arg Ala Phe Ser Ser Arg Ala Met
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Thr Phe Ser Asp Tyr Ala Trp
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ile Ile Phe Ser Pro Asn Ala Met
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ile Ile Phe Ser Pro Asn Ala Met
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 31

Gly Ile Thr Asn Arg Ile Thr Thr Met
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Ser Val Arg Thr Ile Asn Asp Met
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ile Ile Phe Ser Pro Asn Ala Met
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Arg Thr Phe Arg Ser Tyr Thr Met
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ile Ile Phe Ser Pro Asn Ala Met
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Arg Thr Phe Ser Ser Tyr Val Met
1               5

<210> SEQ ID NO 37
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Leu Glu Asn Pro Pro Phe Ala Ile
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ser Thr Val Thr Ile Ser Thr Val
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Ile Ile Phe Asn Pro Asn Ala Met
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ile Ile Phe Ser Pro Asn Ala Leu
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ile Ile Phe Ser Pro Asn Ala Met
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42
```

```
Gly Ile Ile Phe Ser Pro Asn Ala Leu
1               5
```

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Gly Ile Phe Glu Ser Thr Phe Asp Ala Thr Ala Met
1               5                   10
```

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Gly Ser Ile Phe Ser Thr Asn Val Met
1               5
```

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Gly Arg Thr Phe Asp Lys Tyr Arg Ile
1               5
```

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Gly Arg Thr Phe Ile Asn Arg Ser Met
1               5
```

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Gly Phe Thr Phe Ser Met Tyr Gly Met
1               5
```

<210> SEQ ID NO 48
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 48

Gly Leu Thr Phe Ser Ser Tyr Gly Met
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Arg Thr Phe Ser Ser Tyr Ala Met
1               5

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Arg Asp Ala Ser Asp Gly Thr Phe Ser Arg Tyr Val Met
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Arg Thr Phe Gly Ser Leu His Met
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Phe Thr Phe Asp Asp Tyr Val Ile
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Phe Arg Leu Asn Asp Tyr Tyr Val
1               5

```
<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ile Ile Phe Arg Ile Asn Thr Met
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Phe Thr Leu Gly Tyr Phe Ala Ile
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Leu Ala Phe Asn Thr Lys Thr Met
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Phe Thr Phe Ser Arg Tyr Leu Met
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Arg Ile Phe Gly Ser Leu His Met
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59
```

```
Gly Ser Ile Ser Ser Ile Lys Ala Met
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Arg Thr Phe Ser Arg Asp Ala Met
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Arg Thr Phe Ser Ser Tyr Ala Met
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Arg Thr Phe Ser Ile Tyr Ala Met
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Leu Ala Phe Ser Thr Lys Thr Met
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Arg Thr Phe Ser Ser Asn Thr Met
1               5

<210> SEQ ID NO 65
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 65

Gly Arg Thr Phe Ser Ser Tyr Gly Met
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Arg Ala Leu Ser Ala Tyr Ile Met
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Arg Thr Phe Asn Thr Tyr Asn Ile
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Arg Ser Phe Ser Ser Tyr Asn Met
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Arg Thr Phe Ser Ser Tyr Thr Met
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Thr Phe Phe Arg Ile Asn Tyr Met
1               5
```

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Arg Thr Phe Ser Ser Tyr Ala Met
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Phe Asn Phe Ser Leu Tyr Ser Met
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Arg Ile Leu Ser Ser His Arg Met
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Phe Thr Leu Asp Asn Tyr Ala Ile
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Phe Met Pro Asp Tyr Ser Ala Leu
1               5

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 76

Leu Tyr Ser Leu Arg Thr Arg Leu Gln Tyr Leu
1               5                   10

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Phe Thr Phe Ser Ser Tyr Trp Met
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Phe Thr Phe Ser Asn Phe Trp Met
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Arg Thr Phe Ser Ser Tyr Ala Met
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Arg Thr Phe Ile Asn Arg Ser Met
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Phe Thr Leu Asp Tyr Phe Ala Ile
1               5

<210> SEQ ID NO 82
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 82

Gly Arg Thr Phe Ser Met Tyr Ala Met
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Val His Ser Phe Ser Asn Tyr Ala Leu
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Arg Pro Phe Ile Asn Tyr Asn Met
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Phe Thr Phe Asp Asp Phe Ala Val
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Phe Ser Leu Asp His Ser Ala Ile
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Phe Asp Phe Asn Ile Tyr Trp Met
1               5
```

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Arg Thr Leu Arg Ser Tyr Val Met
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Leu Ile Phe Gly Asp Tyr Val Met
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Arg Thr Phe Ser Asn Leu Ala Met
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Arg Thr Phe Ser Ser Tyr Ala Met
1               5

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ile Thr Thr Gly Gly Asn Thr Ala Asn Thr
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 93

Ile Thr Ile Thr Ser Gly Arg Gly Gly Asn Thr
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Thr Ser Phe Gly Ile Ile
1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ile Thr Thr Gly Gly Ser Tyr Gly Asn Thr
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Leu Pro Ser Gly Arg Thr
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Leu Pro Thr Gly Thr Thr
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ile Ser Arg Ala Gly Ser Thr
1               5

<210> SEQ ID NO 99
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Leu Ser Met Ala Arg Ala
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ile Arg Trp Gly Asn Gly Asn Thr
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ile Thr Arg Ser Gly Ser Thr
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Arg Trp Gly Asn Gly Asn Thr
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ile Ser Arg Ala Gly Asn Thr
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Ser Trp Ser Gly Gly Asn Thr
```

```
<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Thr Lys Asn Gly Arg Thr Thr
1               5

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ile Gly Thr Gly Gly Ser Ser Ser Gly Asn Thr
1               5                   10

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ile Arg Trp Gly Asn Gly Asn Thr
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Met Thr Gly Gly Lys Thr Pro Asp Ala
1               5                   10

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ile Thr Trp Gly Asn Gly Asn Thr
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 110

Ile Tyr Pro Ser Gly Ser Ser Thr
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ile Thr Ser Phe Gly Ile Ile
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ile Thr Ser Phe Gly Ile Ile
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ile Ile Ser Gly Gly Arg Ser
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Thr Ser Phe Gly Ile Ile
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Leu Leu Pro Ser Gly Arg Thr
1               5

<210> SEQ ID NO 116

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ile Ile Ser Phe Gly Ile Lys
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Lys Ser Ser Gly Ala Asp Pro
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ile Ser Ser Ser Gly Ser Ser Thr
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ile Ser Trp Thr Gly Gly Ile Ile
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ile Thr Ser Phe Gly Ile Ile
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121
```

```
Ile Thr Ser Phe Gly Ile Ile
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ile Arg Asp Asp Arg Asp Ala Asn
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ile Ser Ser Gly Gly Asn Thr
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ile Thr Ser Phe Gly Ile Ile
1               5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ile Ser Trp Ser Ala Gly Ser Thr
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ile Thr Ser Ser Gly Ile Ile
1               5

<210> SEQ ID NO 127
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 127

Ile Ser Trp Ser Gly Gly Ser Ser
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ile Thr Tyr Cys Val Met Glu Ile
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ile Ser Ser Asp Ser Thr Thr
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ile Thr Ser Phe Gly Ile Ile
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ile Ile Ser Gly Gly Arg Ser
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ile Thr Ser Phe Gly Ile Ile
1               5

```
<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ile Ile Ser Gly Gly Arg Ser
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ile Gly Ser Arg Gly Ser Ile
1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ile Thr Ser Gly Gly Asn Thr
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ile Ser Trp Asn Gly Ala Tyr Thr
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ile Ser Ser Ser Gly Ser Asn Thr
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138
```

```
Ile Asn Ser Gly Gly Ala Arg Thr
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ile Lys Met Ser Gly Asp Thr
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ile Asn Trp Ser Gly Gly Arg Ile
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Met Arg Trp Asn Thr Gly Ser Glu
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ile Ser Ala Ala Gly Gly Val Thr
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Thr Ser Ser Ser Asp Gly Asp Thr
1               5

<210> SEQ ID NO 144
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 144

Thr Gly Ser Arg Ser Gly Arg Leu
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ile Thr Arg Ala Gly Ser Thr
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ile Ser Asn Ser Asp Gly Ser Thr
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ile Thr Trp Gly Thr Ile Asn Thr
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Val Asn Ser Gly Gly Ala Met Thr
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Thr Ala Ala Gly Gly Val Thr
1               5
```

```
<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Trp Arg Met Tyr Ser Gly Thr
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ile Asn Trp Asn Gly Arg Ser Thr
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ile Asn Trp Ser Gly Gly Arg Ile
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ile Asn Trp Ser Gly Gly Arg Ile
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ile Thr Trp Gly Thr Ser Ser Thr
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 155

Ile Ala Ser Ser Asp Gly Ala Thr
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ile Lys Val Ser Gly Asp Thr
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ile Ser Ser Ser Gly Ser Asn Thr
1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ile Ser Trp Gly Arg Gly Asn Thr
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ile Thr Trp Ser Gly Asn Thr
1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ile Ser Trp Ser Gly Gly Asn Thr
1               5

<210> SEQ ID NO 161
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 161

Ile Ser Ser Gly Gly Ser Thr
1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ile Arg Trp Thr Arg Ser Ser Thr
1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ile Ser Asn Leu Ser Val Arg Thr
1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ile Arg Trp Gly Ser Gly Ser Thr
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ile Ser Arg Ser Asp Gly Asp Thr
1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ile Ser Arg Asp Gly His Thr Tyr
1               5
```

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Thr Tyr Trp Pro Ile Phe Cys His
1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ile Asp Thr Gly Gly Gly Ser Thr
1               5

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Leu Asn Thr Gly Gly Gly Ala Thr
1               5

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ile Ser Trp Asp Gly Ala Thr Thr
1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Ser Ser Gly Ser Tyr Ser
1               5

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 172

Ile Ser Asn Ile Asp Gly Ile Thr
1               5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ile Asn Trp Ser Gly Ala Ser Thr
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ile Thr Trp Asn Ala Glu Ser
1               5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ile Ser Trp Ser Gly Asp Ser Thr
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Leu Ser Ser Ser Asp Gly Ser Thr
1               5

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Val His His Asp Gly Thr Ala
1               5

<210> SEQ ID NO 178
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ile Arg Ser Thr Gly Asp Thr Ile
1               5

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Leu Ser Trp Ser Gly Ile Ser Thr
1               5

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ile Ser Ser Asp Ser Thr Thr
1               5

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ile Asn Trp Ser Asp Asn Thr
1               5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ile Arg Trp Thr Arg Ser Ser Thr
1               5

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Ala Arg Gly Leu Ser Tyr Glu Tyr Asp Tyr
```

```
<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Ala Arg Gly Ala Met Thr Tyr Glu Tyr Asp Tyr
1               5                   10

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asn Ala Lys Thr Phe Asp Gly Thr Arg Trp Arg Asp Tyr
1               5                   10

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Ala Arg Gly Ser Gln Thr Tyr Glu Tyr Asp Tyr
1               5                   10

<210> SEQ ID NO 187
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asn Thr Ala Asp Phe
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Tyr Cys Asn Thr Ala Asp Phe
1               5

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 189

Lys Ala Ser Ser Gly Ser Ser Val Tyr Ile Gly Phe Gly Ser
1               5                   10

<210> SEQ ID NO 190
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asn Thr Thr Asp Phe
1               5

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ala Ala Arg Ile Val Asn Gly Gly Ser Trp Asp Tyr
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asn Ala Asp Phe Tyr Gly Leu Tyr Pro Arg Gln Tyr
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ala Ala Arg Gly Leu Ala Tyr Glu Tyr Glu Tyr
1               5                   10

<210> SEQ ID NO 194
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Lys Ala Ser Ser Gly Ser Ser Val Tyr Ile Gly Val Gly Ser
1               5                   10

<210> SEQ ID NO 195

<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ala Ala Pro Glu Arg Ser Gly Ser Tyr Ala Tyr Thr Pro Ser Arg Leu
1               5                   10                  15

Asn Glu Tyr Ala Tyr
            20

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ala Gly Arg Arg Ser Asn Ala Asp Asn Trp Asp Tyr
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ala Ala Arg Gly Thr Ile Ser Tyr Glu Tyr Asp Tyr
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Thr Arg Ile Val Asn Gly Gly Ser Trp Asp Tyr
1               5                   10

<210> SEQ ID NO 199
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Tyr Asn Cys Asp Phe Trp Gly Leu Ala Tyr Glu Tyr Asp Tyr
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 200

Pro Ala Arg Ile Val Asn Gly Gly Ser Trp Asp Tyr
1               5                   10

<210> SEQ ID NO 201
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Thr Ala Ser Arg Arg Gly Val Val Ser Leu Thr Ser Asn Pro Ser
1               5                   10                  15

Thr Ser Arg Asn Asp Phe Ser Ser
            20

<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asn Ala Lys Thr Phe Asp Gly Thr Arg Trp His Asp Tyr
1               5                   10

<210> SEQ ID NO 203
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asn Ala Lys Ala Phe Asp Gly Thr Arg Trp His Asp Tyr
1               5                   10

<210> SEQ ID NO 204
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Asn Ala Asn Val Tyr Asp Gly Asn Arg Trp Arg Thr Tyr
1               5                   10

<210> SEQ ID NO 205
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Asn Ala Lys Ser Phe Asp Gly Ser Arg Trp Asn Asp Tyr
1               5                   10
```

<210> SEQ ID NO 206
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asn Thr Ala Asp Phe
1               5

<210> SEQ ID NO 207
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Asn Gly Lys Ala Phe Asp Phe Asn Arg Trp His Asp Tyr
1               5                   10

<210> SEQ ID NO 208
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Tyr Arg Lys Gly Gln Tyr Tyr Arg Gly Thr Tyr Trp Asp Asn Phe Glu
1               5                   10                  15

Ser

<210> SEQ ID NO 209
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Ala Val Arg Pro Tyr Gly Ser Gly Thr Tyr Ser Arg Thr Glu Ala
1               5                   10                  15

Tyr Asn Phe

<210> SEQ ID NO 210
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Ala Val Gly Arg Ile Leu Gly Trp Ile Pro Thr Met Tyr Arg Gln
1               5                   10                  15

Ala Ala Ser Tyr Asp Tyr
            20

<210> SEQ ID NO 211

<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Asn Ala Lys Ser Phe Asp Gly Thr Arg Trp Val Glu His
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asn Ala Lys Ala Phe Asp Gly Thr Arg Trp Arg Asp Tyr
1               5                   10

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Asn Val Gln Thr Ile Ile Arg Asn Tyr
1               5

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ser Gln Arg Gly Gln Tyr Phe Thr Glu Gly Tyr Trp Lys Glu Tyr Asp
1               5                   10                  15

Asn

<210> SEQ ID NO 215
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Asn Ala Asn Val Tyr Asp Gly Asn Arg Trp Arg Thr Tyr
1               5                   10

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 216

Ala Ala Gly Thr Lys Tyr Ser Asp Thr Ile Ile Thr Trp Gly Ser
1               5                   10                  15

<210> SEQ ID NO 217
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Asn Ala Lys Ala Phe Asp Gly Thr Arg Trp Tyr Asp Tyr
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ala Ala Arg Thr Ala Leu Gly Gly Thr Tyr Asp Tyr
1               5                   10

<210> SEQ ID NO 219
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

His Thr Pro His Phe
1               5

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Asn Val Val Gly Thr Tyr Trp Thr Gly Ala Asp Trp Arg Pro Phe Asp
1               5                   10                  15

Thr

<210> SEQ ID NO 221
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Asn Ala Ile Thr Phe Tyr Gly Thr Arg Trp Leu Asp Tyr
1               5                   10

<210> SEQ ID NO 222
```

```
<210> SEQ ID NO 222
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Asn Ala Asp Val Tyr Asp Gly Asn Arg Trp Arg Thr Tyr
1               5                   10

<210> SEQ ID NO 223
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Phe Ala Lys Thr Phe Asp Gly Thr Arg Trp Cys Asp Tyr
1               5                   10

<210> SEQ ID NO 224
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Asn Ala Ile Val Tyr Asp Gly Asn Arg Trp Arg Thr Tyr
1               5                   10

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asn Ser Val Gly His
1               5

<210> SEQ ID NO 226
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ala Ala Gln Thr Leu Gly Ser Ser Tyr Tyr Asp Ala
1               5                   10

<210> SEQ ID NO 227
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227
```

```
Ala Ala Val Gln Ser Thr Val Ile Gln Thr Ser Pro Asn Arg Tyr Asn
1               5                   10                  15

Tyr

<210> SEQ ID NO 228
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Ala Ala Arg Leu Gly Trp Gly Leu Thr Ile Ser Asp Arg Ile Tyr
1               5                   10                  15

Glu Tyr

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Lys Ala Ser Leu Pro Trp Phe Asp Gly Ser Ser Pro Asp Tyr
1               5                   10                  15

<210> SEQ ID NO 230
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Ala Ala Arg Val Arg Thr Pro Gly Trp Gly Pro Gln Lys Ser Tyr
1               5                   10                  15

Asp Tyr

<210> SEQ ID NO 231
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asn Ala Asp Tyr Asp Asn Ser Gly Ser Tyr Tyr Tyr Gln Lys Gly Asn
1               5                   10                  15

Tyr Glu Tyr Asp Tyr
            20

<210> SEQ ID NO 232
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232
```

```
Thr Ala Asp Gly Pro Pro Asp Tyr Gly Lys Tyr Asp Tyr
1               5                   10
```

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

```
Ala Ala Val Lys Tyr Trp Gly Arg Arg Gln Arg Ala Asp Glu Tyr Asp
1               5                   10                  15

Tyr
```

<210> SEQ ID NO 234
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

```
Ala Ala Glu Leu Ser Leu Asn Pro Gly Lys Arg Leu Thr Leu Glu Ile
1               5                   10                  15

Leu Lys Tyr Asp Tyr
            20
```

<210> SEQ ID NO 235
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

```
Ala Ala Gly Tyr Gly Ala Gly Asp Val Lys Arg Ala Leu Ser Ser Cys
1               5                   10                  15

Arg Gly Ser Tyr Val Tyr
            20
```

<210> SEQ ID NO 236
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

```
Lys Met Asn His Gln Leu Tyr Ser Asp Ser Ser Tyr Glu Asn Val Tyr
1               5                   10                  15
```

<210> SEQ ID NO 237
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

```
Ala Thr Asp Thr Trp Gly Asn Ser Arg Cys Asp His Asp Met Arg Tyr
```

```
<210> SEQ ID NO 238
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Glu Ser Glu Ala Leu Leu Glu Thr Thr Pro Ser Arg Arg Pro Tyr Glu
1               5                   10                  15

Tyr Asn Tyr

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ala Lys Gly Gln Arg Glu Tyr Tyr Asn Asp Phe Glu Phe Asp Tyr
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Arg Thr Leu Gly Cys Ser Tyr Tyr Glu Arg Ala Asp Glu Tyr Asn Tyr
1               5                   10                  15

<210> SEQ ID NO 241
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Tyr Leu Glu Ile Pro Glu Ser Arg Gly Ala Phe
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Ala Gly Glu Trp Gly Ile Arg Pro Tyr Asn Tyr Asp Tyr
1               5                   10

<210> SEQ ID NO 243
<211> LENGTH: 21
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 243

Asn Thr Asp Tyr Asp Asn Ser Gly Ser Tyr Tyr Tyr Gln Lys Gly Asn
1               5                   10                  15

Tyr Glu Tyr Asp Tyr
            20

<210> SEQ ID NO 244
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asn Ala Asn Tyr Asp Asn Asn Gly Ser Tyr Tyr Tyr Gln Lys Gly Asn
1               5                   10                  15

Tyr Glu Tyr Asp Tyr
            20

<210> SEQ ID NO 245
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ala Ala Ala Ala Leu Leu Glu Thr Thr Pro Ser Arg Arg Pro Ser Ala
1               5                   10                  15

Tyr Asn Tyr

<210> SEQ ID NO 246
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ala Gly Ala Trp Gly Tyr Ala Gly Ile Ile Pro Arg Gly Ala Tyr Asp
1               5                   10                  15

Asp

<210> SEQ ID NO 247
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ala Ala Ala Arg Ile Arg Thr Pro Gly Trp Gly Pro Gln Lys Ser Tyr
1               5                   10                  15

Asp Tyr

<210> SEQ ID NO 248
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Ala Gly Val Val Thr Ala Gln Ala Ile Met Ala Ala Arg Asp Phe
1               5                   10                  15

Asp Tyr

<210> SEQ ID NO 249
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Ala Asp Arg Ser Arg Glu Gly Arg Thr Arg Pro Asn Glu Tyr Asp
1               5                   10                  15

Tyr

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Lys Val Arg Ala Glu Asp Thr Asp Tyr
1               5

<210> SEQ ID NO 251
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ala Ala Pro Glu Arg Ser Gly Ser Tyr Ala Tyr Thr Pro Ser Arg Leu
1               5                   10                  15

Asn Glu Tyr Ala Tyr
            20

<210> SEQ ID NO 252
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Asn Ala Asp Phe Tyr Gly Leu Tyr Pro Arg Gln Tyr
1               5                   10

<210> SEQ ID NO 253
<211> LENGTH: 18
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 253

Ala Ala Asp Arg Tyr Tyr Arg Thr Asp Ile Tyr Arg Ala Ser Ser Tyr
1               5                   10                  15

Glu Tyr

<210> SEQ ID NO 254
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ala Lys Gly Trp Thr Val Asp Val Asn His Ile Glu Asp
1               5                   10

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Ala Lys Tyr Gly Gly Thr Asp Leu Leu Ser Arg Tyr Glu Tyr
1               5                   10                  15

<210> SEQ ID NO 256
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ala Ser Val Tyr Ser Phe Asp Pro Gly Arg Cys Gly Pro Ile Ala Thr
1               5                   10                  15

Met Val Gly His Tyr
            20

<210> SEQ ID NO 257
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ala Thr Asp Ala Ala Gly Gly Arg Gly Ser Phe Phe Ile Asp His Lys
1               5                   10                  15

Arg Thr Cys Pro Ser Glu Glu Tyr Asp Ser
            20                  25

<210> SEQ ID NO 258
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 258

Thr Ala Asp Gly Pro Pro Asp Tyr Gly Lys Tyr Asp Tyr
1               5                   10

<210> SEQ ID NO 259
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ala Arg Val Ser Val Ile Arg Pro Pro Tyr Gly Val Tyr Ser Asp Phe
1               5                   10                  15

Gly Ser

<210> SEQ ID NO 260
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Thr Leu Tyr Gly Ser Gly Ala Ala Glu Lys Phe His Ser
1               5                   10

<210> SEQ ID NO 261
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ala Ala Asn Trp Gly Arg Arg Arg Val Pro Thr Thr Val His Glu Tyr
1               5                   10                  15

Asp Tyr

<210> SEQ ID NO 262
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ala Ala Ala Arg Leu Gly Trp Gly Leu Thr Ile Ser Asp Arg Ile Tyr
1               5                   10                  15

Glu Tyr

<210> SEQ ID NO 263
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 263

Ala Thr Asp Thr Trp Gly Asn Ser Arg Cys Asp His Asp Met Arg Tyr
1               5                   10                  15

<210> SEQ ID NO 264
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ala Ala Gly Ser Phe Ser Asp Asn Lys Tyr Tyr Thr Arg Ser Gln Asp
1               5                   10                  15

Tyr Glu His

<210> SEQ ID NO 265
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ala Ala Ser Ser Trp Cys Gln Thr Phe Asp Ala Lys Tyr Gly Tyr
1               5                   10                  15

<210> SEQ ID NO 266
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ala Ala Asp Asn Gln His Asp Ile Pro Leu Arg Pro Gly
1               5                   10

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

His Pro Ser Asp Thr Thr Gly Trp Thr Arg Gly Arg Ala Tyr
1               5                   10

<210> SEQ ID NO 268
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ala Thr Ala Cys Thr Arg Leu Trp Lys Pro Gly Arg Asp Tyr
1               5                   10

```
<210> SEQ ID NO 269
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Met Arg Asp Phe Tyr Thr
1               5

<210> SEQ ID NO 270
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ala Ala Ala Ser Thr Ile Lys His Cys Tyr Thr Ala Val Ser Tyr Tyr
1               5                   10                  15

Thr Lys Asp Ala Gln Tyr Asp Tyr
            20

<210> SEQ ID NO 271
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Asn Val Val Gly Thr Tyr Trp Thr Gly Ala Asp Trp Arg Pro Phe Asp
1               5                   10                  15

Thr

<210> SEQ ID NO 272
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gly Val Ala Arg Asp Ser Arg Ser Tyr Tyr Asn Phe Arg Leu Asn Gln
1               5                   10                  15

Glu Asp Glu Tyr Asp Tyr
            20

<210> SEQ ID NO 273
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ala Ala Ser His Gly Ile Gly Arg Val Val Ala Glu Ser Leu Tyr Asp
1               5                   10                  15

Tyr
```

<210> SEQ ID NO 274
<211> LENGTH: 185
<212> TYPE: PRT
<213> ORGANISM: Salmonella typhimurium

<400> SEQUENCE: 274

Met Lys His Lys Leu Met Thr Ser Thr Ile Ala Ser Leu Met Phe Val
1               5                   10                  15

Ala Gly Ala Ala Val Ala Ala Asp Pro Thr Pro Val Ser Val Ser Gly
            20                  25                  30

Gly Thr Ile His Phe Glu Gly Lys Leu Val Asn Ala Ala Cys Ala Val
        35                  40                  45

Ser Thr Lys Ser Ala Asp Gln Thr Val Thr Leu Gly Gln Tyr Arg Thr
    50                  55                  60

Ala Ser Phe Thr Ala Ile Gly Asn Thr Thr Ala Gln Val Pro Phe Ser
65                  70                  75                  80

Ile Val Leu Asn Asp Cys Asp Pro Lys Val Ala Ala Asn Ala Ala Val
                85                  90                  95

Ala Phe Ser Gly Gln Ala Asp Asn Thr Asn Pro Asn Leu Leu Ala Val
            100                 105                 110

Ser Ser Ala Asp Asn Ser Thr Thr Ala Thr Gly Val Gly Ile Glu Ile
        115                 120                 125

Leu Asp Asn Thr Ser Ser Pro Leu Lys Pro Asp Gly Ala Thr Phe Ser
    130                 135                 140

Ala Lys Gln Ser Leu Val Glu Gly Thr Asn Thr Leu Arg Phe Thr Ala
145                 150                 155                 160

Arg Tyr Lys Ala Thr Ala Ala Thr Thr Pro Gly Gln Ala Asn Ala
                165                 170                 175

Asp Ala Thr Phe Ile Met Lys Tyr Glu
            180                 185

<210> SEQ ID NO 275
<211> LENGTH: 495
<212> TYPE: PRT
<213> ORGANISM: Salmonella typhimurium

<400> SEQUENCE: 275

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
            165                 170                 175

Gln Lys Tyr Lys Val Ser Asp Thr Ala Ala Thr Val Thr Gly Tyr Ala
        180                 185                 190

Asp Thr Thr Ile Ala Leu Asp Asn Ser Thr Phe Lys Ala Ser Ala Thr
    195                 200                 205

Gly Leu Gly Gly Thr Asp Gln Lys Ile Asp Gly Asp Leu Lys Phe Asp
210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
            245                 250                 255

Val Thr Leu Ala Gly Gly Ala Thr Ser Pro Leu Thr Gly Gly Leu Pro
        260                 265                 270

Ala Thr Ala Thr Glu Asp Val Lys Asn Val Gln Val Ala Asn Ala Asp
    275                 280                 285

Leu Thr Glu Ala Lys Ala Ala Leu Thr Ala Ala Gly Val Thr Gly Thr
290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
            325                 330                 335

Gln Asn Lys Asp Gly Ser Ile Ser Ile Asn Thr Thr Lys Tyr Thr Ala
        340                 345                 350

Asp Asp Gly Thr Ser Lys Thr Ala Leu Asn Lys Leu Gly Gly Ala Asp
    355                 360                 365

Gly Lys Thr Glu Val Val Ser Ile Gly Gly Lys Thr Tyr Ala Ala Ser
370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
            405                 410                 415

Ala Gln Val Asp Thr Leu Arg Ser Asp Leu Gly Ala Val Gln Asn Arg
        420                 425                 430

Phe Asn Ser Ala Ile Thr Asn Leu Gly Asn Thr Val Asn Asn Leu Thr
    435                 440                 445

Ser Ala Arg Ser Arg Ile Glu Asp Ser Asp Tyr Ala Thr Glu Val Ser
450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
            485                 490                 495

<210> SEQ ID NO 276
<211> LENGTH: 80
<212> TYPE: PRT
<213> ORGANISM: Salmonella typhimurium

<400> SEQUENCE: 276

Met Ala Thr Pro Trp Ser Gly Tyr Leu Asp Asp Val Ser Ala Lys Phe
1               5                   10                  15

Asp Thr Gly Val Asp Asn Leu Gln Thr Gln Val Thr Glu Ala Leu Asp
            20                  25                  30

```
Lys Leu Ala Ala Lys Pro Ser Asp Pro Ala Leu Leu Ala Ala Tyr Gln
            35                  40                  45

Ser Lys Leu Ser Glu Tyr Asn Leu Tyr Arg Asn Ala Gln Ser Asn Thr
 50                  55                  60

Val Lys Val Phe Lys Asp Ile Asp Ala Ala Ile Ile Gln Asn Phe Arg
 65                  70                  75                  80

<210> SEQ ID NO 277
<211> LENGTH: 185
<212> TYPE: PRT
<213> ORGANISM: Salmonella enteritidis

<400> SEQUENCE: 277

Met Lys His Lys Leu Met Thr Ser Thr Ile Ala Ser Leu Met Phe Val
 1               5                  10                  15

Ala Gly Ala Ala Val Ala Ala Asp Pro Thr Pro Val Ser Val Ser Gly
            20                  25                  30

Gly Thr Ile His Phe Glu Gly Lys Leu Val Asn Ala Ala Cys Ala Val
            35                  40                  45

Ser Thr Lys Ser Ala Asp Gln Thr Val Thr Leu Gly Gln Tyr Arg Thr
 50                  55                  60

Ala Ser Phe Thr Ala Ile Gly Asn Thr Thr Ala Gln Val Pro Phe Ser
 65                  70                  75                  80

Ile Val Leu Asn Asp Cys Asp Pro Lys Val Ala Thr Ala Ala Val
                 85                  90                  95

Ala Phe Ser Gly Gln Ala Asp Asn Thr Asn Pro Asn Leu Leu Ala Val
            100                 105                 110

Ser Ser Ala Asp Asn Ser Thr Thr Ala Thr Gly Val Gly Ile Glu Ile
            115                 120                 125

Leu Asp Asn Thr Ser Ser Pro Leu Lys Pro Asp Gly Ala Thr Phe Ser
130                 135                 140

Ala Lys Gln Ala Leu Val Glu Gly Thr Asn Thr Leu Arg Phe Thr Ala
145                 150                 155                 160

Arg Tyr Lys Ala Thr Ala Thr Ala Thr Thr Pro Gly Gln Ala Asn Ala
                165                 170                 175

Asp Ala Thr Phe Ile Met Lys Tyr Glu
            180                 185

<210> SEQ ID NO 278
<211> LENGTH: 505
<212> TYPE: PRT
<213> ORGANISM: Salmonella enteritidis

<400> SEQUENCE: 278

Met Ala Gln Val Ile Asn Thr Asn Ser Leu Ser Leu Leu Thr Gln Asn
 1               5                  10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
            35                  40                  45

Ala Ile Ala Asn Arg Phe Thr Ser Asn Ile Lys Gly Leu Thr Gln Ala
 50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ser
                85                  90                  95
```

```
Val Gln Ala Thr Asn Gly Thr Asn Ser Asp Ser Asp Leu Lys Ser Ile
                100                 105                 110

Gln Asp Glu Ile Gln Gln Arg Leu Glu Glu Ile Asp Arg Val Ser Asn
            115                 120                 125

Gln Thr Gln Phe Asn Gly Val Lys Val Leu Ser Gln Asp Asn Gln Met
        130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Gly Pro Lys Glu Ala Thr Val Gly Asp Leu Lys Ser Ser Phe Lys Asn
            180                 185                 190

Val Thr Gly Tyr Asp Thr Tyr Ala Ala Gly Ala Asp Lys Tyr Arg Val
        195                 200                 205

Asp Ile Asn Ser Gly Ala Val Val Thr Asp Ala Ala Pro Asp Lys
            210                 215                 220

Val Tyr Val Asn Ala Ala Asn Gly Gln Leu Thr Thr Asp Asp Ala Glu
225                 230                 235                 240

Asn Asn Thr Ala Val Asp Leu Phe Lys Thr Thr Lys Ser Thr Ala Gly
                245                 250                 255

Thr Ala Glu Ala Lys Ala Ile Ala Gly Ala Ile Lys Gly Gly Lys Glu
            260                 265                 270

Gly Asp Thr Phe Asp Tyr Lys Gly Val Thr Phe Thr Ile Asp Thr Lys
        275                 280                 285

Thr Gly Asp Asp Gly Asn Gly Lys Val Ser Thr Thr Ile Asn Gly Glu
            290                 295                 300

Lys Val Thr Leu Thr Val Ala Asp Ile Ala Thr Gly Ala Thr Asp Val
305                 310                 315                 320

Asn Ala Ala Thr Leu Gln Ser Ser Lys Asn Val Tyr Thr Ser Val Val
                325                 330                 335

Asn Gly Gln Phe Thr Phe Asp Asp Lys Thr Lys Asn Glu Ser Ala Lys
            340                 345                 350

Leu Ser Asp Leu Glu Ala Asn Asn Ala Val Lys Gly Glu Ser Lys Ile
        355                 360                 365

Thr Val Asn Gly Ala Glu Tyr Thr Ala Asn Ala Thr Gly Asp Lys Ile
        370                 375                 380

Thr Leu Ala Gly Lys Thr Met Phe Ile Asp Lys Thr Ala Ser Gly Val
385                 390                 395                 400

Ser Thr Leu Ile Asn Glu Asp Ala Ala Ala Lys Lys Ser Thr Ala
                405                 410                 415

Asn Pro Leu Ala Ser Ile Asp Ser Ala Leu Ser Lys Val Asp Ala Val
            420                 425                 430

Arg Ser Ser Leu Gly Ala Ile Gln Asn Arg Phe Asp Ser Ala Ile Thr
        435                 440                 445

Asn Leu Gly Asn Thr Val Thr Asn Leu Asn Ser Ala Arg Ser Arg Ile
        450                 455                 460

Glu Asp Ala Asp Tyr Ala Thr Glu Val Ser Asn Met Ser Lys Ala Gln
465                 470                 475                 480

Ile Leu Gln Gln Ala Gly Thr Ser Val Leu Ala Gln Ala Asn Gln Val
                485                 490                 495

Pro Gln Asn Val Leu Ser Leu Leu Arg
            500                 505
```

<210> SEQ ID NO 279
<211> LENGTH: 80
<212> TYPE: PRT
<213> ORGANISM: Salmonella enteritidis

<400> SEQUENCE: 279

Met Ala Thr Pro Trp Ser Gly Tyr Leu Asp Asp Val Ser Ala Lys Phe
1               5                   10                  15

Asp Thr Gly Val Asp Asn Leu Gln Thr Gln Val Thr Glu Ala Leu Asp
            20                  25                  30

Lys Leu Ala Ala Lys Pro Ser Asp Pro Ala Leu Leu Ala Ala Tyr Gln
        35                  40                  45

Ser Lys Leu Ser Glu Tyr Asn Leu Tyr Arg Asn Ala Gln Ser Asn Thr
    50                  55                  60

Val Lys Val Phe Lys Asp Ile Asp Ala Ala Ile Ile Gly Asn Phe Arg
65                  70                  75                  80

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gly Arg Thr Ser Ser Ser Ala Tyr Thr
1               5

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Thr Arg Thr Ser Ser Ser Ser Tyr Thr
1               5

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gly Arg Thr Ser Ser Ser Ala Tyr Thr
1               5

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Gly Arg Thr Ser Pro Ser Ser Tyr Thr
1               5

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gly Ser Thr Leu Ser Asn Tyr Ala Val
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gly Arg Thr Phe Ser Ser Leu Ala Met
1               5

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gly Arg Thr Phe Ser Ser Leu Ala Met
1               5

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Thr Ala Ile Leu Ser Ile Asp Ser Met
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Gly Asp Ile Ser Thr Ile Asp Val Met
1               5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 289

Gly Phe Thr Phe Ser Ser Ser Ile Met
1               5

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gly Asp Ile Ser Ser Ile Ser Val Met
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gly Phe Thr Phe Ser Thr Asn Ile Leu
1               5

<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Thr Ser Ile Leu Ser Ile Asn Ala Met
1               5

<210> SEQ ID NO 293
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Gly Ser Ile Ser Ser Ile Thr Ala Met
1               5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gly Ser Ile Ser Ser Ile Thr Ala Met
1               5

<210> SEQ ID NO 295
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 295

Gly Phe Thr Phe Ser Ser Ala Ile Met
1               5

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Thr Ser Ile Leu Ser Ile Asp Ala Met
1               5

<210> SEQ ID NO 297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Ser Ile Ser Ser Ile Thr Ala Met
1               5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gly Ser Ala Phe Ser Gly Asp Ala Met
1               5

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Ser Ala Phe Ser Gly Gly Asp Ala Met
1               5                   10

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gly Ser Ala Phe Ser Gly Asp Ala Met
1               5
```

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gly Leu Thr Phe Asn Asn Tyr Ala Met
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gly Ile Asp Ser Ser Phe Tyr Val Met
1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gly Ile Asp Ser Ser Phe Tyr Val Met
1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gly Leu Thr Phe Ser Ser Tyr Ala Met
1               5

<210> SEQ ID NO 305
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Glu Ser Ile Phe Ser Arg Asn Ala
1               5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 306

Gly Ile Thr Ser Ser Leu Tyr Val Met
1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gly Leu Thr Phe Asn Asn Tyr Ala Met
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gly Ile Asp Ser Ser Phe Tyr Val Met
1               5

<210> SEQ ID NO 309
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gly Ser Gly Ile Leu Phe Arg Ile Ser Ala
1               5                   10

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ala Arg Thr Leu Ser Asn Tyr Ala Met
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gly Ser Ala Phe Ser Gly Asp Ala Met
1               5

<210> SEQ ID NO 312
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gly Leu Thr Phe His Asn Tyr Ala Met
1               5

<210> SEQ ID NO 313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gly Ser Ala Phe Ser Gly Asp Ala Met
1               5

<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Arg Thr Phe Ser Thr Tyr Ala
1               5

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gly Ser Ala Phe Ser Gly Asp Ala Met
1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gly Leu Thr Phe Asn Asn Tyr Ala Met
1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gly Ser Ala Phe Ser Gly Asp Ala Met
```

```
1               5
```

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

```
Gly Ser Ala Phe Ser Gly Asp Ala Met
1               5
```

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

```
Gly Ser Ala Phe Ser Gly Asp Ala Met
1               5
```

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

```
Gly Ser Ala Phe Ser Gly Asp Ala Met
1               5
```

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

```
Ile Ser Gly Phe Ser Gly Asp Ala Met
1               5
```

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

```
Gly Ile Ile Ser Ser Ala Tyr Val Met
1               5
```

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic

```
                         peptide

<400> SEQUENCE: 323

Gly Ile Ala Phe Ser Thr Tyr Gly Met
1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Gly Ser Ala Phe Ser Gly Asp Ala Met
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Gly Ser Ala Phe Ser Gly Asp Ala Met
1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Ser Ala Phe Ser Gly Asp Ala Met
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Gly Ser Ala Phe Ser Gly Asp Ala Met
1               5

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gly Ser Ala Phe Ser Gly Gly Asp Ala Met
1               5                   10

<210> SEQ ID NO 329
```

```
<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gly Ile Thr Phe Ser Ser Asp Ala Met
1               5

<210> SEQ ID NO 330
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ile Ser Trp Ser Gly Thr Thr Thr
1               5

<210> SEQ ID NO 331
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ile Ser Tyr Ser Gly Thr Thr Thr
1               5

<210> SEQ ID NO 332
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Ile Ser Trp Ser Gly Thr Thr Thr
1               5

<210> SEQ ID NO 333
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ile Ser Trp Ser Gly Thr Thr Thr
1               5

<210> SEQ ID NO 334
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334
```

Ile Ser Ser Gly Gly Ser Thr
1               5

<210> SEQ ID NO 335
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ile Ser Arg Ser Gly Asp Tyr Thr
1               5

<210> SEQ ID NO 336
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ile Thr Arg Ser Gly Asp Tyr Thr
1               5

<210> SEQ ID NO 337
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ile Ala Arg Gly Gly Ser Thr
1               5

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Ile Ala Arg Gly Gly Thr Ile
1               5

<210> SEQ ID NO 339
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ile Pro Ser Phe Gly Ser Ala
1               5

<210> SEQ ID NO 340
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 340

Ile Ala Ser Gly Gly Ser Val
1               5

<210> SEQ ID NO 341
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Ile Thr Pro Phe Gly Ser Ala
1               5

<210> SEQ ID NO 342
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ile Ala Pro Gly Gly Thr Thr
1               5

<210> SEQ ID NO 343
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ile Ala Arg Gly Gly Met Ile
1               5

<210> SEQ ID NO 344
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ile Ala Arg Gly Gly Met Thr
1               5

<210> SEQ ID NO 345
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Ile Pro Ser Phe Gly Ser Ala
1               5

```
<210> SEQ ID NO 346
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ile Ala Arg Gly Gly Ser Thr
1               5

<210> SEQ ID NO 347
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Ile Ala Arg Gly Gly Met Thr
1               5

<210> SEQ ID NO 348
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ile Ser Ser Gly Ala Ile Thr
1               5

<210> SEQ ID NO 349
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ile Ser Ser Gly Gly Ile Ala
1               5

<210> SEQ ID NO 350
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Ile Ser Ser Gly Gly Ile Pro
1               5

<210> SEQ ID NO 351
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351
```

```
Ile Ser Arg Asp Gly Thr Asn Thr
1               5

<210> SEQ ID NO 352
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Leu Gly Thr Pro Asp Ser Ala
1               5

<210> SEQ ID NO 353
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ile Ser Ser Ala Asp Ser Pro
1               5

<210> SEQ ID NO 354
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ile Gly Trp Ser Gly Gly Ser Thr
1               5

<210> SEQ ID NO 355
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Ile Gly Ser Asp Gly Ser Thr
1               5

<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ile Asn Ser Gly Asp Ser Pro
1               5

<210> SEQ ID NO 357
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 357

Ile Ser Arg Asp Gly Thr Ser Thr
1               5

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Ile Ser Met Thr Ser Ala Asp Ser Pro
1               5

<210> SEQ ID NO 359
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Ile Ser Ser Gly Gly Ser Thr
1               5

<210> SEQ ID NO 360
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Ile Ser Arg Ser Gly Gly Ser Ile
1               5

<210> SEQ ID NO 361
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ile Ser Ser Gly Gly Ile Thr
1               5

<210> SEQ ID NO 362
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ile Ser Arg Asp Gly Thr Asn Thr
1               5
```

```
<210> SEQ ID NO 363
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ile Ser Ser Gly His Ile Thr
1               5

<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ile Ser Arg Ser Gly Asp Asn Ile
1               5

<210> SEQ ID NO 365
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ile Ser Ser Gly Gly Ile Glu
1               5

<210> SEQ ID NO 366
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ile Ser Arg Asp Gly Thr Asn Thr
1               5

<210> SEQ ID NO 367
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ile Ser Ser Gly Gly Ile Thr
1               5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 368

Ile Ser Ser Gly Gly Ile Ala
1               5

<210> SEQ ID NO 369
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ile Ser Ser Gly Ala Ile Thr
1               5

<210> SEQ ID NO 370
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Ile Ser Ser Gly Gly Ile Thr
1               5

<210> SEQ ID NO 371
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ile Ser Ser Gly Gly Ile Thr
1               5

<210> SEQ ID NO 372
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ile Thr Ser Gly Asp Ser Pro
1               5

<210> SEQ ID NO 373
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Ile Thr Gly Asn Gly Asp Asp
1               5

<210> SEQ ID NO 374
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 374

Ile Ser Ser Gly Gly Ile Thr
1               5

<210> SEQ ID NO 375
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ile Ser Ser Gly Gly Ile Thr
1               5

<210> SEQ ID NO 376
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Ile Ser Ser Gly Gly Ile Thr
1               5

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Ile Ser Ser Gly Gly Ile Pro
1               5

<210> SEQ ID NO 378
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ile Ser Ser Gly Gly Ile Thr
1               5

<210> SEQ ID NO 379
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ile Ser Ser Gly Asp Ile Thr
1               5
```

```
<210> SEQ ID NO 380
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Ala Ala Asp Arg Arg Ser Thr Ile Gly Ser Pro Arg Gln Gln Tyr Ala
1               5                   10                  15

Tyr

<210> SEQ ID NO 381
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ala Ala Asp Arg Arg Ser Thr Ile Gly Ser Pro Arg Gln Gln Tyr Ala
1               5                   10                  15

Tyr

<210> SEQ ID NO 382
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ala Ala Asp Arg Arg Ser Thr Ile Gly Thr Pro Arg Glu Gln Tyr Ala
1               5                   10                  15

Tyr

<210> SEQ ID NO 383
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ala Ala Asp Arg Arg Ser Thr Ile Gly Ser Pro Arg Gln Gln Tyr Ala
1               5                   10                  15

Tyr

<210> SEQ ID NO 384
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

His Thr Tyr Asp Phe Gln Gly Trp Gly Leu Arg Ser Asp Tyr
1               5                   10
```

<210> SEQ ID NO 385
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ala Ala Thr Lys Ile Val Thr Pro Trp Thr Ser Thr Tyr Tyr Tyr Thr
1               5                   10                  15

Lys Ala Tyr Glu Trp Asp Tyr
            20

<210> SEQ ID NO 386
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ala Ala Thr Lys Ile Val Thr Pro Trp Thr Ser Thr Tyr Tyr Tyr Thr
1               5                   10                  15

Lys Ala Tyr Glu Trp Asp Tyr
            20

<210> SEQ ID NO 387
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ala Ala Asp Pro Gly Gly Ala Ser Pro Leu Ser
1               5                   10

<210> SEQ ID NO 388
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ala Val Asp Thr Gly Ser Pro Arg Leu Thr
1               5                   10

<210> SEQ ID NO 389
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Asn Thr Arg Leu Tyr
1               5

<210> SEQ ID NO 390
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Ala Val Asp Thr Gly Ser Pro Arg Leu Thr
1               5                   10

<210> SEQ ID NO 391
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Asn Thr Gln Leu Tyr
1               5

<210> SEQ ID NO 392
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Ala Ala Asp Pro Gly Gly Gln Ser Pro Leu Ser
1               5                   10

<210> SEQ ID NO 393
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ala Val Asp Asn Gly Asp Pro Arg Leu His
1               5                   10

<210> SEQ ID NO 394
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Ala Leu Asp Asn Gly Asp Pro Arg Leu His
1               5                   10

<210> SEQ ID NO 395
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Asn Thr Arg Leu Tyr
```

```
1               5

<210> SEQ ID NO 396
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Ala Ala Asp Pro Gly Gly Ala Ser Gly Leu Ser
1               5                   10

<210> SEQ ID NO 397
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Ala Leu Tyr Asn Gly Asp Pro Arg Leu His
1               5                   10

<210> SEQ ID NO 398
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Asn Arg Ile Gln Ala Val Leu Arg Gly Asn Ser Gly
1               5                   10

<210> SEQ ID NO 399
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Asn Ser Ile Thr Ala Val Leu Arg Gly Asn Ser Gly
1               5                   10

<210> SEQ ID NO 400
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Asn Ser Ile Ser Ala Val Leu Arg Gly Asn Gly Val
1               5                   10

<210> SEQ ID NO 401
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
                       peptide

<400> SEQUENCE: 401

Gly Val Gly Arg Gly Thr Gly Tyr Ala Tyr Thr Ala Ile Asn Glu Tyr
1               5                   10                  15

Asp Tyr Ser Lys
            20

<210> SEQ ID NO 402
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Tyr Gly Leu Tyr Arg Gln Val Tyr
1               5

<210> SEQ ID NO 403
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Tyr Gly Leu Tyr Arg Gln Val His
1               5

<210> SEQ ID NO 404
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Ala Ala Arg Arg Thr Thr Ala Trp Gly Lys Gly Thr Asp Tyr
1               5                   10

<210> SEQ ID NO 405
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Arg Val Val Leu Ala Thr Ser Pro Tyr Asn Tyr
1               5                   10

<210> SEQ ID NO 406
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Tyr Gly Leu Tyr Arg Gln Val His
1               5
```

<210> SEQ ID NO 407
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Gly Val Gly Arg Gly Ser Gly Tyr Ala Tyr Ser Ala Ile Asn Glu Tyr
1               5                   10                  15

Asp Tyr Ser Ser
            20

<210> SEQ ID NO 408
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Tyr Gly Leu Tyr Arg Gln Val His
1               5

<210> SEQ ID NO 409
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Asn Ile Val Gly Arg Thr Asp Ser
1               5

<210> SEQ ID NO 410
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Gly Arg Ala Arg Gly Thr Gly Tyr Ala Tyr Thr Ala Leu Asn Gln Tyr
1               5                   10                  15

Asp Tyr Asp Tyr
            20

<210> SEQ ID NO 411
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Asn Ser Ile Lys Ala Val Leu Arg Gly Asn Ser Gly
1               5                   10

<210> SEQ ID NO 412

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gly Val Gly Arg Gly Ser Gly Tyr Ala Tyr Thr Ala Ile Asn Glu Tyr
1               5                   10                  15

Asp Tyr Ser Lys
            20

<210> SEQ ID NO 413
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Asn Ser Ile Thr Ala Val Leu Arg Gly Asn Ser Gly
1               5                   10

<210> SEQ ID NO 414
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Gly Arg Ala Arg Gly Thr Gly Tyr Ala His Thr Ala Leu Asn Gln Tyr
1               5                   10                  15

Asp Tyr Asp Tyr
            20

<210> SEQ ID NO 415
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Asn Leu Ile Lys Ala Val Leu Arg Gly Asn Ser Gly
1               5                   10

<210> SEQ ID NO 416
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gly Val Gly Arg Gly Thr Gly Tyr Ala Tyr Thr Ala Ile Arg Glu His
1               5                   10                  15

Asp Tyr Ser Ser
            20

<210> SEQ ID NO 417
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Asn Ser Ile Thr Ala Val Leu Arg Gly Asn Ser Gly
1               5                   10

<210> SEQ ID NO 418
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Asn Thr Ile Lys Ala Val Leu Arg Gly Asn Ala Gly
1               5                   10

<210> SEQ ID NO 419
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Asn Ser Ile Thr Ala Val Leu Arg Gly Asn Ser
1               5                   10

<210> SEQ ID NO 420
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Asn Ile Ile Ser Ala Val Leu Arg Gly Asn Gly Gly
1               5                   10

<210> SEQ ID NO 421
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Asn Thr Ile Thr Gly Val Leu Arg Gly Asn Ser Gly
1               5                   10

<210> SEQ ID NO 422
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422
```

```
Tyr Gly Leu Tyr Arg Gln Val Tyr
1               5

<210> SEQ ID NO 423
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Asn Ile Gly Met Tyr
1               5

<210> SEQ ID NO 424
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Asn Ser Ile Ser Ala Val Leu Arg Gly Asn Ser Gly
1               5                   10

<210> SEQ ID NO 425
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Asn Ser Ile Ser Ala Val Leu Arg Gly Asn Gly Gly
1               5                   10

<210> SEQ ID NO 426
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Asn Ser Ile Thr Ala Val Leu Arg Gly Asn Ser Asp
1               5                   10

<210> SEQ ID NO 427
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Asn Ile Ile Lys Thr Val Leu Arg Gly Asn Ala Val
1               5                   10

<210> SEQ ID NO 428
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 428

Asn Ser Ile Thr Ala Val Leu Arg Gly Asn Ser Gly
1               5                   10

<210> SEQ ID NO 429
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Asn Thr Ile Thr Arg Leu Leu Tyr Gly Met Asp Tyr
1               5                   10

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

```
<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Gly Gly Gly Gly Ser
1               5

<210> SEQ ID NO 446
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Gly Gly Gly Gly Ser Gly Gly Gly Gly Ser Gly Gly Gly Gly Ser
1               5                   10                  15

<210> SEQ ID NO 447
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Gly Gly Gly Gly Ser Gly Gly Gly Gly Ser Gly Gly Gly Gly Ser Gly
1               5                   10                  15
Gly Gly Gly Ser Gly Gly Gly Gly Ser
            20                  25

<210> SEQ ID NO 448
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Gly Gly Gly Ser Gly Gly Gly Ser
1               5

<210> SEQ ID NO 449
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Gly Gly Gly Gly Gly Gly Gly Gly Gly Gly
1               5                   10

<210> SEQ ID NO 450
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Gly Gly Ala Glu Ala Ala Ala Lys Glu Ala Ala Lys Glu Ala Ala
1               5                   10                  15
Ala Lys Glu Ala Ala Ala Lys Glu Ala Ala Ala Lys Gly Gly
            20                  25                  30

<210> SEQ ID NO 451
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Gly Gly Gly Ala Ala Pro Ala Ala Ala Pro Lys Gln Glu Ala Ala
1               5                   10                  15
Ala Pro Ala Pro Ala Ala Lys Ala Glu Ala Pro Ala Ala Ala Pro Ala
            20                  25                  30
Ala Thr Gly Gly
        35
```

<210> SEQ ID NO 452
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 452

Gly Gly Gly Gly Ser Gly Gly Leu Gly Gly Ser Gly Gly Gly Gly Ser
1               5                   10                  15

<210> SEQ ID NO 453
<211> LENGTH: 86
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 453

Met Glu Leu Lys His Ser Ile Ser Asp Tyr Thr Glu Ala Glu Phe Leu
1               5                   10                  15

Gln Leu Val Thr Thr Ile Cys Asn Ala Asp Thr Ser Ser Glu Glu Glu
            20                  25                  30

Leu Val Lys Leu Val Thr His Phe Glu Glu Met Thr Glu His Pro Ser
        35                  40                  45

Gly Ser Asp Leu Ile Tyr Tyr Pro Lys Glu Gly Asp Asp Ser Pro
    50                  55                  60

Ser Gly Ile Val Asn Thr Val Lys Gln Trp Arg Ala Ala Asn Gly Lys
65                  70                  75                  80

Ser Gly Phe Lys Gln Gly
                85

<210> SEQ ID NO 454
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 454

Met Glu Ser Lys Arg Asn Lys Pro Gly Lys Ala Thr Gly Lys Gly Lys
1               5                   10                  15

Pro Val Gly Asp Lys Trp Leu Asp Asp Ala Gly Lys Asp Ser Gly Ala
            20                  25                  30

Pro Ile Pro Asp Arg Ile Ala Asp Lys Leu Arg Asp Lys Glu Phe Lys
        35                  40                  45

Ser Phe Asp Asp Phe Arg Lys Ala Val Trp Glu Glu Val Ser Lys Asp
    50                  55                  60

Pro Glu Leu Ser Lys Asn Leu Asn Pro Cys Asn Lys Ser Ser Val Ser
65                  70                  75                  80

Lys Gly Tyr Ser Pro Phe Thr Pro Lys Asn Gln Gln Val Gly Arg
            85                  90                  95

Lys Val Tyr Glu Leu His His Asp Lys Pro Ile Ser Gln Gly Gly Glu
                100                 105                 110

Val Tyr Asp Met Asp Asn Ile Arg Val Thr Thr Pro Lys Arg His Ile
            115                 120                 125

Asp Ile His Arg Gly Lys

130

<210> SEQ ID NO 455
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Leu Thr Asp Thr Leu Gln Ala Glu Thr Asp Gln Leu Glu Asp Glu Lys
1               5                   10                  15

Ser Ala Leu Gln Thr Glu Ile Ala Asn Leu Leu Lys Glu Lys Glu Lys
            20                  25                  30

Leu Glu Phe Ile Leu Ala Ala
        35

<210> SEQ ID NO 456
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Arg Ile Ala Arg Leu Glu Glu Lys Val Lys Thr Leu Lys Ala Gln Asn
1               5                   10                  15

Ser Glu Leu Ala Ser Thr Ala Asn Met Leu Arg Glu Gln Val Ala Gln
            20                  25                  30

Leu Lys Gln Lys Val Met Asn
        35

<210> SEQ ID NO 457
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Arg Met Lys Gln Leu Glu Asp Lys Ile Glu Glu Leu Leu Ser Lys Ile
1               5                   10                  15

Tyr His Leu Glu Asn Glu Ile Ala Arg Leu Lys Lys Leu Ile Gly Glu
            20                  25                  30

Arg

<210> SEQ ID NO 458
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg

<210> SEQ ID NO 459
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Arg Met Lys Gln Ile Glu Asp Lys Leu Glu Glu Ile Leu Ser Lys Leu
1               5                   10                  15

Tyr His Ile Glu Asn Glu Leu Ala Arg Ile Lys Lys Leu Leu Gly
            20                  25                  30

<210> SEQ ID NO 460
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Glu Arg Val Val Ile Asn Ile Ser Gly Leu Arg Phe Glu Thr Gln Leu
1               5                   10                  15

Lys Thr Leu Ala Gln Phe Pro Glu Thr Leu Leu Gly Asp Pro Lys Lys
            20                  25                  30

Arg Met Arg Tyr Phe Asp Pro Leu Arg Asn Glu Tyr Phe Phe Asp Arg
        35                  40                  45

Asn Arg Pro Ser Phe Asp Ala Ile Leu Tyr Tyr Tyr Gln Ser Gly Gly
    50                  55                  60

Arg Leu Arg Arg Pro Val Asn Val Pro Leu Asp Ile Phe Ser Glu Glu
65                  70                  75                  80

Ile Arg Phe Tyr Glu Leu Gly
                85

<210> SEQ ID NO 461
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Ala Thr Pro Trp Ser Gly Tyr Leu Asp Asp Val Ser Ala Lys Phe Asp
1               5                   10                  15

Thr Gly Val Asp Asn Leu Gln Thr Gln Val Thr Glu Ala Leu Asp Lys
            20                  25                  30

Leu Ala Ala Lys Pro Ser Asp Pro Ala Leu Leu Ala Ala Tyr Gln Ser
        35                  40                  45

Lys Leu Ser Glu Tyr Asn Leu Tyr Arg Asn Ala Gln Ser Asn Thr Val
    50                  55                  60

Lys Val Phe Lys Asp Ile Asp Ala Ala Ile Gln Asn Phe Arg Gly
65                  70                  75                  80

Gly Ser Gly Gly Thr Thr Ile Ser Asp Ala Glu Ile Trp Asp Met Val
                85                  90                  95

Ser Gln Asn Ile Ser Ala Ile Gly Asp Ser Tyr Leu Gly Val Tyr Glu
            100                 105                 110

```
Asn Val Val Ala Val Tyr Thr Asp Phe Tyr Gln Ala Phe Ser Asp Ile
            115                 120                 125

Leu Ser Lys Met Gly Gly Trp Leu Leu Pro Gly Lys Asp Gly Asn Thr
130                 135                 140

Val Lys Leu Asp Val Thr Ser Leu Lys Asn Asp Leu Asn Ser Leu Val
145                 150                 155                 160

Asn Lys Tyr Asn Gln Ile Asn Ser Asn Thr Val Leu Phe Pro Ala Gln
            165                 170                 175

Ser Gly Ser Gly Val Lys Val Ala Thr Glu Ala Glu Ala Arg Gln Trp
            180                 185                 190

Leu Ser Glu Leu Asn Leu Pro Asn Ser Cys Leu Lys Ser Tyr Gly Ser
            195                 200                 205

Gly Tyr Val Val Thr Val Asp Leu Thr Pro Leu Gln Lys Met Val Gln
            210                 215                 220

Asp Ile Asp Gly Leu Gly Ala Pro Gly Lys Asp Ser Lys Leu Glu Met
225                 230                 235                 240

Asp Asn Ala Lys Tyr Gln Ala Trp Gln Ser Gly Phe Lys Ala Gln Glu
            245                 250                 255

Glu Asn Met Lys Thr Thr Leu Gln Thr Leu Thr Gln Lys Tyr Ser Asn
            260                 265                 270

Ala Asn Ser Leu Tyr Asp Asn Leu Val Lys Val Leu Ser Ser Thr Ile
            275                 280                 285

Ser Ser Ser Leu Glu Thr Ala Lys Ser Phe Leu Gln Gly
            290                 295                 300

<210> SEQ ID NO 462
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
        35                  40                  45

Ala Thr Ile Thr Ser Phe Gly Ile Ile Asn Tyr Ala Asp Ser Val Lys
    50                  55                  60

Asp Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
            85                  90                  95

Ala Lys Thr Phe Asp Gly Thr Arg Trp His Asp Tyr Trp Gly Gln Gly
            100                 105                 110

Thr Gln Val Thr Val Ser Ser Gly Gly Gly Ser Gly Gly Gly Gly
            115                 120                 125

Ser Gly Gly Gly Gly Ser Gln Val Lys Leu Glu Glu Ser Gly Gly Gly
        130                 135                 140

Leu Val Gln Pro Gly Gly Ser Leu Glu Val Ser Cys Ala Ala Ser Gly
145                 150                 155                 160

Ile Ile Phe Ser Pro Asn Ala Met Gly Trp Tyr Arg Gln Ala Pro Gly
            165                 170                 175
```

```
Glu Gln Arg Glu Leu Val Ala Thr Ile Thr Ser Phe Gly Ile Ile Asn
                180                 185                 190

Tyr Ala Asp Ser Val Lys Asp Arg Phe Thr Ile Ser Arg Asp Asn Ala
            195                 200                 205

Lys Asn Thr Val Tyr Leu Gln Met Thr Ser Leu Lys Pro Glu Asp Thr
210                 215                 220

Ala Val Tyr Tyr Cys Asn Ala Lys Thr Phe Asp Gly Thr Arg Trp His
225                 230                 235                 240

Asp Tyr Trp Gly Gln Gly Thr Gln Val Thr Val Ser Ser
                245                 250

<210> SEQ ID NO 463
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
        35                  40                  45

Ala Thr Ile Thr Ser Phe Gly Ile Ile Asn Tyr Ala Asp Ser Val Lys
    50                  55                  60

Asp Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ala Lys Thr Phe Asp Gly Thr Arg Trp His Asp Tyr Trp Gly Gln Gly
            100                 105                 110

Thr Gln Val Thr Val Ser Ser Gly Gly Gly Gly Ser Gly Gly Gly Gly
        115                 120                 125

Ser Gly Gly Gly Gly Ser Gln Val Lys Leu Glu Glu Ser Gly Gly Gly
    130                 135                 140

Leu Val Gln Pro Gly Gly Ser Leu Glu Val Ser Cys Ala Ala Ser Gly
145                 150                 155                 160

Ile Ile Phe Ser Pro Asn Ala Met Gly Trp Tyr Arg Gln Ala Pro Gly
                165                 170                 175

Glu Gln Arg Glu Leu Val Ala Thr Ile Thr Ser Phe Gly Ile Ile Asn
            180                 185                 190

Tyr Ala Asp Ser Val Lys Asp Arg Phe Thr Ile Ser Arg Asp Asn Ala
        195                 200                 205

Lys Asn Thr Val Tyr Leu Gln Met Thr Ser Leu Lys Pro Glu Asp Thr
    210                 215                 220

Ala Val Tyr Tyr Cys Asn Ala Lys Thr Phe Asp Gly Thr Arg Trp His
225                 230                 235                 240

Asp Tyr Trp Gly Gln Gly Thr Gln Val Thr Val Ser Ser Gly Gly Gly
                245                 250                 255

Gly Ser Gly Gly Gly Gly Ser Gly Gly Gly Gly Ser Gln Val Lys Leu
            260                 265                 270

Glu Glu Ser Gly Gly Gly Leu Val Gln Pro Gly Gly Ser Leu Glu Val
```

```
                275                 280                 285
Ser Cys Ala Ala Ser Gly Ile Ile Phe Ser Pro Asn Ala Met Gly Trp
        290                 295                 300

Tyr Arg Gln Ala Pro Gly Glu Gln Arg Glu Leu Val Ala Thr Ile Thr
305                 310                 315                 320

Ser Phe Gly Ile Ile Asn Tyr Ala Asp Ser Val Lys Asp Arg Phe Thr
                325                 330                 335

Ile Ser Arg Asp Asn Ala Lys Asn Thr Val Tyr Leu Gln Met Thr Ser
            340                 345                 350

Leu Lys Pro Glu Asp Thr Ala Val Tyr Tyr Cys Asn Ala Lys Thr Phe
                355                 360                 365

Asp Gly Thr Arg Trp His Asp Tyr Trp Gly Gln Gly Thr Gln Val Thr
        370                 375                 380

Val Ser Ser
385

<210> SEQ ID NO 464
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

Gln Val Gln Leu Val Glu Ser Gly Gly Gly Leu Val Gln Pro Gly Gly
1               5                   10                  15

Ser Leu Thr Leu Ser Cys Ile Val Ser Gly Arg Ser Val Ser Ile Asn
            20                  25                  30

Pro Met Tyr Trp Tyr Arg Gln Gly Pro Gly Lys Gln Arg Glu Leu Val
        35                  40                  45

Val Ser Leu Leu Pro Ser Gly Arg Thr His Asp Ala His Phe Ala Lys
    50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Thr Ala Asp Phe Trp Gly Gln Gly Thr Gln Val Thr Val Ser Ser Gly
            100                 105                 110

Gly Gly Gly Ser Gly Gly Gly Gly Ser Gly Gly Gly Gly Ser Gln Val
        115                 120                 125

Gln Leu Val Glu Ser Gly Gly Gly Leu Val Gln Pro Gly Gly Ser Leu
    130                 135                 140

Thr Leu Ser Cys Ile Val Ser Gly Arg Ser Val Ser Ile Asn Pro Met
145                 150                 155                 160

Tyr Trp Tyr Arg Gln Gly Pro Gly Lys Gln Arg Glu Leu Val Val Ser
                165                 170                 175

Leu Leu Pro Ser Gly Arg Thr His Asp Ala His Phe Ala Lys Gly Arg
            180                 185                 190

Phe Ile Ile Ser Arg Asp Asn Ala Lys Asn Thr Val Tyr Leu Gln Met
        195                 200                 205

Asn Ser Leu Lys Pro Glu Asp Thr Ala Val Tyr Tyr Cys Asn Thr Ala
    210                 215                 220

Asp Phe Trp Gly Gln Gly Thr Gln Val Thr Val Ser Ser
225                 230                 235
```

-continued

```
<210> SEQ ID NO 465
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

Gln Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Ser Asn Asn
            20                  25                  30

Ala Met Gly Trp Phe Arg Gln Ala Pro Gly Lys Gln Arg Glu Leu Val
        35                  40                  45

Ala Ala Ile Ser Arg Ala Gly Asn Thr Asn Tyr Ala Asp Ser Met Lys
    50                  55                  60

Gly Arg Val Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Ala Ser Ser Gly Ser Ser Val Tyr Ile Gly Val Gly Ser Trp Gly Gln
            100                 105                 110

Gly Thr Gln Val Thr Val Ser Ser Gly Gly Gly Ser Gly Gly Gly
        115                 120                 125

Gly Ser Gly Gly Gly Ser Gln Val Gln Leu Val Glu Ser Gly Gly
    130                 135                 140

Gly Leu Val Gln Ala Gly Asp Ser Leu Arg Leu Ser Cys Thr Ala Ser
145                 150                 155                 160

Gly Arg Thr Phe Ser Asn Asn Ala Met Gly Trp Phe Arg Gln Ala Pro
                165                 170                 175

Gly Lys Gln Arg Glu Leu Val Ala Ala Ile Ser Arg Ala Gly Asn Thr
            180                 185                 190

Asn Tyr Ala Asp Ser Met Lys Gly Arg Val Thr Ile Ser Gly Asp Asn
        195                 200                 205

Ala Lys Asn Thr Val Tyr Leu Gln Met Asn Ser Leu Lys Pro Glu Asp
    210                 215                 220

Thr Ala Val Tyr Tyr Cys Lys Ala Ser Ser Gly Ser Ser Val Tyr Ile
225                 230                 235                 240

Gly Val Gly Ser Trp Gly Gln Gly Thr Gln Val Thr Val Ser Ser
                245                 250                 255

<210> SEQ ID NO 466
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

Met Gln Val Lys Leu Glu Glu Ser Gly Gly Gly Leu Val Gln Pro Gly
1               5                   10                  15

Gly Ser Leu Glu Val Ser Cys Ala Ala Ser Gly Ile Ile Phe Ser Pro
            20                  25                  30

Asn Ala Met Gly Trp Tyr Arg Gln Ala Pro Gly Glu Gln Arg Glu Leu
        35                  40                  45
```

```
Val Ala Thr Ile Thr Ser Phe Gly Ile Ile Asn Tyr Ala Asp Ser Val
 50                  55                  60

Lys Asp Arg Phe Thr Ile Ser Arg Asp Asn Ala Lys Asn Thr Val Tyr
 65                  70                  75                  80

Leu Gln Met Thr Ser Leu Lys Pro Glu Asp Thr Ala Val Tyr Tyr Cys
                 85                  90                  95

Asn Ala Lys Thr Phe Asp Gly Thr Arg Trp His Asp Tyr Trp Gly Gln
            100                 105                 110

Gly Thr Gln Val Thr Val Ser Ser Glu Leu Lys His Ser Ile Ser Asp
        115                 120                 125

Tyr Thr Glu Ala Glu Phe Leu Gln Leu Val Thr Thr Ile Cys Asn Ala
130                 135                 140

Asp Thr Ser Ser Glu Glu Leu Val Lys Leu Val Thr His Phe Glu
145                 150                 155                 160

Glu Met Thr Glu His Pro Ser Gly Ser Asp Leu Ile Tyr Tyr Pro Lys
                165                 170                 175

Glu Gly Asp Asp Asp Ser Pro Ser Gly Ile Val Asn Thr Val Lys Gln
            180                 185                 190

Trp Arg Ala Ala Asn Gly Lys Ser Gly Phe Lys Gln Gly
        195                 200                 205

<210> SEQ ID NO 467
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Met Gln Val Lys Leu Glu Glu Ser Gly Gly Gly Leu Val Gln Pro Gly
  1               5                  10                  15

Gly Ser Leu Glu Val Ser Cys Ala Ala Ser Gly Ile Ile Phe Ser Pro
             20                  25                  30

Asn Ala Met Gly Trp Tyr Arg Gln Ala Pro Gly Glu Gln Arg Glu Leu
         35                  40                  45

Val Ala Thr Ile Thr Ser Phe Gly Ile Ile Asn Tyr Ala Asp Ser Val
 50                  55                  60

Lys Asp Arg Phe Thr Ile Ser Arg Asp Asn Ala Lys Asn Thr Val Tyr
 65                  70                  75                  80

Leu Gln Met Thr Ser Leu Lys Pro Glu Asp Thr Ala Val Tyr Tyr Cys
                 85                  90                  95

Asn Ala Lys Thr Phe Asp Gly Thr Arg Trp His Asp Tyr Trp Gly Gln
            100                 105                 110

Gly Thr Gln Val Thr Val Ser Ser Glu Ser Lys Arg Asn Lys Pro Gly
        115                 120                 125

Lys Ala Thr Gly Lys Gly Lys Pro Val Gly Asp Lys Trp Leu Asp Asp
130                 135                 140

Ala Gly Lys Asp Ser Gly Ala Pro Ile Pro Asp Arg Ile Ala Asp Lys
145                 150                 155                 160

Leu Arg Asp Lys Glu Phe Lys Ser Phe Asp Phe Arg Lys Ala Val
                165                 170                 175

Trp Glu Glu Val Ser Lys Asp Pro Glu Leu Ser Lys Asn Leu Asn Pro
            180                 185                 190

Cys Asn Lys Ser Ser Val Ser Lys Gly Tyr Ser Pro Phe Thr Pro Lys
        195                 200                 205
```

Asn Gln Gln Val Gly Gly Arg Lys Val Tyr Glu Leu His Ala Asp Lys
    210                 215                 220

Pro Ile Ser Gln Gly Gly Glu Val Tyr Asp Met Asp Asn Ile Arg Val
225                 230                 235                 240

Thr Thr Pro Lys Arg His Ile Asp Ile His Arg Gly Lys
                245                 250

<210> SEQ ID NO 468
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
        35                  40                  45

Ala Thr Ile Thr Ser Phe Gly Ile Ile Asn Tyr Ala Asp Ser Val Lys
    50                  55                  60

Asp Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ala Lys Thr Phe Asp Gly Thr Arg Trp His Asp Tyr Trp Gly Gln Gly
            100                 105                 110

Thr Gln Val Thr Val Ser Ser Gly Gly Gly Ser Gly Gly Gly Ser Arg
        115                 120                 125

Met Lys Gln Leu Glu Asp Lys Ile Glu Glu Leu Ser Lys Ile Tyr
    130                 135                 140

His Leu Glu Asn Glu Ile Ala Arg Leu Lys Lys Leu Ile Gly Glu Arg
145                 150                 155                 160

<210> SEQ ID NO 469
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
        35                  40                  45

Ala Thr Ile Thr Ser Phe Gly Ile Ile Asn Tyr Ala Asp Ser Val Lys
    50                  55                  60

Asp Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

```
Ala Lys Thr Phe Asp Gly Thr Arg Trp His Asp Tyr Trp Gly Gln Gly
            100                 105                 110

Thr Gln Val Thr Val Ser Ser Gly Gly Gly Ser Gly Gly Gly Ser Arg
            115                 120                 125

Met Lys Gln Ile Glu Asp Lys Ile Glu Ile Leu Ser Lys Ile Tyr
130                 135                 140

His Ile Glu Asn Glu Ile Ala Arg Ile Lys Lys Leu Ile Gly Glu Arg
145                 150                 155                 160

<210> SEQ ID NO 470
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
        35                  40                  45

Ala Thr Ile Thr Ser Phe Gly Ile Ile Asn Tyr Ala Asp Ser Val Lys
    50                  55                  60

Asp Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ala Lys Thr Phe Asp Gly Thr Arg Trp His Asp Tyr Trp Gly Gln Gly
            100                 105                 110

Thr Gln Val Thr Val Ser Ser Gly Gly Gly Ser Gly Gly Gly Ser Arg
            115                 120                 125

Met Lys Gln Ile Glu Asp Lys Leu Glu Glu Ile Leu Ser Lys Leu Tyr
130                 135                 140

His Ile Glu Asn Glu Leu Ala Arg Ile Lys Lys Leu Leu Gly
145                 150                 155

<210> SEQ ID NO 471
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
        35                  40                  45

Ala Thr Ile Thr Ser Phe Gly Ile Ile Asn Tyr Ala Asp Ser Val Lys
    50                  55                  60

Asp Arg Phe Thr Ile Ser Arg Asp Asn Ala Lys Asn Thr Val Tyr Leu
65                  70                  75                  80
```

Gln Met Thr Ser Leu Lys Pro Glu Asp Thr Ala Val Tyr Tyr Cys Asn
                85                  90                  95

Ala Lys Thr Phe Asp Gly Thr Arg Trp His Asp Tyr Trp Gly Gln Gly
            100                 105                 110

Thr Gln Val Thr Val Ser Ser Gly Gly Gly Gly Gly Gly Gly Gly
        115                 120                 125

Gly Leu Thr Asp Thr Leu Gln Ala Glu Thr Asp Gln Leu Glu Asp Glu
    130                 135                 140

Lys Ser Ala Leu Gln Thr Glu Ile Ala Asn Leu Leu Lys Glu Lys Glu
145                 150                 155                 160

Lys Leu Glu Phe Ile Leu Ala Ala
            165

<210> SEQ ID NO 472
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
        35                  40                  45

Ala Thr Ile Thr Ser Phe Gly Ile Ile Asn Tyr Ala Asp Ser Val Lys
    50                  55                  60

Asp Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ala Lys Thr Phe Asp Gly Thr Arg Trp His Asp Tyr Trp Gly Gln Gly
            100                 105                 110

Thr Gln Val Thr Val Ser Ser Gly Gly Gly Gly Gly Gly Gly Gly
        115                 120                 125

Gly Arg Ile Ala Arg Leu Glu Glu Lys Val Lys Thr Leu Lys Ala Gln
    130                 135                 140

Asn Ser Glu Leu Ala Ser Thr Ala Asn Met Leu Arg Glu Gln Val Ala
145                 150                 155                 160

Gln Leu Lys Gln Lys Val Met Asn
            165

<210> SEQ ID NO 473
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
            35                  40                  45

Ala Thr Ile Thr Ser Phe Gly Ile Ile Asn Tyr Ala Asp Ser Val Lys
 50                  55                  60

Asp Arg Phe Thr Ile Ser Arg Asp Asn Ala Lys Asn Thr Val Tyr Leu
 65                  70                  75                  80

Gln Met Thr Ser Leu Lys Pro Glu Asp Thr Ala Val Tyr Tyr Cys Asn
                 85                  90                  95

Ala Lys Thr Phe Asp Gly Thr Arg Trp His Asp Tyr Trp Gly Gln Gly
            100                 105                 110

Thr Gln Val Thr Val Ser Ser Gly Gly Gly Ser Glu Arg Val Val
        115                 120                 125

Ile Asn Ile Ser Gly Leu Arg Phe Glu Thr Gln Leu Lys Thr Leu Ala
130                 135                 140

Gln Phe Pro Glu Thr Leu Leu Gly Asp Pro Lys Lys Arg Met Arg Tyr
145                 150                 155                 160

Phe Asp Pro Leu Arg Asn Glu Tyr Phe Phe Asp Arg Asn Arg Pro Ser
                165                 170                 175

Phe Asp Ala Ile Leu Tyr Tyr Tyr Gln Ser Gly Arg Leu Arg Arg
            180                 185                 190

Pro Val Asn Val Pro Leu Asp Ile Phe Ser Glu Glu Ile Arg Phe Tyr
                195                 200                 205

Glu Leu Gly
    210

<210> SEQ ID NO 474
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
            35                  40                  45

Ala Thr Ile Thr Ser Phe Gly Ile Ile Asn Tyr Ala Asp Ser Val Lys
 50                  55                  60

Asp Arg Phe Thr Ile Ser Arg Asp Asn Ala Lys Asn Thr Val Tyr Leu
 65                  70                  75                  80

Gln Met Thr Ser Leu Lys Pro Glu Asp Thr Ala Val Tyr Tyr Cys Asn
                 85                  90                  95

Ala Lys Thr Phe Asp Gly Thr Arg Trp His Asp Tyr Trp Gly Gln Gly
            100                 105                 110

Thr Gln Val Thr Val Ser Ser Gly Gly Gly Gly Ser Gly Gly Gly Gly
        115                 120                 125

Ser Gly Gly Gly Gly Ser Gly Gly Ser Gly Gly Gly Gly Ser
130                 135                 140

Ala Leu Ser Asn Gln Ile Thr Phe Thr Thr Gln Gln Gly Asp Ile
145                 150                 155                 160

Tyr Thr Val Ile Pro Gln Val Thr Leu Asn Glu Pro Cys Val Cys Gln

```
                  165                 170                 175

Val Gln Ile Leu Ser Val Arg Asp Gly Val Gly Gly Gln Ser His Thr
            180                 185                 190

Gln Gln Lys Gln Thr Leu Ser Leu Pro Ala Asn Gln Pro Ile Glu Leu
        195                 200                 205

Ser Arg Leu Ser Val Asn Ile Ser Ser Glu Asp Ser Val Lys Ile Ile
    210                 215                 220

Val Thr Val Ser Asp Gly Gln Ser Leu His Leu Ser Gln Gln Trp Pro
225                 230                 235                 240

Pro Ser Ala Gln

<210> SEQ ID NO 475
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
        35                  40                  45

Ala Thr Ile Thr Ser Phe Gly Ile Ile Asn Tyr Ala Asp Ser Val Lys
    50                  55                  60

Asp Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
            85                  90                  95

Ala Lys Thr Phe Asp Gly Thr Arg Trp His Asp Tyr Trp Gly Gln Gly
        100                 105                 110

Thr Gln Val Thr Val
        115

<210> SEQ ID NO 476
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Gln Val Gln Leu Val Glu Ser Gly Gly Gly Leu Val Gln Pro Gly Gly
1               5                   10                  15

Ser Leu Thr Leu Ser Cys Ile Val Ser Gly Arg Ser Val Ser Ile Asn
            20                  25                  30

Pro Met Tyr Trp Tyr Arg Gln Gly Pro Gly Lys Gln Arg Glu Leu Val
        35                  40                  45

Val Ser Leu Leu Pro Ser Gly Arg Thr His Asp Ala His Phe Ala Lys
    50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95
```

Thr Ala Asp Phe Trp Gly Gln Gly Thr Gln Val Thr Val
            100                 105

<210> SEQ ID NO 477
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

Gln Val Gln Leu Val Glu Ser Gly Gly Leu Val Gln Ala Gly Asp
1               5                   10                  15

Ser Leu Arg Leu Ser Cys Thr Ala Ser Gly Arg Thr Phe Ser Asn Asn
            20                  25                  30

Ala Met Gly Trp Phe Arg Gln Ala Pro Gly Lys Gln Arg Glu Leu Val
        35                  40                  45

Ala Ala Ile Ser Arg Ala Gly Asn Thr Asn Tyr Ala Asp Ser Met Lys
    50                  55                  60

Gly Arg Val Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Ala Ser Ser Gly Ser Ser Val Tyr Ile Gly Val Gly Ser Trp Gly Gln
            100                 105                 110

Gly Thr Gln Val Thr Val
        115

<210> SEQ ID NO 478
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

Gln Val Gln Leu Val Glu Ser Gly Gly Gly Leu Val Gln Pro Gly Gly
1               5                   10                  15

Ser Leu Thr Leu Ser Cys Ile Val Ser Gly Arg Ser Val Ser Ile Asn
            20                  25                  30

Pro Met Tyr Trp Tyr Arg Gln Gly Pro Gly Lys Gln Arg Glu Leu Val
        35                  40                  45

Val Ser Leu Leu Pro Ser Gly Arg Thr His Asp Ala His Phe Ala Lys
    50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Thr Ala Asp Phe Trp Gly Gln Gly Thr Gln Val Thr Val Ser Ser
            100                 105                 110

<210> SEQ ID NO 479
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Gln Val Gln Leu Val Glu Ser Gly Gly Leu Val Gln Ala Gly Asp
1               5                   10                  15

Ser Leu Arg Leu Ser Cys Thr Ala Ser Gly Arg Thr Phe Ser Asn Asn
            20                  25                  30

Ala Met Gly Trp Phe Arg Gln Ala Pro Gly Lys Gln Arg Glu Leu Val
        35                  40                  45

Ala Ala Ile Ser Arg Ala Gly Asn Thr Asn Tyr Ala Asp Ser Met Lys
    50                  55                  60

Gly Arg Val Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Ala Ser Ser Gly Ser Ser Val Tyr Ile Gly Val Gly Ser Trp Gly Gln
            100                 105                 110

Gly Thr Gln Val Thr Val Ser Ser
        115                 120

<210> SEQ ID NO 480
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
        35                  40                  45

Ala Thr Ile Thr Ser Phe Gly Ile Ile Asn Tyr Ala Asp Ser Val Lys
    50                  55                  60

Asp Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ala Lys Thr Phe Asp Gly Thr Arg Trp His Asp Tyr Trp Gly Gln Gly
            100                 105                 110

Thr Gln Val Thr Val Ser Ser
        115

<210> SEQ ID NO 481
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 481

Gln Val Lys Leu Glu Glu Ser Gly Gly Gly Leu Val Gln Pro Gly Gly
1               5                   10                  15

Ser Leu Glu Val Ser Cys Ala Ala Ser Gly Ile Ile Phe Ser Pro Asn
            20                  25                  30

Ala Met Gly Trp Tyr Arg Gln Ala Pro Gly Glu Gln Arg Glu Leu Val
            35                  40                  45

Ala Thr Ile Thr Ser Phe Gly Ile Ile Asn Tyr Ala Asp Ser Val Lys
 50                  55                  60

Asp Arg Phe Thr Ile Ser Arg Asp Asn Ala Lys Asn Thr Val Tyr Leu
 65                  70                  75                  80

Gln Met Thr Ser Leu Lys Pro Glu Asp Thr Ala Val Tyr Tyr Cys Asn
                 85                  90                  95

Ala Lys Ala Phe Asp Gly Thr Arg Trp His Asp Tyr Trp Gly Gln Gly
            100                 105                 110

Thr Gln Val Thr Val Ser Ser
        115

<210> SEQ ID NO 482
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Gln Val Lys Leu Glu Glu Ser Gly Gly Gly Leu Val Gln Ala Gly Gly
 1               5                  10                  15

Ser Leu Arg Leu Ser Cys Ala Val Ser Gly Ser Ile Phe Ser Thr Asn
            20                  25                  30

Val Met Gly Trp Phe Arg Gln Ala Pro Gly Lys Gln Arg Gly Phe Val
            35                  40                  45

Ala His Ile Thr Ser Gly Gly Asn Thr Asp Tyr Ala Asp Ser Val Asn
 50                  55                  60

Gly Arg Phe Thr Met Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Gln Thr Leu Gly Ser Ser Tyr Tyr Asp Ala Trp Gly Gln Gly Thr
            100                 105                 110

Gln Val Thr Val Ser Ser
        115

<210> SEQ ID NO 483
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ser Ile Asn Trp Ser Gly Arg Ile Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Asn Ala Asp Tyr Asp Asn Ser Gly Ser Tyr Tyr Gln Lys Gly Asn
            100                 105                 110

Tyr Glu Tyr Asp Tyr Trp Gly Gln Gly Thr Gln Val Thr Val Ser Ser
        115                 120                 125

<210> SEQ ID NO 484
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 484

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Ser Ser Ser Ala
            20                  25                  30

Tyr Thr Ala Trp Phe Arg Gln Ala Pro Gly Asn Glu Arg Glu Phe Val
        35                  40                  45

Ala Ser Ile Ser Trp Ser Gly Thr Thr Thr Tyr Tyr Ala Asp Pro Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Asp Arg Arg Ser Thr Ile Gly Ser Pro Arg Gln Gln Tyr Ala
            100                 105                 110

Tyr Trp Gly Gln Gly Thr Gln Val Thr Val Ser Ser
        115                 120

<210> SEQ ID NO 485
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 485

Gln Val Gln Leu Gln Glu Ser Gly Gly Gly Leu Val Gln Ala Gly Gly
1               5                   10                  15

Ser Leu Arg Leu Ser Cys Ala Ala Ser Thr Arg Thr Ser Ser Ser Ser
            20                  25                  30

Tyr Thr Ala Trp Phe Arg Gln Ala Pro Gly Asn Glu Arg Glu Phe Val
        35                  40                  45

Ala Ser Ile Ser Tyr Ser Gly Thr Thr Thr Tyr Tyr Ala Asp Pro Val
    50                  55                  60

Lys Gly Arg Phe Thr Ile Ser Arg Asp Ser Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Asp Arg Arg Ser Thr Ile Gly Ser Pro Arg Gln Gln Tyr Ala
            100                 105                 110

Tyr Trp Gly Gln Gly Thr Gln Val Thr Val Ser Ser
        115                 120

<210> SEQ ID NO 486
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 486

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Ser Ser Ser Ala
            20                  25                  30

Tyr Thr Ala Trp Phe Arg Gln Ala Pro Gly Asn Glu Arg Glu Phe Val
        35                  40                  45

Ala Ser Ile Ser Trp Ser Gly Thr Thr Thr Tyr His Ala His Pro Val
    50                  55                  60

Lys Gly Arg Phe Thr Ile Phe Arg Asp Asn Ala Lys Asn Thr Val Tyr
65                  70                  75                  80

Leu Gln Met Asn Ser Leu Lys Pro Asp Asp Thr Gly Val Tyr Tyr Cys
                85                  90                  95

Ala Ala Asp Arg Arg Ser Thr Ile Gly Thr Pro Arg Glu Gln Tyr Ala
            100                 105                 110

Tyr Trp Gly Gln Gly Thr Gln Val Thr Val Ser Ser
        115                 120

<210> SEQ ID NO 487
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 487

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Leu Ser Asn Tyr
            20                  25                  30

Ala Val Glu Trp Tyr Arg Gln Ala Pro Gly Asn Gln Arg Glu Tyr Val
        35                  40                  45

Ala Arg Ile Ser Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys His
                85                  90                  95

Thr Tyr Asp Phe Gln Gly Trp Gly Leu Arg Ser Asp Tyr Trp Gly Gln
            100                 105                 110

Gly Thr Gln Val Thr Val Ser Ser
        115                 120

<210> SEQ ID NO 488
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 488

```
Gln Val Gln Leu Gln Glu Ser Gly Gly Arg Leu Val Gln Ala Gly Gly
1               5                   10                  15

Ser Leu Arg Leu Ser Cys Ala Ala Ser Gly Arg Thr Phe Ser Ser Leu
            20                  25                  30

Ala Met Gly Trp Phe Arg Gln Ala Pro Gly Lys Glu Arg Glu Phe Val
        35                  40                  45

Ala Ala Ile Ser Arg Ser Gly Asp Tyr Thr Tyr Phe Ser Asp Ser Val
    50                  55                  60

Lys Gly Arg Phe Ala Ile Ser Arg Asp Asn Ala Lys Asp Thr Val Ser
65                  70                  75                  80

Leu Gln Met Asn Asn Leu Lys Pro Asp Asp Thr Ala Val Tyr Thr Cys
                85                  90                  95

Ala Ala Thr Lys Ile Val Thr Pro Trp Thr Ser Thr Tyr Tyr Tyr Thr
            100                 105                 110

Lys Ala Tyr Glu Trp Asp Tyr Trp Gly Gln Gly Thr Gln Val Thr Val
        115                 120                 125

Ser Ser
    130
```

<210> SEQ ID NO 489
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 489

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Val Ala Phe Asn Ser Arg
            20                  25                  30

Ile Met Gly Trp Tyr Arg Gln Ala Pro Gly Lys Gln Arg Glu Leu Val
        35                  40                  45

Ala Leu Ile Thr Ser Gly Gly Ser Thr Asn Tyr Ala Asp Ser Val Lys
    50                  55                  60

Gly Arg Phe Thr Ile Ser Arg Asn Asn Ala Lys Lys Thr Val Tyr Leu
65                  70                  75                  80

Gln Met Asn Ser Leu Lys Pro Glu Asp Thr Ala Val Tyr Tyr Cys Asn
                85                  90                  95

Ile Arg Asn Tyr Trp Gly Gln Gly Thr Gln Val Thr Val Ser Ser
            100                 105                 110
```

<210> SEQ ID NO 490
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Asn Thr Tyr
            20                  25                  30

Tyr Met Gly Trp Phe Arg Gln Ala Pro Gly Lys Glu Arg Glu Phe Val
```

```
                35                  40                  45
Ser Ala Ile Arg Trp Ser Asp Gly Gly Thr Trp Tyr Ala Asp Ser Met
         50                  55                  60
Lys Gly Arg Phe Thr Ile Ser Arg Asp Asn Ala Lys Asn Thr Gly Tyr
 65                  70                  75                  80
Leu Gln Met Asn Ser Leu Lys Pro Glu Asp Thr Ala Ile Tyr Tyr Cys
                 85                  90                  95
Asn Ala Asn Val Tyr Asp Gly Asn Arg Trp Arg Thr Tyr Trp Gly Gln
            100                 105                 110
Gly Thr Gln Val Thr Val Ser Ser
            115                 120
```

<210> SEQ ID NO 491
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

```
Gln Val Lys Leu Glu Glu Ser Gly Gly Gly Leu Val Arg Ala Gly Gly
  1               5                  10                  15
Ser Leu Thr Leu Ser Cys Gly Ala Ser Arg Gly Thr Phe Arg Thr Tyr
             20                  25                  30
Ser Met Gly Trp Phe Arg Gln Ala Pro Gly Lys Glu Arg Glu Phe Val
             35                  40                  45
Ala Ala Ile Thr Trp Asn Gly Lys Tyr Thr Tyr Tyr Gly Asp Ser Val
         50                  55                  60
Gln Gly Arg Phe Thr Ile Ser Lys Asp Asn Ala Lys Asn Thr Val Ser
 65                  70                  75                  80
Leu Gln Met Asn Arg Leu Asn Pro Glu Asp Thr Ala Val Tyr Tyr Cys
                 85                  90                  95
Ala Ala Asn Pro Ile Pro Thr Ala Gln Pro Pro Gly Ile Met Ala Ala
            100                 105                 110
Arg Ser Tyr Val His Trp Gly Gln Gly Thr Gln Val Thr Val Ser Ser
            115                 120                 125
```

<210> SEQ ID NO 492
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 492

```
Gln Val Gln Leu Gln Gln Ser Gly Gly Gly Leu Val Gln Ala Gly Gly
  1               5                  10                  15
Ser Leu Arg Leu Ser Cys Ala Ala Ser Gly Arg Thr Ser Pro Ser Ser
             20                  25                  30
Tyr Thr Ala Trp Phe Arg Gln Ala Pro Gly Asn Glu Arg Glu Phe Val
             35                  40                  45
Ala Ser Ile Ser Trp Ser Gly Thr Thr Tyr Tyr Ala Asp Pro Val
         50                  55                  60
Lys Gly Arg Phe Thr Ile Ser Arg Asp Asn Ala Lys Asn Thr Val Tyr
 65                  70                  75                  80
Leu Gln Met Asn Ser Leu Lys Pro Asp Asp Thr Ala Val Tyr Tyr Cys
```

```
                85                  90                  95

Ala Ala Asp Arg Arg Ser Thr Ile Gly Ser Pro Arg Gln Gln Tyr Ala
            100                 105                 110

Tyr Trp Gly Gln Gly Thr Gln Val Thr Val Ser Ser
        115                 120

<210> SEQ ID NO 493
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Gln Val Gln Leu Gln Glu Ser Gly Gly Arg Leu Val Gln Ala Gly Gly
1               5                   10                  15

Ser Leu Arg Leu Ser Cys Ala Ala Ser Gly Arg Thr Phe Ser Ser Leu
            20                  25                  30

Ala Met Gly Trp Phe Arg Gln Ala Pro Gly Lys Glu Arg Glu Phe Val
        35                  40                  45

Ala Ala Ile Thr Arg Ser Gly Asp Tyr Thr Tyr Phe Ser Asp Ser Val
    50                  55                  60

Lys Gly Arg Phe Ala Ile Ser Arg Asp Asn Ala Lys Asp Thr Val Ser
65                  70                  75                  80

Leu Gln Met Asn Asn Leu Lys Pro Asp Thr Ala Val Tyr Thr Cys
                85                  90                  95

Ala Ala Thr Lys Ile Val Thr Pro Trp Thr Ser Thr Tyr Tyr Tyr Thr
            100                 105                 110

Lys Ala Tyr Glu Trp Asp Tyr Trp Gly Gln Gly Thr Gln Val Thr Val
        115                 120                 125

Ser Ser
    130

<210> SEQ ID NO 494
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

Gln Val Gln Leu Gln Glu Ser Gly Gly Gly Leu Val Gln Ala Gly Lys
1               5                   10                  15

Ser Leu Arg Leu Ser Cys Ala Ala Ser Thr Ala Ile Leu Ser Ile Asp
            20                  25                  30

Ser Met Gly Trp Asn Arg Gln Ala Val Gly Asn Gln Arg Glu Leu Val
        35                  40                  45

Ala Val Ile Ala Arg Gly Gly Ser Thr Lys Tyr Ala Asp Ser Val Lys
    50                  55                  60

Gly Arg Phe Thr Ile Thr Arg Asp Ile Ser Lys Asn Thr Ile Tyr Leu
65                  70                  75                  80

Gln Met Asn Ser Leu Lys Pro Glu Asp Thr Gly Val Tyr Tyr Cys Ala
                85                  90                  95

Ala Asp Pro Gly Gly Ala Ser Pro Leu Ser Trp Gly Gln Gly Thr Gln
            100                 105                 110

Val Thr Val Ser Leu
```

-continued

```
          115

<210> SEQ ID NO 495
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 495

Gln Val Gln Leu Gln Glu Ser Gly Gly Gly Met Val Gln Ala Gly Gly
1               5                   10                  15

Ser Leu Arg Leu Ala Cys Thr Ala Ser Gly Asp Ile Ser Thr Ile Asp
            20                  25                  30

Val Met Gly Trp Asn Arg Gln Ala Pro Gly Lys His Arg Glu Leu Val
        35                  40                  45

Ala Ile Ile Ala Arg Gly Gly Thr Ile Lys Tyr Ala Asp Ser Val Lys
    50                  55                  60

Gly Arg Phe Thr Ile Ser Arg Asp Asn Thr Lys Asn Thr Val Thr Val
65                  70                  75                  80

Tyr Leu Gln Met Asn Asn Val Asn Ala Glu Asp Thr Ala Val Tyr Tyr
                85                  90                  95

Cys Ala Val Asp Thr Gly Ser Pro Arg Leu Thr Trp Gly Gln Gly Thr
            100                 105                 110

Gln Val Thr Val Ser Ser
        115

<210> SEQ ID NO 496
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Ser Ser Ser
            20                  25                  30

Ile Met Ala Trp Tyr Arg Gln Ala Pro Gly Lys Gln Arg Glu Ala Ile
        35                  40                  45

Ala Ser Ile Pro Ser Phe Gly Ser Ala Val Tyr Ala Asp Ser Val Lys
    50                  55                  60

Asp Arg Phe Thr Ile Ser Arg Asp Asn Asn Lys Asn Met Val Tyr Leu
65                  70                  75                  80

Gln Met Asn Ser Leu Lys Pro Glu Asp Thr Ala Val Tyr Tyr Cys Asn
                85                  90                  95

Thr Arg Leu Tyr Trp Gly Gln Gly Thr Gln Val Thr Val Ser Ser
            100                 105                 110

<210> SEQ ID NO 497
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 497
```

Gln Val Gln Leu Gln Glu Ser Gly Gly Gly Leu Val Gln Ala Gly Gly
1               5                   10                  15

Ser Leu Arg Leu Ala Cys Thr Ala Ser Gly Asp Ile Ser Ser Ile Ser
            20                  25                  30

Val Met Gly Trp Asn Arg Gln Ala Pro Gly Lys Gln Gln Arg Glu Leu
        35                  40                  45

Val Ala Ala Ile Ala Ser Gly Gly Ser Val Lys Tyr Ala Asp Ser Val
    50                  55                  60

Lys Gly Arg Phe Thr Ile Ser Arg Asp Asn Thr Lys Asn Thr Val Tyr
65                  70                  75                  80

Leu Gln Met Asn Ser Val Asn Ala Glu Asp Thr Ala Val Tyr Tyr Cys
                85                  90                  95

Ala Val Asp Thr Gly Ser Pro Arg Leu Thr Trp Gly Gln Gly Thr Gln
            100                 105                 110

Val Thr Val Ser Ser
            115

<210> SEQ ID NO 498
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 498

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Ser Thr Asn
            20                  25                  30

Ile Leu Ala Trp Tyr Arg Gln Ala Pro Gly Lys Gln Arg Glu Ala Ile
        35                  40                  45

Ala Ser Ile Thr Pro Phe Gly Ser Ala Val Tyr Ala Asn Ser Val Lys
    50                  55                  60

Asp Arg Phe Thr Ile Ser Arg Asp Asn Asn Lys Asn Met Val Tyr Leu
65                  70                  75                  80

Gln Met Asn Ser Leu Lys Pro Glu Asp Thr Ala Val Tyr Ser Cys Asn
                85                  90                  95

Thr Gln Leu Tyr Trp Gly Gln Gly Thr Gln Val Thr Val Ser Thr
            100                 105                 110

<210> SEQ ID NO 499
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 499

Gln Val Gln Leu Gln Glu Ser Gly Gly Gly Leu Val Gln Ala Gly Gly
1               5                   10                  15

Ser Leu Arg Leu Ser Cys Ala Ala Ser Thr Ser Ile Leu Ser Ile Asn
            20                  25                  30

Ala Met Gly Trp Asn Arg Glu Ala Pro Gly Asn Arg Arg Glu Met Val
        35                  40                  45

Ala Ile Ile Ala Pro Gly Gly Thr Asn Tyr Ala Asp Ser Val Lys
    50                  55                  60

Gly Arg Phe Thr Ile Thr Arg Asp Ile Ser Lys Asn Thr Ile Tyr Leu
65                  70                  75                  80

Gln Met Asn Asn Leu Lys Pro Glu Asp Thr Gly Val Tyr Tyr Cys Ala
                85                  90                  95

Ala Asp Pro Gly Gly Gln Ser Pro Leu Ser Trp Gly Gln Gly Thr Gln
            100                 105                 110

Val Thr Val Ser Leu
        115

<210> SEQ ID NO 500
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ser Ile Ser Ser Ile Thr
            20                  25                  30

Ala Met Gly Trp Asn Arg Gln Ala Pro Gly Asn Gln Arg Glu Leu Val
        35                  40                  45

Ala Val Ile Ala Arg Gly Gly Met Ile Lys Tyr Asp Asp Ser Val Lys
    50                  55                  60

Gly Arg Phe Thr Ile Ser Arg Asp Ile Ala Lys Asn Thr Val Phe Leu
65                  70                  75                  80

Gln Met Asp Ser Leu Lys Pro Glu Asp Thr Gly Val Tyr Tyr Cys Ala
                85                  90                  95

Val Asp Asn Gly Asp Pro Arg Leu His Trp Gly Gln Gly Ile Gln Val
            100                 105                 110

Thr Val Ser Ser
        115

<210> SEQ ID NO 501
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ser Ser Ile Thr
            20                  25                  30

Ala Met Gly Trp Asn Arg Gln Ala Pro Gly Asn Gln Arg Asp Leu
        35                  40                  45

Val Ala Val Ile Ala Arg Gly Gly Met Thr Lys Tyr Ala Asp Ser Val
    50                  55                  60

Gln Gly Arg Phe Thr Ile Ser Arg Asp Ile Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Leu Asp Asn Gly Asp Pro Arg Leu His Trp Gly Gln Gly Ile Gln
            100                 105                 110

Val Thr Val Ser Ser
        115

<210> SEQ ID NO 502
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 502

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Ser Ser Ala
            20                  25                  30

Ile Met Ala Trp Tyr Arg Gln Ala Pro Gly Lys Gln Arg Glu Ala Ile
        35                  40                  45

Ala Ser Ile Pro Ser Phe Gly Ser Ala Val Tyr Ala Asp Ser Val Lys
    50                  55                  60

Asp Arg Phe Thr Ile Ser Arg Asp Asn Asn Lys Asn Met Val Tyr Leu
65                  70                  75                  80

Gln Met Asp Ser Leu Lys Pro Glu Asp Thr Ala Val Tyr Tyr Cys Asn
                85                  90                  95

Thr Arg Leu Tyr Trp Gly Gln Gly Thr Gln Val Thr Val Ser Thr
            100                 105                 110

<210> SEQ ID NO 503
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 503

Gln Val Gln Leu Gln Glu Ser Gly Gly Gly Leu Val Gln Ala Gly Gly
1               5                   10                  15

Ser Leu Arg Leu Ser Cys Ala Ala Ser Thr Ser Ile Leu Ser Ile Asp
            20                  25                  30

Ala Met Gly Trp Asn Arg Gln Ala Pro Gly Asn Gln Arg Arg Asp Leu
        35                  40                  45

Val Ala Val Ile Ala Arg Gly Gly Ser Thr Gln Tyr Ala Asp Ser Val
    50                  55                  60

Lys Gly Arg Phe Thr Ile Thr Arg Asp Ile Ser Lys Asn Thr Ile Tyr
65                  70                  75                  80

Leu Gln Met Asn Ser Leu Lys Pro Glu Tyr Thr Gly Val Tyr Tyr Cys
                85                  90                  95

Ala Ala Asp Pro Gly Gly Ala Ser Gly Leu Ser Trp Gly Gln Gly Thr
            100                 105                 110

Gln Val Thr Val Ser Leu
        115

<210> SEQ ID NO 504
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 504

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ser Ser Ile Thr
            20                  25                  30

Ala Met Gly Trp Asn Arg Gln Ala Pro Gly Asn Gln Gln Arg Asp Leu
        35                  40                  45

Val Ala Val Ile Ala Arg Gly Gly Met Thr Lys Tyr Ala Asp Ser Val
    50                  55                  60

Gln Gly Arg Phe Thr Ile Ser Arg Asp Ile Ala Asn Asn Thr Val Tyr
65                  70                  75                  80

Leu Gln Met Asn Ser Leu Lys Pro Glu Asp Thr Gly Val Tyr Tyr Cys
                85                  90                  95

Ala Leu Tyr Asn Gly Asp Pro Arg Leu His Trp Gly Gln Gly Ile Gln
            100                 105                 110

Val Thr Val Ser Ser
        115

<210> SEQ ID NO 505
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 505

Gln Val Gln Leu Gln Glu Ser Gly Gly Gly Leu Val Gln Ala Gly Gly
1               5                   10                  15

Ser Leu Ser Leu Ser Cys Thr Ala Ser Gly Ser Ala Phe Ser Gly Asp
            20                  25                  30

Ala Met Gly Trp Tyr Arg Arg Ala Pro Gly Lys Gln Arg Glu Phe Val
        35                  40                  45

Ala Gly Ile Ser Ser Gly Ala Ile Thr Asn Tyr Met Asp Ser Val Lys
    50                  55                  60

Gly Arg Phe Thr Ile Ser Arg Asp Asn Ala Lys Asn Thr Val Tyr Leu
65                  70                  75                  80

Gln Met Thr Lys Leu Lys Pro Glu Asp Thr Ala Val Tyr Tyr Cys Asn
                85                  90                  95

Arg Ile Gln Ala Val Leu Arg Gly Asn Ser Gly Trp Gly Gln Gly Thr
            100                 105                 110

Gln Val Thr Val Ser Ser
        115

<210> SEQ ID NO 506
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 506

Gln Val Gln Leu Gln Glu Ser Gly Gly Gly Leu Val Gln Pro Gly Gly
1               5                   10                  15

Ser Leu Ser Leu Ser Cys Thr Ala Ser Gly Ser Ala Phe Ser Gly Gly
            20                  25                  30

Asp Ala Met Gly Trp Tyr Arg Arg Ala Pro Gly Lys Gln Arg Glu Phe
            35                  40                  45

Val Ala Gly Ile Ser Ser Gly Gly Ile Ala Asn Tyr Met Asp Ser Val
 50                  55                  60

Lys Gly Arg Phe Thr Ile Ser Arg Asp Asn Ala Lys Lys Ala Val Tyr
 65                  70                  75                  80

Leu Gln Met Thr Ser Leu Lys Pro Glu Asp Thr Ala Leu Tyr Tyr Cys
                85                  90                  95

Asn Ser Ile Thr Ala Val Leu Arg Gly Asn Ser Gly Trp Gly Gln Gly
            100                 105                 110

Thr Gln Val Thr Val Ser Ser
        115

<210> SEQ ID NO 507
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Gln Val Gln Leu Gln Glu Ser Gly Gly Gly Leu Val Gln Ala Gly Gly
 1               5                  10                  15

Ser Leu Thr Leu Ser Cys Thr Ala Ser Gly Ser Ala Phe Ser Gly Asp
            20                  25                  30

Ala Met Gly Trp Tyr Arg Arg Ala Pro Gly Lys Glu Arg Glu Phe Val
            35                  40                  45

Ala Gly Ile Ser Ser Gly Gly Ile Pro Asn Tyr Met Gly Ser Val Gln
 50                  55                  60

Gly Arg Phe Thr Ile Ser Arg Asp Asn Ala Lys Asn Thr Val Tyr Leu
 65                  70                  75                  80

Gln Met Arg Arg Leu Lys Pro Glu Asp Thr Ala Val Tyr Tyr Cys Asn
                85                  90                  95

Ser Ile Ser Ala Val Leu Arg Gly Asn Gly Val Trp Gly Gln Gly Thr
            100                 105                 110

Gln Val Thr Val Ser Ser
        115

<210> SEQ ID NO 508
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Leu Thr Phe Asn Asn Tyr
            20                  25                  30

Ala Met Gly Trp Phe Arg Gln Ala Pro Gly Lys Glu Arg Glu Phe Val
            35                  40                  45

Ala Thr Ile Ser Arg Asp Gly Thr Asn Thr Arg Tyr Ala Asp Ser Val
 50                  55                  60

Lys Gly Arg Phe Thr Ile Ser Arg Asp Asn Ala Lys Asn Thr Val Asp
 65                  70                  75                  80

-continued

Leu Gln Met Asn Ser Leu Lys Pro Glu Asp Thr Ala Val Tyr Tyr Cys
                85                  90                  95

Gly Val Gly Arg Gly Thr Gly Tyr Ala Tyr Thr Ala Ile Asn Glu Tyr
            100                 105                 110

Asp Tyr Ser Lys Trp Gly Gln Gly Thr Gln Val Thr Val Ser Ser
        115                 120                 125

<210> SEQ ID NO 509
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Asp Ser Ser Phe Tyr
            20                  25                  30

Val Met Ala Trp Tyr Arg Gln Ala Pro Gly Lys Gln Arg Glu Leu Val
        35                  40                  45

Ala Ser Leu Gly Thr Pro Asp Ser Ala Thr Tyr Ala Asp Phe Val Lys
    50                  55                  60

Gly Arg Phe Ile Ile Ser Arg Asp Asn Ala Lys Ser Thr Val Tyr Leu
65                  70                  75                  80

Gln Met Asn Ser Leu Lys Pro Glu Asp Thr Ala Val Tyr Tyr Cys Tyr
                85                  90                  95

Gly Leu Tyr Arg Gln Val Tyr Trp Gly Gln Gly Thr Gln Val Thr Val
            100                 105                 110

Ser Ser

<210> SEQ ID NO 510
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

Gln Val Gln Leu Gln Glu Ser Gly Gly Gly Leu Val Gln Ala Gly Gly
1               5                   10                  15

Ser Leu Arg Leu Ser Cys Val Ala Ser Gly Ile Asp Ser Ser Phe Tyr
            20                  25                  30

Val Met Ala Trp Tyr Arg Gln Ala Pro Gly Lys Gln Arg Glu Leu Val
        35                  40                  45

Ala Ser Ile Ser Ser Ala Asp Ser Pro Arg Tyr Glu Asp Phe Val Lys
    50                  55                  60

Gly Arg Phe Thr Ile Ser Arg Asp Asn Gly Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Gly Leu Tyr Arg Gln Val His Trp Gly Gln Gly Thr Gln Val Thr Val
            100                 105                 110

Ser Ser

<210> SEQ ID NO 511

```
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Gln Val Gln Leu Gln Gln Ser Gly Gly Gly Leu Val Gln Ala Gly Gly
1               5                   10                  15

Ser Leu Arg Leu Ser Cys Ala Ala Ser Gly Leu Thr Phe Ser Ser Tyr
            20                  25                  30

Ala Met Gly Trp Phe Arg Gln Ala Pro Gly Lys Glu Arg Glu Phe Ile
        35                  40                  45

Val Ala Ile Gly Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu His Met Asn Ser Leu Lys Pro Glu Asp Thr Ala Val Tyr Tyr Cys
                85                  90                  95

Ala Ala Arg Arg Thr Thr Ala Trp Gly Lys Gly Thr Asp Tyr Trp Gly
            100                 105                 110

Gln Gly Thr Gln Val Thr Val Ser Ser
        115                 120

<210> SEQ ID NO 512
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 512

Gln Val Gln Leu Gln Glu Ser Gly Gly Gly Leu Val Gln Ala Gly Gly
1               5                   10                  15

Ser Leu Arg Leu Ser Cys Ala Ala Ser Glu Ser Ile Phe Ser Arg Asn
            20                  25                  30

Ala Met Gly Trp Tyr Arg Gln Ala Pro Gly Lys Glu Arg Asp Leu Val
        35                  40                  45

Ala Pro Gly Lys Glu Arg Glu Leu Val Ala Gly Ile Gly Ser Asp Gly
    50                  55                  60

Ser Thr Asn Tyr Ala Glu Ser Val Lys Gly Arg Phe Thr Ile Ser Arg
65                  70                  75                  80

Asp Asn Ala Lys Asn Thr Val Tyr Leu Gln Met Asn Ser Leu Lys Pro
                85                  90                  95

Glu Asp Thr Ala Val Tyr Tyr Cys Arg Val Val Leu Ala Thr Ser Pro
            100                 105                 110

Tyr Asn Tyr Trp Gly Gln Gly Thr Gln Val Thr Val Ser Ser
        115                 120                 125

<210> SEQ ID NO 513
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 513
```

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Thr Ser Ser Leu Tyr
            20                  25                  30

Val Met Ala Trp Tyr Arg Gln Ala Pro Gly Lys Gln Arg Glu Leu Val
        35                  40                  45

Ala His Ile Asn Ser Gly Asp Ser Pro Arg Tyr Ala Asp Phe Val Gln
    50                  55                  60

Gly Arg Phe Thr Ile Ser Arg Asp Asn Gly Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Gly Leu Tyr Arg Gln Val His Trp Gly Gln Gly Thr Gln Val Thr Val
            100                 105                 110

Ser Ser

<210> SEQ ID NO 514
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 514

Gln Val Gln Leu Gln Glu Ser Gly Gly Gly Leu Val Gln Ala Gly Gly
1               5                   10                  15

Ser Leu Arg Leu Ala Cys Ala Ala Ser Gly Leu Thr Phe Asn Asn Tyr
            20                  25                  30

Ala Met Gly Trp Phe Arg Gln Ala Pro Gly Lys Glu Arg Glu Phe Val
        35                  40                  45

Ala Thr Ile Ser Arg Asp Gly Thr Ser Thr Arg Tyr Ala Asp Ser Val
    50                  55                  60

Lys Gly Arg Phe Thr Ile Ser Arg Asp Asn Ala Lys Asn Thr Val Asn
65                  70                  75                  80

Leu Gln Met Asn Arg Leu Lys Pro Glu Asp Thr Ala Val Tyr Tyr Cys
                85                  90                  95

Gly Val Gly Arg Gly Ser Gly Tyr Ala Tyr Ser Ala Ile Asn Glu Tyr
            100                 105                 110

Asp Tyr Ser Ser Trp Gly Gln Gly Thr Gln Val Thr Val Ser Ser
        115                 120                 125

<210> SEQ ID NO 515
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Asp Ser Ser Phe Tyr
            20                  25                  30

Val Met Ala Trp Tyr Arg Gln Ala Pro Gly Gln Gln Arg Glu Leu Val
        35                  40                  45

Ala Ser Ile Ser Met Thr Ser Ala Asp Ser Pro Arg Tyr Ala Asp Phe

Val Lys Gly Arg Phe Thr Ile Ser Arg Asp Asn Ala Lys Ser Thr Val
65                  70                  75                  80

Tyr Leu Gln Met Asn Ser Leu Lys Pro Glu Asp Thr Ala Val Tyr Tyr
                85                  90                  95

Cys Tyr Gly Leu Tyr Arg Gln Val His Trp Gly Gln Gly Thr Gln Val
                100                 105                 110

Thr Val Ser Ser
        115

<210> SEQ ID NO 516
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 516

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Gly Ile Leu Phe Arg
                20                  25                  30

Ile Ser Ala Met Gly Trp Tyr Arg Gln Ala Pro Gly Lys Glu Arg Asp
                35                  40                  45

Leu Val Ala Gly Ile Ser Ser Gly Gly Ser Thr Asn Tyr Ala Asp Ser
            50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Asn Ile Val Gly Arg Thr Asp Ser Trp Gly Gln Gly Thr Gln Val
                100                 105                 110

Thr Val Ser Ser
        115

<210> SEQ ID NO 517
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 517

Gln Val Gln Leu Gln Glu Ser Gly Gly Gly Ser Val Gln Ala Gly Gly
1               5                   10                  15

Ser Leu Arg Leu Ser Cys Ala Ala Ser Ala Arg Thr Leu Ser Asn Tyr
                20                  25                  30

Ala Met Gly Trp Phe Arg Gln Ala Pro Gly Lys Glu Arg Glu Phe Val
                35                  40                  45

Ala Thr Ile Ser Arg Ser Gly Gly Ser Ile His Tyr Ala Asp Ser Val
            50                  55                  60

Lys Gly Arg Phe Thr Ile Ser Arg Asp Asn Ala Lys Asn Thr Val Asn
65                  70                  75                  80

Leu Gln Met Asn Ser Leu Lys Val Glu Asp Thr Ala Val Tyr Tyr Cys
                85                  90                  95

Gly Arg Ala Arg Gly Thr Gly Tyr Ala Tyr Thr Ala Leu Asn Gln Tyr

Asp Tyr Asp Tyr Trp Gly Gln Gly Thr Gln Val Thr Val Ser Ser
            115                 120                 125

<210> SEQ ID NO 518
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 518

Gln Val Gln Leu Gln Glu Ser Gly Gly Gly Leu Val Gln Ala Gly Gly
1               5                   10                  15

Ser Leu Thr Leu Ser Cys Thr Thr Ser Gly Ser Ala Phe Ser Gly Asp
            20                  25                  30

Ala Met Gly Trp Tyr Arg Arg Ala Pro Gly Gln Glu Arg Glu Phe Val
        35                  40                  45

Ala Gly Ile Ser Ser Gly Gly Ile Thr Asn Tyr Met Asn Phe Val Lys
    50                  55                  60

Gly Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ser Ile Lys Ala Val Leu Arg Gly Asn Ser Gly Trp Gly Gln Gly Thr
            100                 105                 110

Gln Val Thr Val Ser Ser
        115

<210> SEQ ID NO 519
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 519

Gln Val Gln Leu Gln Glu Ser Gly Gly Gly Leu Val Gln Ala Gly Gly
1               5                   10                  15

Ser Leu Arg Leu Ser Cys Ala Ala Ser Gly Leu Thr Phe His Asn Tyr
            20                  25                  30

Ala Met Gly Trp Phe Arg Gln Ala Pro Gly Lys Glu Arg Glu Phe Val
        35                  40                  45

Ala Thr Ile Ser Arg Asp Gly Thr Asn Thr His Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Val Tyr Tyr Cys
                85                  90                  95

Gly Val Gly Arg Gly Ser Gly Tyr Ala Tyr Thr Ala Ile Asn Glu Tyr
            100                 105                 110

Asp Tyr Ser Lys Trp Gly Gln Gly Thr Gln Val Thr Val Ser Ser
        115                 120                 125

<210> SEQ ID NO 520
<211> LENGTH: 118
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 520

```
Gln Val Gln Leu Gln Glu Ser Gly Gly Gly Leu Val Gln Ala Gly Gly
1               5                   10                  15

Ser Leu Ser Leu Ser Cys Thr Ala Ser Gly Ser Ala Phe Ser Gly Asp
            20                  25                  30

Ala Met Gly Trp Tyr Arg Arg Ala Pro Gly Lys Gln Arg Asp Phe Val
        35                  40                  45

Ala Gly Ile Ser Ser Gly His Ile Thr Asn Tyr Met Asp Ser Val Lys
    50                  55                  60

Gly Arg Phe Thr Ile Ser Arg Asp Asn Ala Lys Asn Thr Val Tyr Leu
65                  70                  75                  80

Gln Met Thr Lys Leu Lys Pro Glu Asp Thr Ala Val Tyr Tyr Cys Asn
                85                  90                  95

Ser Ile Thr Ala Val Leu Arg Gly Asn Ser Gly Trp Gly Gln Gly Thr
            100                 105                 110

Gln Val Thr Val Ser Ser
        115
```

<210> SEQ ID NO 521
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 521

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Ala Met Gly Trp Phe Arg Gln Ala Pro Gly Lys Glu Arg Glu Phe Val
        35                  40                  45

Ala Thr Ile Ser Arg Ser Gly Asp Asn Ile Tyr Tyr Ala Asp Ser Val
    50                  55                  60

Lys Gly Arg Phe Thr Ile Ser Arg Asp Asn Ala Lys Asn Thr Val Ser
65                  70                  75                  80

Leu Gln Met Asn Ser Leu Lys Val Glu Asp Thr Ala Val Tyr Tyr Cys
                85                  90                  95

Gly Arg Ala Arg Gly Thr Gly Tyr Ala His Thr Ala Leu Asn Gln Tyr
            100                 105                 110

Asp Tyr Asp Tyr Trp Gly Gln Gly Thr Gln Val Thr Val Ser Ser
        115                 120                 125
```

<210> SEQ ID NO 522
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 522

```
Gln Val Gln Leu Gln Glu Ser Gly Gly Gly Leu Val Gln Ala Gly Gly
1               5                   10                  15
```

```
Ser Leu Ser Leu Ser Cys Arg Val Ser Gly Ser Ala Phe Ser Gly Asp
            20                  25                  30

Ala Met Gly Trp Tyr Arg Arg Ala Pro Gly Lys Gln Arg Glu Phe Val
            35                  40                  45

Ala Gly Ile Ser Ser Gly Gly Ile Glu Asn Tyr Met Asp Ser Val Lys
    50                  55                  60

Gly Arg Phe Thr Ile Ser Arg Asp Asn Ala Lys Asn Thr Val Tyr Leu
65                  70                  75                  80

Arg Met Ser Ser Leu Lys Pro Glu Asp Thr Ala Val Tyr Tyr Cys Asn
                85                  90                  95

Leu Ile Lys Ala Val Leu Arg Gly Asn Ser Gly Trp Gly Gln Gly Thr
            100                 105                 110

Gln Val Thr Val Ser Ser
            115

<210> SEQ ID NO 523
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 523

Gln Val Gln Leu Gln Glu Ser Gly Gly Gly Leu Val Gln Ala Gly Gly
1               5                   10                  15

Ser Leu Arg Leu Ser Cys Ala Ala Ser Gly Leu Thr Phe Asn Asn Tyr
            20                  25                  30

Ala Met Gly Trp Phe Arg Gln Ala Pro Gly Lys Glu Arg Glu Phe Val
            35                  40                  45

Ala Thr Ile Ser Arg Asp Gly Thr Asn Thr Arg Tyr Ala Asp Ser Val
    50                  55                  60

Lys Gly Arg Phe Thr Ile Ser Arg Asp Asn Ala Lys Asn Thr Val Asn
65                  70                  75                  80

Leu Gln Met Asn Ser Leu Lys Pro Glu Asp Thr Ala Val Tyr Tyr Cys
                85                  90                  95

Gly Val Gly Arg Gly Thr Gly Tyr Ala Tyr Thr Ala Ile Arg Glu His
            100                 105                 110

Asp Tyr Ser Ser Trp Gly Gln Gly Thr Gln Val Thr Val Ser Ser
            115                 120                 125

<210> SEQ ID NO 524
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 524

Gln Val Gln Leu Gln Glu Ser Gly Gly Gly Leu Val Gln Ala Gly Gly
1               5                   10                  15

Ser Leu Ser Leu Ser Cys Thr Ala Ser Gly Ser Ala Phe Ser Gly Asp
            20                  25                  30

Ala Met Gly Trp Tyr Arg Arg Ala Pro Gly Lys Gln Arg Glu Phe Val
            35                  40                  45

Ala Gly Ile Ser Ser Gly Gly Ile Thr Asn Tyr Met Asn Ser Val Lys
    50                  55                  60
```

```
Gly Arg Phe Thr Ile Ser Arg Asp Asn Ala Lys Asn Thr Val Tyr Leu
65                  70                  75                  80

His Met Thr Gly Val Lys Pro Ala Asp Thr Ala Val Tyr Tyr Cys Asn
                85                  90                  95

Ser Ile Thr Ala Val Leu Arg Gly Asn Ser Gly Trp Gly Pro Gly Thr
            100                 105                 110

Gln Val Thr Val Ser Ser
        115

<210> SEQ ID NO 525
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 525

Gln Val Gln Leu Gln Glu Ser Gly Gly Gly Leu Val Gln Pro Gly Gly
1               5                   10                  15

Ser Leu Thr Leu Ser Cys Thr Ala Ser Gly Ser Ala Phe Ser Gly Asp
            20                  25                  30

Ala Met Gly Trp Tyr Arg Arg Ala Pro Gly Lys Gln Arg Glu Phe Val
        35                  40                  45

Ala Gly Ile Ser Ser Gly Gly Ile Ala Asn Tyr Met Asp Ser Thr Glu
    50                  55                  60

Gly Arg Phe Thr Ile Ser Arg Asp Asp Ala Lys Asn Thr Val Tyr Leu
65                  70                  75                  80

Gln Met Thr Gly Val Lys Pro Ala Asp Thr Ala Val Tyr Tyr Cys Asn
                85                  90                  95

Thr Ile Lys Ala Val Leu Arg Gly Asn Ala Gly Trp Gly Gln Gly Thr
            100                 105                 110

Gln Val Thr Val Ser Ser
        115

<210> SEQ ID NO 526
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 526

Gln Val Gln Leu Gln Glu Ser Gly Gly Gly Leu Val Gln Ala Gly Gly
1               5                   10                  15

Ser Leu Ser Leu Ser Cys Thr Ala Ser Gly Ser Ala Phe Ser Gly Asp
            20                  25                  30

Ala Met Gly Trp Tyr Arg Arg Ala Pro Gly Lys Gln Arg Glu Phe Val
        35                  40                  45

Ala Gly Ile Ser Ser Gly Ala Ile Thr Asn Tyr Met Asp Ser Val Lys
    50                  55                  60

Gly Arg Phe Thr Ile Ser Arg Asp Asn Ala Lys Asn Met Val Tyr Leu
65                  70                  75                  80

Gln Met Thr Lys Leu Lys Pro Glu Asp Thr Ala Val Tyr Tyr Cys Asn
                85                  90                  95

Ser Ile Thr Ala Val Leu Arg Gly Asn Ser Gly Trp Gly Gln Gly Thr
            100                 105                 110
```

Gln Val Thr Val Ser Ser
        115

<210> SEQ ID NO 527
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 527

Gln Val Gln Leu Gln Glu Ser Gly Gly Gly Leu Val Gln Ala Gly Gly
1               5                   10                  15

Ser Leu Ser Leu Ser Cys Thr Ala Ser Gly Ser Ala Phe Ser Gly Asp
            20                  25                  30

Ala Met Gly Trp Tyr Arg Arg Ala Pro Gly Lys Gln Arg Glu Phe Val
        35                  40                  45

Ala Gly Ile Ser Ser Gly Gly Ile Thr Asn Tyr Met Asp Ser Val Lys
    50                  55                  60

Gly Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ile Ile Ser Ala Val Leu Arg Gly Asn Gly Gly Trp Gly Gln Gly Thr
            100                 105                 110

Gln Val Thr Val Ser Ser
        115

<210> SEQ ID NO 528
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 528

Gln Val Gln Leu Gln Gln Ser Gly Gly Gly Leu Val Gln Ala Gly Gly
1               5                   10                  15

Ser Leu Ser Leu Ser Cys Thr Ala Ser Ile Ser Gly Phe Ser Gly Asp
            20                  25                  30

Ala Met Gly Trp Tyr Arg Arg Ala Pro Gly Lys Gln Arg Glu Phe Val
        35                  40                  45

Ala Gly Ile Ser Ser Gly Gly Ile Thr Asn Tyr Met Asp Ser Val Lys
    50                  55                  60

Gly Arg Phe Thr Ile Ser Arg Asp Asn Ala Lys Asn Thr Val Tyr Leu
65                  70                  75                  80

Gln Met Thr Asn Leu Lys Pro Glu Asp Thr Ala Val Tyr Tyr Cys Asn
                85                  90                  95

Thr Ile Thr Gly Val Leu Arg Gly Asn Ser Gly Trp Gly Gln Gly Thr
            100                 105                 110

Gln Val Thr Val Ser Ser
        115

<210> SEQ ID NO 529
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 529

Gln Val Gln Leu Gln Glu Ser Gly Gly Gly Leu Val Gln Ala Gly Gly
1               5                   10                  15

Ser Leu Arg Leu Ser Cys Ala Gly Ser Gly Ile Ile Ser Ser Ala Tyr
            20                  25                  30

Val Met Ala Trp Tyr Arg Gln Arg Pro Gly Lys Gln Arg Glu Leu Val
        35                  40                  45

Ala Ser Ile Thr Ser Gly Asp Ser Pro Arg Tyr Glu Asp Phe Val Lys
    50                  55                  60

Gly Arg Phe Thr Ile Ser Arg Asp Asn Ala Lys Ser Thr Val Tyr Leu
65                  70                  75                  80

Gln Met Asn Ser Leu Lys Pro Glu Asp Thr Ala Val Tyr Tyr Cys Tyr
                85                  90                  95

Gly Leu Tyr Arg Gln Val Tyr Trp Gly Gln Gly Thr Gln Val Thr Val
            100                 105                 110

Ser Ser

<210> SEQ ID NO 530
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 530

Gln Val Gln Leu Gln Gln Ser Gly Gly Gly Leu Val Gln Ala Gly Gly
1               5                   10                  15

Ser Leu Lys Leu Ser Cys Ala Ala Ser Gly Ile Ala Phe Ser Thr Tyr
            20                  25                  30

Gly Met Asn Trp Phe Arg Gln Thr Pro Gly Lys Gln Arg Glu Tyr Val
        35                  40                  45

Ala Tyr Ile Thr Gly Asn Gly Asp Asp Asn Val Ala Gln Ser Met Glu
    50                  55                  60

Gly Arg Phe Thr Ile Ser Arg Asp Asn Ala Lys Asn Thr Gly Tyr Leu
65                  70                  75                  80

Gln Met Asn Ser Leu Lys Pro Glu Asp Thr Gly Val Tyr Tyr Cys Asn
                85                  90                  95

Ile Gly Met Tyr Trp Gly Gln Gly Thr Gln Val Thr Val Ser Ser
            100                 105                 110

<210> SEQ ID NO 531
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 531

Gln Val Gln Leu Gln Glu Ser Gly Gly Gly Leu Val Gln Ala Gly Gly
1               5                   10                  15

Ser Leu Ser Leu Ser Cys Thr Ala Ser Gly Ser Ala Phe Ser Gly Asp
            20                  25                  30

Ala Met Gly Trp Tyr Arg Arg Ala Pro Gly Lys Gln Arg Glu Phe Val

```
                35                  40                  45

Ala Gly Ile Ser Ser Gly Gly Ile Thr Asn Tyr Met Gly Phe Val Lys
        50                  55                  60

Gly Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ser Ile Ser Ala Val Leu Arg Gly Asn Ser Gly Trp Gly Gln Gly Thr
            100                 105                 110

Gln Val Thr Val Ser Ala
        115

<210> SEQ ID NO 532
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 532

Gln Val Gln Leu Gln Glu Ser Gly Gly Gly Leu Val Gln Ala Gly Gly
1               5                   10                  15

Ser Leu Ser Leu Ser Cys Thr Ala Ser Gly Ser Ala Phe Ser Gly Asp
            20                  25                  30

Ala Met Gly Trp Tyr Arg Arg Ala Pro Gly Lys Gln Arg Asp Phe Val
        35                  40                  45

Ala Gly Ile Ser Ser Gly Gly Ile Thr Asn Tyr Met Asp Ser Val Lys
        50                  55                  60

Gly Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ser Ile Ser Ala Val Leu Arg Gly Asn Gly Trp Gly Gln Gly Thr
            100                 105                 110

Gln Val Thr Val Ser Ser
        115

<210> SEQ ID NO 533
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 533

Gln Val Gln Leu Gln Glu Ser Gly Gly Gly Leu Val Gln Pro Gly Gly
1               5                   10                  15

Ser Leu Ser Leu Ser Cys Thr Ala Ser Gly Ser Ala Phe Ser Gly Asp
            20                  25                  30

Ala Met Gly Trp Tyr Arg Arg Ala Pro Gly Lys Gln Arg Glu Phe Val
        35                  40                  45

Ala Gly Ile Ser Ser Gly Gly Ile Thr Asn Tyr Met Asp Ser Val Lys
        50                  55                  60

Asp Arg Phe Thr Ile Ser Arg Asp Asn Ala Lys Asn Thr Leu Tyr Leu
65                  70                  75                  80

Gln Met Thr Asn Leu Lys Pro Glu Asp Thr Ala Val Tyr Tyr Cys Asn
```

```
                    85                  90                  95

Ser Ile Thr Ala Val Leu Arg Gly Asn Ser Asp Trp Gly Gln Gly Thr
                100                 105                 110

Gln Val Thr Val Ser Ser
        115

<210> SEQ ID NO 534
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 534

Gln Val Gln Leu Gln Glu Ser Gly Gly Gly Leu Val Gln Ala Gly Gly
1               5                   10                  15

Ser Leu Ser Leu Ser Cys Thr Thr Ser Gly Ser Ala Phe Ser Gly Asp
                20                  25                  30

Ala Met Gly Trp Tyr Arg Arg Ala Pro Gly Lys Gln Arg Glu Phe Val
            35                  40                  45

Ala Gly Ile Ser Ser Gly Gly Ile Pro Asn Tyr Met Gly Phe Val Arg
        50                  55                  60

Gly Arg Phe Thr Ile Ser Arg Asp Asn Thr Lys Asn Thr Val Tyr Leu
65                  70                  75                  80

Gln Met Thr Ser Leu Lys Pro Asp Asp Thr Ala Val Tyr Tyr Cys Asn
                85                  90                  95

Ile Ile Lys Thr Val Leu Arg Gly Asn Ala Val Trp Gly Gln Gly Thr
                100                 105                 110

Gln Val Thr Val Ser Ser
        115

<210> SEQ ID NO 535
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 535

Gln Val Gln Leu Gln Glu Ser Gly Gly Gly Leu Val Gln Ala Gly Gly
1               5                   10                  15

Ser Leu Ser Leu Ser Cys Thr Ala Ser Gly Ser Ala Phe Ser Gly Gly
                20                  25                  30

Asp Ala Met Gly Trp Tyr Arg Arg Ala Pro Gly Lys Gln Arg Glu Phe
            35                  40                  45

Val Ala Gly Ile Ser Ser Gly Gly Ile Thr Asn Tyr Met Asp Phe Val
        50                  55                  60

Lys Gly Arg Phe Thr Ile Ser Arg Asp Asn Ala Lys Asn Thr Val Tyr
65                  70                  75                  80

Leu Gln Met Thr Ser Leu Lys Pro Glu Asp Thr Ala Val Tyr Tyr Cys
                85                  90                  95

Asn Ser Ile Thr Ala Val Leu Arg Gly Asn Ser Gly Trp Gly Gln Gly
                100                 105                 110

Thr Gln Val Thr Val Ser Ser
        115
```

```
<210> SEQ ID NO 536
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 536

Gln Val Gln Leu Gln Glu Ser Gly Gly Gly Leu Val Gln Ala Gly Gly
1               5                   10                  15

Ser Leu Arg Leu Ser Cys Val Ala Ser Gly Ile Thr Phe Ser Ser Asp
            20                  25                  30

Ala Met Gly Trp Tyr Arg Gln Ala Pro Gly Lys Gln Arg Glu Phe Val
        35                  40                  45

Ala Gly Ile Ser Ser Gly Asp Ile Thr Asn Tyr Pro Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Thr Ile Thr Arg Leu Leu Tyr Gly Met Asp Tyr Trp Gly Lys Gly Thr
            100                 105                 110

Leu Val Thr Val Ser Ser
        115

<210> SEQ ID NO 537
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 537

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Gly Tyr
            20                  25                  30

Ala Ile Gly Trp Phe Arg Gln Ala Pro Gly Lys Glu Arg Glu Trp Val
        35                  40                  45

Ser Cys Ile Ile Tyr Arg Asp Gly Ser Pro Ala Tyr Ala Asp Ser Val
    50                  55                  60

Trp Gly Arg Phe Thr Ile Ser Arg Asp Asn Ala Lys Asn Asn Val Tyr
65                  70                  75                  80

Leu Glu Met Asn Ser Leu Lys Pro Glu Asp Thr Ala Val Tyr Tyr Cys
                85                  90                  95

Ala Ala Arg Pro Gly Gly Ala Cys Ser Arg Tyr Pro Ser Asn Tyr Asp
            100                 105                 110

Thr Trp Gly Gln Gly Thr Gln Val Thr Ala Ser Ser
        115                 120

<210> SEQ ID NO 538
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 538
```

Gln Val Lys Leu Glu Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Thr Gly Gly Asn Thr Ala Asn Thr Ala Tyr Ala Asp
    50                  55                  60

Ser Val Lys Gly Arg Phe Thr Ile Ser Arg Asp Lys Ala Lys Asn Thr
65                  70                  75                  80

Val Tyr Leu Gln Met Asn Ser Leu Lys Pro Glu Asp Thr Ala Val Tyr
                85                  90                  95

Tyr Cys Ala Ala Arg Gly Leu Ser Tyr Glu Tyr Asp Tyr Trp Gly Gln
            100                 105                 110

Gly Thr Gln Val Thr Val Ser Ser
        115                 120

<210> SEQ ID NO 539
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 539

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Ile Thr Ser Gly Arg Gly Gly Asn Thr Ala Tyr Ala
    50                  55                  60

Asp Ser Val Lys Gly Arg Phe Thr Ile Ser Arg Asp Asn Ala Lys Asn
65                  70                  75                  80

Thr Val Tyr Leu Gln Met Asn Thr Leu Lys Pro Glu Asp Thr Ala Val
                85                  90                  95

Tyr Tyr Cys Ala Ala Arg Gly Ala Met Thr Tyr Glu Tyr Asp Tyr Trp
            100                 105                 110

Gly Gln Gly Thr Gln Val Thr Val Ser Ser
        115                 120

<210> SEQ ID NO 540
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 540

Gln Val Gln Leu Val Glu Ser Gly Gly Gly Leu Val Gln Ala Gly Gly
1               5                   10                  15

Ser Leu Arg Leu Ser Cys Ala Ala Ser Gly Ile Ile Phe Ser Pro Asn
            20                  25                  30

Ala Met Gly Trp Tyr Arg Gln Ala Pro Gly Lys Gln Arg Glu Leu Val
        35                  40                  45

```
Ser Thr Ile Thr Ser Phe Gly Ile Ile Asn Tyr Ala Asp Ser Val Lys
    50                  55                  60

Asp Thr Ile Ser Arg Asp Asn Ala Lys Asn Thr Val Tyr Leu Gln Met
65                  70                  75                  80

Thr Ser Leu Lys Pro Glu Asp Thr Ala Val Tyr Tyr Cys Asn Ala Lys
                85                  90                  95

Thr Phe Asp Gly Thr Arg Trp Arg Asp Tyr Trp Gly Gln Gly Ala Gln
            100                 105                 110

Val Thr Val Ser Ser
        115
```

<210> SEQ ID NO 541
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 541

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Asn Ile Phe Ser Ile Asn
                20                  25                  30

Ala Met Gly Trp Tyr Arg Gln Ala Pro Gly Lys Gln Arg Glu Leu Val
            35                  40                  45

Ala Ala Ile Thr Thr Gly Gly Ser Tyr Gly Asn Thr Asn Tyr Ala Asp
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Ala Ala Arg Gly Ser Gln Thr Tyr Glu Tyr Asp Tyr Trp Gly
            100                 105                 110

Gln Gly Thr Gln Val Thr Val Ser Ser
        115                 120
```

<210> SEQ ID NO 542
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 542

```
Gln Val Lys Leu Glu Glu Ser Gly Gly Gly Leu Val Gln Pro Gly Gly
1               5                   10                  15

Ser Leu Thr Leu Ser Cys Ala Ser Gly Arg Ile Phe Ser Ile Tyr
                20                  25                  30

Asp Met Gly Trp Phe Arg Gln Ala Pro Gly Lys Glu Arg Glu Leu Val
            35                  40                  45

Ser Ala Ile Thr Trp Gly Asn Gly Asn Thr Ala Tyr Gly Asp Ser Val
    50                  55                  60

Lys Gly Arg Phe Ser Ile Ser Arg Asp Phe Ala Lys Asn Thr Val Tyr
65                  70                  75                  80

Leu Gln Ile Asp Ser Leu Lys Ala Glu Asp Thr Ala Val Tyr Tyr Cys
                85                  90                  95
```

```
Pro Ala Arg Ile Val Asn Gly Gly Ser Trp Asp Tyr Trp Gly Gln Gly
            100                 105                 110

Thr Gln Val Thr Val Ser Ser
        115

<210> SEQ ID NO 543
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 543

Gln Val Lys Leu Glu Glu Ser Gly Gly Gly Leu Val Gln Pro Gly Gly
1               5                   10                  15

Ser Leu Thr Leu Ser Cys Ala Ala Ser Gly Arg Ile Phe Ser Ile Tyr
            20                  25                  30

Asp Met Gly Trp Phe Arg Gln Ala Pro Gly Lys Glu Arg Glu Leu Val
        35                  40                  45

Ser Ala Ile Thr Trp Gly Asn Gly Asn Thr Ala Tyr Gly Asp Ser Val
    50                  55                  60

Lys Gly Arg Phe Ser Ile Ser Arg Asp Phe Ala Lys Asn Thr Val Tyr
65                  70                  75                  80

Leu Gln Ile Asp Ser Leu Lys Ala Glu Asp Thr Ala Val Tyr Tyr Cys
                85                  90                  95

Pro Ala Arg Ile Val Asn Gly Gly Ser Trp Asp Tyr Trp Gly Gln Gly
            100                 105                 110

Thr Gln Val Thr Val Ser Ser
        115

<210> SEQ ID NO 544
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 544

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Met Phe Ser Ser Tyr
            20                  25                  30

Asp Met Gly Trp Phe Arg Gln Ala Pro Gly Lys Glu Arg Asp Ile Val
        35                  40                  45

Ala Ala Ile Thr Lys Asn Gly Arg Thr Thr Ser Tyr Ala Asn Ser Val
    50                  55                  60

Lys Gly Arg Phe Thr Ile Ser Arg Asp Asn Thr Lys Ser Thr Val Tyr
65                  70                  75                  80

Leu Gln Ile His Ser Leu Lys Pro Glu Asp Thr Ala Val Tyr Tyr Cys
                85                  90                  95

Ala Gly Arg Arg Ser Asn Ala Asp Asn Trp Asp Tyr Trp Gly Gln Gly
            100                 105                 110

Thr Gln Val Thr Val Ser Ser
        115

<210> SEQ ID NO 545
```

```
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 545

Gln Val Lys Leu Glu Glu Ser Gly Gly Gly Leu Val Gln Ala Gly Gly
1               5                   10                  15

Ser Leu Arg Leu Ser Cys Ala Val Ser Gly Ser Ile Phe Ser Ile Asn
            20                  25                  30

Ala Val Gly Trp Tyr Arg Gln Ala Pro Gly Lys Gln Arg Glu Leu Val
        35                  40                  45

Ala Ala Ile Gly Thr Gly Gly Ser Ser Gly Asn Thr Ala Tyr Ala
    50                  55                  60

Asp Ser Val Lys Gly Arg Phe Thr Ile Ser Asn Asp Ala Ala Lys Asn
65                  70                  75                  80

Thr Val Tyr Leu Gln Met Asn Ser Leu Lys Pro Asp Asp Thr Ala Val
                85                  90                  95

Tyr Tyr Cys Ala Ala Arg Gly Thr Ile Ser Tyr Glu Tyr Asp Tyr Trp
            100                 105                 110

Gly Gln Gly Thr Gln Val Thr Val Ser Ser
        115                 120

<210> SEQ ID NO 546
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 546

Gln Val Gln Leu Val Glu Ser Gly Gly Gly Leu Val Gln Ala Gly Gly
1               5                   10                  15

Ser Leu Thr Leu Ser Cys Ile Val Ser Gly Ile Ser Val Asn Ile Asn
            20                  25                  30

Pro Met Tyr Trp Tyr Arg Pro Gly Pro Gly Asn Gln Arg Glu Leu Val
        35                  40                  45

Val Ser Leu Leu Pro Thr Gly Thr Thr His Asp Ala His Phe Thr Lys
    50                  55                  60

Gly Arg Phe Ile Ile Ser Lys Asp Asp Ala Lys Asn Thr Val Tyr Leu
65                  70                  75                  80

Leu Met Asn Ser Leu Lys Pro Glu Asp Thr Ala Val Tyr Tyr Cys Asn
                85                  90                  95

Thr Ala Asp Phe Trp Gly Gln Gly Thr Gln Val Thr Val Ser Ser
            100                 105                 110

<210> SEQ ID NO 547
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

Gln Val Lys Leu Glu Glu Ser Gly Gly Gly Leu Val Gln Ala Gly Gly
1               5                   10                  15
```

```
Ser Leu Arg Leu Ser Cys Ala Ala Ser Gly Ser Thr Phe Ser Ile Asn
            20                  25                  30

Ala Met Gly Trp Phe Arg Gln Ala Pro Gly Lys Gln Arg Glu Leu Val
        35                  40                  45

Ala Ala Ile Ser Arg Ala Gly Ser Thr Asn Thr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Ala Ser Ser Gly Ser Ser Val Tyr Ile Gly Phe Gly Trp Gly Gln
            100                 105                 110

Gly Thr Gln Val Thr Val Ser Ser
        115                 120

<210> SEQ ID NO 548
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

Gln Val Gln Leu Val Glu Ser Glu Ser Gly Leu Val Leu Ala Gly Gly
1               5                   10                  15

Ser Leu Thr Leu Thr Arg Phe Cys Ser Val Ser Ser Val Ser Ile Asn
            20                  25                  30

Pro Met Tyr Trp Tyr Arg Gln Gly Pro Gly Lys Gln Arg Glu Leu Val
        35                  40                  45

Leu Ile Leu Leu Ser Met Ala Arg Ala Gln Asn Ala His Phe Pro Asn
    50                  55                  60

Gly Gln Phe Leu Ile Ser Ile Tyr Glu Asp Asp Asn Thr Met Tyr Leu
65                  70                  75                  80

Gln Leu Ser Ile Gln Lys Pro Glu Asp Ala Asp Val Tyr Asp Cys Asn
                85                  90                  95

Thr Thr Asp Phe Trp Gly Gln Gly Thr Gln Val Thr Val Ser Ser
            100                 105                 110

<210> SEQ ID NO 549
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 549

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser Arg Leu
            20                  25                  30

Ala Met Gly Trp Phe Arg Gln Ala Pro Gly Lys Glu Arg Glu Phe Val
        35                  40                  45

Val Ala Ile Ser Trp Ser Gly Gly Asn Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Asn Ala Glu Asp Thr Ala Val Tyr Tyr Cys
                85                  90                  95

Ala Ala Pro Glu Arg Ser Gly Ser Tyr Ala Tyr Thr Pro Ser Arg Leu
            100                 105                 110

Asn Glu Tyr Ala Tyr Trp Gly Gln Gly Thr Gln Val Thr Val Ser Ser
        115                 120                 125

<210> SEQ ID NO 550
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 550

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Phe Ser Ser Tyr
            20                  25                  30

Asp Met Gly Trp Phe Arg Gln Ala Pro Gly Lys Glu Arg Glu Leu Val
        35                  40                  45

Ala Ala Ile Arg Trp Gly Asn Gly Asn Thr Ala Tyr Gly Asp Ser Val
    50                  55                  60

Lys Gly Arg Phe Ser Ile Ser Arg Asp Phe Ala Lys Asn Thr Val Tyr
65                  70                  75                  80

Leu His Ile Asp Ser Leu Lys Ala Glu Asp Thr Ala Val Tyr Tyr Cys
                85                  90                  95

Ala Ala Arg Gly Leu Ala Tyr Glu Tyr Glu Tyr Trp Gly Gln Gly Thr
            100                 105                 110

Gln Val Thr Val Ser Ser
        115

<210> SEQ ID NO 551
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 551

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Phe Ser Ser Tyr
            20                  25                  30

Asp Met Gly Trp Phe Arg Gln Ala Pro Gly Lys Glu Arg Glu Leu Val
        35                  40                  45

Ala Ala Ile Arg Trp Gly Asn Gly Asn Thr Ala Tyr Gly Asp Ser Val
    50                  55                  60

Lys Gly Arg Phe Ser Ile Ser Arg Asp Phe Ala Lys Asn Thr Val Tyr
65                  70                  75                  80

Leu His Ile Asp Ser Leu Lys Ala Glu Asp Thr Ala Val Tyr Tyr Cys
                85                  90                  95

Ala Ala Arg Ile Val Asn Gly Gly Ser Trp Asp Tyr Trp Gly Gln Gly
            100                 105                 110

Thr Gln Val Thr Val Ser Ser
        115
```

<210> SEQ ID NO 552
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 552

Gln Val Gln Leu Val Glu Ser Gly Gly Gly Ser Val Gln Pro Ala Gly
1               5                   10                  15

Ser Leu Arg Leu Ser Cys Ala Val Ser Gly Ile Ile Phe Ser Pro Asn
            20                  25                  30

Ala Leu Gly Trp Tyr Arg Pro Ala Pro Gly Lys Glu Arg Glu Leu Val
        35                  40                  45

Ala Ser Ile Ile Ser Gly Gly Arg Ser Asp Tyr Ala Asp Ser Val Lys
    50                  55                  60

Asp Arg Phe Thr Ile Ala Arg Asp Asn Pro Lys Asn Thr Val Thr Leu
65                  70                  75                  80

Gln Met Asn Ser Leu Lys Pro Glu Asp Thr Ala Ile Tyr Tyr Cys Asn
                85                  90                  95

Ala Asn Val Tyr Asp Gly Asn Arg Trp Arg Thr Tyr Trp Gly Gln Gly
            100                 105                 110

Thr Gln Val Thr Val Ser Ser
        115

<210> SEQ ID NO 553
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 553

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Arg Ser Tyr
            20                  25                  30

Thr Met Gly Trp Phe Arg Gln Ala Pro Gly Leu Glu Arg Glu Ile Ile
        35                  40                  45

Ala Ala Ile Ser Trp Ser Ala Gly Ser Thr Arg Tyr Ala Asp Ser Met
    50                  55                  60

Ser Asp Arg Phe Thr Ile Ser Arg Asp Asn Ala Lys Asn Thr Val Tyr
65                  70                  75                  80

Leu Gly Met Asp Ser Leu Lys Pro Glu Asp Thr Ala Val Tyr Tyr Cys
                85                  90                  95

Ala Ala Gly Thr Lys Tyr Ser Asp Thr Ile Ile Thr Trp Gly Ser Trp
            100                 105                 110

Gly Gln Gly Thr Gln Val Thr Val Ser Ser
        115                 120

<210> SEQ ID NO 554
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 554

Gln Val Gln Leu Val Glu Ser Gly Gly Gly Leu Val Gln Pro Gly Gly
1               5                   10                  15

Ser Leu Arg Leu Ser Cys Ala Val Ser Gly Ser Thr Val Thr Ile Ser
            20                  25                  30

Thr Val Gly Trp Tyr Arg Gln Ala Pro Gly Asn Gln Arg Val Leu Val
        35                  40                  45

Ala Ser Ile Ser Ser Asp Ser Thr Thr Asn Tyr Ala His Ser Val Lys
    50                  55                  60

Gly Thr Ile Ser Arg His Asn Ala Glu Asn Pro Val Ser Arg Leu Gln
65                  70                  75                  80

Met Asn Ser Leu Lys Pro Glu Asp Thr Ala Val Tyr Tyr Cys Asn Val
                85                  90                  95

Val Gly Thr Tyr Trp Thr Gly Ala Asp Trp Arg Pro Phe Asp Thr Trp
            100                 105                 110

Gly Arg Gly Thr Gln Val Thr Val Ser Ser
        115                 120

<210> SEQ ID NO 555
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 555

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Ser Phe Ser Ser Tyr
            20                  25                  30

Asn Met Gly Trp Phe Arg Gln Ala Pro Gly Lys Glu Arg Glu Phe Val
        35                  40                  45

Ala Ala Ile Thr Trp Ser Gly Asn Thr Tyr Tyr Ala Asp Ser Val Lys
    50                  55                  60

Gly Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Phe Cys Lys Val Arg
                85                  90                  95

Ala Glu Asp Thr Asp Tyr Trp Gly Arg Gly Thr Gln Val Thr Val Ser
            100                 105                 110

Ser

<210> SEQ ID NO 556
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 556

Gln Val Lys Leu Glu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Gly Met Thr Trp Val Arg Gln Ala Pro Gly Lys Gly Leu Glu Trp Val
        35                  40                  45

Ser Ala Ile Asn Ser Gly Gly Ala Arg Thr Ser Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                85                  90                  95

Ala Lys Ala Ser Leu Pro Trp Phe Asp Gly Ser Ser Pro Asp Tyr Trp
            100                 105                 110

Gly Gln Gly Thr Gln Val Thr Val Ser Ser
            115                 120

<210> SEQ ID NO 557
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 557

Gln Val Lys Leu Glu Glu Ser Gly Gly Gly Leu Val Gln Ala Gly Gly
 1               5                   10                  15

Ser Leu Arg Leu Ser Cys Ala Ala Ser Gly Leu Thr Phe Ser Ser Tyr
                20                  25                  30

Gly Met Gly Trp Phe Arg Gln Pro Gly Lys Glu Arg Glu Ser Val
            35                  40                  45

Ala Ala Ile Lys Met Ser Gly Asp Thr Tyr Thr Asp Ser Val Lys
        50                  55                  60

Gly Arg Phe Thr Ile Ser Arg Asp Asn Ala Lys Asn Thr Val Tyr Leu
 65                  70                  75                  80

Gln Met Asp Ser Leu Lys Pro Glu Asp Thr Ala Val Tyr Phe Cys Ala
                85                  90                  95

Ala Ala Arg Val Arg Thr Pro Gly Trp Gly Pro Gln Lys Ser Tyr Asp
            100                 105                 110

Tyr Trp Gly Gln Gly Thr Gln Val Thr Val Ser Ser
            115                 120

<210> SEQ ID NO 558
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 558

Gln Val Lys Leu Glu Glu Ser Gly Gly Gly Leu Val Gln Ala Gly Gly
 1               5                   10                  15

Ser Leu Arg Leu Ser Cys Ala Ala Ser Gly Arg Thr Phe Gly Ser Leu
                20                  25                  30

His Met Gly Trp Phe Arg Gln Ala Pro Gly Lys Glu Arg Glu Phe Val
            35                  40                  45

Ser Ala Ile Ser Ala Ala Gly Val Thr Asp Tyr Ala Asp Ser Ala
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

```
Ala Ala Val Lys Tyr Trp Gly Arg Arg Gln Arg Ala Asp Glu Tyr Asp
            100                 105                 110

Tyr Trp Gly Gln Gly Thr Gln Val Thr Val Ser Ser
        115                 120

<210> SEQ ID NO 559
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 559

Gln Val Arg Leu Glu Lys Ser Gly Gly Gly Leu Val Gln Pro Gly Gly
1               5                   10                  15

Ser Leu Thr Leu Ser Cys Thr Ala Ser Gly Ser Ile Ser Ser Ile Lys
            20                  25                  30

Ala Met Gly Trp Tyr Arg Gln Ala Pro Gly Lys Gln Arg Glu Leu Ala
        35                  40                  45

Ala Leu Trp Arg Met Tyr Ser Gly Thr Ala Tyr Gly Asp Ser Val Lys
    50                  55                  60

Gly Arg Ser Asn Leu Ser Val Asn His Thr Asn Asn Thr Ala Tyr Leu
65                  70                  75                  80

Gln Met Asn Ser Leu Arg Pro Glu Asp Thr Ala Val Tyr Trp Cys Tyr
                85                  90                  95

Leu Glu Ile Pro Glu Ser Arg Gly Ala Phe Trp Gly His Gly Thr Gln
            100                 105                 110

Val Thr Val Ser Ser
        115

<210> SEQ ID NO 560
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 560

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Arg Asp
            20                  25                  30

Ala Met Gly Trp Phe Arg Gln Ala Pro Gly Lys Glu Arg Glu Phe Val
        35                  40                  45

Ala Thr Ile Asn Trp Asn Gly Arg Ser Thr Tyr Tyr Thr Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Glu Trp Gly Ile Arg Pro Tyr Asn Tyr Asp Tyr Trp Gly
            100                 105                 110

Gln Gly Thr Gln Val Thr Val Ser Ser
        115                 120

<210> SEQ ID NO 561
```

<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 561

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ser Ile Asn Trp Ser Gly Gly Arg Ile Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Thr Asp Tyr Asp Asn Ser Gly Ser Tyr Tyr Tyr Gln Lys Gly Asn
            100                 105                 110

Tyr Glu Tyr Asp Tyr Trp Gly Gln Gly Thr Gln Val Thr Val Ser Ser
        115                 120                 125

<210> SEQ ID NO 562
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 562

Gln Val Gln Leu Val Glu Ser Gly Gly Gly Leu Val Gln Pro Gly Gly
1               5                   10                  15

Ser Leu Lys Val Ser Cys Ala Ala Ser Gly Ile Ile Phe Ser Pro Asn
            20                  25                  30

Ala Met Gly Trp Tyr Arg Gln Ala Pro Gly Lys Gln Arg Asp Leu Val
        35                  40                  45

Ala Thr Ile Thr Ser Ser Gly Ile Ile Asn Tyr Ala Asp Ser Val Lys
    50                  55                  60

Gly Thr Ile Ser Arg Asp Asn Ala Lys Asn Thr Val Tyr Leu Gln Met
65                  70                  75                  80

Thr Ser Leu Lys Pro Glu Asp Thr Ala Val Tyr Tyr Cys Asn Ala Lys
                85                  90                  95

Ala Phe Asp Gly Thr Arg Trp Tyr Asp Tyr Trp Gly Gln Gly Thr Gln
            100                 105                 110

Val Thr Val Ser Ser
        115

<210> SEQ ID NO 563
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 563

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Glu Ala Pro Gly Lys Glu Arg Arg Phe Val
        35                  40                  45

Ala Ser Ile Ser Trp Ser Gly Ser Ser Tyr Ala Asp Ser Val
    50                  55                  60

Lys Gly Thr Ile Ser Arg Asp Tyr Ala Glu Asn Met Val Tyr Leu Gln
65                  70                  75                  80

Met Asn Ser Leu Lys Pro Glu Asp Thr Ala Thr Tyr Tyr Cys Ala Ala
                85                  90                  95

Arg Thr Ala Leu Gly Gly Thr Tyr Asp Tyr Trp Gly Gln Gly Thr Gln
            100                 105                 110

Val Thr Val Ser Ser
            115

<210> SEQ ID NO 564
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 564

Gln Val Gln Leu Ala Glu Ser Gly Val Gly Leu Val Glu Pro Ala Gly
1               5                   10                  15

Ser Leu Lys Phe Ser Cys Ala Ala Ser Gly Ile Ile Phe Asn Pro Asn
            20                  25                  30

Ala Met Gly Trp His Arg Gln Ala Pro Glu Asn Gln Arg Glu Leu Val
        35                  40                  45

Ala Thr Ile Thr Ser Phe Gly Ile Ile Asn Tyr Ala Asp Ser Val Lys
    50                  55                  60

Asp Ser Ile Ser Arg Asp His Asp Thr Asn Ala Val Tyr Leu Gln Met
65                  70                  75                  80

Thr Asn Leu Arg Pro Asp Asp Pro Ala Val Tyr Tyr Cys Asn Ala Ile
                85                  90                  95

Thr Phe Tyr Gly Thr Arg Trp Leu Asp Tyr Trp Gly Gln Gly Thr Gln
            100                 105                 110

Val Thr Val Ser Ser
            115

<210> SEQ ID NO 565
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 565

Gln Val Gln Leu Val Glu Ser Gly Gly Gly Leu Val Gln Pro Gly Gly
1               5                   10                  15

Ser Leu Arg Leu Ser Cys Ala Val Ser Gly Ile Ile Phe Ser Pro Asn
            20                  25                  30

Ala Leu Gly Trp Tyr Arg Gln Ala Pro Gly Lys Glu Arg Glu Leu Val
        35                  40                  45
```

Ala Ser Ile Ile Ser Gly Gly Arg Ser Asp Tyr Ala Asp Ser Val Lys
            50                  55                  60

Asp Thr Ile Ala Arg Asp Asn Pro Lys Asn Thr Val Thr Leu Gln Met
65                  70                  75                  80

Asn Ser Leu Lys Pro Glu Asp Thr Ala Ile Tyr Tyr Cys Asn Ala Asp
                85                  90                  95

Val Tyr Asp Gly Asn Arg Trp Arg Thr Tyr Trp Gly Gln Gly Thr Gln
            100                 105                 110

Val Thr Val Ser Ser
        115

<210> SEQ ID NO 566
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 566

Gln Val Lys Leu Glu Glu Ser Gly Gly Gly Leu Val Gln Pro Gly Gly
1               5                   10                  15

Ser Leu Lys Val Ser Cys Ala Ala Ser Gly Ile Ile Phe Ser Pro Asn
            20                  25                  30

Ala Met Gly Trp Tyr Arg Gln Ala Pro Gly Lys Gln Arg Glu Leu Val
        35                  40                  45

Ala Thr Ile Thr Ser Phe Gly Ile Ile Asn Tyr Ala Asp Ser Val Lys
    50                  55                  60

Asp Thr Ile Ser Arg Asp Asn Ala Lys Asn Thr Val Tyr Leu Gln Met
65                  70                  75                  80

Thr Ser Leu Lys Pro Glu Asp Thr Ala Val Phe Tyr Cys Phe Ala Lys
                85                  90                  95

Thr Phe Asp Gly Thr Arg Trp Cys Asp Tyr Trp Gly Gln Gly Thr Gln
            100                 105                 110

Val Thr Val Ser Ser
        115

<210> SEQ ID NO 567
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 567

Gln Val Gln Leu Val Glu Ser Gly Ala Gly Leu Val Gln Pro Gly Gly
1               5                   10                  15

Ser Leu Arg Leu Ser Cys Ala Val Ser Gly Ile Ile Phe Ser Pro Asn
            20                  25                  30

Ala Leu Gly Trp Tyr Arg Gln Ala Pro Gly Lys Glu Arg Glu Leu Val
        35                  40                  45

Ala Ser Ile Ile Ser Gly Gly Arg Ser Asp Tyr Ala Asp Ser Val Lys
    50                  55                  60

Asp Thr Ile Ala Arg Asp Asn Pro Lys Asn Ala Val Thr Leu Gln Met
65                  70                  75                  80

Asn Ser Leu Lys Pro Glu Asp Thr Ala Ile Tyr Tyr Cys Asn Ala Ile
                85                  90                  95

```
Val Tyr Asp Gly Asn Arg Trp Arg Thr Tyr Trp Gly Gln Gly Thr Gln
            100                 105                 110

Val Thr Val Ser Ser
        115

<210> SEQ ID NO 568
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 568

Gln Val Lys Leu Glu Glu Ser Gly Glu Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Ala Trp Phe Arg Gln Ala Pro Gly Lys Glu Arg Glu Phe Val
        35                  40                  45

Ala Arg Ile Arg Trp Thr Arg Ser Ser Thr Val Tyr Ala Asp Ser Val
    50                  55                  60

Lys Gly Thr Ile Ser Gly Asp Asn Ala Lys Asn Thr Met Tyr Leu Gln
65                  70                  75                  80

Met Asn Ser Leu Lys Pro Glu Asp Thr Ala Val Tyr Tyr Cys Ala Ala
                85                  90                  95

Asp Arg Tyr Tyr Arg Thr Asp Ile Tyr Arg Ala Ser Ser Tyr Glu Tyr
            100                 105                 110

Trp Gly Gln Gly Thr Gln Val Thr Val Ser Ser
        115                 120

<210> SEQ ID NO 569
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 569

Gln Val Lys Leu Glu Glu Ser Gly Gly Gly Leu Val Gln Ala Gly Gly
1               5                   10                  15

Ser Leu Arg Leu Ser Cys Val Val Ser Gly Arg Pro Phe Ile Asn Tyr
            20                  25                  30

Asn Met Gly Trp Phe Arg Gln Ala Pro Gly Lys Glu His Glu Phe Val
        35                  40                  45

Ala Ala Ile Ser Trp Ser Gly Asp Ser Thr Tyr Tyr Glu Asp Ser Val
    50                  55                  60

Lys Gly Thr Val Ser Arg Asp Asn Ala Lys Asn Thr Val Tyr Leu Gln
65                  70                  75                  80

Met Asn Asn Leu Lys Pro Glu Asp Thr Ala Val Tyr Tyr Cys Ala Ala
                85                  90                  95

Asp Asn Gln His Asp Ile Pro Leu Arg Pro Gly Gly Trp Gln Gly Thr
            100                 105                 110

Gln Val Thr Val Ser Ser
        115

<210> SEQ ID NO 570
<211> LENGTH: 126
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 570

Gln Val Gln Leu Val Glu Ser Gly Gly Gly Leu Val Glu Ala Gly Gly
1               5                   10                  15

Ser Leu Thr Leu Ser Cys Ala Ala Ser Gly Leu Ala Phe Asn Thr Lys
            20                  25                  30

Thr Met Ala Trp Phe Arg Gln Ala Pro Asp Lys Glu Arg Ala Val Val
        35                  40                  45

Ala Thr Ile Thr Trp Gly Thr Ile Asn Thr Ser Tyr Ala Asp Ser Val
    50                  55                  60

Lys Gly Arg Phe Thr Ile Ser Arg Asp Asn Ala Lys Asn Met Val Tyr
65                  70                  75                  80

Leu Arg Met Asp Ser Leu Lys Pro Glu Asp Thr Asp Val Tyr Tyr Cys
                85                  90                  95

Glu Ser Glu Ala Leu Leu Glu Thr Thr Pro Ser Arg Arg Pro Tyr Glu
            100                 105                 110

Tyr Asn Tyr Trp Gly Pro Gly Thr Gln Val Thr Val Ser Ser
        115                 120                 125

<210> SEQ ID NO 571
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 571

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Ile Phe Gly Ser Leu
            20                  25                  30

His Met Gly Trp Phe Arg Gln Ala Pro Gly Lys Glu Arg Glu Phe Val
        35                  40                  45

Ser Pro Ile Thr Ala Ala Gly Gly Val Thr Asp Tyr Asp Ser Ser Asn
    50                  55                  60

Glu Gly Ile His Ser Val Leu His Lys Gln Arg Gln Glu His Val Ser
65                  70                  75                  80

Ser Pro Met Asn Ser Leu Lys Pro Asp Thr His Gly Arg Leu Leu Leu
                85                  90                  95

Cys Arg Thr Leu Gly Cys Ser Tyr Tyr Glu Arg Ala Asp Glu Tyr Asn
            100                 105                 110

Tyr Trp Gly Gln Gly Thr Gln Val Thr Val Ser Ser
        115                 120

<210> SEQ ID NO 572
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 572

Gln Val Lys Leu Glu Glu Ser Gly Gly Gly Leu Val Gln Ala Gly Gly
```

```
                1               5                   10                  15
            Ser Leu Arg Leu Ser Cys Ala Val Ser Gly Ser Ile Phe Ser Thr Asn
                            20                  25                  30
            Leu Met Gly Trp Tyr Arg Gln Ala Pro Gly Lys Gln Arg Gly Phe Val
                        35                  40                  45
            Ala His Ile Thr Ser Gly Gly Asn Thr Asp Tyr Leu Asp Ser Val Lys
                    50                  55                  60
            Gly Arg Phe Thr Ile Ser Arg Asp Asn Ala Lys Asn Thr Val Tyr Leu
             65                 70                  75                  80
            Gln Met Asn Ser Leu Lys Pro Glu Asp Thr Ala Val Tyr Tyr Cys Ala
                            85                  90                  95
            Ala Gln Thr Leu Gly Ser Ser Tyr Tyr Asp Ala Trp Gly Gln Gly Thr
                        100                 105                 110
            Gln Val Thr Val Ser Ser
                    115

<210> SEQ ID NO 573
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Gly Phe Thr Leu Asp Gly Tyr Ala Ile
1               5

<210> SEQ ID NO 574
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Ile Ile Tyr Arg Asp Gly Ser Pro
1               5

<210> SEQ ID NO 575
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Ala Ala Arg Pro Gly Gly Ala Cys Ser Arg Tyr Pro Ser Asn Tyr Asp
1               5                   10                  15

Thr

<210> SEQ ID NO 576
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Gln Val Lys Leu Glu Glu Ser Gly Gly Gly Leu Val Gln Ala Gly Gly
```

Ser Leu Arg Leu Ser Cys Ala Val Ser
            20                  25

<210> SEQ ID NO 577
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 578
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 579
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Gln Val Lys Leu Glu Glu Ser Gly Gly Gly Leu Val Arg Ala Gly Gly
1               5                   10                  15

Ser Leu Thr Leu Ser Cys Gly Ala Ser
            20                  25

<210> SEQ ID NO 580
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Gln Val Gln Leu Gln Gln Ser Gly Gly Gly Leu Val Gln Ala Gly Gly
1               5                   10                  15

Ser Leu Arg Leu Ser Cys Ala Ala Ser
            20                  25

<210> SEQ ID NO 581
<211> LENGTH: 25
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 581

Gln Val Gln Leu Gln Glu Ser Gly Gly Arg Leu Val Gln Ala Gly Gly
1               5                   10                  15

Ser Leu Arg Leu Ser Cys Ala Ala Ser
            20                  25

<210> SEQ ID NO 582
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Gln Val Gln Leu Gln Glu Ser Gly Gly Gly Leu Val Gln Ala Gly Lys
1               5                   10                  15

Ser Leu Arg Leu Ser Cys Ala Ala Ser
            20                  25

<210> SEQ ID NO 583
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Gln Val Gln Leu Gln Glu Ser Gly Gly Gly Met Val Gln Ala Gly Gly
1               5                   10                  15

Ser Leu Arg Leu Ala Cys Thr Ala Ser
            20                  25

<210> SEQ ID NO 584
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 585
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Gln Val Gln Leu Gln Glu Ser Gly Gly Gly Leu Val Gln Ala Gly Gly
1               5                   10                  15

Ser Leu Arg Leu Ala Cys Thr Ala Ser
            20                  25
```

<210> SEQ ID NO 586
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Gln Val Gln Leu Gln Glu Ser Gly Gly Gly Ser Val Gln Ala Gly Gly
1               5                   10                  15

Ser Leu Arg Leu Ser Cys Ala Ala Ser
            20                  25

<210> SEQ ID NO 587
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Gln Val Gln Leu Gln Glu Ser Gly Gly Gly Leu Val Gln Ala Gly Gly
1               5                   10                  15

Ser Leu Ser Leu Ser Cys Thr Ala Ser
            20                  25

<210> SEQ ID NO 588
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Gln Val Gln Leu Gln Glu Ser Gly Gly Gly Leu Val Gln Pro Gly Gly
1               5                   10                  15

Ser Leu Ser Leu Ser Cys Thr Ala Ser
            20                  25

<210> SEQ ID NO 589
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Gln Val Gln Leu Gln Glu Ser Gly Gly Gly Leu Val Gln Ala Gly Gly
1               5                   10                  15

Ser Leu Thr Leu Ser Cys Thr Ala Ser
            20                  25

<210> SEQ ID NO 590
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

```
Gln Val Gln Leu Gln Glu Ser Gly Gly Gly Leu Val Gln Ala Gly Gly
1               5                   10                  15

Ser Leu Thr Leu Ser Cys Thr Thr Ser
            20                  25

<210> SEQ ID NO 591
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Gln Val Gln Leu Gln Glu Ser Gly Gly Gly Leu Val Gln Ala Gly Gly
1               5                   10                  15

Ser Leu Ser Leu Ser Cys Arg Val Ser
            20                  25

<210> SEQ ID NO 592
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Gln Val Gln Leu Gln Glu Ser Gly Gly Gly Leu Val Gln Pro Gly Gly
1               5                   10                  15

Ser Leu Thr Leu Ser Cys Thr Ala Ser
            20                  25

<210> SEQ ID NO 593
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Gln Val Gln Leu Gln Gln Ser Gly Gly Gly Leu Val Gln Ala Gly Gly
1               5                   10                  15

Ser Leu Ser Leu Ser Cys Thr Ala Ser
            20                  25

<210> SEQ ID NO 594
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Gln Val Gln Leu Gln Glu Ser Gly Gly Gly Leu Val Gln Ala Gly Gly
1               5                   10                  15

Ser Leu Arg Leu Ser Cys Ala Gly Ser
            20                  25

<210> SEQ ID NO 595
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 595

Gln Val Gln Leu Gln Gln Ser Gly Gly Gly Leu Val Gln Ala Gly Gly
1               5                   10                  15

Ser Leu Lys Leu Ser Cys Ala Ala Ser
            20                  25

<210> SEQ ID NO 596
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Gln Val Gln Leu Gln Glu Ser Gly Gly Gly Leu Val Gln Ala Gly Gly
1               5                   10                  15

Ser Leu Ser Leu Ser Cys Thr Thr Ser
            20                  25

<210> SEQ ID NO 597
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Gln Val Gln Leu Gln Glu Ser Gly Gly Gly Leu Val Gln Ala Gly Gly
1               5                   10                  15

Ser Leu Arg Leu Ser Cys Val Ala Ser
            20                  25

<210> SEQ ID NO 598
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 599
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Gln Val Lys Leu Glu Glu Ser Gly Gly Gly Leu Val Gln Ala Gly Gly
1               5                   10                  15

Ser Leu Arg Leu Ser Cys Ala Ala Ser
            20                  25
```

<210> SEQ ID NO 600
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Gln Val Lys Leu Glu Glu Ser Gly Gly Gly Leu Val Gln Pro Gly Gly
1               5                   10                  15

Ser Leu Thr Leu Ser Cys Ala Ala Ser
            20                  25

<210> SEQ ID NO 601
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Gln Val Lys Leu Glu Glu Ser Gly Glu Gly Leu Val Gln Ala Gly Gly
1               5                   10                  15

Ser Leu Arg Leu Ser Cys Ala Ala Ser
            20                  25

<210> SEQ ID NO 602
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Gln Val Gln Leu Val Glu Ser Gly Gly Gly Leu Val Gln Ala Gly Gly
1               5                   10                  15

Ser Leu Thr Leu Ser Cys Ile Val Ser
            20                  25

<210> SEQ ID NO 603
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Gln Val Gln Leu Val Glu Ser Glu Ser Gly Leu Val Leu Ala Gly Gly
1               5                   10                  15

Ser Leu Thr Leu Thr Arg Phe Cys Ser
            20                  25

<210> SEQ ID NO 604
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

```
Gln Val Gln Leu Val Glu Ser Gly Gly Gly Ser Val Gln Pro Ala Gly
1               5                   10                  15

Ser Leu Arg Leu Ser Cys Ala Val Ser
            20                  25

<210> SEQ ID NO 605
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Gln Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 606
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Gln Val Lys Leu Glu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 607
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Gln Val Arg Leu Glu Lys Ser Gly Gly Gly Leu Val Gln Pro Gly Gly
1               5                   10                  15

Ser Leu Thr Leu Ser Cys Thr Ala Ser
            20                  25

<210> SEQ ID NO 608
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Gln Val Gln Leu Val Glu Ser Gly Gly Gly Leu Val Gln Pro Gly Gly
1               5                   10                  15

Ser Leu Lys Val Ser Cys Ala Ala Ser
            20                  25

<210> SEQ ID NO 609
<211> LENGTH: 25
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 609

Gln Val Gln Leu Ala Glu Ser Gly Val Gly Leu Val Glu Pro Ala Gly
1               5                   10                  15

Ser Leu Lys Phe Ser Cys Ala Ala Ser
            20                  25

<210> SEQ ID NO 610
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Gln Val Lys Leu Glu Glu Ser Gly Gly Gly Leu Val Gln Pro Gly Gly
1               5                   10                  15

Ser Leu Lys Val Ser Cys Ala Ala Ser
            20                  25

<210> SEQ ID NO 611
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Gln Val Gln Leu Val Glu Ser Gly Ala Gly Leu Val Gln Pro Gly Gly
1               5                   10                  15

Ser Leu Arg Leu Ser Cys Ala Val Ser
            20                  25

<210> SEQ ID NO 612
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Gln Val Lys Leu Glu Glu Ser Gly Gly Gly Leu Val Gln Ala Gly Gly
1               5                   10                  15

Ser Leu Arg Leu Ser Cys Val Val Ser
            20                  25

<210> SEQ ID NO 613
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Gln Val Gln Leu Val Glu Ser Gly Gly Gly Leu Val Glu Ala Gly Gly
1               5                   10                  15

Ser Leu Thr Leu Ser Cys Ala Ala Ser
```

20          25

<210> SEQ ID NO 614
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Tyr Trp Tyr Arg Gln Gly Pro Gly Lys Gln Arg Glu Leu Val Val Ser
1               5                   10                  15

<210> SEQ ID NO 615
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Gly Trp Phe Arg Gln Ala Pro Gly Lys Gln Arg Glu Leu Val Ala Ala
1               5                   10                  15

<210> SEQ ID NO 616
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Gly Trp Tyr Arg Gln Ala Pro Gly Glu Gln Arg Glu Leu Val Ala Thr
1               5                   10                  15

<210> SEQ ID NO 617
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Gly Trp Phe Arg Gln Ala Pro Gly Lys Gln Arg Gly Phe Val Ala His
1               5                   10                  15

<210> SEQ ID NO 618
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Gly Trp Phe Arg Gln Ala Pro Gly Lys Glu Arg Glu Phe Val Ala Ser
1               5                   10                  15

<210> SEQ ID NO 619
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 619

Ala Trp Phe Arg Gln Ala Pro Gly Asn Glu Arg Glu Phe Val Ala Ser
1               5                   10                  15

<210> SEQ ID NO 620
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Glu Trp Tyr Arg Gln Ala Pro Gly Asn Gln Arg Glu Tyr Val Ala Arg
1               5                   10                  15

<210> SEQ ID NO 621
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Gly Trp Phe Arg Gln Ala Pro Gly Lys Glu Arg Glu Phe Val Ala Ala
1               5                   10                  15

<210> SEQ ID NO 622
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Gly Trp Tyr Arg Gln Ala Pro Gly Lys Gln Arg Glu Leu Val Ala Leu
1               5                   10                  15

<210> SEQ ID NO 623
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Gly Trp Phe Arg Gln Ala Pro Gly Lys Glu Arg Glu Phe Val Ser Ala
1               5                   10                  15

<210> SEQ ID NO 624
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

Gly Trp Asn Arg Gln Ala Val Gly Asn Gln Arg Glu Leu Val Ala Val
1               5                   10                  15

<210> SEQ ID NO 625

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

Gly Trp Asn Arg Gln Ala Pro Gly Lys His Arg Glu Leu Val Ala Ile
1               5                   10                  15

<210> SEQ ID NO 626
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Ala Trp Tyr Arg Gln Ala Pro Gly Lys Gln Arg Glu Ala Ile Ala Ser
1               5                   10                  15

<210> SEQ ID NO 627
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Gly Trp Asn Arg Gln Ala Pro Gly Lys Gln Gln Arg Glu Leu Val Ala
1               5                   10                  15

Ala

<210> SEQ ID NO 628
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Gly Trp Asn Arg Glu Ala Pro Gly Asn Arg Arg Glu Met Val Ala Ile
1               5                   10                  15

<210> SEQ ID NO 629
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Gly Trp Asn Arg Gln Ala Pro Gly Asn Gln Arg Glu Leu Val Ala Val
1               5                   10                  15

<210> SEQ ID NO 630
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 630

Gly Trp Asn Arg Gln Ala Pro Gly Asn Gln Gln Arg Asp Leu Val Ala
1               5                   10                  15

Val

<210> SEQ ID NO 631
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Gly Trp Asn Arg Gln Ala Pro Gly Asn Gln Arg Arg Asp Leu Val Ala
1               5                   10                  15

Val

<210> SEQ ID NO 632
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Gly Trp Tyr Arg Arg Ala Pro Gly Lys Gln Arg Glu Phe Val Ala Gly
1               5                   10                  15

<210> SEQ ID NO 633
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Gly Trp Tyr Arg Arg Ala Pro Gly Lys Glu Arg Glu Phe Val Ala Gly
1               5                   10                  15

<210> SEQ ID NO 634
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Gly Trp Phe Arg Gln Ala Pro Gly Lys Glu Arg Glu Phe Val Ala Thr
1               5                   10                  15

<210> SEQ ID NO 635
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Ala Trp Tyr Arg Gln Ala Pro Gly Lys Gln Arg Glu Leu Val Ala Ser
1               5                   10                  15
```

<210> SEQ ID NO 636
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Gly Trp Phe Arg Gln Ala Pro Gly Lys Glu Arg Glu Phe Ile Val Ala
1               5                   10                  15

Ile

<210> SEQ ID NO 637
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Gly Trp Tyr Arg Gln Ala Pro Gly Lys Glu Arg Asp Leu Val Ala Pro
1               5                   10                  15

<210> SEQ ID NO 638
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Ala Trp Tyr Arg Gln Ala Pro Gly Lys Gln Arg Glu Leu Val Ala His
1               5                   10                  15

<210> SEQ ID NO 639
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Ala Trp Tyr Arg Gln Ala Pro Gly Gln Gln Arg Glu Leu Val Ala Ser
1               5                   10                  15

<210> SEQ ID NO 640
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Gly Trp Tyr Arg Gln Ala Pro Gly Lys Glu Arg Asp Leu Val Ala Gly
1               5                   10                  15

<210> SEQ ID NO 641
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 641

Gly Trp Tyr Arg Arg Ala Pro Gly Gln Glu Arg Glu Phe Val Ala Gly
1               5                   10                  15

<210> SEQ ID NO 642
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Gly Trp Tyr Arg Arg Ala Pro Gly Lys Gln Arg Asp Phe Val Ala Gly
1               5                   10                  15

<210> SEQ ID NO 643
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Ala Trp Tyr Arg Gln Arg Pro Gly Lys Gln Arg Glu Leu Val Ala Ser
1               5                   10                  15

<210> SEQ ID NO 644
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 644

Asn Trp Phe Arg Gln Thr Pro Gly Lys Gln Arg Glu Tyr Val Ala Tyr
1               5                   10                  15

<210> SEQ ID NO 645
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Gly Trp Phe Arg Gln Ala Pro Gly Lys Glu Arg Glu Trp Val Ser Cys
1               5                   10                  15

<210> SEQ ID NO 646
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Gly Trp Tyr Arg Gln Ala Pro Gly Lys Gln Arg Glu Leu Val Ala Ala
1               5                   10                  15

<210> SEQ ID NO 647

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Gly Trp Tyr Arg Gln Ala Pro Gly Lys Gln Arg Glu Leu Val Ser Thr
1               5                   10                  15

<210> SEQ ID NO 648
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Gly Trp Phe Arg Gln Ala Pro Gly Lys Glu Arg Glu Leu Val Ser Ala
1               5                   10                  15

<210> SEQ ID NO 649
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Gly Trp Phe Arg Gln Ala Pro Gly Lys Glu Arg Glu Leu Val Ala Ala
1               5                   10                  15

<210> SEQ ID NO 650
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Gly Trp Phe Arg Gln Ala Pro Gly Lys Glu Arg Asp Ile Val Ala Ala
1               5                   10                  15

<210> SEQ ID NO 651
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Tyr Trp Tyr Arg Pro Gly Pro Gly Asn Gln Arg Glu Leu Val Val Ser
1               5                   10                  15

<210> SEQ ID NO 652
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652
```

Tyr Trp Tyr Arg Gln Gly Pro Gly Lys Gln Arg Glu Leu Val Leu Ile
1               5                   10                  15

<210> SEQ ID NO 653
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Gly Trp Phe Arg Gln Ala Pro Gly Lys Glu Arg Glu Phe Val Val Ala
1               5                   10                  15

<210> SEQ ID NO 654
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Gly Trp Tyr Arg Pro Ala Pro Gly Lys Glu Arg Glu Leu Val Ala Ser
1               5                   10                  15

<210> SEQ ID NO 655
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Gly Trp Phe Arg Gln Ala Pro Gly Leu Glu Arg Glu Ile Ile Ala Ala
1               5                   10                  15

<210> SEQ ID NO 656
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Gly Trp Tyr Arg Gln Ala Pro Gly Asn Gln Arg Val Leu Val Ala Ser
1               5                   10                  15

<210> SEQ ID NO 657
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Thr Trp Val Arg Gln Ala Pro Gly Lys Gly Leu Glu Trp Val Ser Ala
1               5                   10                  15

<210> SEQ ID NO 658
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 658

Gly Trp Phe Arg Gln Gly Pro Gly Lys Glu Arg Glu Ser Val Ala Ala
1               5                   10                  15

<210> SEQ ID NO 659
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Gly Trp Tyr Arg Gln Ala Pro Gly Lys Gln Arg Glu Leu Ala Ala Leu
1               5                   10                  15

<210> SEQ ID NO 660
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Gly Trp Tyr Arg Gln Ala Pro Gly Lys Gln Arg Asp Leu Val Ala Thr
1               5                   10                  15

<210> SEQ ID NO 661
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Gly Trp Phe Arg Glu Ala Pro Gly Lys Glu Arg Arg Phe Val Ala Ser
1               5                   10                  15

<210> SEQ ID NO 662
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Gly Trp His Arg Gln Ala Pro Glu Asn Gln Arg Glu Leu Val Ala Thr
1               5                   10                  15

<210> SEQ ID NO 663
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Gly Trp Tyr Arg Gln Ala Pro Gly Lys Glu Arg Glu Leu Val Ala Ser
1               5                   10                  15
```

```
<210> SEQ ID NO 664
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Gly Trp Tyr Arg Gln Ala Pro Gly Lys Gln Arg Glu Leu Val Ala Thr
1               5                   10                  15

<210> SEQ ID NO 665
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Ala Trp Phe Arg Gln Ala Pro Gly Lys Glu Arg Glu Phe Val Ala Arg
1               5                   10                  15

<210> SEQ ID NO 666
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Gly Trp Phe Arg Gln Ala Pro Gly Lys Glu His Glu Phe Val Ala Ala
1               5                   10                  15

<210> SEQ ID NO 667
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Ala Trp Phe Arg Gln Ala Pro Asp Lys Glu Arg Ala Val Val Ala Thr
1               5                   10                  15

<210> SEQ ID NO 668
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Gly Trp Phe Arg Gln Ala Pro Gly Lys Glu Arg Glu Phe Val Ser Pro
1               5                   10                  15

<210> SEQ ID NO 669
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669
```

```
Gly Trp Tyr Arg Gln Ala Pro Gly Lys Gln Arg Gly Phe Val Ala His
1               5                   10                  15

<210> SEQ ID NO 670
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 670

His Asp Ala His Phe Ala Lys Gly Arg Phe Ile Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 671
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 671

Asn Tyr Ala Asp Ser Met Lys Gly Arg Val Thr Ile Ser Gly Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 672
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 672

Asn Tyr Ala Asp Ser Val Lys Asp Arg Phe Thr Ile Ser Arg Asp Asn
1               5                   10                  15

Ala Lys Asn Thr Val Tyr Leu Gln Met Thr Ser Leu Lys Pro Glu Asp
            20                  25                  30

Thr Ala Val Tyr Tyr Cys
        35

<210> SEQ ID NO 673
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 673

Asp Tyr Ala Asp Ser Val Asn Gly Arg Phe Thr Met Ser Arg Asp Asn
1               5                   10                  15

Ala Lys Asn Thr Val Tyr Leu Gln Met Asn Ser Leu Lys Pro Glu Asp
            20                  25                  30
```

-continued

```
                20                  25                  30

Thr Ala Val Tyr Tyr Cys
        35

<210> SEQ ID NO 674
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 674

Tyr Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 675
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 675

Tyr Tyr Ala Asp Pro Val Lys Gly Arg Phe Thr Ile Ser Arg Asp Asn
1               5                   10                  15

Ala Lys Asn Thr Val Tyr Leu Gln Met Asn Ser Leu Lys Pro Asp Asp
            20                  25                  30

Thr Ala Val Tyr Tyr Cys
        35

<210> SEQ ID NO 676
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 676

Tyr Tyr Ala Asp Pro Val Lys Gly Arg Phe Thr Ile Ser Arg Asp Ser
1               5                   10                  15

Ala Lys Asn Thr Val Tyr Leu Gln Met Asn Ser Leu Lys Pro Asp Asp
            20                  25                  30

Thr Ala Val Tyr Tyr Cys
        35

<210> SEQ ID NO 677
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 677

Tyr His Ala His Pro Val Lys Gly Arg Phe Thr Ile Phe Arg Asp Asn
1               5                   10                  15
```

Ala Lys Asn Thr Val Tyr Leu Gln Met Asn Ser Leu Lys Pro Asp Asp
            20                  25                  30

Thr Gly Val Tyr Tyr Cys
        35

<210> SEQ ID NO 678
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 678

Asn Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 679
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 679

Tyr Phe Ser Asp Ser Val Lys Gly Arg Phe Ala Ile Ser Arg Asp Asn
1               5                   10                  15

Ala Lys Asp Thr Val Ser Leu Gln Met Asn Asn Leu Lys Pro Asp Asp
            20                  25                  30

Thr Ala Val Tyr Thr Cys
        35

<210> SEQ ID NO 680
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 680

Asn Tyr Ala Asp Ser Val Lys Gly Arg Phe Thr Ile Ser Arg Asn Asn
1               5                   10                  15

Ala Lys Lys Thr Val Tyr Leu Gln Met Asn Ser Leu Lys Pro Glu Asp
            20                  25                  30

Thr Ala Val Tyr Tyr Cys
        35

<210> SEQ ID NO 681
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 681

Trp Tyr Ala Asp Ser Met Lys Gly Arg Phe Thr Ile Ser Arg Asp Asn
1               5                   10                  15

Ala Lys Asn Thr Gly Tyr Leu Gln Met Asn Ser Leu Lys Pro Glu Asp
            20                  25                  30

Thr Ala Ile Tyr Tyr Cys
        35

<210> SEQ ID NO 682
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 682

Tyr Tyr Gly Asp Ser Val Gln Gly Arg Phe Thr Ile Ser Lys Asp Asn
1               5                   10                  15

Ala Lys Asn Thr Val Ser Leu Gln Met Asn Arg Leu Asn Pro Glu Asp
            20                  25                  30

Thr Ala Val Tyr Tyr Cys
        35

<210> SEQ ID NO 683
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 683

Lys Tyr Ala Asp Ser Val Lys Gly Arg Phe Thr Ile Thr Arg Asp Ile
1               5                   10                  15

Ser Lys Asn Thr Ile Tyr Leu Gln Met Asn Ser Leu Lys Pro Glu Asp
            20                  25                  30

Thr Gly Val Tyr Tyr Cys
        35

<210> SEQ ID NO 684
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 684

Lys Tyr Ala Asp Ser Val Lys Gly Arg Phe Thr Ile Ser Arg Asp Asn
1               5                   10                  15

Thr Lys Asn Thr Val Thr Val Tyr Leu Gln Met Asn Asn Val Asn Ala
            20                  25                  30

Glu Asp Thr Ala Val Tyr Tyr Cys
        35                  40

<210> SEQ ID NO 685
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 685

Lys Tyr Ala Asp Ser Val Lys Gly Arg Phe Thr Ile Ser Arg Asp Asn

```
                  1               5                  10                 15
Thr Lys Asn Thr Val Tyr Leu Gln Met Asn Ser Val Asn Ala Glu Asp
                 20                 25                 30

Thr Ala Val Tyr Tyr Cys
        35

<210> SEQ ID NO 686
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 686

Val Tyr Ala Asn Ser Val Lys Asp Arg Phe Thr Ile Ser Arg Asp Asn
1               5                   10                  15

Asn Lys Asn Met Val Tyr Leu Gln Met Asn Ser Leu Lys Pro Glu Asp
                20                  25                  30

Thr Ala Val Tyr Ser Cys
        35

<210> SEQ ID NO 687
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 687

Asn Tyr Ala Asp Ser Val Lys Gly Arg Phe Thr Ile Thr Arg Asp Ile
1               5                   10                  15

Ser Lys Asn Thr Ile Tyr Leu Gln Met Asn Asn Leu Lys Pro Glu Asp
                20                  25                  30

Thr Gly Val Tyr Tyr Cys
        35

<210> SEQ ID NO 688
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 688

Lys Tyr Asp Asp Ser Val Lys Gly Arg Phe Thr Ile Ser Arg Asp Ile
1               5                   10                  15

Ala Lys Asn Thr Val Phe Leu Gln Met Asp Ser Leu Lys Pro Glu Asp
                20                  25                  30

Thr Gly Val Tyr Tyr Cys
        35

<210> SEQ ID NO 689
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 689
```

```
Lys Tyr Ala Asp Ser Val Gln Gly Arg Phe Thr Ile Ser Arg Asp Ile
1               5                   10                  15
Ala Lys Asn Thr Val Tyr Leu Gln Met Asn Ser Leu Lys Pro Glu Asp
            20                  25                  30
Thr Gly Val Tyr Tyr Cys
        35

<210> SEQ ID NO 690
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 690

Val Tyr Ala Asp Ser Val Lys Asp Arg Phe Thr Ile Ser Arg Asp Asn
1               5                   10                  15
Asn Lys Asn Met Val Tyr Leu Gln Met Asp Ser Leu Lys Pro Glu Asp
            20                  25                  30
Thr Ala Val Tyr Tyr Cys
        35

<210> SEQ ID NO 691
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 691

Gln Tyr Ala Asp Ser Val Lys Gly Arg Phe Thr Ile Thr Arg Asp Ile
1               5                   10                  15
Ser Lys Asn Thr Ile Tyr Leu Gln Met Asn Ser Leu Lys Pro Glu Tyr
            20                  25                  30
Thr Gly Val Tyr Tyr Cys
        35

<210> SEQ ID NO 692
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 692

Lys Tyr Ala Asp Ser Val Gln Gly Arg Phe Thr Ile Ser Arg Asp Ile
1               5                   10                  15
Ala Asn Asn Thr Val Tyr Leu Gln Met Asn Ser Leu Lys Pro Glu Asp
            20                  25                  30
Thr Gly Val Tyr Tyr Cys
        35

<210> SEQ ID NO 693
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 693
```

Asn Tyr Met Asp Ser Val Lys Gly Arg Phe Thr Ile Ser Arg Asp Asn
1               5                   10                  15

Ala Lys Asn Thr Val Tyr Leu Gln Met Thr Lys Leu Lys Pro Glu Asp
            20                  25                  30

Thr Ala Val Tyr Tyr Cys
            35

<210> SEQ ID NO 694
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 694

Asn Tyr Met Asp Ser Val Lys Gly Arg Phe Thr Ile Ser Arg Asp Asn
1               5                   10                  15

Ala Lys Lys Ala Val Tyr Leu Gln Met Thr Ser Leu Lys Pro Glu Asp
            20                  25                  30

Thr Ala Leu Tyr Tyr Cys
            35

<210> SEQ ID NO 695
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 695

Asn Tyr Met Gly Ser Val Gln Gly Arg Phe Thr Ile Ser Arg Asp Asn
1               5                   10                  15

Ala Lys Asn Thr Val Tyr Leu Gln Met Arg Arg Leu Lys Pro Glu Asp
            20                  25                  30

Thr Ala Val Tyr Tyr Cys
            35

<210> SEQ ID NO 696
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 696

Arg Tyr Ala Asp Ser Val Lys Gly Arg Phe Thr Ile Ser Arg Asp Asn
1               5                   10                  15

Ala Lys Asn Thr Val Asp Leu Gln Met Asn Ser Leu Lys Pro Glu Asp
            20                  25                  30

Thr Ala Val Tyr Tyr Cys
            35

<210> SEQ ID NO 697
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 697

Thr Tyr Ala Asp Phe Val Lys Gly Arg Phe Ile Ile Ser Arg Asp Asn
1               5                   10                  15

Ala Lys Ser Thr Val Tyr Leu Gln Met Asn Ser Leu Lys Pro Glu Asp
            20                  25                  30

Thr Ala Val Tyr Tyr Cys
        35

<210> SEQ ID NO 698
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 698

Arg Tyr Glu Asp Phe Val Lys Gly Arg Phe Thr Ile Ser Arg Asp Asn
1               5                   10                  15

Gly Lys Asn Thr Val Tyr Leu Gln Met Asn Ser Leu Lys Pro Glu Asp
            20                  25                  30

Thr Ala Val Tyr Tyr Cys
        35

<210> SEQ ID NO 699
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 699

Tyr Tyr Ala Asp Ser Val Lys Gly Arg Phe Thr Ile Ser Arg Asp Asn
1               5                   10                  15

Ala Lys Asn Thr Val Tyr Leu His Met Asn Ser Leu Lys Pro Glu Asp
            20                  25                  30

Thr Ala Val Tyr Tyr Cys
        35

<210> SEQ ID NO 700
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 700

Asn Tyr Ala Glu Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 701
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 701

Arg Tyr Ala Asp Phe Val Gln Gly Arg Phe Thr Ile Ser Arg Asp Asn
1               5                   10                  15

Gly Lys Asn Thr Val Tyr Leu Gln Met Asn Ser Leu Lys Pro Glu Asp
            20                  25                  30

Thr Ala Val Tyr Tyr Cys
        35

<210> SEQ ID NO 702
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 702

Arg Tyr Ala Asp Ser Val Lys Gly Arg Phe Thr Ile Ser Arg Asp Asn
1               5                   10                  15

Ala Lys Asn Thr Val Asn Leu Gln Met Asn Arg Leu Lys Pro Glu Asp
            20                  25                  30

Thr Ala Val Tyr Tyr Cys
        35

<210> SEQ ID NO 703
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 703

Arg Tyr Ala Asp Phe Val Lys Gly Arg Phe Thr Ile Ser Arg Asp Asn
1               5                   10                  15

Ala Lys Ser Thr Val Tyr Leu Gln Met Asn Ser Leu Lys Pro Glu Asp
            20                  25                  30

Thr Ala Val Tyr Tyr Cys
        35

<210> SEQ ID NO 704
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 704

His Tyr Ala Asp Ser Val Lys Gly Arg Phe Thr Ile Ser Arg Asp Asn
1               5                   10                  15

Ala Lys Asn Thr Val Asn Leu Gln Met Asn Ser Leu Lys Val Glu Asp
            20                  25                  30

Thr Ala Val Tyr Tyr Cys
        35

<210> SEQ ID NO 705
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 705

Asn Tyr Met Asn Phe Val Lys Gly Arg Phe Thr Ile Ser Arg Asp Asn
1               5                   10                  15

Ala Lys Asn Thr Val Tyr Leu Gln Met Thr Ser Leu Lys Pro Glu Asp
            20                  25                  30

Thr Ala Val Tyr Tyr Cys
        35

<210> SEQ ID NO 706
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 706

His Tyr Ala Asp Ser Val Lys Gly Arg Phe Thr Ile Ser Arg Asp Asn
1               5                   10                  15

Ala Lys Asn Thr Val Asp Leu Gln Met Asn Ser Leu Lys Pro Glu Asp
            20                  25                  30

Thr Ala Val Tyr Tyr Cys
        35

<210> SEQ ID NO 707
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 707

Tyr Tyr Ala Asp Ser Val Lys Gly Arg Phe Thr Ile Ser Arg Asp Asn
1               5                   10                  15

Ala Lys Asn Thr Val Ser Leu Gln Met Asn Ser Leu Lys Val Glu Asp
            20                  25                  30

Thr Ala Val Tyr Tyr Cys
        35

<210> SEQ ID NO 708
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 708

Asn Tyr Met Asp Ser Val Lys Gly Arg Phe Thr Ile Ser Arg Asp Asn
1               5                   10                  15

Ala Lys Asn Thr Val Tyr Leu Arg Met Ser Ser Leu Lys Pro Glu Asp
            20                  25                  30

Thr Ala Val Tyr Tyr Cys
        35

<210> SEQ ID NO 709
<211> LENGTH: 38
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 709

Arg Tyr Ala Asp Ser Val Lys Gly Arg Phe Thr Ile Ser Arg Asp Asn
1               5                   10                  15

Ala Lys Asn Thr Val Asn Leu Gln Met Asn Ser Leu Lys Pro Glu Asp
            20                  25                  30

Thr Ala Val Tyr Tyr Cys
        35

<210> SEQ ID NO 710
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 710

Asn Tyr Met Asn Ser Val Lys Gly Arg Phe Thr Ile Ser Arg Asp Asn
1               5                   10                  15

Ala Lys Asn Thr Val Tyr Leu His Met Thr Gly Val Lys Pro Ala Asp
            20                  25                  30

Thr Ala Val Tyr Tyr Cys
        35

<210> SEQ ID NO 711
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 711

Asn Tyr Met Asp Ser Thr Glu Gly Arg Phe Thr Ile Ser Arg Asp Asp
1               5                   10                  15

Ala Lys Asn Thr Val Tyr Leu Gln Met Thr Gly Val Lys Pro Ala Asp
            20                  25                  30

Thr Ala Val Tyr Tyr Cys
        35

<210> SEQ ID NO 712
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 712

Asn Tyr Met Asp Ser Val Lys Gly Arg Phe Thr Ile Ser Arg Asp Asn
1               5                   10                  15

Ala Lys Asn Met Val Tyr Leu Gln Met Thr Lys Leu Lys Pro Glu Asp
            20                  25                  30

Thr Ala Val Tyr Tyr Cys
        35

<210> SEQ ID NO 713
<211> LENGTH: 38
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 713

Asn Tyr Met Asp Ser Val Lys Gly Arg Phe Thr Ile Ser Arg Asp Asn
1               5                   10                  15

Ala Lys Asn Thr Val Tyr Leu Gln Met Thr Ser Leu Lys Pro Glu Asp
            20                  25                  30

Thr Ala Val Tyr Tyr Cys
        35

<210> SEQ ID NO 714
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 714

Asn Tyr Met Asp Ser Val Lys Gly Arg Phe Thr Ile Ser Arg Asp Asn
1               5                   10                  15

Ala Lys Asn Thr Val Tyr Leu Gln Met Thr Asn Leu Lys Pro Glu Asp
            20                  25                  30

Thr Ala Val Tyr Tyr Cys
        35

<210> SEQ ID NO 715
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 715

Arg Tyr Glu Asp Phe Val Lys Gly Arg Phe Thr Ile Ser Arg Asp Asn
1               5                   10                  15

Ala Lys Ser Thr Val Tyr Leu Gln Met Asn Ser Leu Lys Pro Glu Asp
            20                  25                  30

Thr Ala Val Tyr Tyr Cys
        35

<210> SEQ ID NO 716
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 716

Asn Val Ala Gln Ser Met Glu Gly Arg Phe Thr Ile Ser Arg Asp Asn
1               5                   10                  15

Ala Lys Asn Thr Gly Tyr Leu Gln Met Asn Ser Leu Lys Pro Glu Asp
            20                  25                  30

Thr Gly Val Tyr Tyr Cys
        35

<210> SEQ ID NO 717
<211> LENGTH: 38
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 717

Asn Tyr Met Gly Phe Val Lys Gly Arg Phe Thr Ile Ser Arg Asp Asn
1               5                   10                  15

Ala Lys Asn Thr Val Tyr Leu Gln Met Thr Ser Leu Lys Pro Glu Asp
            20                  25                  30

Thr Ala Val Tyr Tyr Cys
        35

<210> SEQ ID NO 718
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 718

Asn Tyr Met Asp Ser Val Lys Asp Arg Phe Thr Ile Ser Arg Asp Asn
1               5                   10                  15

Ala Lys Asn Thr Leu Tyr Leu Gln Met Thr Asn Leu Lys Pro Glu Asp
            20                  25                  30

Thr Ala Val Tyr Tyr Cys
        35

<210> SEQ ID NO 719
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 719

Asn Tyr Met Gly Phe Val Arg Gly Arg Phe Thr Ile Ser Arg Asp Asn
1               5                   10                  15

Thr Lys Asn Thr Val Tyr Leu Gln Met Thr Ser Leu Lys Pro Asp Asp
            20                  25                  30

Thr Ala Val Tyr Tyr Cys
        35

<210> SEQ ID NO 720
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 720

Asn Tyr Met Asp Phe Val Lys Gly Arg Phe Thr Ile Ser Arg Asp Asn
1               5                   10                  15

Ala Lys Asn Thr Val Tyr Leu Gln Met Thr Ser Leu Lys Pro Glu Asp
            20                  25                  30

Thr Ala Val Tyr Tyr Cys
        35

<210> SEQ ID NO 721
<211> LENGTH: 38

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 721

Asn Tyr Pro Asp Ser Val Lys Gly Arg Phe Ala Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 722
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 722

Ala Tyr Ala Asp Ser Val Trp Gly Arg Phe Thr Ile Ser Arg Asp Asn
1               5                   10                  15

Ala Lys Asn Asn Val Tyr Leu Glu Met Asn Ser Leu Lys Pro Glu Asp
            20                  25                  30

Thr Ala Val Tyr Tyr Cys
        35

<210> SEQ ID NO 723
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 723

Ala Tyr Ala Asp Ser Val Lys Gly Arg Phe Thr Ile Ser Arg Asp Lys
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 724
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 724

Ala Tyr Ala Asp Ser Val Lys Gly Arg Phe Thr Ile Ser Arg Asp Asn
1               5                   10                  15

Ala Lys Asn Thr Val Tyr Leu Gln Met Asn Thr Leu Lys Pro Glu Asp
            20                  25                  30

Thr Ala Val Tyr Tyr Cys
        35

<210> SEQ ID NO 725
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 725

Asn Tyr Ala Asp Ser Val Lys Asp Thr Ile Ser Arg Asp Asn Ala Lys
1               5                   10                  15

Asn Thr Val Tyr Leu Gln Met Thr Ser Leu Lys Pro Glu Asp Thr Ala
            20                  25                  30

Val Tyr Tyr Cys
        35

<210> SEQ ID NO 726
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 726

Ala Tyr Gly Asp Ser Val Lys Gly Arg Phe Ser Ile Ser Arg Asp Phe
1               5                   10                  15

Ala Lys Asn Thr Val Tyr Leu Gln Ile Asp Ser Leu Lys Ala Glu Asp
            20                  25                  30

Thr Ala Val Tyr Tyr Cys
        35

<210> SEQ ID NO 727
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 727

Ser Tyr Ala Asn Ser Val Lys Gly Arg Phe Thr Ile Ser Arg Asp Asn
1               5                   10                  15

Thr Lys Ser Thr Val Tyr Leu Gln Ile His Ser Leu Lys Pro Glu Asp
            20                  25                  30

Thr Ala Val Tyr Tyr Cys
        35

<210> SEQ ID NO 728
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 728

Ala Tyr Ala Asp Ser Val Lys Gly Arg Phe Thr Ile Ser Asn Asp Ala
1               5                   10                  15

Ala Lys Asn Thr Val Tyr Leu Gln Met Asn Ser Leu Lys Pro Asp Asp
            20                  25                  30

Thr Ala Val Tyr Tyr Cys
        35
```

```
<210> SEQ ID NO 729
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 729

His Asp Ala His Phe Thr Lys Gly Arg Phe Ile Ile Ser Lys Asp Asp
1               5                   10                  15

Ala Lys Asn Thr Val Tyr Leu Leu Met Asn Ser Leu Lys Pro Glu Asp
            20                  25                  30

Thr Ala Val Tyr Tyr Cys
        35

<210> SEQ ID NO 730
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 730

Asn Thr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 731
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 731

Gln Asn Ala His Phe Pro Asn Gly Gln Phe Leu Ile Ser Ile Tyr Glu
1               5                   10                  15

Asp Asp Asn Thr Met Tyr Leu Gln Leu Ser Ile Gln Lys Pro Glu Asp
            20                  25                  30

Ala Asp Val Tyr Asp Cys
        35

<210> SEQ ID NO 732
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 732

Asn Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Asn Ala Glu Asp
            20                  25                  30

Thr Ala Val Tyr Tyr Cys
        35
```

<210> SEQ ID NO 733
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 733

Ala Tyr Gly Asp Ser Val Lys Gly Arg Phe Ser Ile Ser Arg Asp Phe
1               5                   10                  15

Ala Lys Asn Thr Val Tyr Leu His Ile Asp Ser Leu Lys Ala Glu Asp
            20                  25                  30

Thr Ala Val Tyr Tyr Cys
        35

<210> SEQ ID NO 734
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 734

Asp Tyr Ala Asp Ser Val Lys Asp Arg Phe Thr Ile Ala Arg Asp Asn
1               5                   10                  15

Pro Lys Asn Thr Val Thr Leu Gln Met Asn Ser Leu Lys Pro Glu Asp
            20                  25                  30

Thr Ala Ile Tyr Tyr Cys
        35

<210> SEQ ID NO 735
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 735

Arg Tyr Ala Asp Ser Met Ser Asp Arg Phe Thr Ile Ser Arg Asp Asn
1               5                   10                  15

Ala Lys Asn Thr Val Tyr Leu Gly Met Asp Ser Leu Lys Pro Glu Asp
            20                  25                  30

Thr Ala Val Tyr Tyr Cys
        35

<210> SEQ ID NO 736
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 736

Asn Tyr Ala His Ser Val Lys Gly Thr Ile Ser Arg His Asn Ala Glu
1               5                   10                  15

Asn Pro Val Ser Arg Leu Gln Met Asn Ser Leu Lys Pro Glu Asp Thr
            20                  25                  30

Ala Val Tyr Tyr Cys
        35

<210> SEQ ID NO 737
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 737

Tyr Tyr Ala Asp Ser Val Lys Gly Thr Ile Ser Arg Asp Asn Ala Lys
1               5                   10                  15

Asn Thr Val Tyr Leu Gln Met Asn Ser Leu Lys Pro Glu Asp Thr Ala
            20                  25                  30

Val Tyr Phe Cys
        35

<210> SEQ ID NO 738
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 738

Ser Tyr Ala Asp Ser Val Lys Gly Arg Phe Thr Ile Ser Arg Asp Asn
1               5                   10                  15

Ala Lys Asn Thr Leu Tyr Leu Gln Met Asn Ser Leu Lys Pro Glu Asp
            20                  25                  30

Thr Ala Val Tyr Tyr Cys
        35

<210> SEQ ID NO 739
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 739

Tyr Tyr Thr Asp Ser Val Lys Gly Arg Phe Thr Ile Ser Arg Asp Asn
1               5                   10                  15

Ala Lys Asn Thr Val Tyr Leu Gln Met Asp Ser Leu Lys Pro Glu Asp
            20                  25                  30

Thr Ala Val Tyr Phe Cys
        35

<210> SEQ ID NO 740
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 740

Asp Tyr Ala Asp Ser Ala Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys

-continued

```
                35

<210> SEQ ID NO 741
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 741

Ala Tyr Gly Asp Ser Val Lys Gly Arg Ser Asn Leu Ser Val Asn His
1               5                   10                  15

Thr Asn Asn Thr Ala Tyr Leu Gln Met Asn Ser Leu Arg Pro Glu Asp
            20                  25                  30

Thr Ala Val Tyr Trp Cys
        35

<210> SEQ ID NO 742
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 742

Tyr Tyr Thr Glu Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 743
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 743

Asn Tyr Ala Asp Ser Val Lys Gly Thr Ile Ser Arg Asp Asn Ala Lys
1               5                   10                  15

Asn Thr Val Tyr Leu Gln Met Thr Ser Leu Lys Pro Glu Asp Thr Ala
            20                  25                  30

Val Tyr Tyr Cys
        35

<210> SEQ ID NO 744
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 744

Ser Tyr Ala Asp Ser Val Lys Gly Thr Ile Ser Arg Asp Tyr Ala Glu
1               5                   10                  15

Asn Met Val Tyr Leu Gln Met Asn Ser Leu Lys Pro Glu Asp Thr Ala
            20                  25                  30
```

Thr Tyr Tyr Cys
        35

<210> SEQ ID NO 745
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 745

Asn Tyr Ala Asp Ser Val Lys Asp Ser Ile Ser Arg Asp His Asp Thr
1               5                   10                  15

Asn Ala Val Tyr Leu Gln Met Thr Asn Leu Arg Pro Asp Asp Pro Ala
            20                  25                  30

Val Tyr Tyr Cys
        35

<210> SEQ ID NO 746
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 746

Asp Tyr Ala Asp Ser Val Lys Asp Thr Ile Ala Arg Asp Asn Pro Lys
1               5                   10                  15

Asn Thr Val Thr Leu Gln Met Asn Ser Leu Lys Pro Glu Asp Thr Ala
            20                  25                  30

Ile Tyr Tyr Cys
        35

<210> SEQ ID NO 747
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 747

Asn Tyr Ala Asp Ser Val Lys Asp Thr Ile Ser Arg Asp Asn Ala Lys
1               5                   10                  15

Asn Thr Val Tyr Leu Gln Met Thr Ser Leu Lys Pro Glu Asp Thr Ala
            20                  25                  30

Val Phe Tyr Cys
        35

<210> SEQ ID NO 748
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 748

Asp Tyr Ala Asp Ser Val Lys Asp Thr Ile Ala Arg Asp Asn Pro Lys
1               5                   10                  15

Asn Ala Val Thr Leu Gln Met Asn Ser Leu Lys Pro Glu Asp Thr Ala
            20                  25                  30

```
Ile Tyr Tyr Cys
        35

<210> SEQ ID NO 749
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 749

Val Tyr Ala Asp Ser Val Lys Gly Thr Ile Ser Gly Asp Asn Ala Lys
1               5                   10                  15

Asn Thr Met Tyr Leu Gln Met Asn Ser Leu Lys Pro Glu Asp Thr Ala
            20                  25                  30

Val Tyr Tyr Cys
        35

<210> SEQ ID NO 750
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 750

Tyr Tyr Glu Asp Ser Val Lys Gly Thr Val Ser Arg Asp Asn Ala Lys
1               5                   10                  15

Asn Thr Val Tyr Leu Gln Met Asn Asn Leu Lys Pro Glu Asp Thr Ala
            20                  25                  30

Val Tyr Tyr Cys
        35

<210> SEQ ID NO 751
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 751

Ser Tyr Ala Asp Ser Val Lys Gly Arg Phe Thr Ile Ser Arg Asp Asn
1               5                   10                  15

Ala Lys Asn Met Val Tyr Leu Arg Met Asp Ser Leu Lys Pro Glu Asp
            20                  25                  30

Thr Asp Val Tyr Tyr Cys
        35

<210> SEQ ID NO 752
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 752

Asp Tyr Leu Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
```

```
                    20                  25                  30

Thr Ala Val Tyr Tyr Cys
        35

<210> SEQ ID NO 753
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Trp Gly Gln Gly Thr Gln Val Thr Val Ser Ser
1               5                   10

<210> SEQ ID NO 754
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Trp Gly Gln Gly Thr Gln Val Thr Val Ser Leu
1               5                   10

<210> SEQ ID NO 755
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Trp Gly Gln Gly Thr Gln Val Thr Val Ser Thr
1               5                   10

<210> SEQ ID NO 756
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 756

Trp Gly Gln Gly Ile Gln Val Thr Val Ser Ser
1               5                   10

<210> SEQ ID NO 757
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

Trp Gly Pro Gly Thr Gln Val Thr Val Ser Ser
1               5                   10

<210> SEQ ID NO 758
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 758

Trp Gly Gln Gly Thr Gln Val Thr Val Ser Ala
1               5                   10

<210> SEQ ID NO 759
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 759

Trp Gly Lys Gly Thr Leu Val Thr Val Ser Ser
1               5                   10

<210> SEQ ID NO 760
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 760

Trp Gly Gln Gly Thr Gln Val Thr Ala Ser Ser
1               5                   10

<210> SEQ ID NO 761
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 761

Trp Gly Gln Gly Ala Gln Val Thr Val Ser Ser
1               5                   10

<210> SEQ ID NO 762
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 762

Trp Gly Arg Gly Thr Gln Val Thr Val Ser Ser
1               5                   10

<210> SEQ ID NO 763
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 763

Trp Gly His Gly Thr Gln Val Thr Val Ser Ser
1               5                   10

<210> SEQ ID NO 764
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 764

Trp Gln Gly Thr Gln Val Thr Val Ser Ser
1               5                   10

<210> SEQ ID NO 765
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 765

Gly Ser Ile Phe Ser Thr Asn Leu Met
1               5

<210> SEQ ID NO 766
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 766

Gly Val Ala Phe Asn Ser Arg Ile Met
1               5

<210> SEQ ID NO 767
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 767

Gly Arg Thr Phe Asn Thr Tyr Tyr Met
1               5

<210> SEQ ID NO 768
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 768

Arg Gly Thr Phe Arg Thr Tyr Ser Met
1               5

<210> SEQ ID NO 769
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 769

Ile Thr Ser Gly Gly Asn Thr
1               5

<210> SEQ ID NO 770
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 770

Ile Thr Ser Gly Gly Ser Thr
1               5

<210> SEQ ID NO 771
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 771

Ile Arg Trp Ser Asp Gly Gly Thr
1               5

<210> SEQ ID NO 772
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 772

Ile Thr Trp Asn Gly Lys Tyr Thr
1               5

<210> SEQ ID NO 773
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 773

Ala Ala Gln Thr Leu Gly Ser Ser Tyr Tyr Asp Ala
1               5                   10

<210> SEQ ID NO 774
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 774

Asn Ile Arg Asn Tyr
1               5

<210> SEQ ID NO 775
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 775

Asn Ala Asn Val Tyr Asp Gly Asn Arg Trp Arg Thr Tyr
1               5                   10

<210> SEQ ID NO 776
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 776

Ala Ala Asn Pro Ile Pro Thr Ala Gln Pro Pro Gly Ile Met Ala Ala
1               5                   10                  15

Arg Ser Tyr Val His
            20

<210> SEQ ID NO 777
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

Gln Val Gln Leu Val Glu Ser Gly Gly Gly Leu Val Gln Pro Gly Gly
1               5                   10                  15

Ser Leu Thr Leu Ser Cys Ile Val Ser
            20                  25

<210> SEQ ID NO 778
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 778

Gln Val Gln Leu Val Glu Ser Gly Gly Gly Leu Val Gln Ala Gly Asp
1               5                   10                  15

Ser Leu Arg Leu Ser Cys Thr Ala Ser
            20                  25

<210> SEQ ID NO 779
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 779

Gln Val Lys Leu Glu Glu Ser Gly Gly Gly Leu Val Gln Pro Gly Gly
1               5                   10                  15

Ser Leu Glu Val Ser Cys Ala Ala Ser
            20                  25
```

<210> SEQ ID NO 780
<211> LENGTH: 343
<212> TYPE: PRT
<213> ORGANISM: Salmonella enterica

<400> SEQUENCE: 780

Met Leu Asn Ile Gln Asn Tyr Ser Ala Ser Pro His Pro Gly Ile Val
1               5                   10                  15

Ala Glu Arg Pro Gln Thr Pro Ser Ala Ser Glu His Val Glu Thr Ala
            20                  25                  30

Val Val Pro Ser Thr Thr Glu His Arg Gly Thr Asp Ile Ile Ser Leu
        35                  40                  45

Ser Gln Ala Ala Thr Lys Ile Gln Gln Ala Gln Gln Thr Leu Gln Ser
    50                  55                  60

Thr Pro Pro Ile Ser Glu Glu Asn Asn Asp Glu Arg Thr Leu Ala Arg
65                  70                  75                  80

Gln Gln Leu Thr Ser Ser Leu Asn Ala Leu Ala Lys Ser Gly Val Ser
                85                  90                  95

Leu Ser Ala Glu Gln Asn Glu Asn Leu Arg Ser Ala Phe Ser Ala Pro
            100                 105                 110

Thr Ser Ala Leu Phe Ser Ala Ser Pro Met Ala Gln Pro Arg Thr Thr
        115                 120                 125

Ile Ser Asp Ala Glu Ile Trp Asp Met Val Ser Gln Asn Ile Ser Ala
    130                 135                 140

Ile Gly Asp Ser Tyr Leu Gly Val Tyr Glu Asn Val Ala Val Tyr
145                 150                 155                 160

Thr Asp Phe Tyr Gln Ala Phe Ser Asp Ile Leu Ser Lys Met Gly Gly
                165                 170                 175

Trp Leu Leu Pro Gly Lys Asp Gly Asn Thr Val Lys Leu Asp Val Thr
            180                 185                 190

Ser Leu Lys Asn Asp Leu Asn Ser Leu Val Asn Lys Tyr Asn Gln Ile
        195                 200                 205

Asn Ser Asn Thr Val Leu Phe Pro Ala Gln Ser Gly Ser Gly Val Lys
    210                 215                 220

Val Ala Thr Glu Ala Glu Ala Arg Gln Trp Leu Ser Glu Leu Asn Leu
225                 230                 235                 240

Pro Asn Ser Cys Leu Lys Ser Tyr Gly Ser Gly Tyr Val Val Thr Val
                245                 250                 255

Asp Leu Thr Pro Leu Gln Lys Met Val Gln Asp Ile Asp Gly Leu Gly
            260                 265                 270

Ala Pro Gly Lys Asp Ser Lys Leu Glu Met Asp Asn Ala Lys Tyr Gln
        275                 280                 285

Ala Trp Gln Ser Gly Phe Lys Ala Gln Glu Asn Met Lys Thr Thr
    290                 295                 300

Leu Gln Thr Leu Thr Gln Lys Tyr Ser Asn Ala Asn Ser Leu Tyr Asp
305                 310                 315                 320

Asn Leu Val Lys Val Leu Ser Ser Thr Ile Ser Ser Ser Leu Glu Thr
                325                 330                 335

Ala Lys Ser Phe Leu Gln Gly
            340

<210> SEQ ID NO 781
<211> LENGTH: 6
<212> TYPE: PRT
<213> ORGANISM: Artificial Sequence

```
<220> FEATURE:
<223> OTHER INFORMATION: Description of Artificial Sequence: Synthetic
      6xHis tag

<400> SEQUENCE: 781

His His His His His His
1               5
```

ANTIBODIES AGAINST MICROORGANISMS AND USES THEREOF

CROSS REFERENCE TO RELATED APPLICATIONS

This application is a Divisional of U.S. patent application Ser. No. 16/300,457, filed on Nov. 9, 2018, which is a U.S. National of International Application No. PCT/IB2017/000684, filed May 19, 2017, which claims priority to U.S. Provisionals with Ser. No. 62/339,732 and 62/339,735 both filed on May 20, 2016 both of which are incorporated by reference herein.

BACKGROUND OF THE INVENTION

*Salmonella* bacteria are a major cause of foodborne illness, making infections caused by these pathogens a significant public health and economic concern. In terms of healthcare costs, loss of work due to illness and premature deaths, non-typhoidal *Salmonella* are estimated to be among the top five costliest foodborne pathogens along with *Toxoplasma gondii, Listeria monocytogenes, Norovirus* and *Campylobacter*. The most well-known sources of *Salmonella* infection include contaminated meat and poultry products, as well as eggs and fresh produce. Thus, there are significant economic costs to the food companies and restaurants supplying the contaminated poultry products. Increased foreign trade, distribution and travel have made salmonellae a widespread problem. As such, methods of controlling *Salmonella* contamination of poultry products are a viable approach to reducing infections in humans.

Current methods of controlling *Salmonella* in pre-harvest flocks include vaccination and the use of antibiotics, and while advances have been made in reducing the frequency of contamination in poultry products, there is still mounting pressure on commercial growers to eliminate these pathogens from pre-harvest production facilities. Several vaccines against salmonellae are commercially available but the production and use of vaccines can be expensive and labor intensive. Antibiotics are also commonly used to control pathogen colonization and prevent disease in livestock but there are concerns that misuse in livestock may be contributing to antibiotic resistance in both animals and humans. Furthermore, antibiotics have been shown to modify natural microbial communities in the gastrointestinal tracts of chickens, which could compromise the health of the birds. Therefore, a need exists for alternatives to antibiotics as well as methods to prevent and treat *Salmonella* colonization of domestic animals in order to reduce the incidence of *Salmonella*-associated health problems due to contaminated food products.

SUMMARY OF THE INVENTION

In certain embodiments, described herein, is the use of an antibody for preventing infection in a domestic animal by a pathogenic Enterobacteriaceae bacterial population. In certain embodiments, preventing infection in the domestic animal by the pathogenic Enterobacteriaceae bacterial population prevents transmission of disease to a human. In certain embodiments, the antibody is selected from the group comprised of: a heavy chain antibody (hcIgG); a variable region fragment of a heavy chain antibody ($V_HH$); a single chain antibody; a polypeptide; an immunoglobulin new antigen receptor (IgNAR); a variable region fragment of an immunoglobulin new antigen receptor; or any fragment thereof that retains a capacity to specifically bind a target antigen. In certain embodiments, the antibody is a variable region fragment of a heavy chain antibody ($V_HH$). In certain embodiments, the antibody is altered to reduce immunogenicity in the domestic animal. In certain embodiments, the domestic animal is a chicken. In certain embodiments, the antibody originates from a species of the Camelidae family, or from a species of the Chondrichthyes class. In certain embodiments, the Camelidae species is a llama. In certain embodiments, the bacterial population comprises *Salmonella* bacteria. In certain embodiments, the bacterial population comprises *Salmonella enterica*. In certain embodiments, the bacterial population comprises *Salmonella enterica* serotype Typhimurium, Enteritidis, Newport, Heidelberg, *Gallinarum*, Hadar, Javiana, *Infantis*, Montevideo, Muenchen, Braenderup, Saintpaul, Thompson, Agona, Litchfield, Anatum, Berta, Mbandaka, Oranienburg, Poona, Uganda, Senftenberg, Weltevreden, I 4,[5],12:-, I 13,23:b:-, or any combination thereof. In certain embodiments, the domestic animal is from the superorder Galloanserae. In certain embodiments, the domestic animal is a poultry animal. In certain embodiments, the poultry animal is a chicken, turkey, duck, or goose. In certain embodiments, the poultry animal is a chicken. In certain embodiments, wherein the antibody specifically binds a *Salmonella* biomolecule. In certain embodiments, the antibody specifically binds a *Salmonella* biomolecule that functions in bacterial motility. In certain embodiments, the antibody reduces bacterial motility compared to a negative control antibody. In certain embodiments, the antibody reduces bacterial adhesion compared to a negative control antibody. In certain embodiments, the antibody reduces bacterial invasion compared to a negative control antibody. In certain embodiments, the *Salmonella* biomolecule is a *Salmonella* derived polypeptide. In certain embodiments, the biomolecule is a component of a flagellum. In certain embodiments, the biomolecule comprises a polypeptide derived from the flagella filament structural protein (FliC). In certain embodiments, the biomolecule comprises a polypeptide derived from the protein PrgI. In certain embodiments, the biomolecule comprises a polypeptide derived from the Fimbrial protein A (FimA). In certain embodiments, the antibody is monoclonal. In certain embodiments, the antibody is polyclonal. In certain embodiments, the antibody is incorporated into a spray for application to the exterior of a domestic animal. In certain embodiments, the antibody is formulated for oral administration. In certain embodiments, the antibody is formulated for injection. In certain embodiments, the antibody is formulated as a liquid. In certain embodiments, the antibody is not a chicken antibody. In certain embodiments, the antibody is not an IgY. In certain embodiments, the antibody does not specifically bind bacterial lipopolysaccharide (LPS).

In certain embodiments, described herein, is the use of an antibody for reducing a pathogenic Enterobacteriaceae bacterial population in a domestic animal. In certain embodiments, reducing the pathogenic Enterobacteriaceae bacterial population in a domestic animal prevents transmission of disease to a human. In certain embodiments, the antibody is selected from the group comprising a heavy chain antibody (hcIgG); a variable region fragment of a heavy chain antibody; a single chain antibody; a nanobody; a polypeptide; an immunoglobulin new antigen receptor (IgNAR); a variable region fragment of an immunoglobulin new antigen receptor; or any fragment thereof that retains a capacity to specifically bind a target antigen. In certain embodiments, the antibody is a variable region fragment of a heavy chain antibody (V$_H$H). In certain embodiments, the antibody is altered to reduce immunogenicity in a domestic animal. In certain embodiments, the domestic animal is a chicken. In certain embodiments, the antibody originates from a species of the Camelidae family, or from a species of the Chondrichthyes class. In certain embodiments, the Camelidae species is a llama. In certain embodiments, the bacterial population comprises *Salmonella* bacteria. In certain embodiments, the bacterial population comprises *Salmonella* enterica. In certain embodiments, the bacterial population comprises *Salmonella* enterica serotype Typhimurium, Enteritidis, Newport, Heidelberg, *Gallinarum*, Hadar, Javiana, *Infantis*, Montevideo, Muenchen, Braenderup, Saintpaul, Thompson, Agona, Litchfield, Anatum, Berta, Mbandaka, Oranienburg, Poona, Uganda, Senftenberg, Weltevreden, I 4,[5],12:i:-, I 13,23:b:-, or any combination thereof. In certain embodiments, the domestic animal is from the superorder Galloanserae. In certain embodiments, the domestic animal is a poultry animal. In certain embodiments, the poultry animal is a chicken, turkey, duck, or goose. In certain embodiments, the poultry animal is a chicken. In certain embodiments, the antibody specifically binds a *Salmonella* biomolecule. In certain embodiments, the antibody specifically binds a *Salmonella* biomolecule that functions in bacterial motility. In certain embodiments, the antibody reduces bacterial motility compared to a negative control antibody. In certain embodiments, wherein the antibody reduces bacterial adhesion compared to a negative control antibody. In certain embodiments, the antibody reduces bacterial invasion compared to a negative control antibody. In certain embodiments, the *Salmonella* biomolecule is a *Salmonella* derived polypeptide. In certain embodiments, the biomolecule is a component of a flagellum. In certain embodiments, the biomolecule comprises a polypeptide derived from the flagella filament structural protein (FliC). In certain embodiments, the biomolecule comprises a polypeptide derived from the PrgI protein. In certain embodiments, the biomolecule comprises a polypeptide derived from the Fimbrial protein A (FimA). In certain embodiments, the antibody is monoclonal. In certain embodiments, the antibody is polyclonal. In certain embodiments, the antibody is incorporated into a spray for application to the exterior of a domestic animal. In certain embodiments, the antibody is formulated for oral administration. In certain embodiments, the antibody is formulated for injection. In certain embodiments, the antibody is formulated as a liquid. In certain embodiments, the antibody is not a chicken antibody. In certain embodiments, the antibody is not an IgY. In certain embodiments, the antibody does not specifically bind bacterial lipopolysaccharide (LPS).

In certain embodiments, described herein, is the use of a variable region fragment of a heavy chain antibody (V$_H$H) which specifically binds a *Salmonella* FliC protein, a *Salmonella* PrgI protein, a *Salmonella* FimA protein, or any combination thereof, for preventing infection with a pathogenic *Salmonella enterica* bacterial population in a domestic poultry animal.

In certain embodiments, described herein, is the use of a variable region fragment of a heavy chain antibody (V$_H$H) which specifically binds a *Salmonella* FliC protein, a *Salmonella* PrgI protein, a *Salmonella* FimA protein, or any combination thereof, for reducing a pathogenic *Salmonella enterica* bacterial population in a domestic poultry animal.

In certain embodiments, described herein, is an animal feed comprising an antibody that specifically binds an Enterobacteriaceae bacterial species. In certain embodiments, the animal feed comprises water. In certain embodiments, the animal feed comprises corn or a corn derivative. In certain embodiments, the animal feed comprises wheat or a wheat derivative. In certain embodiments, the animal feed comprises a poultry feed. In certain embodiments, the animal feed comprises a chicken feed. In certain embodiments, the animal feed comprises a probiotic, a prebiotic, a vitamin supplement, an additive spray, a toxin binder, a short chain fatty acid, a medium chain fatty acid, yeast, a yeast extract, sugar, a digestive enzyme, a digestive compound, an essential mineral, an essential salt, fiber, or any combination thereof. In certain embodiments, the antibody is selected from the group comprising: a heavy chain antibody (hcIgG); a variable region fragment of a heavy chain antibody; a single chain antibody; a nanobody; a polypeptide; an immunoglobulin new antigen receptor (IgNAR); a variable region fragment of an immunoglobulin new antigen receptor; or any fragment thereof that retains a capacity to specifically bind a target antigen. In certain embodiments, the antibody is a variable region fragment of a heavy chain antibody (V$_H$H). In certain embodiments, the antibody has been altered to reduce immunogenicity in a domestic animal. In certain embodiments, the domestic animal is a chicken. In certain embodiments, the antibody originates from a species of the Camelidae family, or from a species of the Chondrichthyes class. In certain embodiments, the Camelidae species is a llama. In certain embodiments, the bacterial population comprises *Salmonella* bacteria. In certain embodiments, the bacterial population comprises *Salmonella enterica*. In certain embodiments, the bacterial population comprises *Salmonella enterica* serotype Typhimurium, Enteritidis, Newport, Heidelberg, *Gallinarum*, Hadar, Javiana, *Infantis*, Montevideo, Muenchen, Braenderup, Saintpaul, Thompson, Agona, Litchfield, Anatum, Berta, Mbandaka, Oranienburg, Poona, Uganda, Senftenberg, Weltevreden, I 4,[5],12:i:-, I 13,23:b:-, or any combination thereof. In certain embodiments, the domestic animal is from the superorder Galloanserae. In certain embodiments, the domestic animal is a poultry animal. In certain embodiments, the poultry animal is a chicken, turkey, duck, or goose. In certain embodiments, the poultry animal is a chicken. In certain embodiments, the antibody specifically binds a *Salmonella* biomolecule. In certain embodiments, the antibody specifically binds a *Salmonella* biomolecule that functions in bacterial motility. In certain embodiments, the antibody reduces bacterial motility compared to a negative control antibody. In certain embodiments, the antibody reduces bacterial adhesion compared to a negative control antibody. In certain embodiments, the antibody reduces bacterial invasion compared to a negative control antibody. In certain embodiments, the *Salmonella* biomolecule is a *Salmonella* derived polypeptide. In certain embodiments, the biomolecule is a component of a flagellum. In certain embodiments, the biomolecule comprises a polypeptide derived from the flagella filament structural protein (FliC). In certain embodiments, the biomolecule comprises a polypeptide derived from the PrgI protein. In certain embodiments, the biomolecule comprises a polypeptide derived from the Fimbrial protein A (FimA). In certain embodiments, the antibody is monoclonal. In certain embodiments, the antibody is polyclonal. In certain embodiments, the antibody is incorporated into a spray for application to the exterior of a domestic animal. In certain embodiments, the antibody is formulated for oral administration. In certain embodiments, the antibody is formulated for injection. In certain embodiments, the antibody is formulated as a liquid. In certain embodiments, the antibody is not a chicken antibody. In certain embodiments, the antibody is not an IgY. In certain embodiments, the antibody does not specifically bind bacterial lipopolysaccharide (LPS).

In certain embodiments, described herein, is a domestic poultry feed comprising a variable region fragment of a heavy chain antibody ($V_HH$) which specifically binds a *Salmonella* flagella FliC protein, a *Salmonella* PrgI protein, a *Salmonella* FimA protein, or any combination thereof.

In certain embodiments, described herein, is a substance for introduction to an alimentary canal of a domestic poultry animal, the substance comprising a liquid, a gel, a spray, a tablet, or a pellet, for administration to the animal, which comprises a variable region fragment of a heavy chain antibody ($V_HH$) which specifically binds a *Salmonella* FliC protein, a *Salmonella* PrgI protein, a *Salmonella* FimA protein, or any combination thereof.

In certain embodiments, described herein, is a method for preventing infection with an Enterobacteriaceae bacterial population in a domestic animal, the method comprising introducing an antibody to an alimentary canal of the domestic animal. In certain embodiments, the antibody is selected from the group comprising: a heavy chain antibody (hcIgG); a variable region fragment of a heavy chain antibody ($V_HH$); a single chain antibody; a nanobody; a polypeptide; an immunoglobulin new antigen receptor (IgNAR); a variable region fragment of an immunoglobulin new antigen receptor; or any fragment thereof that retains a capacity to specifically bind a target antigen. In certain embodiments, the antibody is introduced to the alimentary canal of the domestic animal in an admixture of the antibody and a nutritional source. In certain embodiments, the nutritional source comprises water. In certain embodiments, the nutritional source comprises corn or a corn derivative. In certain embodiments, the nutritional source comprises wheat or a wheat derivative. In certain embodiments, the nutritional source comprises a poultry feed. In certain embodiments, the nutritional source comprises a chicken feed. In certain embodiments, the feed comprises a probiotic, a prebiotic, a vitamin supplement, an additive spray, a toxin binder, a short chain fatty acid, a medium chain fatty acid, yeast, a yeast extract, sugar, a digestive enzyme, a digestive compound, an essential mineral, an essential salt, fiber, or any combination thereof. In certain embodiments, the antibody is selected from the group comprising: a heavy chain antibody (hcIgG); a variable region fragment of a heavy chain antibody; a single chain antibody; a nanobody; a polypeptide; an immunoglobulin new antigen receptor (IgNAR); a variable region fragment of an immunoglobulin new antigen receptor; or any fragment thereof that retains a capacity to specifically bind a target antigen. In certain embodiments, the antibody is a variable region fragment of a heavy chain antibody ($V_HH$). In certain embodiments, wherein the antibody has been altered to reduce immunogenicity in a domestic animal. In certain embodiments, the domestic animal is a chicken. In certain embodiments, the antibody originates from a species of the Camelidae family, or from a species of the Chondrichthyes class. In certain embodiments, the Camelidae species is a llama. In certain embodiments, the bacterial population comprises *Salmonella* bacteria. In certain embodiments, the bacterial population comprises *Salmonella enterica*. In certain embodiments, the bacterial population comprises *Salmonella enterica* serotype Typhimurium, Enteritidis, Newport, Heidelberg, *Gallinarum*, Hadar, Javiana, *Infantis*, Montevideo, Muenchen, Braenderup, Saintpaul, Thompson, Agona, Litchfield, Anatum, Berta, Mbandaka, Oranienburg, Poona, Uganda, Senftenberg, Weltevreden, I 4,[5],12:i:-, I 13,23:b:-, or any combination thereof. In certain embodiments, the domestic animal is from the superorder Galloanserae. In certain embodiments, the domestic animal is a poultry animal. In certain embodiments, the poultry animal is a chicken, turkey, duck, or goose. In certain embodiments, the poultry animal is a chicken. In certain embodiments, the antibody specifically binds a *Salmonella* biomolecule. In certain embodiments, the antibody specifically binds a *Salmonella* biomolecule that functions in bacterial motility. In certain embodiments, the antibody reduces bacterial adhesion compared to a negative control antibody. In certain embodiments, the antibody reduces bacterial invasion compared to a negative control antibody. In certain embodiments, the antibody reduces bacterial motility compared to a negative control antibody. In certain embodiments, the *Salmonella* biomolecule is a *Salmonella* derived polypeptide. In certain embodiments, the biomolecule is a component of a flagellum. In certain embodiments, the biomolecule comprises a polypeptide derived from the flagella filament structural protein (FliC). In certain embodiments, the biomolecule comprises a polypeptide derived from the PrgI protein. In certain embodiments, the biomolecule comprises a polypeptide derived from the Fimbrial protein A (FimA). In certain embodiments, the antibody is monoclonal. In certain embodiments, the antibody is polyclonal. In certain embodiments, the antibody is incorporated into a spray for application to the exterior of a domestic animal. In certain embodiments, the antibody is formulated for oral administration. In certain embodiments, the antibody is formulated for injection. In certain embodiments, the antibody is formulated as a liquid. In certain embodiments, the antibody is not a chicken antibody. In certain embodiments, the antibody is not an IgY. In certain embodiments, the antibody does not specifically bind bacterial lipopolysaccharide (LPS).

In certain embodiments, described herein, is a method for reducing an Enterobacteriaceae bacterial population in a domestic animal, the method comprising introducing an antibody to an alimentary canal of the domestic animal. In certain embodiments, the antibody is introduced to the alimentary canal of the domestic animal in an admixture of the antibody and a nutritional source. In certain embodiments, the nutritional source comprises water. In certain embodiments, the nutritional source comprises corn or a corn derivative. In certain embodiments, the nutritional source comprises wheat or a wheat derivative. In certain embodiments, the nutritional source comprises a poultry feed. In certain embodiments, the nutritional source comprises a chicken feed. In certain embodiments, the nutritional source comprises a probiotic, a prebiotic, a vitamin supplement, an additive spray, a toxin binder, a short chain fatty acid, a medium chain fatty acid, yeast, a yeast extract, sugar, a digestive enzyme, a digestive compound, an essential mineral, an essential salt, fiber, or any combination thereof. In certain embodiments, the antibody is selected from the group comprising: a heavy chain antibody (hcIgG); a variable region fragment of a heavy chain antibody; a single chain antibody; a nanobody; a polypeptide; an immunoglobulin new antigen receptor (IgNAR); a variable region fragment of an immunoglobulin new antigen receptor; or any fragment thereof that retains a capacity to specifically bind a target antigen. In certain embodiments, the antibody is a variable region fragment of a heavy chain antibody ($V_HH$). In certain embodiments, the antibody has been altered to reduce immunogenicity in a domestic animal. In certain embodiments, the domestic animal is a chicken. In certain embodiments, the antibody originates from a species of the Camelidae family, or from a species of the Chondrichthyes class. In certain embodiments, the Camelidae species is a llama. In certain embodiments, wherein the bacterial population comprises *Salmonella* bacteria. In certain embodiments, the bacterial population comprises *Salmonella enterica*. In certain embodiments, the bacterial population comprises *Salmonella enterica* serotype Typhimurium, Enteritidis, Newport, Heidelberg, *Gallinarum*, Hadar, Javiana, *Infantis*, Montevideo, Muenchen, Braenderup, Saintpaul, Thompson, Agona, Litchfield, Anatum, Berta, Mbandaka, Oranienburg, Poona, Uganda, Senftenberg, Weltevreden, I 4,[5],12:i:-, I 13,23:b:-, or any combination thereof. In certain embodiments, the domestic animal is from the superorder Galloanserae. In certain embodiments, the domestic animal is a poultry animal. In certain embodiments, the poultry animal is a chicken, turkey, duck, or goose. In certain embodiments, the poultry animal is a chicken. In certain embodiments, the antibody specifically binds a *Salmonella* biomolecule. In certain embodiments, the antibody specifically binds a *Salmonella* biomolecule that functions in bacterial motility. In certain embodiments, the antibody reduces bacterial motility compared to a negative control antibody. In certain embodiments, the antibody reduces bacterial adhesion compared to a negative control antibody. In certain embodiments, the antibody reduces bacterial invasion compared to a negative control antibody. In certain embodiments, the *Salmonella* biomolecule is a *Salmonella* derived polypeptide. In certain embodiments, the biomolecule is a component of a flagellum. In certain embodiments, the biomolecule comprises a polypeptide derived from the flagella filament structural protein (FliC). In certain embodiments, the biomolecule comprises a polypeptide derived from the PrgI protein. In certain embodiments, the biomolecule comprises a polypeptide derived from the Fimbrial protein A (FimA). In certain embodiments, the antibody is monoclonal. In certain embodiments, the antibody is polyclonal. In certain embodiments, the antibody is incorporated into a spray for application to the exterior of a domestic animal. In certain embodiments, the antibody is formulated for oral administration. In certain embodiments, the antibody is formulated for injection. In certain embodiments, the antibody is formulated as a liquid. In certain embodiments, the antibody is not a chicken antibody. In certain embodiments, the antibody is not an IgY. In certain embodiments, the antibody does not specifically bind bacterial lipopolysaccharide (LPS).

In certain embodiments, described herein, is a method for preventing infection with a *Salmonella* enterica bacterial population in a domestic poultry animal, the method comprising introducing to an alimentary canal of the animal a monoclonal variable region fragment of a heavy chain antibody ($V_HH$) which specifically binds a *Salmonella* flagella filament structural protein (FliC), a *Salmonella* PrgI protein, a *Salmonella* FimA protein, or any combination thereof.

In certain embodiments, described herein, is a method for reducing a *Salmonella enterica* bacterial population in a domestic poultry animal, the method comprising introducing to an alimentary canal of the animal a variable region fragment of a heavy chain antibody ($V_HH$) which specifically binds a *Salmonella* flagella filament structural protein (FliC), a *Salmonella* PrgI protein, a *Salmonella* FimA protein, or any combination thereof.

In certain embodiments, described herein, is a heavy chain antibody which specifically binds Enterobacteriaceae. In certain embodiments, the heavy chain antibody is a variable region fragment of a heavy chain antibody; a single chain antibody; a nanobody; a polypeptide; an immunoglobulin new antigen receptor (IgNAR); a variable region fragment of an immunoglobulin new antigen receptor; or any fragment thereof that retains a capacity to specifically bind a target antigen. In certain embodiments, the heavy chain antibody is a variable region fragment of a heavy chain antibody ($V_HH$). In certain embodiments, the heavy chain antibody is altered to reduce immunogenicity in a domestic animal. In certain embodiments, the domestic animal is a chicken. In certain embodiments, the antibody originates from a species of the Camelidae family, or from a species of the Chondrichthyes class. In certain embodiments, the Camelidae species is a llama. In certain embodiments, the heavy chain antibody specifically binds *Salmonella* bacteria. In certain embodiments, the heavy chain antibody specifically binds *Salmonella enterica*. In certain embodiments, the heavy chain antibody specifically binds any of the *Salmonella enterica* serotypes Typhimurium, Enteritidis, Newport, Heidelberg, *Gallinarum*, Hadar, Javiana, *Infantis*, Montevideo, Muenchen, Braenderup, Saintpaul, Thompson, Agona, Litchfield, Anatum, Berta, Mbandaka, Oranienburg, Poona, Uganda, Senftenberg, Weltevreden, I 4,[5],12:i:-, I 13,23:b:-, or any combination thereof. In certain embodiments, the heavy chain antibody specifically binds a *Salmonella* biomolecule. In certain embodiments, the heavy chain antibody specifically binds a *Salmonella* biomolecule that functions in bacterial motility. In certain embodiments, the antibody reduces bacterial motility compared to a negative control antibody. In certain embodiments, the antibody reduces bacterial adhesion compared to a negative control antibody. In certain embodiments, wherein the antibody reduces bacterial invasion compared to a negative control antibody. In certain embodiments, the *Salmonella* biomolecule is a *Salmonella* derived polypeptide. In certain embodiments, the biomolecule is a component of a flagellum. In certain embodiments, the biomolecule comprises a polypeptide derived from the flagella filament structural protein (FliC). In certain embodiments, the biomolecule comprises a polypeptide derived from the PrgI protein. In certain embodiments, the biomolecule comprises a polypeptide derived from the Fimbrial protein A (FimA). In certain embodiments, the heavy chain antibody is monoclonal. In certain embodiments, the heavy chain antibody is polyclonal. In certain embodiments, the heavy chain antibody is incorporated into a spray for application to the exterior of a domestic animal. In certain embodiments, the heavy chain antibody is formulated for injection. In certain embodiments, the heavy chain antibody is formulated as a liquid. In certain embodiments, the heavy chain antibody is not a chicken antibody. In certain embodiments, the heavy chain antibody is not an IgY. In certain embodiments, the heavy chain antibody does not specifically bind bacterial lipopolysaccharide (LPS). In certain embodiments, the peptide sequence of the CDR1 is set forth in any of SEQ ID NOs: 1 to 91. In certain embodiments, the peptide sequence of the CDR2 is set forth in any of SEQ ID NOs: 92 to 182. In certain embodiments, the peptide sequence of the CDR3 is set forth in any of SEQ ID NOs: 183 to 273. In certain embodiments, the peptide sequence of the CDR1 is set forth in any of SEQ ID NOs: 1 to 91, the peptide sequence of the CDR2 is set forth in any of SEQ ID NOs: 92 to 182, and the peptide sequence of the CDR3 is set forth in any of SEQ ID NOs: 183 to 273. In certain embodiments, the peptide sequence of the CDR1 is set forth in SEQ ID NO:1, SEQ ID NO:4, SEQ ID NO: 12, SEQ ID NO: 20, SEQ ID NO: 21, or SEQ ID NO: 60. In certain embodiments, the peptide sequence of the CDR2 is set forth in SEQ ID NO: 92, SEQ ID NO: 95, SEQ ID NO:

103, SEQ ID NO: 111, SEQ ID NO: 112, or SEQ ID NO: 151. In certain embodiments, the peptide sequence of the CDR3 is set forth in SEQ ID NO: 183, SEQ ID NO: 186, SEQ ID NO: 194, SEQ ID NO: 202, SEQ ID NO: 203, or SEQ ID NO: 242. In certain embodiments, the peptide sequence of the CDR1 is set forth in SEQ ID NO: 1, the peptide sequence of the CDR2 is set forth in SEQ ID NO: 92, and the peptide sequence of the CDR3 is set forth in SEQ ID NO: 183. In certain embodiments, the peptide sequence of the CDR1 is set forth in SEQ ID NO: 4, the peptide sequence of the CDR2 is set forth in SEQ ID NO: 95, and the peptide sequence of the CDR3 is set forth in SEQ ID NO: 186. In certain embodiments, the peptide sequence of the CDR1 is set forth in SEQ ID NO: 12, the peptide sequence of the CDR2 is set forth in SEQ ID NO: 103, and the peptide sequence of the CDR3 is set forth in SEQ ID NO: 194. In certain embodiments, the peptide sequence of the CDR1 is set forth in SEQ ID NO: 20, the peptide sequence of the CDR2 is set forth in SEQ ID NO: 111, and the peptide sequence of the CDR3 is set forth in SEQ ID NO: 202. In certain embodiments, the peptide sequence of the CDR1 is set forth in SEQ ID NO: 21, the peptide sequence of the CDR2 is set forth in SEQ ID NO: 112, and the peptide sequence of the CDR3 is set forth in SEQ ID NO: 203. In certain embodiments, the peptide sequence of the CDR1 is set forth in SEQ ID NO: 60, the peptide sequence of the CDR2 is set forth in SEQ ID NO: 151, and the peptide sequence of the CDR3 is set forth in SEQ ID NO: 242. In certain embodiments, the peptide sequence of the CDR1 is set forth in any of SEQ ID NOs: 280 to 329, 573, or 765-768. In certain embodiments, the peptide sequence of the CDR2 is set forth in any of SEQ ID NOs: 330 to 379, 574, or 769-772. In certain embodiments, the peptide sequence of the CDR3 is set forth in any of SEQ ID NOs: 380-429, 575 to 773-776. In certain embodiments, the heavy chain antibody is for use with any of the uses of this disclosure. In certain embodiments, the heavy chain antibody is for use with an animal feed. In certain embodiments, the heavy chain antibody is for use with any of the methods of this disclosure.

In certain embodiments, described herein, is a polypeptide comprising a plurality of variable region fragments of a heavy chain antibody ($V_HHs$) which specifically bind Salmonella enterica. In certain embodiments, the plurality of $V_HHs$ comprise at least three $V_HHs$. In certain embodiments, one or more of the plurality of $V_HHs$ comprise an amino acid sequence with at least 80% identity to the amino acid sequence set forth in SEQ ID NO: 463. In certain embodiments, any one or more of the plurality of $V_HHs$ is identical to another $V_HH$ of the plurality of $V_HHs$. In certain embodiments, a minimum concentration of the polypeptide required for 50% motility inhibition of Salmonella enterica is reduced by at least 20-fold when compared to a minimum concentration of a control polypeptide required for 50% motility inhibition of Salmonella enterica, the control polypeptide comprising a single $V_HH$ that is identical to any one of the plurality of $V_HHs$ of the polypeptide. In certain embodiments, the plurality of $V_HHs$ are covalently coupled to one another by a linker, the linker comprising one or more amino acids. Also described is a polypeptide complex, wherein the polypeptide comprises a first component polypeptide and a second component polypeptide, wherein the first component polypeptide and the second component polypeptide are not covalently linked together and are coupled together by a protein-protein interaction, a small molecule-protein interaction, or a small molecule-small molecule interaction, wherein each of the first and the second component polypeptides comprise a $V_HH$ which specifically binds Salmonella enterica. In certain embodiments, a nucleic acid encodes the polypeptide or the polypeptide complex. In certain embodiments, a plurality of nucleic acids encodes the polypeptide complex. In certain embodiments, a cell comprises the nucleic acid or the plurality of nucleic acids. In certain embodiments, the cell is a yeast cell. In certain embodiments, the yeast is of the genus Pichia. In certain embodiments, a method of producing the polypeptide or the polypeptide complex, comprises (a) incubating the cell in a medium suitable for secretion of the polypeptide from the cell; and (b) purifying the polypeptide from the medium. In certain embodiments, the polypeptide or the polypeptide complex is for use in reducing or preventing a pathogenic Salmonella enterica infection of a human individual or a domestic animal. In certain embodiments, described herein is a use of the polypeptide or the polypeptide complex for reducing or preventing a pathogenic Salmonella enterica infection of a human individual or a domestic animal. In certain embodiments, the use of the polypeptide or polypeptide complex is for oral administration to the human or animal.

In a certain aspect, described herein, is a polypeptide comprising a variable region fragment of a heavy chain antibody ($V_HH$), wherein the $V_HH$ specifically binds a Salmonella enterica virulence factor, wherein the virulence factor is involved in bacterial motility, adhesion, invasion, or biofilm formation. In certain embodiments, the virulence factor comprises a flagellum, FliC, PrgI, FimA, or SipD. In certain embodiments, the virulence factor comprises a flagellum, FliC, PrgI, or FimA. In certain embodiments, the polypeptide that specifically binds a Salmonella enterica virulence factor specifically binds a virulence factor of any of the Salmonella enterica serotypes Typhimurium, Enteritidis, Newport, Heidelberg, Gallinarum, Hadar, Javiana, Infantis, Montevideo, Muenchen, Braenderup, Saintpaul, Thompson, Agona, Litchfield, Anatum, Berta, Mbandaka, Oranienburg, Poona, Uganda, Senftenberg, Weltevreden, I 4,[5],12:i:-, I 13,23:b:-, or any combination thereof. In certain embodiments, the amino acid sequence of the $V_HH$ comprises: a CDR1 sequence set forth in SEQ ID NO: 1, a CDR2 sequence set forth in SEQ ID NO: 92, and a CDR3 sequence set forth in SEQ ID NO: 183; a CDR1 sequence set forth in SEQ ID NO: 4, a CDR2 sequence set forth in SEQ ID NO: 95, and a CDR3 sequence set forth in SEQ ID NO: 186; a CDR1 sequence set forth in SEQ ID NO: 12, a CDR2 sequence set forth in SEQ ID NO: 103, and a CDR3 sequence set forth in SEQ ID NO: 194; a CDR1 sequence set forth in SEQ ID NO: 20, a CDR2 sequence set forth in SEQ ID NO: 111, and a CDR3 sequence set forth in SEQ ID NO: 202 a CDR1 sequence set forth in SEQ ID NO: 21, a CDR2 sequence set forth in SEQ ID NO: 112, and a CDR3 sequence set forth in SEQ ID NO: 203; or a CDR1 sequence set forth in SEQ ID NO: 60, a CDR2 sequence set forth in SEQ ID NO: 151, and a CDR3 sequence set forth in SEQ ID NO: 242. In certain embodiments, the amino acid sequence of the $V_HH$ comprises: a CDR1 sequence set forth in SEQ ID NO: 5, a CDR2 sequence set forth in SEQ ID NO: 96, and a CDR3 sequence set forth in SEQ ID NO: 187; a CDR1 sequence set forth in SEQ ID NO: 285, a CDR2 sequence set forth in SEQ ID NO: 335, and a CDR3 sequence set forth in SEQ ID NO: 385; or a CDR1 sequence set forth in SEQ ID NO: 284, a CDR2 sequence set forth in SEQ ID NO: 334, and a CDR3 sequence set forth in SEQ ID NO: 384. In certain embodiments, the amino acid sequence of the $V_HH$ comprises an amino acid sequence at least 80% identical to that set forth in any one SEQ ID NOs: 478 to 488. In certain embodiments, the amino acid sequence of the $V_H H$ comprises an amino acid sequence identical to that set forth in any one SEQ ID NOs: 478 to 488. In certain embodiments, the $V_H H$ reduces bacterial motility of *Salmonella enterica* compared to a negative control antibody by at least 40%. In certain embodiments, the $V_H H$ reduces biofilm formation by at least 10%. In certain embodiments, described herein is a nucleic acid encoding the polypeptide. In certain embodiments, described herein is a cell comprising the nucleic acid. In certain embodiments, the cell is a yeast cell. In certain embodiments, the yeast is of the genus *Pichia*. In certain embodiments, a method of producing the polypeptide comprises (a) incubating a cell in a medium suitable for secretion of the polypeptide from the cell; and (b) purifying the polypeptide from the medium. In certain embodiments, is described herein is a composition comprising a polypeptide and an animal feed. In certain embodiments, the composition is for use in reducing or preventing infection of a domestic animal with a pathogenic *Salmonella enterica*. In certain embodiments, described herein, is a method of reducing or preventing infection of a domestic animal with a pathogenic *Salmonella enterica* comprising administering to the domestic animal a polypeptide described herein or the composition described herein. In certain embodiments, described herein, is a composition comprising a polypeptide and a pharmaceutically acceptable stabilizer, excipient or diluent. In certain embodiments, the composition is for use in reducing or preventing infection in a human individual with a pathogenic *Salmonella enterica*. In certain embodiments, described herein, is a method of reducing or preventing infection of a human individual with a pathogenic *Salmonella enterica* comprising administering to the human individual a polypeptide, described herein, or the composition described herein. In certain embodiments, is a use of the polypeptide or of the composition for reducing or preventing a pathogenic *Salmonella enterica* infection in a domestic animal. In certain embodiments, is a use of a polypeptide or the composition for reducing or preventing a pathogenic *Salmonella enterica* infection of a human individual.

In a certain aspect, described herein, is an animal feed comprising a nutritional source and a polypeptide comprising a variable region fragment of a heavy chain antibody ($V_H H$), wherein the $V_H H$ specifically binds an Enterobacteriaceae virulence factor, wherein the virulence factor is involved in bacterial motility, adhesion, invasion, or biofilm formation. In certain embodiments, the Enterobacteriaceae is *Salmonella enterica*. In certain embodiments, the amino acid sequence of the $V_H H$ comprises: a CDR1 sequence set forth in SEQ ID NO: 1, a CDR2 sequence set forth in SEQ ID NO: 92, and a CDR3 sequence set forth in SEQ ID NO: 183; a CDR1 sequence set forth in SEQ ID NO: 4, a CDR2 sequence set forth in SEQ ID NO: 95, and a CDR3 sequence set forth in SEQ ID NO: 186; a CDR1 sequence set forth in SEQ ID NO: 12, a CDR2 sequence set forth in SEQ ID NO: 103, and a CDR3 sequence set forth in SEQ ID NO: 194; a CDR1 sequence set forth in SEQ ID NO: 20, a CDR2 sequence set forth in SEQ ID NO: 111, and a CDR3 sequence set forth in SEQ ID NO: 202 a CDR1 sequence set forth in SEQ ID NO: 21, a CDR2 sequence set forth in SEQ ID NO: 112, and a CDR3 sequence set forth in SEQ ID NO: 203; or a CDR1 sequence set forth in SEQ ID NO: 60, a CDR2 sequence set forth in SEQ ID NO: 151, and a CDR3 sequence set forth in SEQ ID NO: 242. In certain embodiments, the amino acid sequence of the VHH comprises: a CDR1 sequence set forth in SEQ ID NO: 5, a CDR2 sequence set forth in SEQ ID NO: 96, and a CDR3 sequence set forth in SEQ ID NO: 187; a CDR1 sequence set forth in SEQ ID NO: 285, a CDR2 sequence set forth in SEQ ID NO: 335, and a CDR3 sequence set forth in SEQ ID NO: 385; or a CDR1 sequence set forth in SEQ ID NO: 284, a CDR2 sequence set forth in SEQ ID NO: 334, and a CDR3 sequence set forth in SEQ ID NO: 384. In certain embodiments, the amino acid sequence of the $V_H H$ comprises an amino acid sequence at least 80% identical to that set forth in any one SEQ ID NOs: 478 to 488. In certain embodiments, the amino acid sequence of the $V_H H$ comprises an amino acid sequence identical to that set forth in any one SEQ ID NOs: 478 to 488.

BRIEF DESCRIPTION OF THE DRAWINGS

FIG. 16A to 16E Show the production system dependency of $V_HH$ activity. Salmonella enterica serovar Typhimurium strain SL1344 clumps Saccharomyces cerevisiae during PBS treatment (A) or treatment with NBX0018 recombinantly produced in Escherichia coli (D). In the presence of Salmonella enterica serovar Typhimurium strain SL1344 lacking the Type-1 Fimbriae (FimA mutant strain), Saccharomyces cerevisiae cells remain unclumped (B). In the presence of Salmonella enterica serovar Typhimurium strain SL1344 with intact Type-1 Fimbriae and excess soluble mannose (C) or NBX0018 recombinantly produced in Pichia pastoris (E), Saccharomyces cerevisiae cells remain unclumped, indicating that the interaction between Type-1 Fimbriae and mannose sugars on the surface of the Saccharomyces cerevisiae cells has been blocked.

DETAILED DESCRIPTION OF THE INVENTION

Figure 1A:
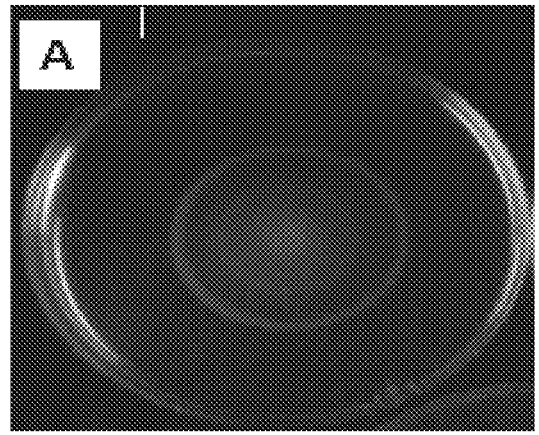
FIGS. 1A, 1B, and 1C show pictures of a plate-based motility assay performed using agar plates.

In certain embodiments, described herein, is the use of an antibody for preventing infection in a domestic animal by a pathogenic Enterobacteriaceae bacterial population.

In certain embodiments, described herein, is the use of an antibody for reducing a pathogenic Enterobacteriaceae bacterial population in a domestic animal.

In certain embodiments, described herein, is the use of an antibody for preventing infection in a human individual by a pathogenic Enterobacteriaceae bacterial population.

In certain embodiments, described herein, is the use of an antibody for reducing a pathogenic Enterobacteriaceae bacterial population in a human individual.

In certain embodiments, described herein, is the use of a variable region fragment of a heavy chain antibody ($V_HH$) which specifically binds a Salmonella FliC protein, a Salmonella PrgI protein, a Salmonella FimA protein, or any combination thereof, for preventing infection with a pathogenic Salmonella enterica bacterial population in a domestic poultry animal.

In certain embodiments, described herein, is the use of a variable region fragment of a heavy chain antibody ($V_HH$) which specifically binds a Salmonella FliC protein, a Salmonella PrgI protein, a Salmonella FimA protein, or any combination thereof, for reducing a pathogenic Salmonella enterica bacterial population in a domestic poultry animal.

In certain embodiments, described herein, is the use of a variable region fragment of a heavy chain antibody ($V_HH$) which specifically binds a Salmonella FliC protein, a Salmonella PrgI protein, a Salmonella FimA protein, or any combination thereof, for preventing infection with a pathogenic Salmonella enterica bacterial population in a human individual.

In certain embodiments, described herein, is the use of a variable region fragment of a heavy chain antibody ($V_HH$) which specifically binds a Salmonella FliC protein, a Salmonella PrgI protein, a Salmonella FimA protein, or any combination thereof, for reducing a pathogenic Salmonella enterica bacterial population in a human individual.

In certain embodiments, described herein, is an animal feed comprising an antibody that specifically binds an Enterobacteriaceae bacterial species.

In certain embodiments, described herein, is a substance for introduction to an alimentary canal of a domestic poultry animal, the substance comprising a liquid, a gel, a spray, a tablet, or a pellet, for administration to the animal, which comprises a variable region fragment of a heavy chain antibody ($V_HH$) which specifically binds a *Salmonella* FliC protein, a *Salmonella* PrgI protein, a *Salmonella* FimA protein, or any combination thereof.

In certain embodiments, described herein, is a method for preventing infection with a *Salmonella* bacterial population in a domestic animal, the method comprising introducing an antibody to an alimentary canal of the domestic animal.

In certain embodiments, described herein, is a method for reducing a *Salmonella* bacterial population in a domestic animal, the method comprising introducing an antibody to an alimentary canal of the domestic animal.

In certain embodiments, described herein, is a method for preventing infection with a *Salmonella enterica* bacterial population in a domestic poultry animal, the method comprising introducing to an alimentary canal of the animal a monoclonal variable region fragment of a heavy chain antibody ($V_HH$) which specifically binds a *Salmonella* flagella filament structural protein (FliC), a *Salmonella* PrgI protein, a *Salmonella* FimA protein, or any combination thereof.

In certain embodiments, described herein, is a method for reducing a *Salmonella enterica* bacterial population in a domestic poultry animal, the method comprising introducing to an alimentary canal of the animal a variable region fragment of a heavy chain antibody ($V_HH$) which specifically binds a *Salmonella* flagella filament structural protein (FliC), a *Salmonella* PrgI protein, a *Salmonella* FimA protein, or any combination thereof.

In certain embodiments, described herein, is a variable region fragment of an antibody which specifically binds *Salmonella*.

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein the term "about refers to an amount that is near the stated amount by about 10%, 5%, or 1%.

As referred to herein "antibody fragment" refers to any portion of a conventional or heavy chain antibody that retains a capacity to specifically bind a target antigen and may include a single chain antibody, a variable region fragment of a heavy chain antibody, a nanobody; a polypeptide or an immunoglobulin new antigen receptor (Ig-NAR).

As referred to herein an "antibody originates from a species" when any of the CDR regions of the antibody were raised in an animal of said species. Antibodies that are raised in a certain species and then optimized by an in vitro method (e.g., phage display) are considered to have originated from that species.

As referred to herein "conventional antibody" refers to any full-sized immunoglobulin that comprises two heavy chain molecules and two light chain molecules joined together by a disulfide bond. In certain embodiments, the antibodies, compositions, animal feeds, and methods described herein do not utilize conventional antibodies.

As referred to herein "heavy chain antibody" refers to an antibody that comprises two heavy chains and lacking the two light chains normally found in a conventional antibody. The heavy chain antibody may originate from a species of the Camelidae family or Chondrichthyes class. Heavy chain antibodies retain specific binding to an antigen in the absence of any light chain.

As referred to herein "poultry" refers to any domesticated or captive raised bird that is kept for its egg, meat, feathers, or combination thereof.

As referred to herein "specific binding" or "specifically binds" refers to binding that occurs between an antibody and its target molecule that is mediated by at least one complementarity determining region (CDR) of the antibody's variable region. Binding that is between the constant region and another molecule, such as Protein A, for example, does not constitute specific binding.

As referred to herein "$V_HH$" refers to an antibody or antibody fragment comprising a single heavy chain variable region which may be derived from natural or synthetic sources. NBXs referred to herein are an example of a $V_HH$.

Figure 26A:
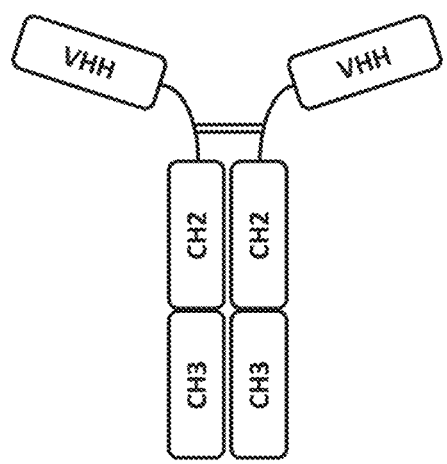
FIG. 26A and FIG. 26B show a schematic of camelid heavy chain only antibodies and their relationship to $V_HH$ domains and complementarity determining regions (CDRs).
Figure 26B:
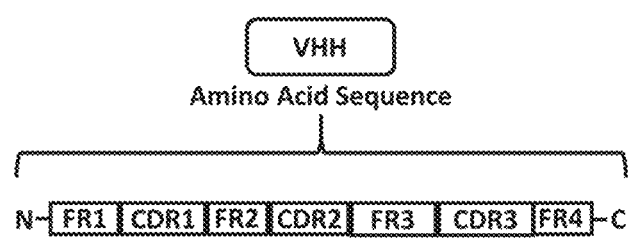

A schematic of camelid heavy chain only antibodies and their relationship to $V_HH$ domains and complementarity determining regions (CDRs) are shown in FIG. 26A and FIG. 26B. (Panel A) A camelid heavy chain only antibody consists of two heavy chains linked by a disulphide bridge. Each heavy chain contains two constant immunoglobulin domains (CH2 and CH3) linked through a hinge region to a variable immunoglobulin domain ($V_HH$). (Panel B) are derived from single $V_HH$ domains. Each $V_HH$ domain contains an amino acid sequence of approximately 110-130 amino acids. The $V_HH$ domain consists of the following regions starting at the N-terminus (N): framework region 1 (FR1), complementarity-determining region 1 (CDR1), framework region 2 (FR2), complementarity-determining region 2 (CDR2), framework region 3 (FR3), complementarity-determining region 3 (CDR3), and framework region 4 (FR4). The domain ends at the C-terminus (C). The complementarity-determining regions are highly variable, determine antigen binding by the antibody, and are held together in a scaffold by the framework regions of the $V_HH$ domain. The framework regions consist of more conserved amino acid sequences; however, some variability exists in these regions.

Use of Antibodies for Preventing or Reducing a Bacterial Population

In certain embodiments, described herein are compositions, methods, and antibodies for use in preventing or reducing a pathogenic bacterial population in a domestic animal. In certain embodiments, described herein are compositions, methods, and antibodies for use in preventing or reducing a pathogenic bacterial population in the alimentary canal in a domestic animal. In certain embodiments, described herein are compositions, methods, and antibodies for use in preventing or reducing attachment of a pathogenic bacterial population in the alimentary canal in a domestic animal. In certain embodiments, described herein are compositions, methods, and antibodies for use in preventing or reducing transmission of a pathogenic bacterial population from a domestic animal to a human. In certain embodiments, described herein are compositions, methods, and antibodies for use in preventing or reducing transmission of a pathogenic bacterial population from the egg, dairy or meat products of a domestic animal to a human. In certain embodiments, described herein are compositions, methods, and antibodies for use in preventing or reducing transmission of a pathogenic bacterial population from a domestic animal to another domestic animal. In certain embodiments, preventing or reducing transmission of a pathogenic or bacterial population comprises reducing disease or symptoms of a disease caused by the bacteria in a human or domestic animal. In certain embodiments, the disease is a gastrointestinal disease with any one or more of the following symptoms in humans: nausea, vomiting, diarrhea, constipation, abdominal cramps, dehydration, fatigue, chills, fever, malnutrition, wasting, or bloody stool.

In certain embodiments, described herein are compositions, methods, and antibodies for use in preventing or reducing a pathogenic bacterial population in a human subject. In certain embodiments, described herein are compositions, methods, and antibodies for use in preventing or reducing a pathogenic bacterial population in the alimentary canal in a human subject. In certain embodiments, described herein are compositions, methods, and antibodies for use in preventing or reducing attachment of a pathogenic bacterial population in the alimentary canal of a human subject. In certain embodiments, described herein are compositions, methods, and antibodies for use in preventing or reducing transmission of a pathogenic bacterial population from a human subject to another human subject. In certain embodiments, preventing or reducing transmission of a pathogenic or bacterial population comprises reducing disease or symptoms of a disease caused by the bacteria in a human. In certain embodiments, the disease is a gastrointestinal disease with any one or more of the following symptoms in humans: nausea, vomiting, diarrhea, constipation, abdominal cramps, dehydration, fatigue, chills, fever, malnutrition, wasting, or bloody stool.

Domestic Animals

In certain embodiments, the uses, compositions and methods described herein are for reducing or preventing a bacterial infection in any domestic animal. In certain embodiments, the domestic animal is a cow, pig, sheep, goat, horse, duck, chicken, goose, turkey or Cornish hen. In certain embodiments, the domestic animal is a pig. In certain embodiments, the domestic animal is from the superorder Galloanserae. In certain embodiments, the domestic animal is a poultry animal. In certain embodiments, the domestic animal is a duck, chicken, goose, turkey or Cornish hen. In certain embodiments, the domestic animal is a duck. In certain embodiments, the domestic animal is a turkey. In certain embodiments, the domestic animal is a chicken. In certain embodiments, the domestic animal is not a cow. In certain embodiments, the domestic animal is not a pig.

Bacteria

In certain embodiments, the bacterial population comprises any member of the Enterobacteriaceae family. In certain embodiments, the bacterial population comprises any member of the genus *Salmonella*. In certain embodiments, the bacterial population comprises any member of the species *Salmonella enterica*. In certain embodiments, the bacterial population comprises any member of the *Salmonella enterica* serotypes Typhimurium, Enteritidis, Newport, Heidelberg, *Gallinarum*, Hadar, Javiana, *Infantis*, Montevideo, Muenchen, Braenderup, Saintpaul, Thompson, Agona, Litchfield, Anatum, Berta, Mbandaka, Oranienburg, Poona, Uganda, Senftenberg, Weltevreden, I 4,[5],12:i:- or I 13,23:b:-. In certain embodiments, the bacterial population is not *E. coli* (*Escherichia coli*).

Antibodies

In certain embodiments, the antibody for the uses, compositions and methods described herein is an IgA, IgG, or IgM antibody. In certain embodiments, the antibody for the uses, compositions and methods described herein is a heavy chain antibody. In certain embodiments, the antibody for the uses, compositions and methods described herein is a $V_HH$. In certain embodiments, the antibody for the uses, compositions and methods described herein is a nanobody; a polypeptide. In certain embodiments, the antibody for the uses, compositions and methods described herein is synthetic. In certain embodiments, the antibody originates from a species of the Camildae family. In certain embodiments, the antibody originates from a species of the Chondrichthyes class. In certain embodiments, the antibody originates from a camel. In certain embodiments, the antibody originates from a llama. In certain embodiments, the antibody originates from a cartilaginous fish. In certain embodiments, the antibody originates from a shark. In certain embodiments, the antibody originates from a human, mouse, rat, rabbit, goat, sheep, horse, cow, donkey or Guinea pig. In certain embodiments, the antibody is a monoclonal antibody. In certain embodiments, the antibody is a polyclonal antibody. In certain embodiments, the antibody is a chimeric or CDR grafted antibody. In certain embodiments, the antibody has been altered to reduce immunogenicity in a poultry species. In certain embodiments, the antibody has been altered to reduce immunogenicity in a duck, chicken, goose, turkey or Cornish hen. In certain embodiments, the antibody has been altered to reduce immunogenicity in chickens. In certain embodiments, the antibody is not a chicken antibody. In certain embodiments, the antibody is not an IgY antibody.

Heavy Chain Antibodies

Heavy chain antibodies are a type of antibody that comprises two heavy chains without associated light chains. Some species such as those from the family Camelidae and Chondrichthyes class raise heavy chain antibodies in response to infection. In some embodiments, the heavy chain antibody is a variable region fragment of a heavy chain antibody ($V_HH$). In some embodiments, the heavy chain antibody is a single chain antibody. In some embodiments, the heavy chain antibody is a nanobody; a polypeptide. In some embodiments, the heavy chain antibody is an immunoglobulin new antigen receptor (IgNAR). In some embodiments, the heavy chain antibody is a variable region fragment of an immunoglobulin new antigen receptor. In some embodiments, the heavy chain antibody is a synthetic or expressed polypeptide. In some embodiments, the variable region fragment of a heavy chain antibody ($V_HH$) is synthetic. In some embodiments, the heavy chain antibody is any fragment thereof that retains a capacity to specifically bind a target antigen. In certain embodiments, the heavy chain antibody comprises a sequence set forth either identically or with at least 80%, 90%, 95%, 98%, or 99% identity to any one of SEQ ID NOs:478-488. In certain embodiments, the heavy chain antibody comprises a sequence set forth either identically or with at least 80%, 90%, 95%, 98%, or 99% identity to any one of SEQ ID NOs:478-572. In certain embodiments, the heavy chain antibody comprises a sequence set forth in any one of SEQ ID NOs:478-488. In certain embodiments, the heavy chain antibody comprises a CDR1 set forth in Table 1 or Table 2. In certain embodiments, the heavy chain antibody comprises a CDR2 set forth in Table 1 or Table 2. In certain embodiments, the heavy chain antibody comprises a CDR3 set forth in Table 1 or Table 2. In a certain embodiment, the heavy chain antibody is any of NBX0001, NBX005, NBX0006, NBX0015, NBX0018, NBX0019, NBX0030, or a combination thereof. In certain embodiments, the heavy chain antibody comprises an amino acid sequence with at least 80%, 90%, 95%, 97%, or 99% identity to SEQ ID NO: 475. In certain embodiments, the heavy chain antibody comprises an amino acid sequence with 100% identity to SEQ ID NO: 475. In certain embodiments, the heavy chain antibody comprises an amino acid sequence with at least 80%, 90%, 95%, 97%, or 99% identity to SEQ ID NO: 476. In certain embodiments, the heavy chain antibody comprises an amino acid sequence with 100% identity to SEQ ID NO: 476. In certain embodiments, the heavy chain antibody comprises an amino acid sequence with at least 80%, 90%, 95%, 97%, or 99% identity to SEQ ID NO: 477. In certain embodiments, the heavy chain antibody comprises an amino acid sequence with 100% identity to SEQ ID NO: 477. In certain embodiments, the heavy chain antibody comprises an amino acid sequence with at least 80%, 90%, 95%, 97%, or 99% identity to SEQ ID NO: 478. In certain embodiments, the heavy chain antibody comprises an amino acid sequence with 100% identity to SEQ ID NO: 478. In certain embodiments, the heavy chain antibody comprises an amino acid sequence with at least 80%, 90%, 95%, 97%, or 99% identity to SEQ ID NO: 479. In certain embodiments, the heavy chain antibody comprises an amino acid sequence with 100% identity to SEQ ID NO: 479. In certain embodiments, the heavy chain antibody comprises an amino acid sequence with at least 80%, 90%, 95%, 97%, or 99% identity to SEQ ID NO: 480. In certain embodiments, the heavy chain antibody comprises an amino acid sequence with 100% identity to SEQ ID NO: 480. In certain embodiments, the heavy chain antibody comprises an amino acid sequence with at least 80%, 90%, 95%, 97%, or 99% identity to SEQ ID NO: 481. In certain embodiments, the heavy chain antibody comprises an amino acid sequence with 100% identity to SEQ ID NO: 481. In certain embodiments, the heavy chain antibody comprises an amino acid sequence with at least 80%, 90%, 95%, 97%, or 99% identity to SEQ ID NO: 482. In certain embodiments, the heavy chain antibody comprises an amino acid sequence with 100% identity to SEQ ID NO: 482. In certain embodiments, the heavy chain antibody comprises an amino acid sequence with at least 80%, 90%, 95%, 97%, or 99% identity to SEQ ID NO: 483. In certain embodiments, the heavy chain antibody comprises an amino acid sequence with 100% identity to SEQ ID NO: 483. In certain embodiments, the heavy chain antibody comprises an amino acid sequence with at least 80%, 90%, 95%, 97%, or 99% identity to SEQ ID NO: 484. In certain embodiments, the heavy chain antibody comprises an amino acid sequence with 100% identity to SEQ ID NO: 484. In certain embodiments, the heavy chain antibody comprises an amino acid sequence with at least 80%, 90%, 95%, 97%, or 99% identity to SEQ ID NO: 485. In certain embodiments, the heavy chain antibody comprises an amino acid sequence with 100% identity to SEQ ID NO: 485. In certain embodiments, the heavy chain antibody comprises an amino acid sequence with at least 80%, 90%, 95%, 97%, or 99% identity to SEQ ID NO: 486. In certain embodiments, the heavy chain antibody comprises an amino acid sequence with 100% identity to SEQ ID NO: 486. In certain embodiments, the heavy chain antibody comprises an amino acid sequence with at least 80%, 90%, 95%, 97%, or 99% identity to SEQ ID NO: 487. In certain embodiments, the heavy chain antibody comprises an amino acid sequence with 100% identity to SEQ ID NO: 487. In certain embodiments, the heavy chain antibody comprises an amino acid sequence with at least 80%, 90%, 95%, 97%, or 99% identity to SEQ ID NO: 488. In certain embodiments, the heavy chain antibody comprises an amino acid sequence with 100% identity to SEQ ID NO: 488.

TABLE 1 unique SEQ IDs for CDRs of the $V_HH$ antibodies of this disclosure

| Clone | NBX | CDR1 Amino Acid Sequence | CDR1 SEQ ID NO: | CDR2 Amino Acid Sequence | CDR2 SEQ ID NO: | CDR3 Amino Acid Sequence | CDR3 SEQ ID NO: | Antigen |
|---|---|---|---|---|---|---|---|---|
| 1 | 0001 | GSIFSINAM | 1 | ITTGGNTANT | 92 | AARGLSYEYDY | 183 | Flagella |
| 2 | 0002 | GSIFSINAM | 2 | ITITSGRGGNT | 93 | AARGAMTYEYDY | 184 | Flagella |
| 3 | 0004 | GIIFSPNAM | 3 | ITSFGII | 94 | NAKTFDGTRWRDY | 185 | Flagella |
| 4 | 0006 | GNIFSINAM | 4 | ITTGGSYGNT | 95 | AARGSQTYEYDY | 186 | Flagella |
| 5 | 0005 | GRSVSINPM | 5 | LLPSGRT | 96 | NTADF | 187 | Flagella |
| 6 | 0011 | GISVNINPM | 6 | LLPTGTT | 97 | YCNTADF | 188 | Flagella |
| 7 | 0012 | GSTFSINAM | 7 | ISRAGST | 98 | KASSGSSVYIGFGS | 189 | Flagella |
| 8 | 0013 | VSINPM | 8 | LLSMARA | 99 | NTTDF | 190 | Flagella |
| 9 | 0017 | GRIFSSYDM | 9 | IRWGNGNT | 100 | AARIVNGGSWDY | 191 | Flagella |

TABLE 1-continued unique SEQ IDs for CDRs of the V$_H$H antibodies of this disclosure

| Clone | NBX | CDR1 Amino Acid Sequence | CDR1 SEQ ID NO: | CDR2 Amino Acid Sequence | CDR2 SEQ ID NO: | CDR3 Amino Acid Sequence | CDR3 SEQ ID NO: | Antigen |
|---|---|---|---|---|---|---|---|---|
| 10 | 0042 | GSIESIRSM | 10 | 1TRSGST | 101 | NADFYGLYPRQY | 192 | Flagella |
| 11 | 0016 | GRIFSSYDM | 11 | IRWGNGNT | 102 | AARGLAYEYEY | 193 | Flagella |
| 12 | 0015 | GRTFSNNAM | 12 | ISRAGNT | 103 | KASSGSSVYIGVGS | 194 | Flagella |
| 13 | 0014 | GRTFSRLAM | 13 | ISWSGGNT | 104 | AAPERSGSYAYTPSRLNEYAY | 195 | Flagella |
| 14 | 0009 | GRMFSSYDM | 14 | ITKNGRTT | 105 | AGRRSNADNWDY | 196 | Flagella |
| 15 | 0010 | GSIFSINAV | 15 | IGTGGSSGNT | 106 | AARGTISYEYDY | 197 | Flagella |
| 16 | 0008 | GRIFSSYDM | 16 | IRWGNGNT | 107 | ATRIVNGGSWDY | 198 | Flagella |
| 17 | 0043 | GRIFS1NPM | 17 | LMTGGKTPDA | 108 | YNCDFWGLAYEYDY | 199 | Flagella |
| 18 | 0007 | GRIFSIYDM | 18 | ITWGNGNT | 109 | PARIVNGGSWDY | 200 | Flagella |
| 19 | 0044 | GFTFSSAWM | 19 | IYPSGSST | 110 | ATASRRGVVSLTSNPSTSRNDFSS | 201 | FliC |
| 20 | 0018 | GIIFSPNAM | 20 | ITSFGII | 111 | NAKTFDGTRWHDY | 202 | FliC |
| 21 | 0019 | GIIFSPNAM | 21 | ITSFGII | 112 | NAKAFDGTRWHDY | 203 | FliC |
| 22 | 0020 | GIIFSPNAL | 22 | IISGGRS | 113 | NANVYDGNRWRTY | 204 | FliC |
| 23 | 0045 | GIIFSPNAM | 23 | ITSFG11 | 114 | NAKSFDGSRAINDY | 205 | FliC |
| 24 | 0046 | GRSVSINPM | 24 | LLPSGRT | 115 | NTADF | 206 | FliC |
| 25 | 0047 | VFILNAM | 25 | 11SFGIK | 116 | NGKAFDFNRWHDY | 207 | FliC |
| 26 | 0048 | REFFTTDAM | 26 | KSSGADP | 117 | YRKGQYYRGTYWDNFES | 208 | FliC |
| 27 | 0049 | VRAFSSRAM | 27 | ISSSGSSI | 118 | AAVRPYGSGTYSRTEAYNF | 209 | FliC |
| 28 | 0050 | GGTFSDYAW | 28 | ISWTGGII | 119 | AAVGRILGWIPTIVIYRQAASYDY | 210 | FliC |
| 29 | 0051 | GIIFSPNAM | 29 | ITSFGII | 120 | NAKSFDGTRWVEH | 211 | FliC |
| 30 | 0052 | GIIFSPNAM | 30 | ITSFGII | 121 | NAKAFDGTRWRDY | 212 | FliC |
| 31 | 0053 | GITNRITTM | 31 | IRDDRDAN | 122 | NVQTIIRNY | 213 | FliC |
| 32 | 0054 | GSVRTINDM | 32 | 1SSGGNT | 123 | SQRGQYFTEGYWKEYDN | 214 | FliC |
| 33 | 0055 | GIIFSPNAM | 33 | ITSFG11 | 124 | NANVYDGNRWRTY | 215 | FliC |

TABLE 1-continued unique SEQ IDs for CDRs of the V$_H$H antibodies of this disclosure

| Clone | NBX | CDR1 Amino Acid Sequence | CDR1 SEQ ID NO: | CDR2 Amino Acid Sequence | CDR2 SEQ ID NO: | CDR3 Amino Acid Sequence | CDR3 SEQ ID NO: | Antigen |
|---|---|---|---|---|---|---|---|---|
| 34 | 0021 | GRTFRSYTM | 34 | ISWSAGST | 125 | AAGTKYSDTIITWGS | 216 | FliC |
| 35 | 0032 | GIIFSPNAM | 35 | ITSSGII | 126 | NAKAFDGTRWYDY | 217 | FliC |
| 36 | 0033 | GRTFSSYVM | 36 | ISWSGGSS | 127 | AARTALGGTYDY | 218 | FliC |
| 37 | 0056 | FLENPPFAI | 37 | ITYCVMEI | 128 | HPHF | 219 | FliC |
| 38 | 0022 | GSTVTISTV | 38 | ISSDSTT | 129 | NVVGTYWTGADWRPFDT | 220 | FliC |
| 39 | 0034 | GIIFNPNAM | 39 | ITSFGII | 130 | NAITFYGTRWLDY | 221 | FliC |
| 40 | 0035 | GIIFSPNAL | 40 | IISGGRS | 131 | NADVYDGNRWRTY | 222 | FliC |
| 41 | 0036 | GIIFSPNAM | 41 | ITSFGII | 132 | FAKTFDGTRWCDY | 223 | FliC |
| 42 | 0037 | GIIFSPNAL | 42 | IISGGRS | 133 | NAIVYDGNRWRTY | 224 | FliC |
| 43 | 0057 | GIFESTFDATAM | 43 | IGSRGSI | 134 | NSVGH | 225 | FimA |
| 44 | 0024 | GSIFSTNVM | 44 | ITSGGNT | 135 | AAQTLGSSYYDA | 226 | FimA |
| 45 | 0058 | GRTFDKYRI | 45 | ISWNGAYT | 136 | AAVQSTVIQTSPNRYNY | 227 | FimA |
| 46 | 0059 | GRTFINRSM | 46 | 1SSSGSNT | 137 | AAARLGWGLTISDRIYEY | 228 | FimA |
| 47 | 0025 | GFTFSMYGM | 47 | INSGGART | 138 | AKASLPWFDGSSPDY | 229 | FimA |
| 48 | 0026 | GLTFSSYGM | 48 | IKMSGDT | 139 | AAARVRTPGWGPQKSYDY | 230 | FimA |
| 49 | 0027 | GRTFSSYAM | 49 | INWSGGRI | 140 | NADYDNSGSYYYQKGNYEYDY | 231 | FimA |
| 50 | 0060 | GRDASDGTESRYVM | 50 | MRWNTGSE | 141 | TADGPPDYGKYDY | 232 | FimA |
| 51 | 0028 | GRTFGSLHM | 51 | ISAAGGVT | 142 | AAVKYWGRRQRADEYDY | 233 | FimA |
| 52 | 0061 | GFTFDDYVI | 52 | TSSSDGDT | 143 | AAELSLNPGKRLTLE1LKYDY | 234 | FimA |
| 53 | 0062 | GFRLNDYYV | 53 | TGSRSGRL | 144 | AAGYGAGDVKRALSSCRGSYVY | 235 | FimA |
| 54 | 0063 | GIIFRINTM | 54 | ITRAGST | 145 | KMNHQLYSDSSYENVY | 236 | FimA |
| 55 | 0064 | GFTLGYFAI | 55 | ISNSDGST | 146 | ATDTWGNSRCDHDMRY | 237 | FimA |
| 56 | 0040 | GLAFNTKTM | 56 | ITWGTINT | 147 | ESEALLETTPSRRPYEYNY | 238 | FimA |

TABLE 1-continued unique SEQ IDs for CDRs of the $V_HH$ antibodies of this disclosure

| Clone | NBX | CDR1 Amino Acid Sequence | CDR1 SEQ ID NO: | CDR2 Amino Acid Sequence | CDR2 SEQ ID NO: | CDR3 Amino Acid Sequence | CDR3 SEQ ID NO: | Antigen |
|---|---|---|---|---|---|---|---|---|
| 57 | 0065 | GFTESRYLM | 57 | VNSGGAMT | 148 | AKGQREYYNDFEFDY | 239 | FimA |
| 58 | 0041 | GRIFGSLHM | 58 | ITAAGGVT | 149 | RTLGCSYYERADEYNY | 240 | FimA |
| 59 | 0029 | GSISSIKAM | 59 | WRMYSGT | 150 | YLEIPESRGAF | 241 | FimA |
| 60 | 0030 | GRTFSRDAM | 60 | INWNGRST | 151 | AAGEWGIRPYNYDY | 242 | FimA |
| 61 | 0031 | GRTFSSYAM | 61 | INWSGGRI | 152 | NTDYDNSGSYYYQKGNYEYDY | 243 | FimA |
| 62 | 0066 | GRTFS1YAM | 62 | ININSGGRI | 153 | NANYDNNGSYYYQKGNYEYDY | 244 | FimA |
| 63 | 0067 | GLAFSTKTM | 63 | 1TWGTSST | 154 | AAAALLETTPSRRPSAYNY | 245 | Prgl |
| 64 | 0068 | GRTFSSNTM | 64 | 1ASSDGAT | 155 | AGAWGYAGIIPRGAYDD | 246 | Prgl |
| 65 | 0069 | GRTESSYGM | 65 | 1KVSGDT | 156 | AAARIRTPGWGPQKSYDY | 247 | Prgl |
| 66 | 0070 | GRALSAYIM | 66 | 1SSSGSNT | 157 | AAGVVTAQAIMAARDFDY | 248 | Prgl |
| 67 | 0071 | VRTFNTYNI | 67 | ISWGRGNT | 158 | AADRSREGRTRPNEYDY | 249 | Prgl |
| 68 | 0023 | GRSFSSYNM | 68 | ITWSGNT | 159 | KVRAEDTDYAAPERSGSY | 250 | Prgl |
| 69 | 0072 | ERTFSSYTM | 69 | ISWSGGNT | 160 | AYTPSRLNEYAY | 251 | Prgl |
| 70 | 0073 | GTFFRINYM | 70 | 1SSGGST | 161 | NADFYGLYPRQY | 252 | Prgl |
| 71 | 0038 | GRTFSSYAM | 71 | IRWTRSST | 162 | AADRYYRTDIYRASSYEY | 253 | Prgl |
| 72 | 0074 | GFNFSLYSM | 72 | ISNLSVRT | 163 | AKGWTVDVNHIED | 254 | Prgl |
| 73 | 0075 | ARILSSFIRM | 73 | IRWGSGST | 164 | AAKYGGTDLLSRYEY | 255 | Prgl |
| 74 | 0076 | GFILDNYAI | 74 | ISRSDGDT | 165 | ASVYSFDPGRCGPIATMVGHY | 256 | Prgl |
| 75 | 0077 | GFMPDYSAL | 75 | ISRDGHTY | 166 | ATDAAGGRGSFFIDHKRTCPSEEYDS | 257 | Prgl |
| 76 | 0078 | LYSLRTRLQYL | 76 | TYWPIECH | 167 | TADGPPDYGKYDY | 258 | Prgl |
| 77 | 0079 | GFTESSYWM | 77 | 1DTGGGST | 168 | ARVSVIRPPYGVYSDFGS | 259 | Prgl |
| 78 | 0080 | GFTESNFWM | 78 | LNTGGGAT | 169 | TLYGSGAAEKFHS | 260 | Prgl |

TABLE 1-continued unique SEQ IDs for CDRs of the V$_H$H antibodies of this disclosure

| Clone | NBX | CDR1 Amino Acid Sequence | CDR1 SEQ ID NO: | CDR2 Amino Acid Sequence | CDR2 SEQ ID NO: | CDR3 Amino Acid Sequence | CDR3 SEQ ID NO: | Antigen |
|---|---|---|---|---|---|---|---|---|
| 79 | 0081 | ARTFSSYAM | 79 | 1SWDGATT | 170 | AANWGRRRVPTTVHEYDV | 261 | Prg1 |
| 80 | 0082 | GRTFINRSM | 80 | GSSGSYS | 171 | AAARLGWGLTISDRIYEY | 262 | Prg1 |
| 81 | 0083 | GFTLDYFA1 | 81 | ISNIDGIT | 172 | ATDTWGNSRCDHDMRY | 263 | Prg1 |
| 82 | 0084 | GRTFSMYAM | 82 | 1NWSGAST | 173 | AAGSFSDNKYYTRSQDYEH | 264 | Prg1 |
| 83 | 0085 | VHSFSNYAL | 83 | 1TWNAES | 174 | AASSWCQTFDAKYGY | 265 | Prg1 |
| 84 | 0039 | GRPFINYNM | 84 | ISWSGDST | 175 | AADNQHDIPLRPG | 266 | Prg1 |
| 85 | 0086 | AFTFDDFAV | 85 | LSSSDGST | 176 | HPSDTTGWTRGRAY | 267 | Prg1 |
| 86 | 0087 | GESLDHSAI | 86 | VHHDGTA | 177 | ATACTRLWKPGRDY | 268 | Prg1 |
| 87 | 0088 | GFDFNIYWM | 87 | IRSTGDTI | 178 | MRDFYT | 269 | Prg1 |
| 88 | 0089 | GRTLRSYVM | 88 | LSWSGIST | 179 | AAASTIKHCYTAVSYYTKDAQYDY | 270 | Prg1 |
| 89 | 0090 | GL1FGDYVM | 89 | ISSDSTT | 180 | NVVGTYWTGADWRPFDT | 271 | Prg1 |
| 90 | 0091 | GRTFSNLAM | 90 | IWSDNT | 181 | GVARDSRSYYNFRLNQEDEYDY | 272 | Prg1 |
| 91 | 0092 | GRTFSSYAM | 91 | IRWTRSST | 182 | AASHGIGRVVAESLYDY | 273 | Prg1 |

TABLE 2 unique SEQ IDs for CDRs of the V$_H$H antibodies of this disclosure

| Clone | NBX | CDR1 Amino Acid Sequence | CDR1 SEQ ID NO: | CDR2 Amino Acid Sequence | CDR2 SEQ ID NO: | CDR3 Amino Acid Sequence | CDR3 SEQ ID NO: | Antigen |
|---|---|---|---|---|---|---|---|---|
| 92 | 0100 | GSIFSTNLM | 765 | ITSGGNT | 769 | AAQTLGSSYYDA | 773 | FimA |
| 93 | 0104 | GVAFNSRIM | 766 | ITSGGST | 770 | NIRNY | 774 | Prg1 |
| 94 | 0105 | GRTFNTYYM | 767 | IRWSDGGT | 771 | NANVYDGNRWRTY | 775 | Prg1 |
| 95 | 0108 | RGTFRTYSM | 768 | ITWNGKYT | 772 | AANPIPTAQPPGIMAARSYVH | 776 | Prg1 |
| 97 | 0200 | GRTSSSAYT | 280 | ISWSGTTT | 330 | AADRRSTIGSPRQQYAY | 380 | FimA |

TABLE 2-continued unique SEQ IDs for CDRs of the V$_H$H antibodies of this disclosure

| Clone | NBX | CDR1 Amino Acid Sequence | CDR1 SEQ ID NO: | CDR2 Amino Acid Sequence | CDR2 SEQ ID NO: | CDR3 Amino Acid Sequence | CDR3 SEQ ID NO: | Antigen |
|---|---|---|---|---|---|---|---|---|
| 98 | 0201 | TRTSSSSYT | 281 | ISYSGTTT | 331 | AADRRSTIGSPRQQYAY | 381 | FimA |
| 99 | 0202 | GRTSSSAYT | 282 | ISWSGTTT | 332 | AADRRSTIGTPREQYAY | 382 | FimA |
| 100 | 0203 | GRTSPSSYT | 283 | ISWSGTTT | 333 | AADRRSTIGSPRQQYAY | 383 | FimA |
| 101 | 0204 | GSTLSNYAV | 284 | ISSGGST | 334 | HTYDFQGWGLRSDY | 384 | FliC |
| 102 | 0205 | GRTFSSLAM | 285 | ISRSGDYT | 335 | AATKIVTPWTSTYYYTKAYEWDY | 385 | FliC |
| 103 | 0206 | GRTFSSLAM | 286 | ITRSGDYT | 336 | AATKIVTPWTSTYYYTKAYEWDY | 386 | FliC |
| 104 | 0207 | TAILSIDSM | 287 | IARGGST | 337 | AADPGGASPLS | 387 | PrgI |
| 105 | 0208 | GDISTIDVM | 288 | IARGGTI | 338 | AVDTGSPRLT | 388 | PrgI |
| 106 | 0209 | GFTFSSSIM | 289 | IPSFGSA | 339 | NTRLY | 389 | PrgI |
| 107 | 0210 | GDISSISVM | 290 | IASGGSV | 340 | AVDTGSPRLT | 390 | PrgI |
| 108 | 0211 | GFTFSTNIL | 291 | ITPFGSA | 341 | NTQLY | 391 | PrgI |
| 109 | 0212 | TSILSINAM | 292 | IAPGGTT | 342 | AADPGGQSPLS | 392 | PrgI |
| 110 | 0213 | GSISSITAM | 293 | IARGGMI | 343 | AVDNGDPRLH | 393 | PrgI |
| 111 | 0214 | GSISSITAM | 294 | IARGGMT | 344 | ALDNGDPRLH | 394 | PrgI |
| 112 | 0215 | GFTFSSAIM | 295 | IPSFGSA | 345 | NTRLY | 395 | PrgI |
| 113 | 0216 | TSILSIDAM | 296 | IARGGST | 346 | AADPGGASGLS | 396 | PrgI |
| 114 | 0217 | GSISSITAM | 297 | IARGGMT | 347 | ALYNGDPRLH | 397 | PrgI |
| 115 | 0218 | GSAFSGDAM | 298 | ISSGAIT | 348 | NRIQAVLRGNSG | 398 | PrgI-SipD |
| 116 | 0219 | GSAFSGGDAM | 299 | ISSGGIA | 349 | NSITAVLRGNSG | 399 | PrgI-SipD |
| 117 | 0220 | GSAFSGDAM | 300 | ISSGGIP | 350 | NSISAVLRGNGV | 400 | PrgI-SipD |
| 118 | 0221 | GLTFNNYAM | 301 | ISRDGTNT | 351 | GVGRGTGYAYTAINEYDYSK | 401 | PrgI-SipD |
| 119 | 0222 | GIDSSFYVM | 302 | LGTPDSA | 352 | YGLYRQVY | 402 | PrgI-SipD |
| 120 | 0223 | GIDSSFYVM | 303 | ISSADSP | 353 | YGLYRQVH | 403 | PrgI-SipD |
| 121 | 0224 | GLTFSSYAM | 304 | IGWSGGST | 354 | AARRTTAWGKGTDY | 404 | PrgI-SipD |

TABLE 2-continued unique SEQ IDs for CDRs of the V<sub>H</sub>H antibodies of this disclosure

| Clone | NBX | CDR1 Amino Acid Sequence | CDR1 SEQ ID NO: | CDR2 Amino Acid Sequence | CDR2 SEQ ID NO: CDR1 SEQ ID NO: | CDR3 Amino Acid Sequence | CDR3 SEQ ID NO: | Antigen |
|---|---|---|---|---|---|---|---|---|
| 122 | 0225 | ESIFSRNA | 305 | IGSDGST | 355 | RVVLATSPYNY | 405 | PrgI-SipD |
| 123 | 0226 | GITSSLYVM | 306 | INSGDSP | 356 | YGLYRQVH | 406 | PrgI-SipD |
| 124 | 0227 | GLTFNNYAM | 307 | ISRDGTST | 357 | GVGRGSGYAYSAINEYDYSS | 407 | PrgI-SipD |
| 125 | 0228 | GIDSSFYVM | 308 | ISMTSADSP | 358 | YGLYRQVH | 408 | PrgI-SipD |
| 126 | 0229 | GSGILFRISA | 309 | ISSGGST | 359 | NIVGRTDS | 409 | PrgI-SipD |
| 127 | 0230 | ARTLSNYAM | 310 | ISRSGGSI | 360 | GRARGTGYAYTALNQYDYDY | 410 | PrgI-SipD |
| 128 | 0231 | GSAFSGDAM | 311 | ISSGGIT | 361 | NSIKAVLRGNSG | 411 | PrgI-SipD |
| 129 | 0232 | GLTFHNYAM | 312 | ISRDGTNT | 362 | GVGRGSGYAYTAINEYDYSK | 412 | PrgI-SipD |
| 130 | 0233 | GSAFSGDAM | 313 | ISSGHIT | 363 | NSITAVLRGNSG | 413 | PrgI-SipD |
| 131 | 0234 | GRTFSTYA | 314 | ISRSGDNI | 364 | GRARGTGYAHTALNQYDYDY | 414 | PrgI-SipD |
| 132 | 0235 | GSAFSGDAM | 315 | ISSGGIE | 365 | NLIKAVLRGNSG | 415 | PrgI-SipD |
| 133 | 0236 | GLTFNNYAM | 316 | ISRDGTNT | 366 | GVGRGTGYAYTAIREHDYSS | 416 | PrgI-SipD |
| 134 | 0237 | GSAFSGDAM | 317 | ISSGGIT | 367 | NSITAVLRGNSG | 417 | SipD |
| 135 | 0238 | GSAFSGDAM | 318 | ISSGGIA | 368 | NTIKAVLRGNAG | 418 | SipD |
| 136 | 0239 | GSAFSGDAM | 319 | ISSGAIT | 369 | NSITAVLRGNS | 419 | SipD |
| 137 | 0240 | GSAFSGDAM | 320 | ISSGGIT | 370 | NIISAVLRGNGG | 420 | SipD |
| 138 | 0241 | ISGFSGDAM | 321 | ISSGGIT | 371 | NTITGVLRGNSG | 421 | SipD |
| 139 | 0242 | GIISSAYVM | 322 | ITSGDSP | 372 | YGLYRQVY | 422 | SipD |
| 140 | 0243 | GIAFSTYGM | 323 | ITGNGDD | 373 | NIGMY | 423 | SipD |
| 141 | 0244 | GSAFSGDAM | 324 | ISSGGIT | 374 | NSISAVLRGNSG | 424 | SipD |
| 142 | 0245 | GSAFSGDAM | 325 | ISSGGIT | 375 | NSISAVLRGNGG | 425 | SipD |
| 143 | 0246 | GSAFSGDAM | 326 | ISSGGIT | 376 | NSITAVLRGNSD | 426 | SipD |
| 144 | 0247 | GSAFSGDAM | 327 | ISSGGIP | 377 | NIIKTVLRGNAV | 427 | SipD |
| 145 | 0248 | GSAFSGGDAM | 328 | ISSGGIT | 378 | NSITAVLRGNSG | 428 | SipD |

TABLE 2-continued unique SEQ IDs for CDRs of the V$_H$H antibodies of this disclosure

| Clone | NBX | CDR1 Amino Acid Sequence | CDR1 SEQ ID NO: | CDR2 Amino Acid Sequence | CDR2 SEQ ID NO: | CDR3 Amino Acid Sequence | CDR3 SEQ ID NO: | Antigen |
|---|---|---|---|---|---|---|---|---|
| 146 | 0249 | GITFSSDAM | 329 | ISSGDIT | 379 | NTITRLLYGMDY | 429 | SipD |
| 147 | 0250 | GFTLDGYAI | 573 | IIYRDGSP | 574 | AARPGGACSRYPSNYDT | 575 | FimA |

Generic Framework Regions

A full heavy chain variable region will generally comprise the structure according to Framework1-CDR1-Framework2-CDR2-Framework 3-CDR3-Framework 4. The CDRs listed in tables 1 and 2 can be combined with the framework regions listed in SEQ ID NOs: 573-613 (FR1); 614-669 (FR2); 670-752 (FR3); and 753-764 (FR4) for recombinant construction of an anti-*Salmonella* V$_H$H.

In Vivo Stability of V$_H$Hs

For passive immunization or oral administration, the V$_H$Hs described herein should be stable in a GI environment. The V$_H$Hs of this disclosure exhibit stability in GI tract fluids from a chicken. In certain instances, the V$_H$Hs exhibit less than 50%, 40%, 30%, 20%, 10%, 5% or less degradation when incubated at 42° for 30 minutes in gizzard extract. In certain embodiments, the V$_H$Hs exhibit less than 50%, 40%, 30%, 20%, 10%, 5% or less degradation when incubated at 37° at a pH of about 3 for 30 minutes to an hour. In certain embodiments, the V$_H$Hs exhibit less than 50%, 40%, 30%, 20%, 10%, 5% or less degradation when incubated with human gastric fluid or an acceptable substitute for 30 minutes to an hour at 37°.

Bacterial Antigens

Flagella/FliC: Flagella are large, whip-like, multi-component structures that are anchored to the cell envelope of the bacteria and project outside of the cell. Each flagellum consists of tens of thousands of molecules of the FliC subunits plus a number of other accessory proteins. An individual *Salmonella* cell possesses many flagella found all over the cell body (peritrichous flagella). Bacteria rotate their flagella in an energy-dependent manner, to propel themselves (swimming motility) towards attractants and away from repellents.

FimA: Type-1 fimbriae are thin appendages found on the surfaces of many bacteria and project out from the cell. Type-1 fimbriae consists of thousands of subunits of FimA plus a number of other accessory proteins. Type-1 fimbriae allow *Salmonella* to bind to eukaryotic cells via a high-affinity interaction between one of the accessory proteins, the lectin domain of FimH, and mannose sugars located on the outside of eukaryotic cells. This interaction allows *Salmonella* to adhere to eukaryotic tissues.

PrgI and SipD: The Type III Secretion System is a needle-like protein complex that protrudes from the surface of Gram-negative bacteria, interacts with host cell membranes, and injects effector proteins into the host cytoplasm. The Type III Secretion System needle is constructed from hundreds of molecules of PrgI. The tip of the needle is constructed from a ring of SipD proteins, which is necessary for the interaction between the secretion system and the eukaryotic cells.

In certain embodiments, the antibodies for use with the compositions and methods described herein specifically bind to any biomolecule of Enterobacteriaceae. In certain embodiments, the antibodies for use with the compositions and methods described herein specifically bind to any biomolecule of *Salmonella*. In certain embodiments, the biomolecule of *Salmonella* may function in bacterial motility. In certain embodiments, the *Salmonella* biomolecule may be a component of the flagellum. In certain embodiments, the *Salmonella* biomolecule may be a protein or polypeptide component of the flagellum. In certain embodiments, the antibody may specifically bind the *Salmonella* flagellin protein (FliC). In certain embodiments, the biomolecule of *Salmonella* may function in bacterial adhesion. In certain embodiments, the antibody may specifically bind the *Salmonella* fimbrial protein subunit A protein (FimA). In certain embodiments, the biomolecule of *Salmonella* may function in bacterial invasion. In certain embodiments, the antibody may specifically bind the *Salmonella* PrgI protein. In certain embodiments, the antibody may specifically bind the *Salmonella* SipD protein. In certain embodiments, the antibody does not specifically bind bacterial lipopolysaccharide (LPS). In certain embodiments, the antibody does not specifically bind bacterial O-antigen. In certain embodiments, the antibody does not specifically bind FimH or OmpD. The specific antigens disclosed herein FliC, FimA, and PrgI are highly variable among *Salmonella* serovars, for example, the sequence identity between Enteritidis and Newport FliC protein is 48%. It will be appreciated by one of skill in the art that antigens derived from the same genes of different serovars will perform similarly. In certain embodiments, the antibody may be raised against a component of *Salmonella* flagellum. In certain embodiments, the antibody may be raised against a protein or polypeptide with at least 40% sequence identity to SEQ ID NO: 274 or SEQ ID NO: 277. In certain embodiments, the antibody may be raised against a protein or polypeptide with at least 40% sequence identity to SEQ ID NO: 275 or SEQ ID NO: 278. In certain embodiments, the antibody may be raised against a protein or polypeptide with at least 40% sequence identity to SEQ ID NO: 276 or SEQ ID NO: 279. In certain embodiments, the antibody may be raised against a component of *Salmonella* flagellum. In certain embodiments, the antibody may be raised against a protein or polypeptide with at least 50% sequence identity to SEQ ID NO: 274 or SEQ ID NO: 277. In certain embodiments, the antibody may be raised against a protein or polypeptide with at least 50% sequence identity to SEQ ID NO: 275 or SEQ ID NO: 278. In certain embodiments, the antibody may be raised against a protein or polypeptide with at least 50% sequence identity to SEQ ID NO: 276 or SEQ ID NO: 279. In certain embodiments, the antibody may be raised against a component of *Salmonella* flagellum. In certain embodiments, the antibody may be raised against a protein or polypeptide with at least 60% sequence identity to SEQ ID NO: 274 or SEQ ID NO: 277. In certain embodiments, the antibody may be raised against a protein or polypeptide with at least 60% sequence identity to SEQ ID NO: 275 or SEQ ID NO: 278. In certain embodiments, the antibody may be raised against a protein or polypeptide with at least 60% sequence identity to SEQ ID NO: 276 or SEQ ID NO: 279. In certain embodiments, the antibody may be raised against a component of *Salmonella* flagellum. In certain embodiments, the antibody may be raised against a protein or polypeptide with at least 70% sequence identity to SEQ ID NO: 274 or SEQ ID NO: 277. In certain embodiments, the antibody may be raised against a protein or polypeptide with at least 70% sequence identity to SEQ ID NO: 275 or SEQ ID NO: 278. In certain embodiments, the antibody may be raised against a protein or polypeptide with at least 70% sequence identity to SEQ ID NO: 276 or SEQ ID NO: 279. In certain embodiments, the antibody may be raised against a protein or polypeptide with at least 80% sequence identity to SEQ ID NO: 274 or SEQ ID NO: 277. In certain embodiments, the antibody may be raised against a protein or polypeptide with at least 80% sequence identity to SEQ ID NO: 275 or SEQ ID NO: 278. In certain embodiments, the antibody may be raised against a protein or polypeptide with at least 80% sequence identity to SEQ ID NO: 276 or SEQ ID NO: 279. In certain embodiments, the antibody may be raised against a protein or polypeptide with at least 90% sequence identity to SEQ ID NO: 274 or SEQ ID NO: 277. In certain embodiments, the antibody may be raised against a protein or polypeptide with at least 90% sequence identity to SEQ ID NO: 275 or SEQ ID NO: 278. In certain embodiments, the antibody may be raised against a protein or polypeptide with at least 90% sequence identity to SEQ ID NO: 276 or SEQ ID NO: 279. In certain embodiments, the antibody may be raised against a protein or polypeptide with at least 95% sequence identity to SEQ ID NO: 274 or SEQ ID NO: 277. In certain embodiments, the antibody may be raised against a protein or polypeptide with at least 95% sequence identity to SEQ ID NO: 275 or SEQ ID NO: 278. In certain embodiments, the antibody may be raised against a protein or polypeptide with at least 95% sequence identity to SEQ ID NO: 276 or SEQ ID NO: 279. In certain embodiments, the antibody may be raised against a protein or polypeptide with at least 98% sequence identity to SEQ ID NO: 274 or SEQ ID NO: 277. In certain embodiments, the antibody may be raised against a protein or polypeptide with at least 98% sequence identity to SEQ ID NO: 275 or SEQ ID NO: 278. In certain embodiments, the antibody may be raised against a protein or polypeptide with at least 98% sequence identity to SEQ ID NO: 276 or SEQ ID NO: 279. In certain embodiments, the antibody may be raised against a protein or polypeptide with 100% sequence identity to SEQ ID NO: 274 or SEQ ID NO: 277. In certain embodiments, the antibody may be raised against a protein or polypeptide with 100% sequence identity to SEQ ID NO: 275 or SEQ ID NO: 278. In certain embodiments, the antibody may be raised against a protein or polypeptide with 100% sequence identity to SEQ ID NO: 276 or SEQ ID NO: 279. In certain embodiments, the antibody may be raised against a protein or polypeptide with at least 40% sequence identity to SEQ ID NO: 460 or SEQ ID NO: 461. In certain embodiments, the antibody may be raised against a protein or polypeptide with at least 50% sequence identity to SEQ ID NO: 460 or SEQ ID NO: 461. In certain embodiments, the antibody may be raised against a protein or polypeptide with at least 60% sequence identity to SEQ ID NO: 460 or SEQ ID NO: 461. In certain embodiments, the antibody may be raised against a protein or polypeptide with at least 70% sequence identity to SEQ ID NO: 460 or SEQ ID NO: 461. In certain embodiments, the antibody may be raised against a protein or polypeptide with at least 80% sequence identity to SEQ ID NO: 460 or SEQ ID NO: 461. In certain embodiments, the antibody may be raised against a protein or polypeptide with at least 90% sequence identity to SEQ ID NO: 460 or SEQ ID NO: 461. In certain embodiments, the antibody may be raised against a protein or polypeptide with at least 95% sequence identity to SEQ ID NO: 460 or SEQ ID NO: 461. In certain embodiments, the antibody may be raised against a protein or polypeptide with at least 98% sequence identity to SEQ ID NO: 460 or SEQ ID NO: 461. In certain embodiments, the antibody may be raised against a protein or polypeptide with 100% sequence identity to SEQ ID NO: 460 or SEQ ID NO: 461.

Reduction in Bacterial Motility

*Salmonella* bacteria possess the ability to move towards attractants and away from repellents by means of flagella-dependent swimming motility. Within the GI tract of an animal *Salmonella* bacteria encounter numerous stimuli to which the bacteria would move towards or away from. Several studies have suggested that correlation exists between motility and the ability of *Salmonella* to colonize the GI tract. In certain embodiments, the antibodies for use with the compositions and methods described herein reduce bacterial motility. In certain embodiments, the antibody that reduces motility targets a component of the bacterial flagellum. In certain embodiments, the antibody that reduces motility targets the FliC antigen. In certain embodiments, the antibodies for use with the compositions and methods described herein reduce bacterial motility in an in vitro assay. In certain embodiments, the antibody reduces bacterial motility compared to a negative control antibody. In certain embodiments, the antibody reduces bacterial motility by at least 10% compared to a negative control antibody. In certain embodiments, the antibody reduces bacterial motility by at least 20% compared to a negative control antibody. In certain embodiments, the antibody reduces bacterial motility by at least 30% compared to a negative control antibody. In certain embodiments, the antibody reduces bacterial motility by at least 40% compared to a negative control antibody. In certain embodiments, the antibody reduces bacterial motility by at least 50% compared to a negative control antibody. In certain embodiments, the antibody reduces bacterial motility by at least 60% compared to a negative control antibody. In certain embodiments, the antibody reduces bacterial motility by at least 70% compared to a negative control antibody. In certain embodiments, motility is reduced at a concentration of less than 10 µM, 25 µM, 50 µM, 75 µM, 100 µM, 125 µM, 150 µM, 175 µM, 200 µM, 300 µM, 400 µM, or 500 µM. In certain embodiments, a negative control antibody is an isotype control, a non-targeting antibody, or a pre-immune serum.

Reduction in Bacterial Adhesion

*Salmonella* bacteria use adhesins located on their surface to contact and attach to epithelial cells prior to invading the epithelial cells. *Salmonella* possesses several putative adhesins that are thought to participate in adhesion to animal epithelial cells. Reduction in adhesion may contribute to decreased ability to colonize an animal. In certain embodiments, the antibodies for use with the compositions and methods described herein reduce bacterial adhesion. In certain embodiments, the antibody that reduces adhesion targets a component of the bacterial fimbriae. In certain embodiments, the antibody that reduces adhesion targets the FimA antigen. In certain embodiments, the antibodies for use with the compositions and methods described herein reduce bacterial adhesion in an in vitro assay. In certain embodiments, the antibody reduces bacterial adhesion compared to a negative control antibody. In certain embodiments, the antibody reduces bacterial adhesion by at least 10% compared to a negative control antibody. In certain embodiments, the antibody reduces bacterial adhesion by at least 20% compared to a negative control antibody. In certain embodiments, the antibody reduces bacterial adhesion by at least 30% compared to a negative control antibody. In certain embodiments, the antibody reduces bacterial adhesion by at least 40% compared to a negative control antibody. In certain embodiments, the antibody reduces bacterial adhesion by at least 50% compared to a negative control antibody. In certain embodiments, the antibody reduces bacterial adhesion by at least 60% compared to a negative control antibody. In certain embodiments, the antibody reduces bacterial adhesion by at least 70% compared to a negative control antibody. In certain embodiments, adhesion is reduced at a concentration of less than 10 µM, 25 µM, 50 µM, 75 µM, 100 µM, 125 µM, 150 µM, 175 µM, 200 µM, 300 µM, 400 µM, or 500 µM. In certain embodiments, a negative control antibody is an isotype control, a non-targeting antibody, or a pre-immune serum.

Reduction in Bacterial Invasion

To successfully colonize the GI tract of an animal, *Salmonella* bacteria invade epithelial cells lining the GI tract. Within vacuoles of the epithelial cells, *Salmonella* can manipulate the environment to enable survival and bacterial proliferation. Loss of epithelial cell invasion has been correlated with decreased animal colonization. In certain embodiments, the antibodies for use with the compositions and methods described herein reduce bacterial invasion. In certain embodiments, the antibody that reduces invasion targets a component of the bacterial needle complex. In certain embodiments, the antibody that reduces invasion targets the PrgI or SipD antigen. In certain embodiments, the antibodies for use with the compositions and methods described herein reduce bacterial invasion in an in vitro assay. In certain embodiments, the antibody reduces bacterial invasion compared to a negative control antibody. In certain embodiments, the antibody reduces bacterial invasion by at least 10% compared to a negative control antibody. In certain embodiments, the antibody reduces bacterial invasion by at least 20% compared to a negative control antibody. In certain embodiments, the antibody reduces bacterial invasion by at least 30% compared to a negative control antibody. In certain embodiments, the antibody reduces bacterial invasion by at least 40% compared to a negative control antibody. In certain embodiments, the antibody reduces bacterial invasion by at least 50% compared to a negative control antibody. In certain embodiments, the antibody reduces bacterial invasion by at least 60% compared to a negative control antibody. In certain embodiments, the antibody reduces bacterial invasion by at least 70% compared to a negative control antibody. In certain embodiments, invasion is reduced at a concentration of less than 10 µM, 25 µM, 50 µM, 75 µM, 100 µM, 125 µM, 150 µM, 175 µM, 200 µM, 300 µM, 400 µM, or 500 µM. In certain embodiments, a negative control antibody is an isotype control, a non-targeting antibody, or a pre-immune serum.

Reduction in Biofilm Formation

Biofilms are multi-cellular bacterial communities that can protect bacteria from host defenses and antibiotics. *Salmonella* can form biofilms on many types of surfaces including chicken intestinal epithelium and this is thought contribute to colonization and disease in animals. Many putative *Salmonella* virulence factors have been implicated in biofilm formation. In certain embodiments, the antibodies for use with the compositions and methods described herein reduce biofilm formation. In certain embodiments, the antibodies for use with the compositions and methods described herein reduce biofilm formation in an in vitro assay. In certain embodiments, the antibody reduces biofilm formation by at least 10%. In certain embodiments, the antibody reduces biofilm formation by at least 20%. In certain embodiments, the antibody reduces biofilm formation by at least 30%. In certain embodiments, the antibody reduces biofilm formation by at least 40%. In certain embodiments, the antibody reduces biofilm formation by at least 50%. In certain embodiments, the antibody reduces biofilm formation by at least 60%. In certain embodiments, the antibody reduces biofilm formation by at least 70%. In certain embodiments, the antibody reduces biofilm formation by at least 80%. In certain embodiments, the antibody reduces biofilm formation by at least 90%. In certain embodiments, invasion is reduced at a concentration of less than 10 µM, 25 µM, 50 µM, 75 µM, 100 µM, 125 µM, 150 µM, 175 µM, 200 µM, 300 µM, 400 µM, or 500 µM. In certain embodiments, a negative control antibody is an isotype control, a non-targeting antibody, or a pre-immune serum.

Multimers of $V_H H$ Proteins

The antibodies and $V_H H$ fragments of this disclosure are useful as multimers. Also known as protein concatemers, these $V_H H$ fragments can be linked together in a single polypeptide comprising 2, 3, 4, 5, 6, 7, 8, 9, 10 or more $V_H Hs$. The $V_H Hs$ can be linked using any of the linkers in Table 3. In certain embodiments, a multimer comprises, the same $V_H H$ repeated 1, 2, 3, 4, 5, 6, 7, 8, 9, 10 or more times. In certain embodiments, a multimer comprises 1, 2, 3, 4, 5, 6, 7, 8, 9, 10 or more different $V_H Hs$. In a certain embodiment, the multimer comprises an amino acid sequence at least 80%, 85%, 90%, 95%, 97%, 99%, or 100% identical to the sequence set forth in SEQ ID NO 462. In a certain embodiment, the multimer comprises an amino acid sequence at least 80%, 85%, 90%, 95%, 97%, 99%, or 100% identical to the sequence set forth in SEQ ID NO 463. In a certain embodiment, the multimer comprises an amino acid sequence at least 80%, 85%, 90%, 95%, 97%, 99%, or 100% identical to the sequence set forth in SEQ ID NO 464. In a certain embodiment, the multimer comprises an amino acid sequence at least 80%, 85%, 90%, 95%, 97%, 99%, or 100% identical to the sequence set forth in SEQ ID NO 465.

TABLE 3

Exemplary linkers for the multimeric NBX of this disclosure

| Linker Name | SEQ ID NO: | Linker Amino Acid Sequence |
|---|---|---|
| 1X G4S Linker | 445 | GGGGS |
| 3X G4S Linker | 446 | GGGGSGGGGSGGGGS |
| 5X G4S Linker | 447 | GGGGSGGGGSGGGGSGGGGSGGGGS |
| 2X G3S Linker | 448 | GGGSGGGS |
| Glycine Only | 449 | GGGGGGGGGG |

TABLE 3-continued

Exemplary linkers for the multimeric NBX of this disclosure

| Linker Name | SEQ ID NO: | Linker Amino Acid Sequence |
|---|---|---|
| Linker | | |
| Helical Linker | 450 | GGAEAAAKEAAAKEAAAKEAAAKEAAAKGG |
| Rigid Proline Linker | 451 | GGGAAPAAAPAKQEAAAPAPAAKAEAPAAAPAATGG |
| Cleavable Linker | 452 | GGGGSGGLGGSGGGGS |

Figure 27A:
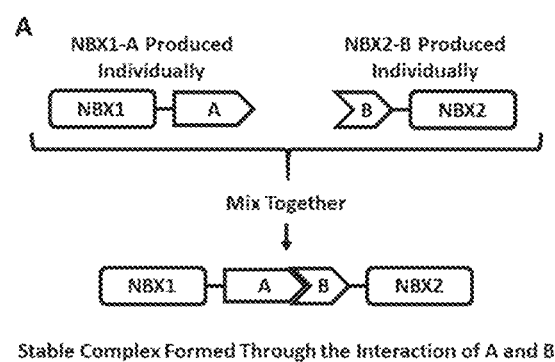
FIG. 27A and FIG. 27B show a schematic to describe the principle behind NBX complex formation via protein-protein interactions. (A) NBX1-A and NBX2-B are two constructs expressed and purified individually. Protein domains A and B form a highly stable interaction. When NBX1-A and NBX2-B are mixed together, a complex is formed, driven by the interaction of A and B, that keeps NBX1 and NBX2 together. (B) Multimers of the same NBX can come together immediately upon production if protein domain A naturally self-oligomerizes.
Figure 27B:
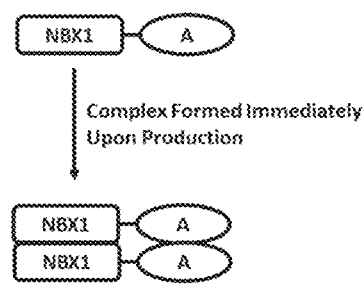

The antibody and V$_H$H fragment multimers of this disclosure can also comprise two separate polypeptides forming a polypeptide complex via protein-protein interactions. FIG. 27A and FIG. 27B show a schematic to describe the principle behind NBX complex formation via protein-protein interactions. (A) NBX1-A and NBX2-B are two constructs expressed and purified individually as component polypeptides. Protein domains A and B form a highly stable interaction. When NBX1-A and NBX2-B are mixed together, a complex is formed, driven by the interaction of A and B, that keeps NBX1 and NBX2 closely associated. (B) Multimers of the same NBX can come together immediately upon production if protein domain A naturally self-oligomerizes. This interaction can also be provided by a protein-small molecule interaction, or a small molecule-small molecule interaction, such as for example biotin-streptavidin. In certain embodiments, the VHHs can be complexed with the aid of any of the heterocomplex forming sequences in SEQ ID NO 453-456 shown in Table 4. In certain embodiments, the V$_H$Hs can be complexed with the aide of any of the complex forming sequences in SEQ ID NO 457-460 shown in Table 4. In a certain embodiment, the multimer comprises an amino acid sequence at least 80%, 85%, 90%, 95%, 97%, or 99% identical to the sequence set forth in SEQ ID NO 466. In a certain embodiment, the multimer comprises an amino acid sequence at least 80%, 85%, 90%, 95%, 97%, or 99% identical to the sequence set forth in SEQ ID NO 467. In a certain embodiment, the multimer comprises an amino acid sequence at least 80%, 85%, 90%, 95%, 97%, or 99% identical to the sequence set forth in SEQ ID NO 468. In a certain embodiment, the multimer comprises an amino acid sequence at least 80%, 85%, 90%, 95%, 97%, or 99% identical to the sequence set forth in SEQ ID NO 469. In a certain embodiment, the multimer comprises an amino acid sequence at least 80%, 85%, 90%, 95%, 97%, or 99% identical to the sequence set forth in SEQ ID NO 470. In a certain embodiment, the multimer comprises an amino acid sequence at least 80%, 85%, 90%, 95%, 97%, or 99% identical to the sequence set forth in SEQ ID NO 471. In a certain embodiment, the multimer comprises an amino acid sequence at least 80%, 85%, 90%, 95%, 97%, or 99% identical to the sequence set forth in SEQ ID NO 472. In a certain embodiment, the multimer comprises an amino acid sequence at least 80%, 85%, 90%, 95%, 97%, or 99% identical to the sequence set forth in SEQ ID NO 473. In a certain embodiment, the multimer comprises an amino acid sequence at least 80%, 85%, 90%, 95%, 97%, or 99% identical to the sequence set forth in SEQ ID NO 474.

In certain embodiments, the multimers formed herein either as a concatemers or protein complexes show an increase in affinity for target antigen. In certain embodiments, this increase in affinity is at least 2-fold more than any V$_H$H by itself. In certain embodiments, this increase in affinity is at least 3-fold more than any V$_H$H by itself. In certain embodiments, this increase in affinity is at least 5-fold more than any V$_H$H by itself. In certain embodiments, this increase in affinity is at least 10-fold more than any V$_H$H by itself. In certain embodiments, this increase in affinity is at least 20-fold more than any V$_H$H by itself. In certain embodiments, this increase in affinity is at least 50-fold more than any V$_H$H by itself. In certain embodiments, this increase in affinity is at least 100-fold more than any V$_H$H by itself. In certain embodiments, this increase in affinity is at least 200-fold more than any V$_H$H by itself. In certain embodiments, this increase in affinity is at least 300-fold more than any V$_H$H by itself.

TABLE 4

Exemplary protein A and protein B partners useful in the construction of NBX multimers.

| Protein A | SEQ ID NO: | Protein A Amino Acid Sequence | SEQ ID NO: | Protein B | Protein B Amino Acid Sequence |
|---|---|---|---|---|---|
| E9 Immunity Protein | 453 | MELKHSISDYTEAEFLQLVTTICNADTSSEEELVKLVTHFEEMTEHPSGSDLIYYPKEGDDDSPSGIVNTVKQWRAANGKSGFKQG | 454 | Colicin E9 | MESKRNKPGKATGKGKPVGDKWLDDAGKDSGAPIPDRIADKLRDKEFKSFDDFRKAVWEEVSKDPELSKNLNPCNKSSVSKGYSPFTPKNQQVGGRKVYELHHDKPISQGGEVYDMDNIRVTTPKRHIDIHRGK |

TABLE 4-continued

Exemplary protein A and protein B partners useful in the construction of NBX multimers.

| Fos Leucine Zipper | 455 | LTDTLQAETDQLEDEKSALQ TEIANLLKEKEKLEFILAA | 456 | Jun Leucine Zipper | RIARLEEKVK TLKAQNSEL ASTANMLR EQVAQLKQ KVMN |
|---|---|---|---|---|---|

Protein A self-oligomerizers useful in the construction of NBX multimers.

| Protein A | | Protein Self-Oligomerization Status | Protein A Amino Acid Sequence |
|---|---|---|---|
| GCN4 PIL | 457 | Dimer | RMKQLEDKIEELLSKIYHLENEIARLKKL IGER |
| GCN4 PII | 457 | Trimer | RMKQIEDKIEEILSKIYHIENEIARIKKLI GER |
| GCN4 PLI | 458 | Tetramer | RMKQIEDKLEEILSKLYHIENELARIKKL LG |
| Kv1.2 T1 | 460 | Tetramer | ERVVINISGLRFETQLKTLAQFPETLLG DPKKRMRYFDPLRNEYFFDRNRPSFD AILYYYQSGGRLRRPVNVPLDIFSEEIRF YELG |

Routes of Administration

In certain embodiments, the heavy chain antibodies and $V_H$Hs for use with the compositions and methods described herein are administered to an animal in any suitable manner. In certain embodiments, the antibodies for use with the compositions and methods described herein are administered to the alimentary canal of an animal. In certain embodiments, the antibodies for use with the compositions and methods described herein are administered to the alimentary canal of an animal orally. In certain embodiments, the antibodies for use with the compositions and methods described herein are administered to the alimentary canal of an animal in liquid form. In certain embodiments, the antibodies for use with the compositions and methods described herein are administered to the alimentary canal of an animal in solid form. In certain embodiments, the antibodies for use with the compositions and methods described herein are administered to the exterior surface of an animal. In certain embodiments, the antibodies for use with the compositions and methods described herein are administered to the exterior surface of an animal in a liquid formulation. In certain embodiments, the antibodies for use with the compositions and methods described herein are administered to the exterior surface of an animal in a spray formulation. In certain embodiments, the antibodies for use with the compositions and methods described herein are administered to the exterior surface of an animal in a gelatinized spray formulation. In certain embodiments, the antibodies for use with the compositions and methods described herein are administered by an injection.

In certain embodiments, the heavy chain antibodies and $V_H$Hs for use with the compositions and methods described herein are administered to a human subject in any suitable manner. In certain embodiments, the antibodies for use with the compositions and methods described herein are administered to the alimentary canal of a human subject. In certain embodiments, the antibodies for use with the compositions and methods described herein are administered to the alimentary canal of a human subject orally. In certain embodiments, the antibodies for use with the compositions and methods described herein are administered to the alimentary canal of a human subject in liquid form. In certain embodiments, the antibodies for use with the compositions and methods described herein are administered to the alimentary canal of a human subject in solid form. In certain embodiments, the antibodies for use with the compositions and methods described herein are administered by an injection. In certain embodiments, the antibodies for use with the compositions and methods described herein are administered intravenously. In certain embodiments, the antibodies for use with the compositions and methods described herein are administered in food or a nutritional supplement.

Antibody Mixtures, Concentrations and Dosage Schedules

In certain embodiments, one or a plurality of heavy chain antibodies or $V_H$H comprising polypeptides is administered in a composition to an animal in any suitable manner described herein. In certain embodiments, a mixture of two or more antibodies that target any combination of two virulence factors comprising of bacterial motility, adhesion, invasion, or biofilm formation are administered simultaneously. In certain embodiments, a mixture of three or more antibodies that target any combination of three virulence factors involved in bacterial motility, adhesion, invasion, or biofilm formation are administered simultaneously. In certain embodiments, a mixture of antibodies that target any combination of flagella/FliC, PrgI, or FimA antigens are administered to the animal. In certain embodiments, more than one distinct antibody is administered to the animal. In certain embodiments, more than two distinct antibodies are administered to the animal. In certain embodiments, more than three distinct antibodies are administered to the animal. In certain embodiments, more than four distinct antibodies are administered to the animal. In certain embodiments, more than five distinct antibodies are administered to the animal. In certain embodiments, the antibodies are administered concurrently. In certain embodiments, the antibodies are administered sequentially. In certain embodiments, antibodies are administered to an animal at a concentration in excess of 1 mg/kg of body weight. In certain embodiments, antibodies are administered to an animal at a concentration in excess of 5 mg/kg of body weight. In certain embodiments, antibodies are administered to an animal at a concentration in excess of 10 mg/kg of body weight. In certain embodiments, antibodies are administered to an animal at a concentration in excess of 50 mg/kg of body weight. In certain embodiments, antibodies are administered to an animal at a concentration in excess of 100 mg/kg of body weight. In certain embodiments, antibodies are administered to an animal at a concentration less than 1 mg/kg of body weight. In certain embodiments, antibodies are administered to an animal at a concentration less than 500 mg/kg of body weight. In certain embodiments, antibodies are administered to an animal at a concentration less than 100 mg/kg of body weight. In certain embodiments, antibodies are administered to an animal at a concentration less than 50 mg/kg of body weight. In certain embodiments, antibodies are administered to an animal at a concentration less than 10 mg/kg of body weight. In certain embodiments, antibodies are administered once a day. In certain embodiments, antibodies are administered twice a day. In certain embodiments, antibodies are administered once a week. In certain embodiments, antibodies are administered twice a week. In certain embodiments, antibodies are administered three times a week. In certain embodiments, antibodies are administered four times a week. In certain embodiments, antibodies are administered once a month. In certain embodiments, antibodies are administered twice a month. In certain embodiments, antibodies are administered three times a month. In certain embodiments, antibodies are administered four times a month.

In certain embodiments, one or a plurality of antibodies or $V_HH$ comprising polypeptides is administered to a human subject in any suitable manner described herein. In certain embodiments, a mixture of any one or more antibodies that target any combination of virulence factors comprising bacterial motility, adhesion, invasion, or biofilm formation are administered simultaneously. In certain embodiments, a mixture of two or more antibodies that target any combination of two virulence factors comprising bacterial motility, adhesion, invasion, or biofilm formation are administered simultaneously. In certain embodiments, a mixture of three or more antibodies that target any combination of three virulence factors involved in bacterial motility, adhesion, invasion, or biofilm formation are administered simultaneously. In certain embodiments, a mixture of antibodies that target any combination of flagella/FliC, PrgI, or FimA antigens are administered to a human subject. In certain embodiments, more than one distinct antibody is administered to a human subject. In certain embodiments, more than two distinct antibodies are administered to a human subject. In certain embodiments, more than three distinct antibodies administered to a human subject. In certain embodiments, more than four distinct antibodies are administered to a human subject. In certain embodiments, more than five distinct antibodies are administered to a human subject. In certain embodiments, the antibodies are administered concurrently. In certain embodiments, the antibodies are administered sequentially. In certain embodiments, antibodies are administered to a human subject at a concentration in excess of 1 mg/kg of body weight. In certain embodiments, antibodies are administered to a human subject at a concentration in excess of 5 mg/kg of body weight. In certain embodiments, antibodies are administered to a human subject at a concentration in excess of 10 mg/kg of body weight. In certain embodiments, antibodies are administered to a human subject at a concentration in excess of 50 mg/kg of body weight. In certain embodiments, antibodies are administered to a human subject at a concentration in excess of 100 mg/kg of body weight. In certain embodiments, antibodies are administered to a human subject at a concentration less than 1 mg/kg of body weight. In certain embodiments, antibodies are administered to a human subject at a concentration less than 500 mg/kg of body weight. In certain embodiments, antibodies are administered to a human subject at a concentration less than 100 mg/kg of body weight. In certain embodiments, antibodies are administered to a human subject at a concentration less than 50 mg/kg of body weight. In certain embodiments, antibodies are administered to a human subject at a concentration less than 10 mg/kg of body weight. In certain embodiments, antibodies are administered to a human subject at a concentration less than 1 mg/kg of body weight. In certain embodiments, antibodies are administered to a human subject at a concentration less than 1 µg/kg of body weight. In certain embodiments, antibodies are administered to a human subject at a concentration less than 1 ng/kg of body weight. In certain embodiments, antibodies are administered once a day. In certain embodiments, antibodies are administered twice a day. In certain embodiments, antibodies are administered once a week. In certain embodiments, antibodies are administered twice a week. In certain embodiments, antibodies are administered three times a week. In certain embodiments, antibodies are administered four times a week. In certain embodiments, antibodies are administered once a month. In certain embodiments, antibodies are administered twice a month. In certain embodiments, antibodies are administered three times a month. In certain embodiments, antibodies are administered four times a month.

Animal Feed

In certain embodiments, the antibodies for use with the compositions and methods described herein are administered in an animal feed. In certain embodiments, the antibodies for use with the compositions and methods described herein are administered mixed with feed. In certain embodiments, the antibodies are administered mixed with feed specific for the type of animal that the antibody is administered to. In certain embodiments, the antibodies are administered mixed with a poultry feed. In certain embodiments, the antibodies are administered mixed with a chicken feed. In certain embodiments, the antibodies are administered mixed with a duck feed. In certain embodiments, the antibodies are administered mixed with a turkey feed. In certain embodiments, the antibodies are administered mixed with a goose feed. In certain embodiments, the antibodies are administered mixed with a grain. In certain embodiments, the grain is whole, milled, or ground. In certain embodiments, the grain is corn, rice, barley, wheat, soybean, alfalfa, grass, hay, straw, or a combination thereof. In certain embodiments, the antibodies are administered in water. In certain embodiments, the antibodies are administered in vitamin supplements. In certain embodiments, the antibodies are mixed with an animal feed or supplement at a concentration of between about 1 ng/kg and about 100 g/kg. In certain embodiments, the antibodies are mixed with an animal feed or supplement at a concentration of between about 1 µg/kg and about 100 g/kg. In certain embodiments, the antibodies are mixed with an animal feed or supplement at a concentration of between about 1 mg/kg and about 100 g/kg. In certain embodiments, the antibodies are mixed with an animal feed or supplement at a concentration of between about 1 mg/kg and about 10 g/kg. In certain embodiments, the antibodies are mixed with an animal feed or supplement at a concentration of between about 10 mg/kg and about 10 g/kg. In certain embodiments, the antibodies are mixed with an animal feed or supplement at a concentration of between about 100 mg/kg and about 10 g/kg. In certain embodiments, the antibodies are mixed with an animal feed or supplement at a concentration of between about 1 g/kg and about 10 g/kg. In certain embodiments, the antibodies are mixed with an animal feed or supplement at a concentration of between about 100 mg/kg and about 1 g/kg. In certain embodiments, the antibodies are mixed with an animal feed or supplement at a concentration of between about 1 mg/kg and about 1 g/kg. In certain embodiments, the antibodies are mixed with an animal feed or supplement at a concentration of between about 1 µg/kg and about 1 g/kg. In certain embodiments, the antibodies are mixed with an animal feed or supplement at a concentration of between about 1 ng/kg and about 1 g/kg. In certain embodiments, the antibodies are mixed with an animal feed or supplement at a concentration of no greater than 10 mg/kg. In certain embodiments, the antibodies are mixed with an animal feed or supplement at a concentration of no greater than 5 mg/kg. In certain embodiments, the antibodies are mixed with an animal feed or supplement at a concentration of no greater than 1 mg/kg. In certain embodiments, the antibodies are mixed with an animal feed or supplement at a concentration of no greater than 5 µg/kg. In certain embodiments, the antibodies are mixed with an animal feed or supplement at a concentration of no greater than 1 µg/kg. In certain embodiments, the antibodies are mixed with an animal feed or supplement at a concentration of no greater than 5 ng/kg. In certain embodiments, the antibodies are mixed with an animal feed or supplement at a concentration of no greater than 1 ng/kg.

Pharmaceutically Acceptable Vehicle, Carrier, Excipient, or Diluent

In certain embodiments, described herein, are compositions of matter that comprise one or more isolated, and purified $V_HH$ polypeptides and a pharmaceutically acceptable vehicle, carrier, or excipient. In certain embodiments, the pharmaceutically acceptable vehicle, carrier, or excipient comprises a pH buffer or pH modifier. In certain embodiments, the pH buffer or pH modifier comprises sodium bicarbonate, HEPES, MOPS, MEPES, phosphate buffer, succinate buffer, citric acid, ascorbic acid, or any combination thereof. In certain embodiments, the pharmaceutically acceptable vehicle, carrier or excipient comprises a salt solution. In certain embodiments, the salt solution comprises sodium chloride, potassium chloride, calcium chloride, hemin chloride, benzethonium chloride, or any combination thereof. In certain embodiments, the pharmaceutically acceptable vehicle, carrier or excipient comprises a carbohydrate. In certain embodiments, the carbohydrate comprises sucrose, dextrose, trehalose, lactose, cellulose, sorbitol, galactose, dextran, xanthan, or any combination thereof. In certain embodiments, the pharmaceutically acceptable vehicle, carrier or excipient comprises an amino acid or protein. In certain embodiments, the amino acid or protein comprises gelatin, egg protein, yeast extract, glutamate, albumin, In certain embodiments, the pharmaceutically acceptable vehicle, carrier or excipient comprises an emulsifier. In certain embodiments, the emulsifier comprises octylphenol ethoxylate (Triton X-100), polysorbate 20, polysorbate 80 (Tween 80), sodium deoxy cholate, or any combination thereof. In certain embodiments, the pharmaceutically acceptable vehicle, carrier or excipient comprises a chelating agent. In certain embodiments, the chelating agent comprises ethylene diamine tetra acetic acid sodium (EDTA), EGTA, or any combination thereof. In certain embodiments, the carrier is poly D,L-lactide-co-glycolide (PLGA). In certain embodiments, the $V_HH$ is diluted in a liquid suitable for consumption by a human individual or a domestic animal.

Nucleic Acids Encoding $V_HH$ Polypeptides

The isolated, and purified $V_HH$ polypeptides of the current disclosure can be produced in cell based protein production systems that have been modified by nucleic acids to express the $V_HH$ polypeptides. Therefore, any of the engineered $V_HH$ polypeptides described herein can be encoded by a nucleic acid. In certain embodiments, the nucleic acid is a plasmid. In certain embodiments, the plasmid comprises an origin or replication for propagation in *E. coli*. In certain embodiments, the nucleic acid is encoded on a plasmid suitable for transforming yeast. In certain embodiments, the plasmid is suitable for homologous recombination in yeast. In certain embodiments, the plasmid comprises a gene for a yeast auxotrophy such as histidine, tryptophan, leucine, lysine, methionine, or uracil. In certain embodiments, the plasmid has a gene that confers antibiotic resistance to ampicillin, kanamycin, neomycin, G418, carbenicillin, chloramphenicol, blasticidin, zeocin, or any combination thereof. In a certain embodiment, the plasmid is pPIC9 SHUTTLE. In certain embodiments, the nucleic acid is a linear single or double stranded DNA molecule able to undergo homologous recombination in yeast. In certain embodiments, the nucleic acid is a double stranded linear DNA molecule that comprises any of the $V_HH$ polypeptides of the current disclosure. In certain embodiments, the nucleic acid is a PCR product that comprises any of the engineered $V_HH$ polypeptides of the current disclosure.

Cell Based Systems for Production of $V_HH$ Polypeptides

The $V_HH$ polypeptides described herein can be isolated and purified from a cellular expression system. The isolated, purified $V_HH$ polypeptides of the current disclosure are purified from a cell based protein production system that has been transformed, transfected, or infected with a nucleic acid encoding an engineered $V_HH$ polypeptide. In certain embodiments, the cell based protein production system is stably transformed with the nucleic acid, such that the nucleic acid integrates into at least one chromosome of the cell based protein production system. In certain embodiments, the eukaryotic system is yeast. In certain embodiments, the yeast is a *Pichia pastoris* strain. In certain embodiments, the yeast is a *Saccharomyces cerevisiae* strain. In certain embodiments, the strain of *Pichia pastoris* is modified to produce a human glycosylation pattern in polypeptides produced using the system. In certain embodiments, the cell based protein purification system is not a mammalian cell line.

Master Cell Bank and Transgenic Yeast

In a certain embodiment, described herein is a master cell bank comprising a yeast or bacteria that comprises a nucleic acid encoding one or more polypeptides integrated into its genome creating a transgenic bacteria or yeast strain. In certain embodiments, the nucleic acid is maintained extrachromosomal, on a plasmid, bacterial artificial chromosome, or yeast artificial chromosome. In certain embodiments, the nucleic acid is integrated into a chromosomal location. In certain embodiments, the yeast is *Pichia pastoris*. In certain embodiments, the *Pichia pastoris* is a GS115 strain. In certain embodiments, the transgenic yeast is created by transformation with linearized plasmid, a PCR product, or a synthesized double stranded DNA molecule. In certain embodiments, the transgenic yeast is created by homologous recombination. In certain embodiments, the master cell bank comprises a cryopreservative suitable for freezing to at least about −80° or below. In certain embodiments, the master cell bank comprises glycerol at between 10 and 30%, and is suitable for long term storage at about −80° or below. In certain embodiments, the master cell bank can preserve a transgenic yeast strain for at least 1, 2, 3, 4, 5, 6, 7, 8, 9, 10 or more years.

Additional Active Ingredients

In certain embodiments, the antibodies for use with the compositions and methods described herein are administered with an additional active ingredient that is effective in controlling bacteria. In certain embodiments, the antibodies are administered with an antibiotic. In certain embodiments, the antibodies are administered with a probiotic. In certain embodiments, the antibodies are administered with a hormone.

Diagnostic and Research Uses

In certain embodiments, any of the antibodies described herein are useful for use in diagnostic assays or for research purposes. Any of the antibodies described herein can be used in an in vitro assay. In certain embodiments, the antibodies described herein are useful in a companion diagnostic.

EXAMPLES

The following illustrative examples are representative of embodiments of the software applications, systems, and methods described herein and are not meant to be limiting in any way Example 1—Purification of Flagella and Recombinant Target Antigens Flagella were isolated from whole-bacterial cells. Bacterial cells were grown overnight at 37° C. with shaking. Overnight cultures were centrifuged and the cell pellets resuspended in 10 mM Tris pH 8.0, 0.9% NaCl. Resuspended cells were homogenized and centrifuged for 20 minutes at 10,000 rpm. Supernatants were subjected to an additional round of centrifugation at 10,000 rpm followed by ultracentrifugation at 45,000 rpm for 1 hour. Pellets were resuspended in 1 ml 10 mM Tris pH 8.0, 0.9% NaCl and checked for purity using SDS-PAGE.

FliC protein was purified from an *E. coli* expression system. FliC was expressed at 30° C. in *E. coli* Rosetta (DE3) pLacI cells (Novagen), induced at an absorbance of ~0.6 at 600 nm by adding 0.4 mM isopropyl-β-D-thiogalactoside (IPTG) and grown for 3.5 more hours before collection. Cells were lysed by sonication in buffer A (250 mM KCl and 10 mM HEPES, pH 7.4) with 25 µg/ml DNase I, 25 µg/ml lysozyme, 14 mM β-mercaptoethanol and 1 mM phenylmethylsulphonyl fluoride. The lysate was applied to a 25 ml Poros MC column (Tosoh Bioscience), washed with five column volumes of buffer A and eluted with 30% (vol/vol) buffer B (250 mM KCl and 500 mM imidazole, pH 7.4). The protein was dialyzed overnight against buffer C (20 mM KCl, 10 mM Tris, pH 8.0 and 14 mM β-mercaptoethanol) at 4° C. The sample was then applied to a 20 ml HiLoad Q column (GE Healthcare). The protein was eluted with a gradient of 0% to 35% buffer D (1.0 M KCl, 10 mM Tris pH 8.0 and 14 mM β-mercaptoethanol). Lastly, the elution was loaded onto a HiLoad 16/60 Superdex 200 prep grade (GE Healthcare) gel filtration column using buffer A plus 14 mM β-mercaptoethanol. The protein sample was then concentrated to 2.3 mg/mL using Amicon concentrators (30 kDa molecular weight cutoff (MWCO); Millipore). The purified protein was stored at −80° C.

PrgI protein was purified form an *E. coli* expression system. PrgI was expressed at 30° C. in *E. coli* Rosetta (DE3) pLacI cells (Novagen), induced at an absorbance of ~0.6 at 600 nm by adding 0.4 mM isopropyl-β-D-thiogalactoside (IPTG) and grown for 3.5 more hours before collection. Cells were lysed by sonication in buffer A (250 mM KCl and 10 mM HEPES, pH 7.4) with 25 µg/ml DNase I, 25 µg/ml lysozyme and 1 mM phenylmethylsulphonyl fluoride. The lysate was applied to a 25 ml Poros MC column (Tosoh Bioscience), washed with five column volumes of buffer A and eluted with 30% (vol/vol) buffer B (250 mM KCl and 500 mM imidazole, pH 7.4). The elution was then loaded onto a HiLoad 16/60 Superdex 200 prep grade (GE Healthcare) gel filtration column using buffer A. The protein sample was then concentrated to 950 uM using Amicon concentrators (3 kDa molecular weight cutoff (MWCO); Millipore). The purified protein was stored at −80° C.

FimA protein was purified form an *E. coli* expression system. FimA was expressed at 18° C. in *E. coli* Rosetta (DE3) pLacI cells (Novagen), induced at an absorbance of ~0.6 at 600 nm by adding 0.4 mM isopropyl-β-D-thiogalactoside (IPTG) and grown for 20 more hours before collection. Cells were lysed by sonication in buffer A (250 mM KCl and 10 mM HEPES, pH 7.4) with 25 µg/ml DNase I, 25 µg/ml lysozyme, 14 mM β-mercaptoethanol and 1 mM phenylmethylsulphonyl fluoride. The lysate was applied to a 25 ml Poros MC column (Tosoh Bioscience), washed with five column volumes of buffer A and eluted with 30% (vol/vol) buffer B (250 mM KCl and 500 mM imidazole, pH 7.4). The protein was dialyzed overnight against buffer C (10 mM KCl, 10 mM Tris, pH 8.8, and 14 mM β-mercaptoethanol) at 4° C. The sample was then applied to a 20 ml HiLoad Q column (GE Healthcare). The protein was in the flow-through of the column. Last, the sample was run on a HiLoad 10/300GL Superdex 75 (GE Healthcare) gel filtration column using buffer A plus 14 mM β-mercaptoethanol. The protein sample was then concentrated to 350 uM using Amicon concentrators (10 kDa molecular mass cutoff; Millipore). The purified protein was stored at −80° C.

Example 2—Generation of Antibodies in Llamas

A single llama was immunized with a mixture of purified flagella and recombinant target antigens, FliC, PrgI and FimA. The llama immunization was performed by Cedarlane where 250 µg of each antigen were pooled and injected for a total of four injections. Antigens were mixed at NRC and supplied frozen on dry ice to Cedarlane. At the time of injection, the antigens were thawed and the volume increased to 1 ml with PBS. The 1 ml antigen-PBS mixture was then mixed with 1 ml of CFA or IFA for a total of 2 ml. A total of 2 ml was immunized per injection. Whole llama blood and sera were collected from the immunized animal on days 0, 35, 42, 75 and 87. Sera from days 35, 42 and 75 were then fractionated to separate $V_H H$ from conventional antibodies. Fractionation was done according to standard protocols by the National Research Council (NRC). ELISA was used to measure reactivity against target antigens in polyclonal and $V_H H$-enriched fractions.

Example 3—In Vitro Generation of Monoclonal Antibodies

RNA isolated from purified llama lymphocytes was used to generate cDNA for cloning into phagemids. The resulting phagemids were used to transform *E. coli* to generate a library of expressed $V_HH$ genes. The phagemid library size was ~2.5×10⁷ total transformants and the estimated number of phagemid containing $V_HH$ inserts was estimated to be ~100%. High affinity antibodies were then selected by panning against *Salmonella* antigens used for llama immunization. A total of two rounds of panning were performed and clones arising from rounds 1 and 2 were sequenced according to their CDR regions. Phage ELISA was then performed on phage bearing unique single domain antibody clones identified from panning/DNA sequencing to prioritize and select single domain antibodies for soluble expression and purification.

Example 4—Motility Assays

Figure 1B:
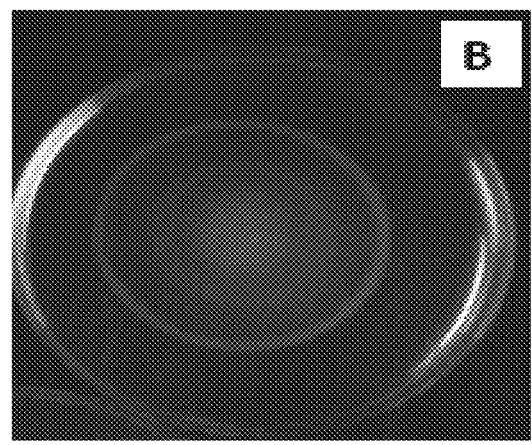
Figure 1C:
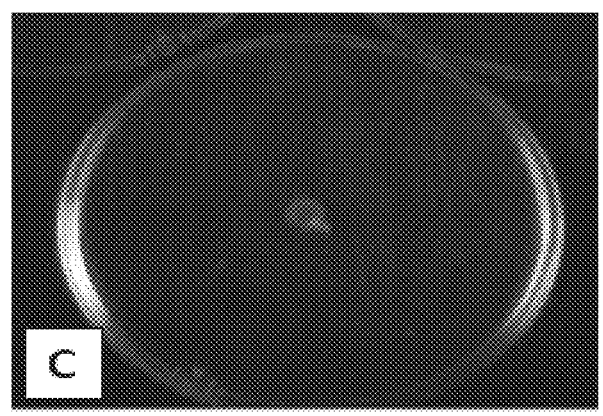
Figure 2A:
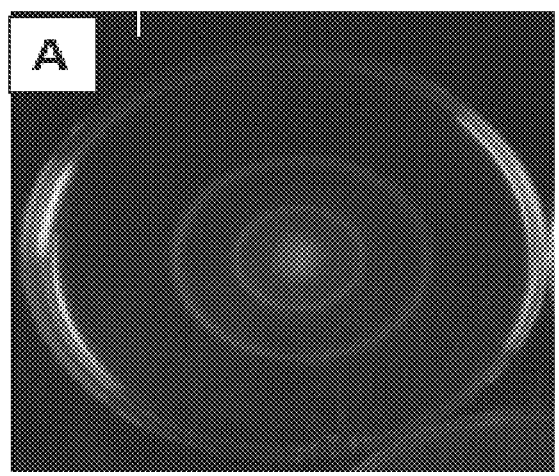
FIGS. 2A, 2B, and 2C show pictures of a plate-based motility assay performed using agar plates.
Figure 2B:
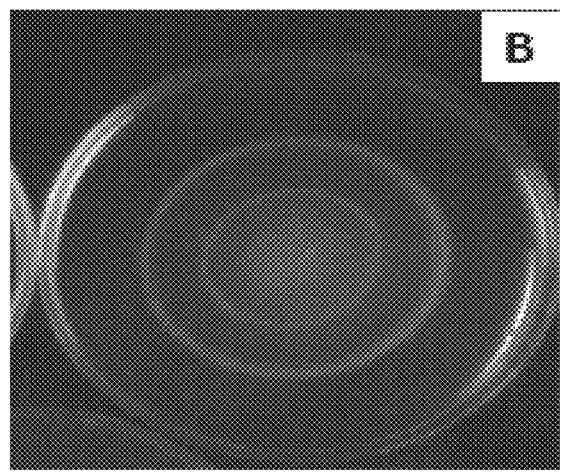
Figure 2C:
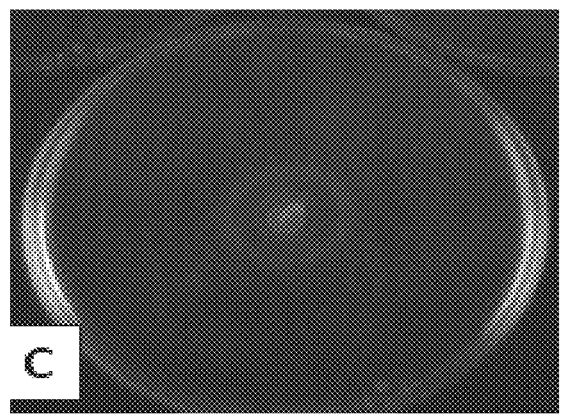
Figure 3A:
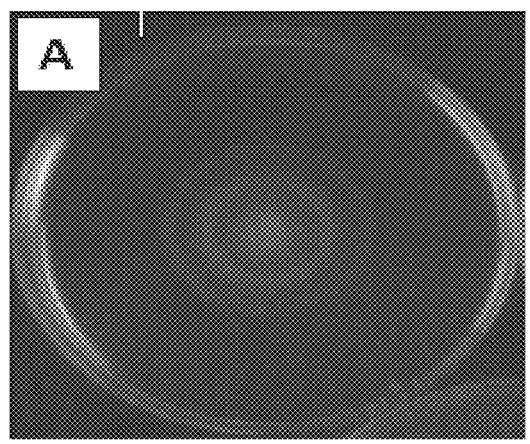
FIGS. 3A, 3B, and 3C show pictures of a plate-based motility assay performed using agar plates.
Figure 3B:
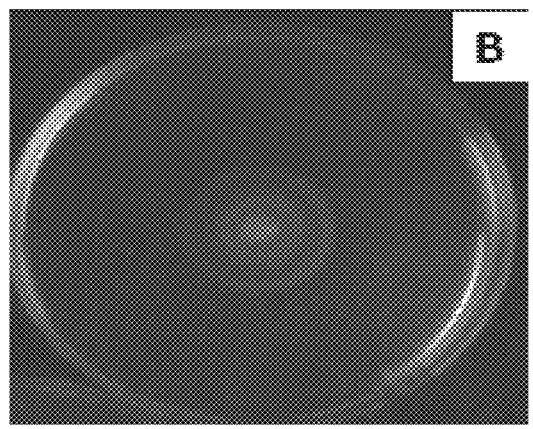
Figure 3C:
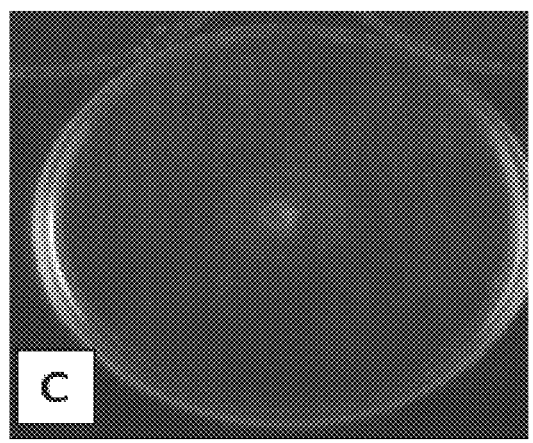
Figure 4A:
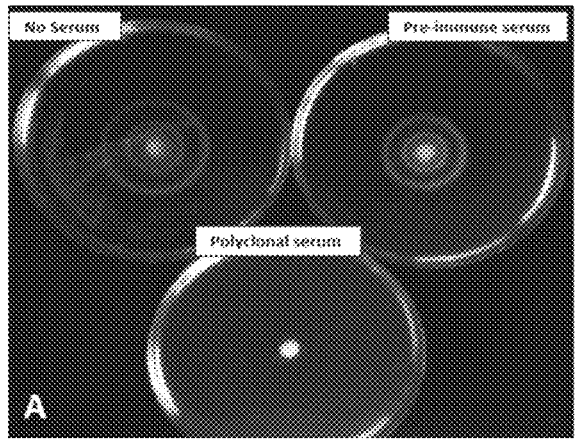
FIGS. 4A, 4B, and 4C show pictures of a plate-based motility assay performed using agar plates.
Figure 4B:
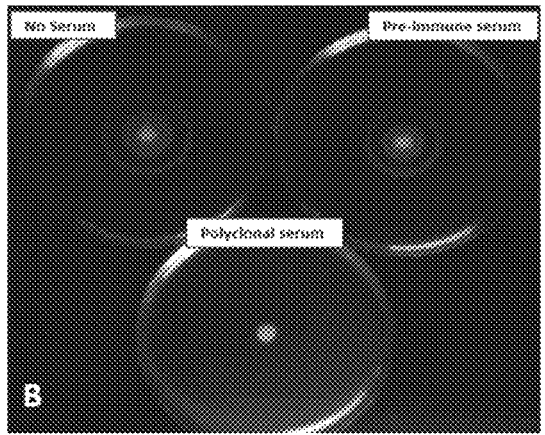
Figure 4C:
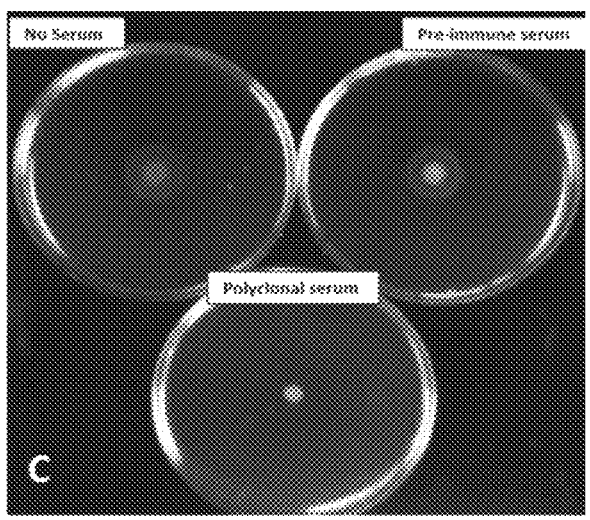
Figure 5:
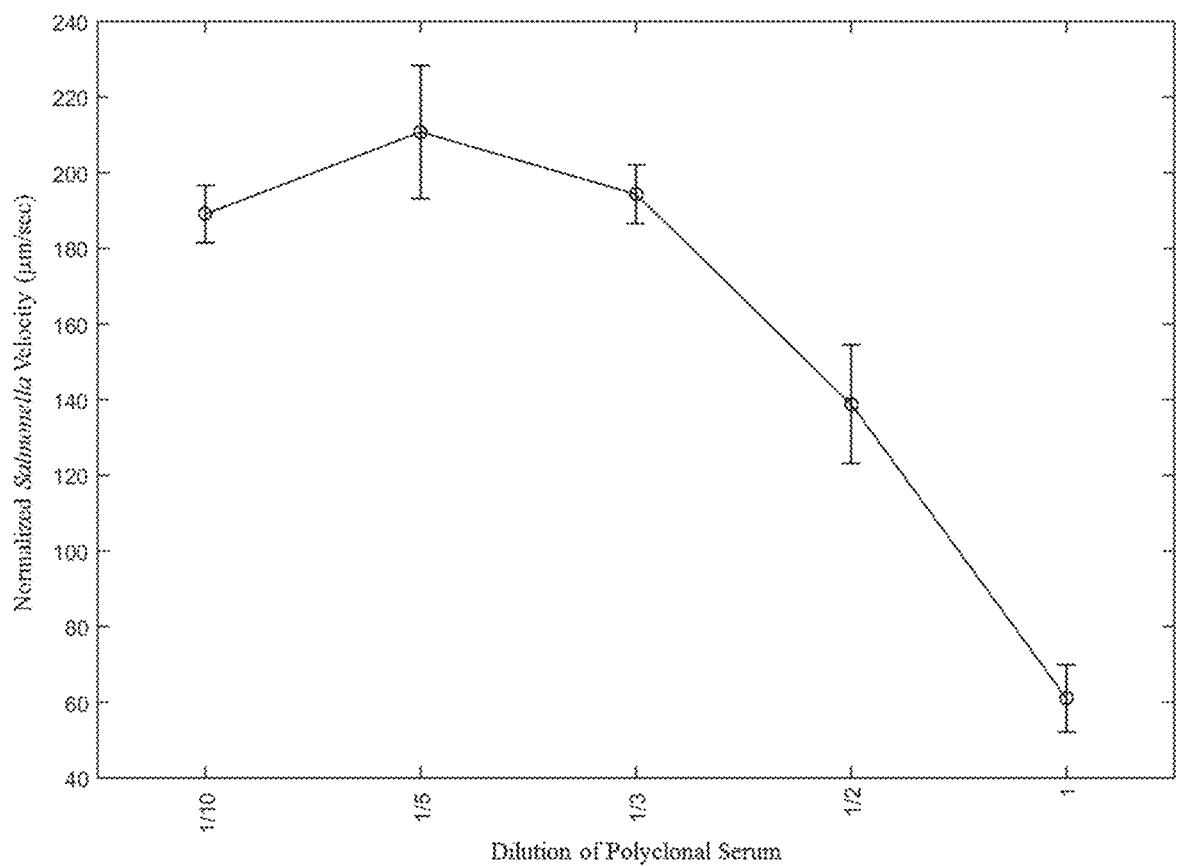
FIG. 5 is a graph that shows the velocity of *Salmonella enterica* serotype Typhimurium strain SL1344 in a live imaging motility assay.
Figure 9:
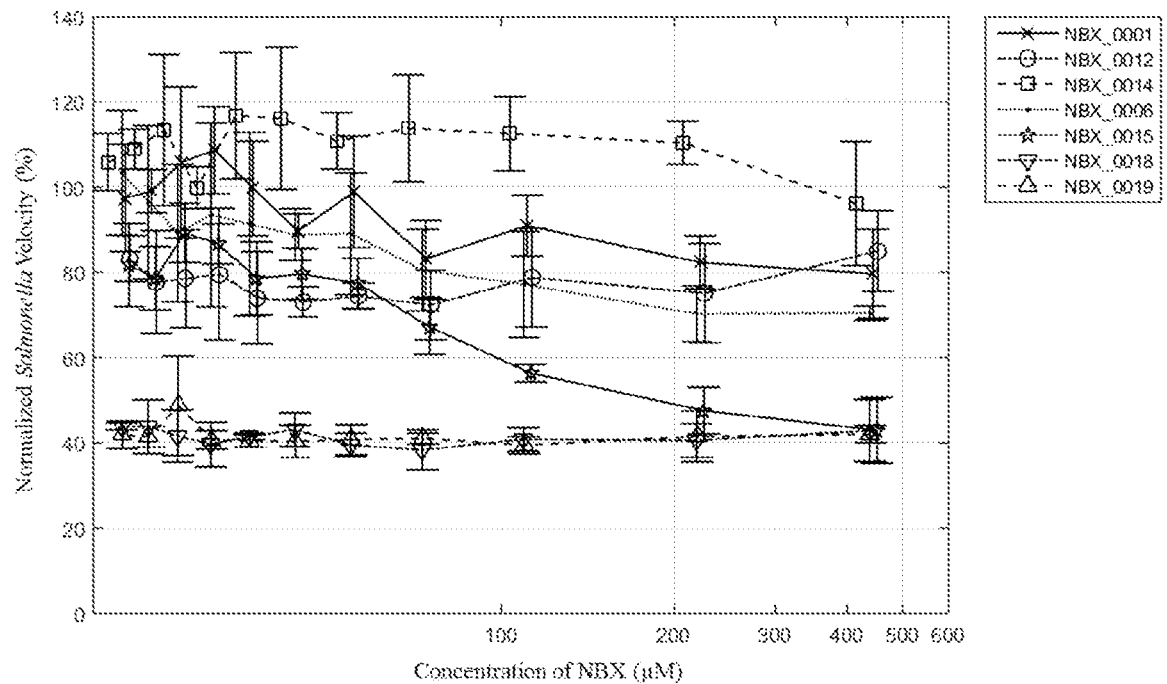
FIG. 9 is a graph that shows the velocity of *Salmonella enterica* serotype Typhimurium strain SL1344 in a live imaging motility assay in the presence of NovoBind NBX0001, NBX0006, NBX0012, NBX0014, NBX0015, NBX0018 and NBX0019.
Figure 10:
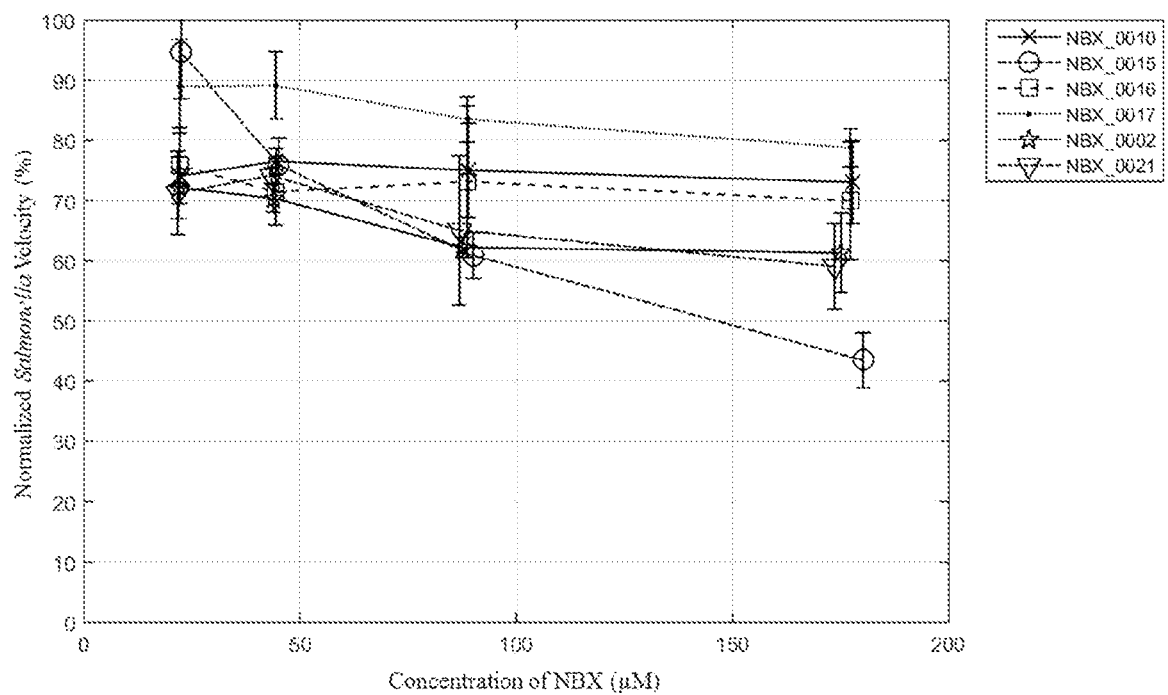
FIG. 10 is a graph that shows the velocity of *Salmonella enterica* serotype Typhimurium strain SL1344 in a live imaging motility assay in the presence of NovoBind NBX0002, NBX0010, NBX0015, NBX0016, NBX0017 and NBX0021.
Figure 11:
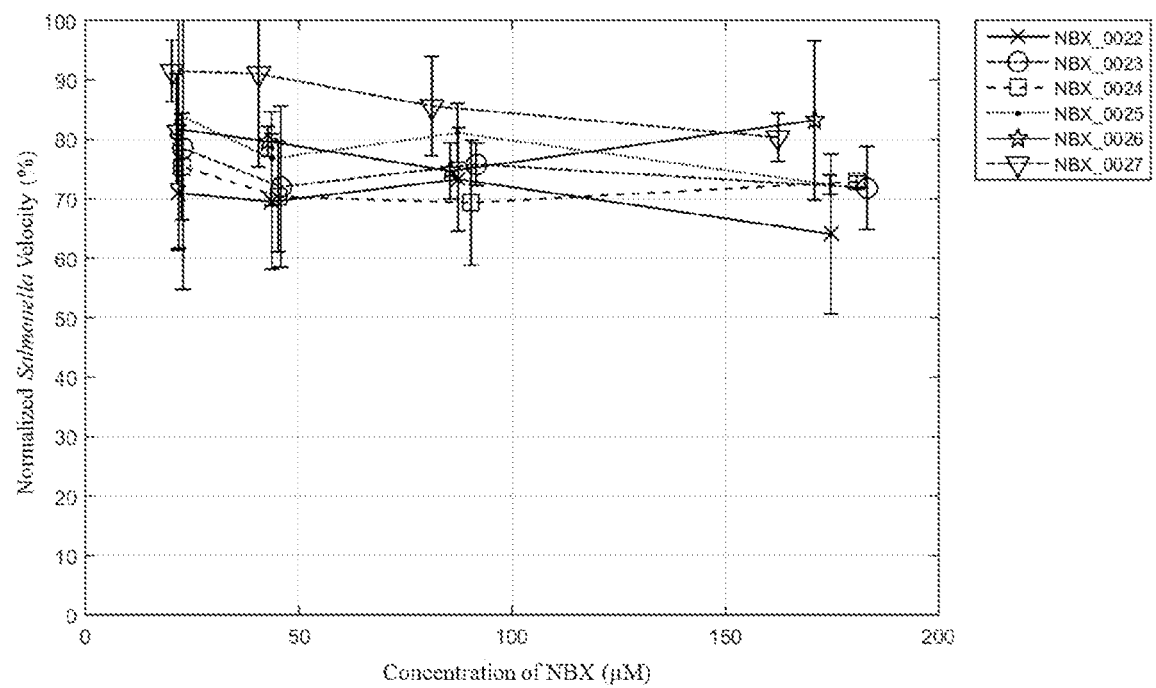
FIG. 11 is a graph that shows the velocity of *Salmonella enterica* serotype Typhimurium strain SL1344 in a live imaging motility assay in the presence of NovoBind NBX0022, NBX0023, NBX0024, NBX0025, NBX0026 and NBX0027.
Figure 12:
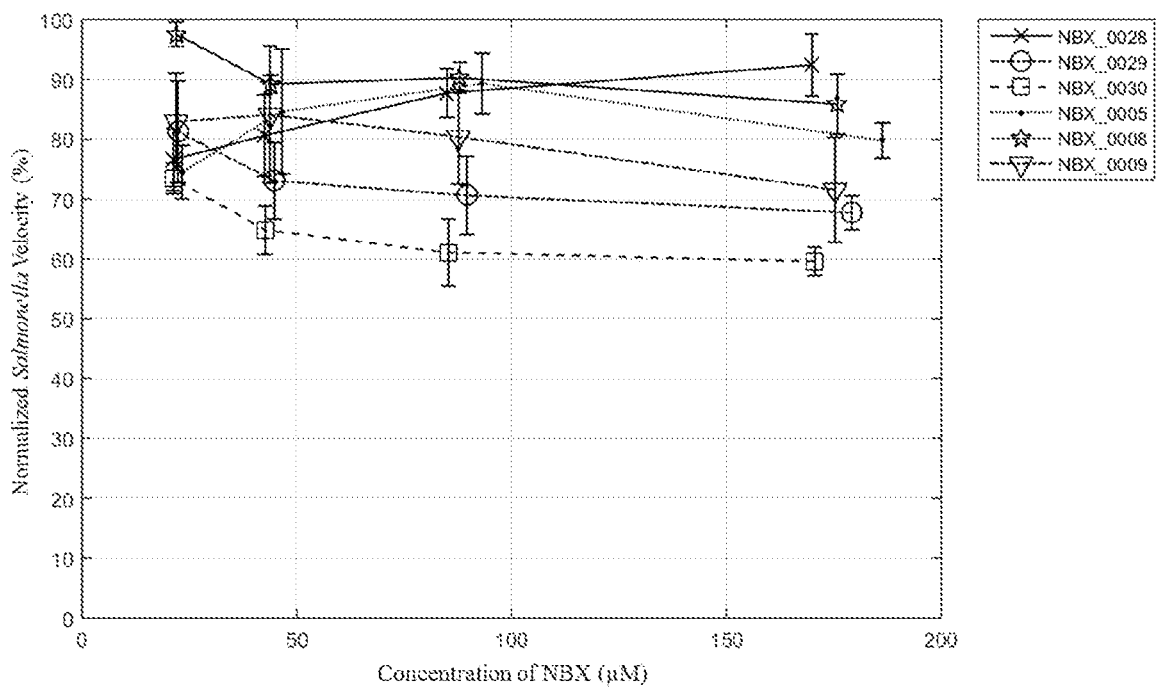
FIG. 12 is a graph that shows the velocity of *Salmonella enterica* serotype Typhimurium strain SL1344 in a live imaging motility assay in the presence of NovoBind NBX0005, NBX0008, NBX0009, NBX0028, NBX0029 and NBX0030.

Inhibition of *Salmonella* motility by polyclonal antibody serum and $V_HH$ antibodies was tested using either a standard plate motility assay or live-imaging microscopy.
Plate-Based Motility Assay Protocol
Plate-based motility assays were used to determine whether llama-derived polyclonal antibody serum was capable of inhibiting the motility of five poultry-contaminating *Salmonella* strains. The strains used were *Salmonella enterica* serotype Typhimurium strain SL1344, *Salmonella enterica* serotype Enteritidis strain PT4, *Salmonella enterica* serotype Enteritidis strain LK5, *Salmonella enterica* serotype Newport and *Salmonella enterica* serotype Heidelberg. Overnight cultures of *Salmonella* were mixed in 1:1 volumes with polyclonal antibody serum, pre-immune serum or PBS. The mixtures were incubated for 30 minutes at room temperature and following incubation, 10 μl from each mixture was spotted in the center of a petri dish containing 0.25% agar and incubated at 37° C. Bacterial motility was determined by measuring the diameter of growth six hours after plating.
Plate-Based Motility Assay Results
FIGS. 1-4 show that the motility of each *Salmonella* strain is inhibited in the presence of polyclonal antibody serum in comparison to pre-immune serum or no serum controls. Referring to FIGS. 1A, 1B, and 1C, the motility of *Salmonella enterica* serotype Typhimurium strain SL1344 is inhibited in the presence of NovoBind polyclonal antibody serum. (A) *Salmonella enterica* serotype Typhimurium strain SL1344 incubated with phosphate buffered saline as a control; (B) *Salmonella enterica* serotype Typhimurium strain SL1344 incubated with pre-immune serum; (C) *Salmonella enterica* serotype Typhimurium strain SL1344 incubated with polyclonal antibody serum. Referring to FIGS. 2A, 2B, and 2C, motility of *Salmonella enterica* serotype Enteritidis strain PT4 is inhibited in the presence of NovoBind polyclonal antibody serum. (A) *Salmonella enterica* serotype Enteritidis strain PT4 incubated with phosphate buffered saline as a control; (B) *Salmonella enterica* serotype Enteritidis strain PT4 incubated with pre-immune serum; (C) *Salmonella enterica* serotype Enteritidis strain PT4 incubated with polyclonal antibody serum. Referring to FIGS. 3A, 3B, and 3C, motility of *Salmonella enterica* serotype Enteritidis strain LK5 is inhibited in the presence of NovoBind polyclonal antibody serum. (A) *Salmonella enterica* serotype Enteritidis strain LK5 incubated with phosphate buffered saline as a control; (B) *Salmonella enterica* serotype Enteritidis strain LK5 incubated with pre-immune serum; (C) *Salmonella enterica* serotype Enteritidis strain LK5 incubated with polyclonal antibody serum. Referring to FIGS. 4A, 4B, and 4C motility of *Salmonella enterica* serotype Enteritidis strain PT4, *Salmonella enterica* serotype Newport and *Salmonella enterica* serotype Heidelberg is inhibited in the presence of NovoBind polyclonal antibody serum. (A) *Salmonella enterica* serotype Enteritidis strain PT4 incubated with phosphate buffered saline, pre-immune serum, or NovoBind polyclonal antibody serum; (B) *Salmonella enterica* serotype Newport phosphate buffered saline, pre-immune serum, or NovoBind polyclonal antibody serum; (C) *Salmonella enterica* serotype Heidelberg incubated with phosphate buffered saline, pre-immune serum, or NovoBind polyclonal antibody serum.
Live Imaging Motility Assay Protocol
Live-imaging microscopy was used to quantify the inhibitory effect of polyclonal antibody serum and monoclonal $V_HH$ antibodies (NBXs) on motility of *Salmonella*. Briefly, an overnight culture of *Salmonella enterica* serotype Typhimurium strain SL1344 was used to inoculate a subculture which was grown at 37° C. in a shaking incubator until logarithmic growth was reached. Five μl of log phase *Salmonella enterica* serotype Typhimurium strain SL1344 was mixed with 10 μl of polyclonal antibody serum or monoclonal $V_HH$ antibodies diluted in PBS as indicated (FIGS. 5, 9-12). Mixtures were incubated at room temperature for 1 hour and observed at 400× magnification with an Olympus IX70 inverted microscope with an Olympus DP80 camera. *Salmonella* motility was tracked and analyzed using Velocity image analysis software and bacterial movement was normalized and expressed as a percentage of a control that was considered to be 100% motile.
Live Imaging Motility Assay Results
FIG. 5 and FIGS. 9-12 show results from live imaging motility assays. Referring to FIG. 5 *Salmonella enterica* serotype Typhimurium strain SL1344 motility is inhibited in the presence of NovoBind polyclonal antibody serum using a live imaging motility assay. The inhibitory effect of NovoBind polyclonal antibody serum decreases with increased dilution of serum. Referring to FIG. 9 the motility of *Salmonella enterica* serotype Typhimurium strain SL1344 is inhibited in the presence of NovoBind NBX0018 and NBX0019. Referring to FIG. 10 the motility of *Salmonella enterica* serotype Typhimurium strain SL1344 is inhibited in the presence of NovoBind NBX0015. Referring to FIG. 11 the motility of *Salmonella enterica* serotype Typhimurium strain SL1344 is inhibited in the presence of NovoBind NBX0022-NBX0027. Referring to FIG. 12 the motility of *Salmonella enterica* serotype Typhimurium strain SL1344 is inhibited in the presence of NovoBind NBX0005, NBX0008, NBX0009, NBX0028, NBX0029 and NBX0030.

Example 5—In Vitro Analysis of Antibody Binding

Figure 6:
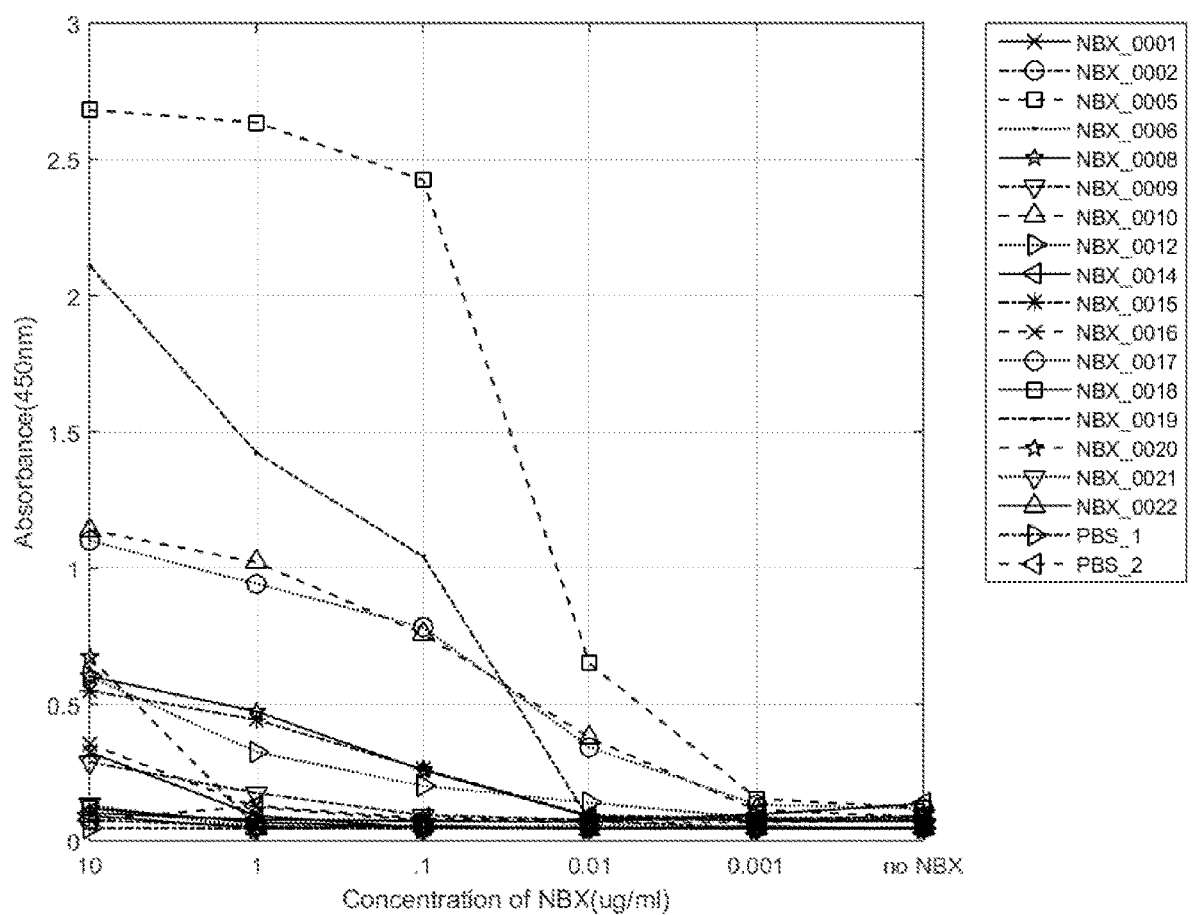
FIG. 6 is a graph that shows the differences in specific binding among 17 different monoclonal $V_H H$ antibodies (NBXs) raised against whole *Salmonella enterica* serotype Typhimurium flagella or recombinant FliC versus a *Salmonella enterica* serotype Typhimurium flagella capture surface.
Figure 7:
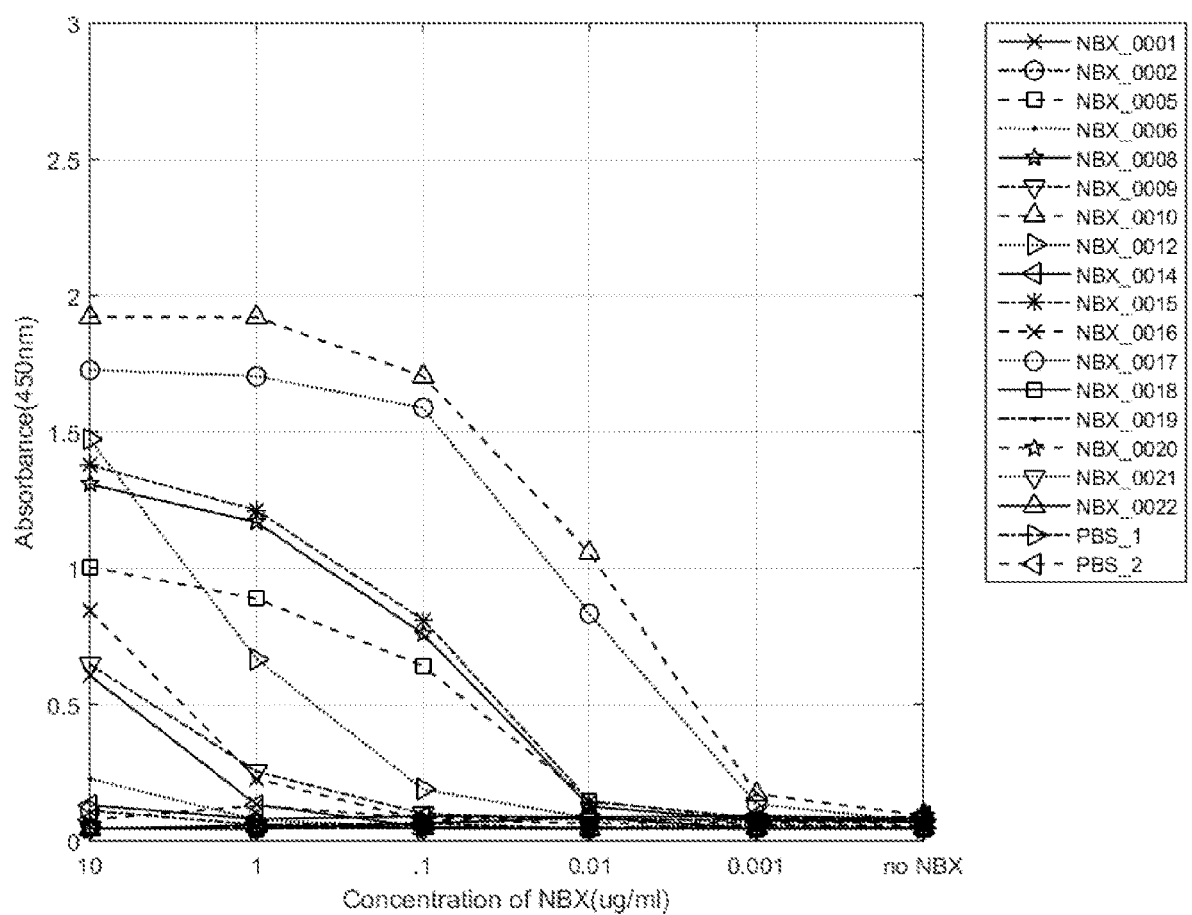
FIG. 7 is a graph that shows the differences in specific binding among 17 different monoclonal $V_H H$ antibodies (NBXs) raised against whole *Salmonella* Typhimurium flagella or recombinant FliC versus a *Salmonella enterica* serotype Enteritidis flagella capture surface.
Figure 8:
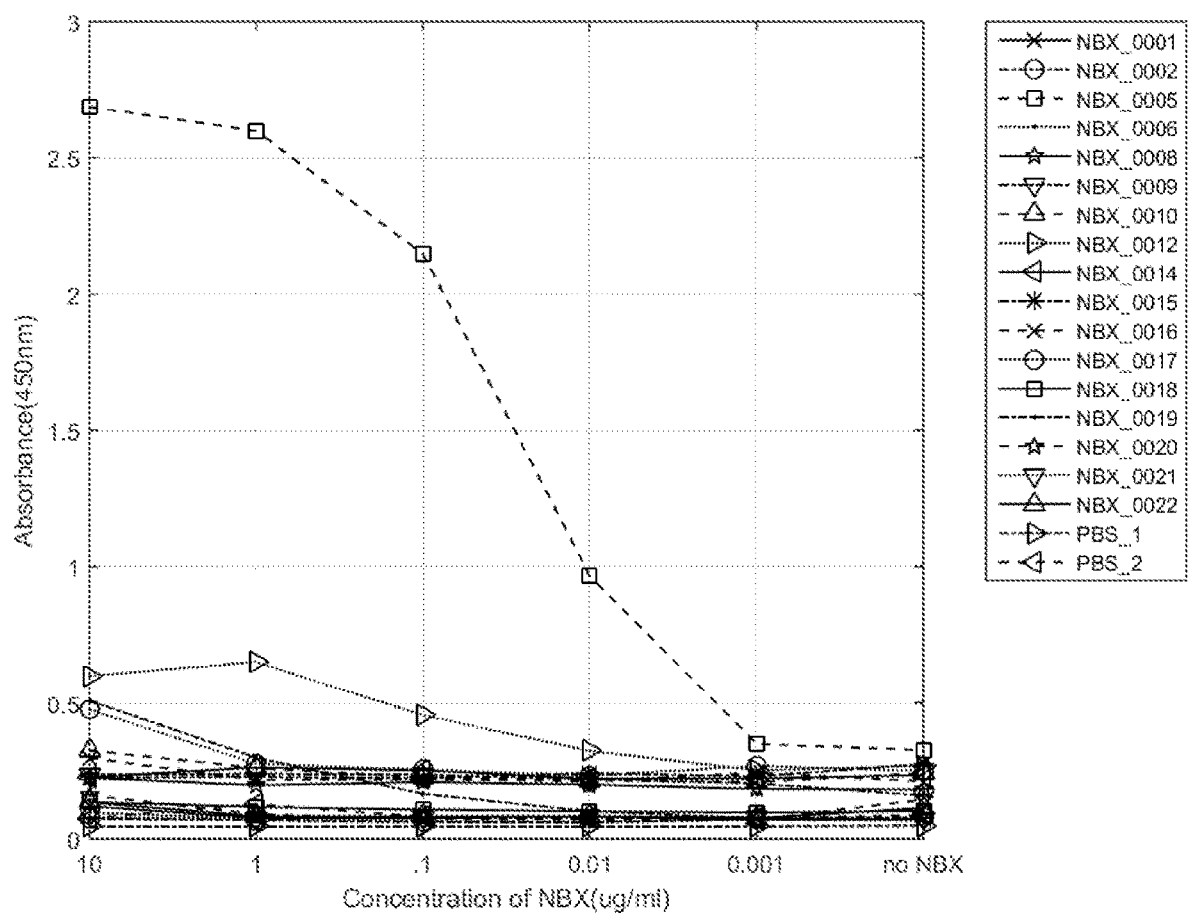
FIG. 8 is a graph that shows the differences in specific binding among 17 different monoclonal $V_H H$ antibodies (NBXs) raised against whole *Salmonella enterica* serotype Typhimurium flagella or recombinant FliC versus a recombinant FliC capture surface.

In Vitro Analysis of Antibody Binding Protocol
Antibody binding was assessed using ELISA. Each well of a microtitre plate was coated with 100 μl containing 0.2 μg of appropriate antigen and plates were incubated overnight at 4° C. Wells were emptied and blocked with 5% skim milk in PBST (PBS 0.1% tween-20), covered with parafilm and incubated at 37° C. for 1 hour. Wells were emptied and 100 μl of the appropriate NBX was added at the appropriate concentration to each well; for wells containing no NBX, 100 μl of PBS was added. Plates were wrapped with parafilm and incubated at room temperature for 1 hour. Following incubation, well contents were removed and wells were washed 3× with PBST. Next, 100 μl of a 1:5000 dilution of anti-6-His-HRP secondary antibody was added to each well, plates were sealed with parafilm and incubated at room temperature for 1 hour. Well contents were removed and wells were again washed 3× with PBST. Signal was detected by adding 100 µl of TMB substrate mixed in equal volume with TMB developing solution to each well for 5 min at room temperature. Reactions were stopped by adding 100 µl of 1 M phosphoric acid and absorbance was read at 450 nm.
In Vitro Analysis of Antibody Binding Results FIGS. 6-8 show results of ELISA based antibody binding assays. FIG. 6 shows the differences in specific binding among 17 different monoclonal NBXs raised against whole *Salmonella enterica* serotype Typhimurium flagella or recombinant FliC versus a *Salmonella enterica* serotype Typhimurium flagella capture surface. FIG. 7 shows the differences in specific binding among 17 different monoclonal NBXs raised against whole *Salmonella enterica* serotype Typhimurium flagella or recombinant FliC versus a *Salmonella enterica* serotype Enteritidis flagella capture surface. FIG. 8 shows the differences in specific binding among 17 different monoclonal NBXs raised against whole *Salmonella enterica* serotype Typhimurium flagella or recombinant FliC versus a recombinant FliC capture surface.

Example 6—Efficacy of $V_HH$ Antibodies (NBXs) in Inhibiting Bacterial Motility In Vitro Shown in Table 5 are the effective in vitro concentrations of different NBX antibodies obtained in a motility assay as performed in Example 4.

TABLE 5

Effect of individual $V_HH$ antibodies (NBXs) on *Salmonella* motility and their effective concentrations

| $V_HH$ | Percent Motility[a] | Effective Concentration[b] (µM) |
|---|---|---|
| NBX0001 | 50% | 90 |
| NBX0002 | 62% | 85 |
| NBX0005 | 80% | 190 |
| NBX0006 | 58% | 85 |
| NBX0008 | 85% | 175 |
| NBX0009 | 72% | 175 |
| NBX0010 | 75% | 90 |
| NBX0012 | 70% | 180 |
| NBX0014 | 70% | 75 |
| NBX0015 | 42% | 450 |
| NBX0016 | 72% | 40 |
| NBX0017 | 78% | 175 |
| NBX0018 | 40% | 30 |
| NBX0019 | 40% | 30 |
| NBX0021 | 60% | 170 |
| NBX0022 | 65% | 170 |
| NBX0023 | 72% | 45 |
| NBX0024 | 70% | 45 |
| NBX0025 | 72% | 170 |
| NBX0026 | 75% | 80 |
| NBX0027 | 80% | 165 |
| NBX0028 | 77% | 25 |
| NBX0029 | 67% | 180 |
| NBX0030 | 60% | 170 |

[a]Percent motility of *Salmonella enterica* serotype *Typhimurium* strain SL1344 normalized to a 100% motile control.
[b]Lowest molar concentration required to achieve lowest percent motility.

Example 7—Efficacy of $V_HH$ Antibodies (NBXs) on Biofilm Formation

Biofilms are multi-cellular bacterial communities. *Salmonella* can form biofilms on many types of surfaces including chicken intestinal epithelium and this contributes to colonization and disease in animals. Therefore, the ability to inhibit biofilm formation may decrease the burden of *Salmonella* in the GI tract of animals. This assay was completed with monomeric NBX.

Figure 13:
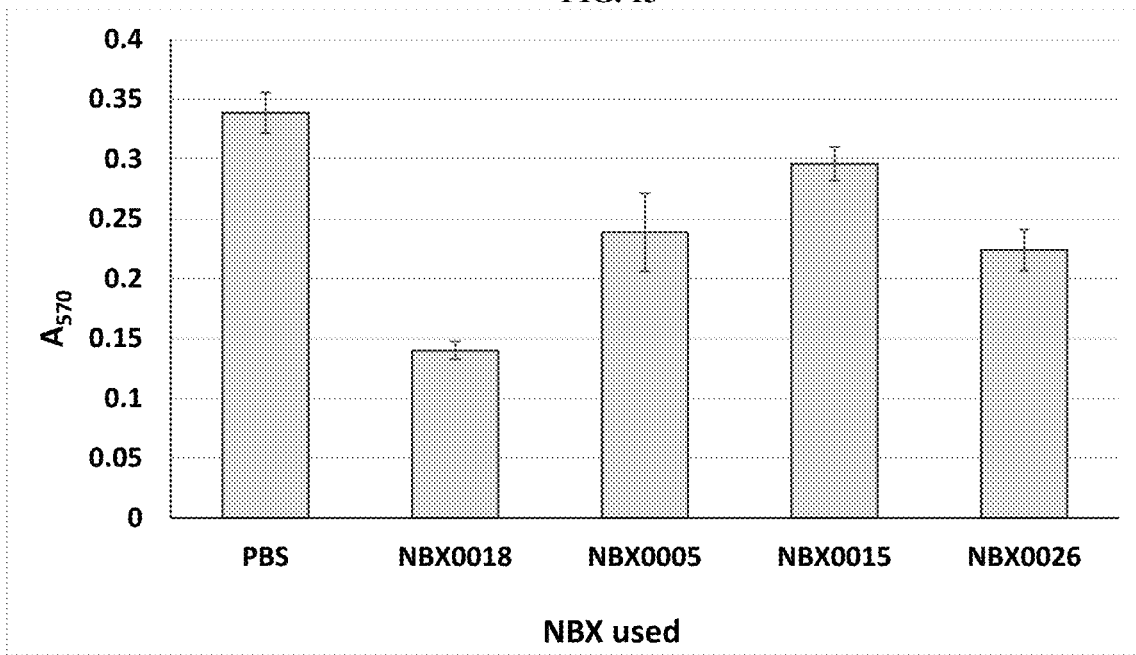
FIG. 13. shows that NBX can inhibit biofilm formation. In the absence of an NBX (PBS), a robust biofilm is formed after 24 hours. Treatment with four different NBXs (NBX0018, NBX0005, NBX0015, NBX0026) reduced biofilm formation by between 12% and 59%. Data presented in the graph represent the mean of five replicate wells and error bars represent the standard deviations.
Figure 14A:
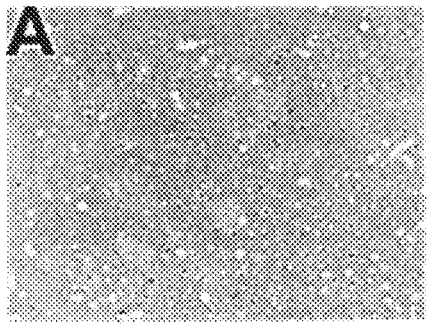
FIG. 14A to 14E Show that multimeric $V_HH$ promote Salmonella aggregation. PBS treatment (A) and NBX0018 (B) fail to aggregate Salmonella enterica serovar Typhimurium strain SL1344 (black dots), while NBX0018-NBX0018 (C) induced small bacterial aggregates. Bacterial aggregates formed by NBX0018-NBX0018-NBX0018 (D) exceeded the size of those formed by the polyclonal antibody positive control (E). Representative aggregates are circled in black for visualization purposes.
Figure 14B:
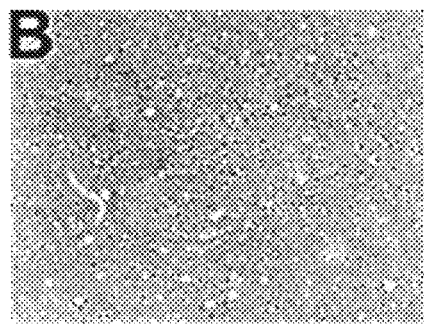
Figure 14C:
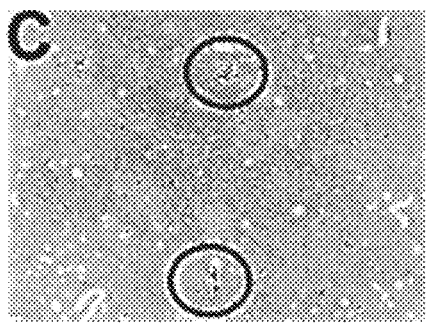
Figure 14D:
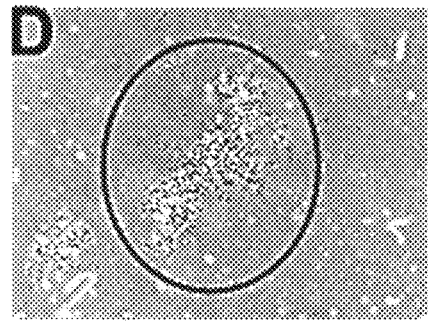
Figure 14E:
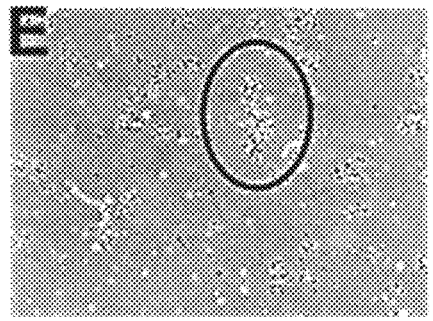

*Salmonella enterica* serovar Typhimurium strain SL1344 was grown overnight in 5 mL of LB media at 37° C. with shaking at 240 RPM. Bacteria were diluted to an $OD_{600}$=0.1 in LB media and grown for 4 hours at 37° C. with shaking at 240 RPM. Four mL of bacterial culture was pelleted by centrifugation and the supernatant was removed. The bacteria were resuspended in 1 mL of LB with no salt. The bacterial culture was pelleted again by centrifugation and the supernatant was removed. The bacteria were resuspended in 1 mL of LB with no salt and the optical density at 600 nm ($OD_{600}$) was measured. The bacteria were diluted to an $OD_{600}$ of 1.25 in LB with no salt. For each condition tested, quintuplicate 96-well plate wells were used. Each well received 80 µl of LB with no salt, 10 µl of bacterial culture in LB with no salt, and 10 µl of NBX stock solution dissolved in PBS or PBS. The final concentration of NBX was 1.0 mg/ml. The 96-well plate was incubated at room temperature for 24 hours. Non-adherent bacteria were removed and adherent biofilms were washed three times with 200 µl of water. Biofilms were fixed to 96-well plates by heat treatment (60° C. for 1 hour). Biofilms were stained with 150 µl of 0.1% (weight/volume) crystal violet for 30 minutes at room temperature. Excess stain was removed and wells were washed three times with 200 µl of water. Plates were inverted and left to dry for 24 hours. Cells were de-stained by addition of 150 µl of 95% (volume/volume) ethanol to wells and incubate 1 hour at room temperature to de-stain crystal violet from the cells. To quantify biofilm formation, absorbance was measured at 570 nm ($A_{570}$) of the solution to determine the amount of crystal violet that had stained the biofilms. FIG. 13 shows that all NBXs tested reduced biofilm formation between 12% and 59% NBX0018 had the highest reduction in biofilm formation followed by NBX0026, NBX0005, and NBX0026.

Example 8—Multimeric $V_HH$ Antibodies Display Enhanced Efficacy

To increase the effectiveness of $V_HHs$ (NBXs), we produced concatemer proteins consisting of up to three NBX subunits linked by 15 amino acid (3×G4S) linker sequences. These protein sequences were constructed and proteins were expressed and produced by means similar to monomeric ($V_HH$) NBX molecules. Multimeric $V_HH$ were assessed in a Live imaging motility assay protocol as per example 4. Results are shown in Table 6. A trimer of NBX0018 inhibits motility at a concentration 300-fold less than a monomer, and the dual NBX0018 inhibits motility at a concentration 20-fold less than the monomer.

TABLE 6

Inhibition of *Salmonella* motility by multimeric $V_HH$

| NBX Construct | Minimum Concentration Required for 50% Motility Inhibition |
|---|---|
| NBX0018 | 510 nM |
| NBX0018-NBX0018 | 24.4 nM |
| NBX0018-NBX0018-NBX0018 | 1.7 nM |
| NBX0005 | >372 µM |
| NBX0005-NBX0005 | 2.6 µM |
| NBX0015 | 52 µM |
| NBX0015-NBX0015 | 25 µM |

Minimum protein concentrations required by NBX constructs to inhibit *Salmonella enterica* serovar *Typhimurium* strain SL1344 motility by >50%.

Example 9—Multimeric V$_H$H Antibodies Aggregate *Salmonella* bacteria

Although bacteria, including *Salmonella* can aggregate into ordered structures known as biofilms, the uncontrolled aggregation of bacteria into clumps has been shown to be detrimental to the ability of *Salmonella* to cause infections in animal models, including chickens. Therefore, we tested the ability of multimeric V$_H$H to induce aggregation of *Salmonella*.

*Salmonella enterica* serovar Typhimurium strain SL1344 was grown overnight in 5 mL of LB media at 37° C. with shaking at 200 RPM. One mL of bacterial culture was pelleted by centrifugation and the supernatant was removed. The bacteria were resuspended in 1 mL of PBS to remove trace amounts of media. The bacterial culture was pelleted again by centrifugation and the supernatant was removed. The bacteria were resuspended in 1 mL of PBS and the optical density at 600 nm (OD$_{600}$) was measured. The bacteria were diluted to an OD$_{600}$ of 1.0 in PBS. 15 µl volumes of bacteria were placed in 1.5 mL centrifuge tubes and 15 µl of PBS (negative control), NBX (test molecules), or 3% anti-*Salmonella enterica* serovar Typhimurium strain SL1344 polyclonal antibody (positive control) were added to appropriate tubes. Mixtures were incubated at 4° C. for 20 hours. 10 µl of each mixture were placed in chamber microscope slides and visualized at 400× magnification. For each microscope slide, 20-30 random fields of view are observed and 3-5 representative images are photographed. If no bacterial aggregations are observed to this point, an additional 20-30 fields of view are observed to confirm lack of aggregates.

FIG. 14 shows that while single monomers of V$_H$H (NBX0018) were ineffective at aggregating *Salmonella* (14B), compared to vehicle control (14A), dimers of V$_H$H (NBX0018-NBX0018) induced aggregation (14C, circled), and trimers (NBX0018-NBX0018-NBX0018) induced a large amount of aggregation (14D, circled), even greater than a positive control antibody (a polyclonal anti-sera) (14E, circled).

Example 10—Multimeric V$_H$H Antibodies Block Cellular Invasion by *Salmonella* bacteria A key process that contributes to the virulence of *Salmonella* is its ability to invade host intestinal epithelial cells. Invasion of host cells can allow *Salmonella* to multiple intracellularly, spread to the lymph nodes and systemic circulation, and potentially infect other organ systems. A method to assess invasion in vitro is the HeLa cell invasion assay. This assay involves incubation of the bacteria and HeLa cells, incubation with an antibiotic to remove external *Salmonella*, then lysis of HeLa cells followed by enumeration of invaded *Salmonella*. The number of *Salmonella* that have invaded HeLa cells can be used to determine if a V$_H$H can block this process.

Figure 15:
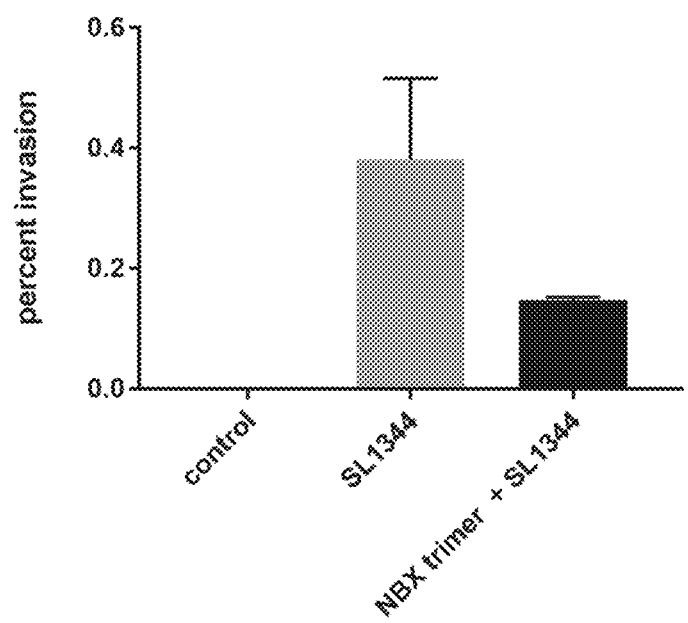
FIG. 15. Shows that multimeric $V_HH$ block HeLa cell invasion by Salmonella enterica serovar Typhimurium strain SL1344 is reduced by more than 50% in the presence of NBX0018-NBX0018-NBX0018 (NBX trimer). Control refers to uninfected HeLa cells treated with PBS throughout the experiment. Shown are the means of duplicate wells and the error bars represent the standard deviations.
Figure 16E:
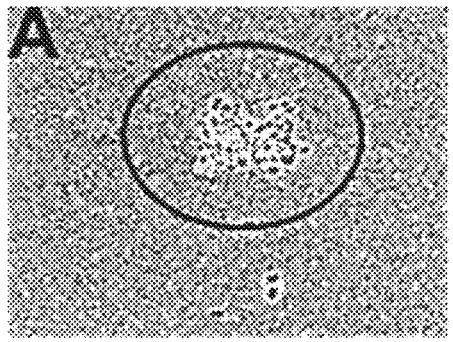
Figure 16E:
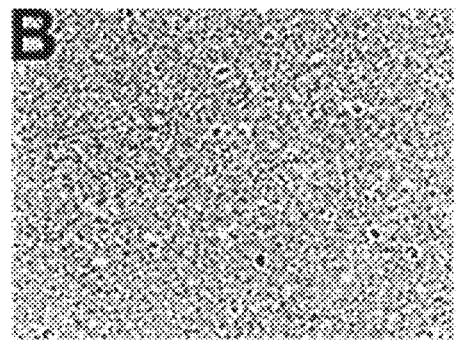
Figure 16E:
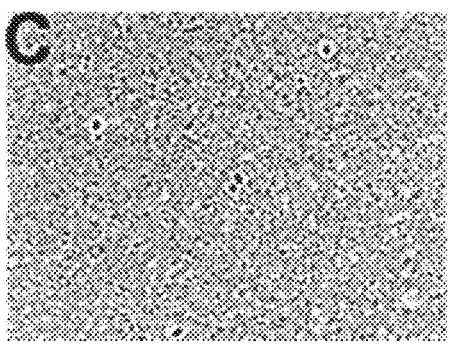
Figure 16E:
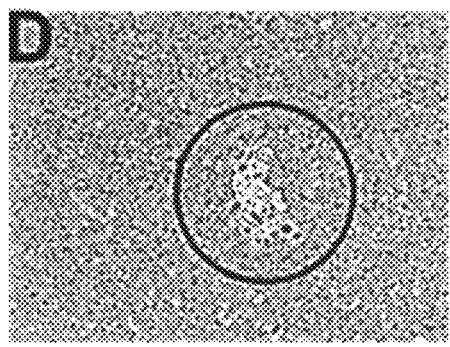
Figure 16E:
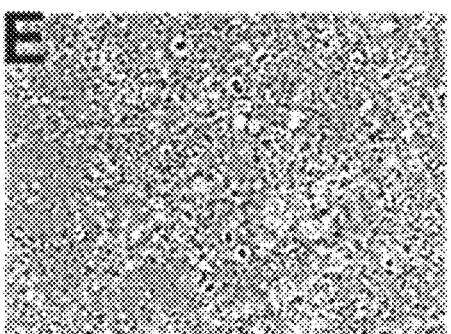
Figure 17:
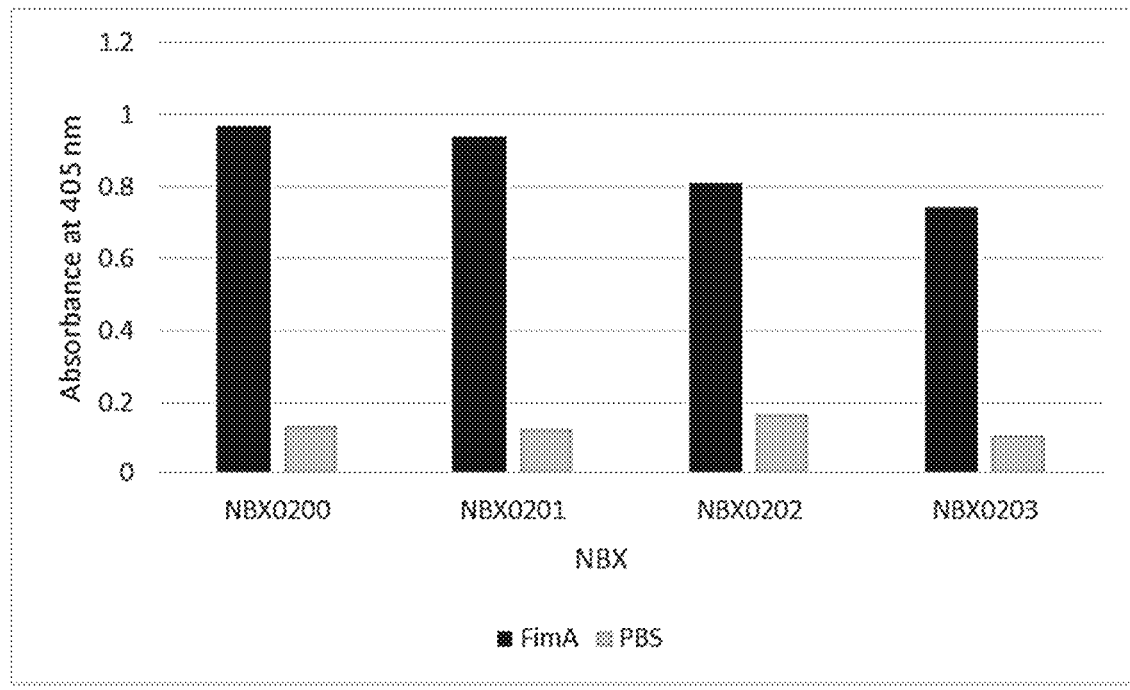
FIG. 17: Shows phage ELISA binding data for NBXs to FimA. Black bars show binding to wells coated with FimA in phosphate-buffered saline (PBS). Grey bars are negative controls that show binding to wells coated with PBS only. In all cases binding to the antigen target is at least four-fold above background.
Figure 18:
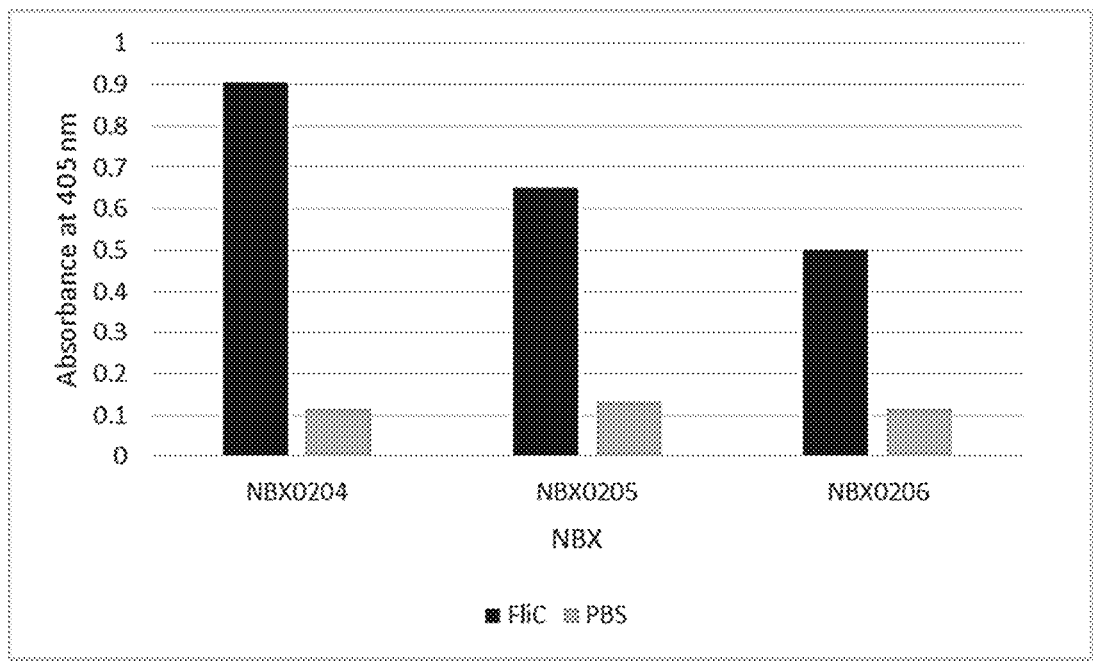
FIG. 18 Shows phage ELISA binding data for NBXs to FliC. Black bars show binding to wells coated with FliC in phosphate-buffered saline (PBS). Grey bars are negative controls that show binding to wells coated with PBS only. In all cases binding to the antigen target is at least four-fold above background.
Figure 19:
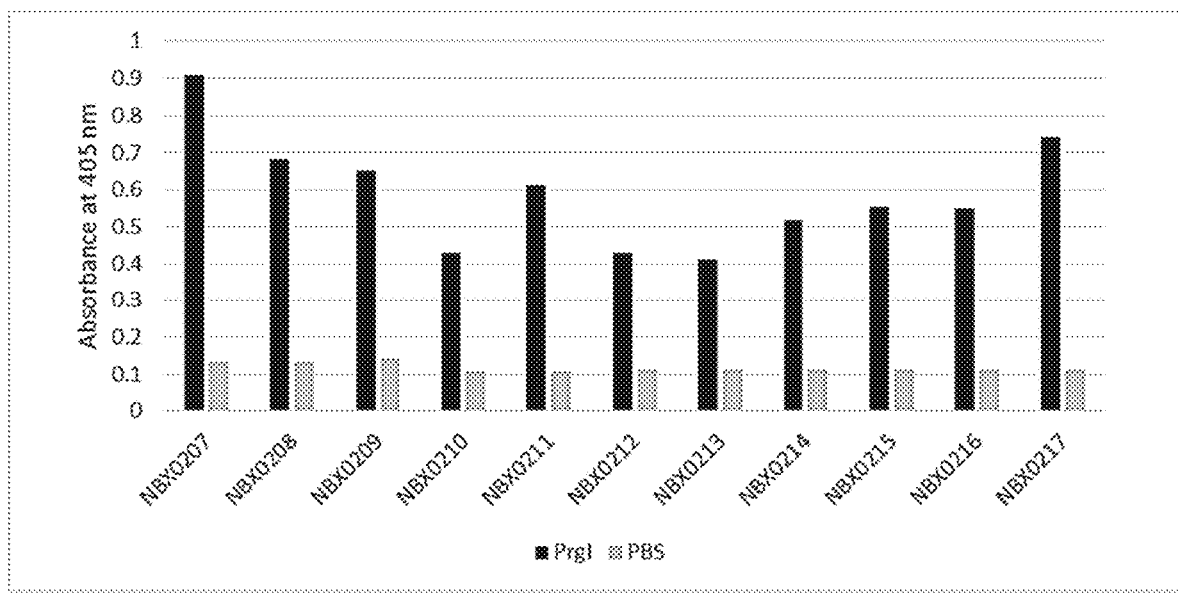
FIG. 19 Shows phage ELISA binding data for NBXs to PrgI. Black bars show binding to wells coated with PrgI in phosphate-buffered saline (PBS). Grey bars are negative controls that show binding to wells coated with PBS only. In all cases binding to the antigen target is at least four-fold above background.
Figure 20:
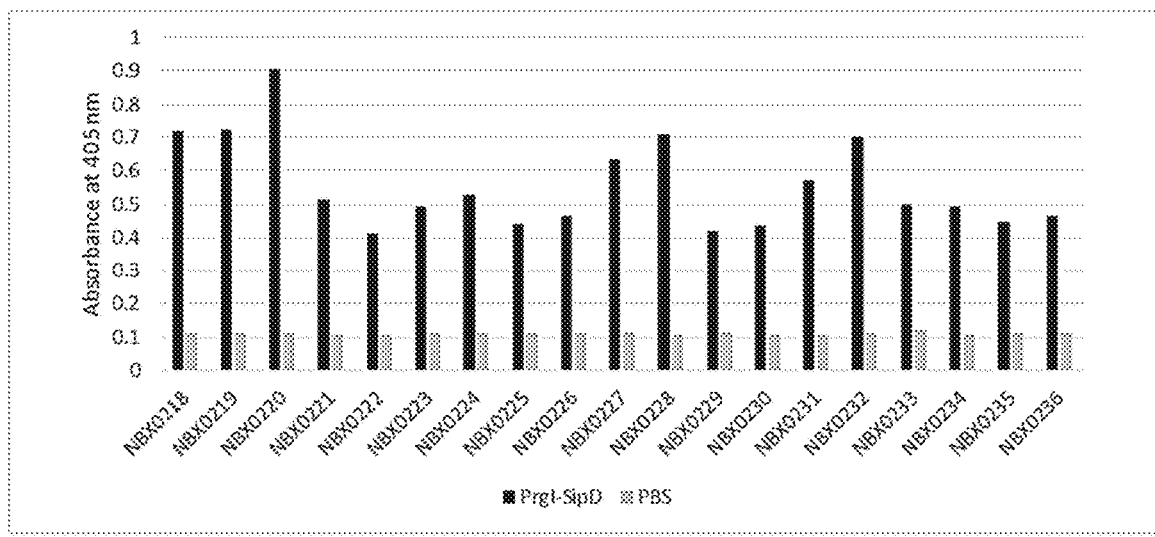
FIG. 20 Shows phage ELISA binding data for NBXs to PrgI-SipD. Black bars show binding to wells coated with PrgI-SipD in phosphate-buffered saline (PBS). Grey bars are negative controls that show binding to wells coated with PBS only. In all cases binding to the antigen target is at least four-fold above background.
Figure 21:
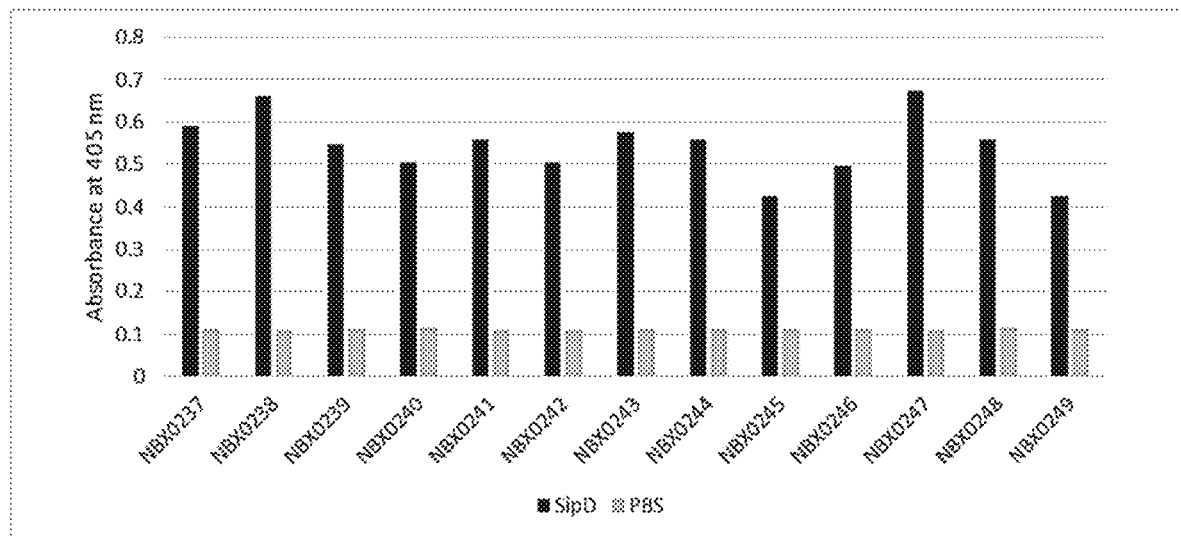
FIG. 21 Shows phage ELISA binding data for NBXs to SipD. Black bars show binding to wells coated with SipD in phosphate-buffered saline (PBS). Grey bars are negative controls that show binding to wells coated with PBS only. In all cases binding to the antigen target is at least four-fold above background.
Figure 22:
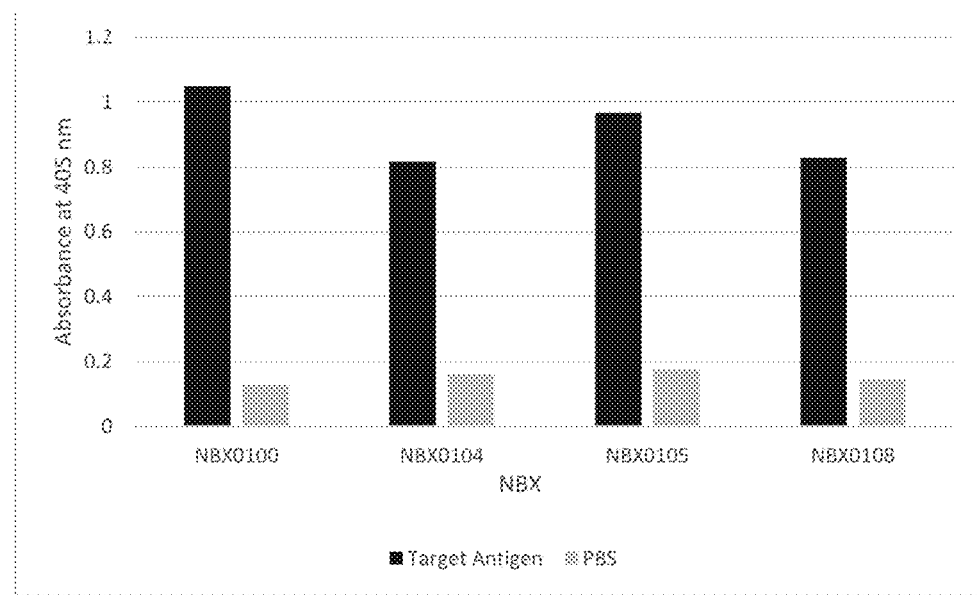
FIG. 22 Shows Phage ELISA binding data. Black bars show binding to wells coated with appropriate antigen target (FimA for NBX0100 and PrgI for NBX0104, NBX0105, and NBX0108) dissolved in phosphate-buffered saline (PBS). Grey bars are negative controls that show binding to wells coated with PBS only. In all cases binding to the antigen target is at least four-fold above background.

HeLa cells (5×10$^4$ cells/well) were seeded in tissue culture media and maintained at 37° C. in 5% CO$_2$. An overnight culture of *Salmonella enterica* serovar Typhimurium strain SL1344, was prepared with shaking at 37° C. After 16 hours of incubation, a subculture was prepared (1:33 in LB Broth with streptomycin) for 3 hours. *Salmonella* were quantified by measuring OD$_{600}$. HeLa cells were incubated with 5×10$^5$ cells/well for 1 hour with or without 1 mg/ml NBX0018-NBX0018-NBX0018. Input *Salmonella* were then plated in serial dilutions. Cells were then washed 3 times with PBS and incubated with gentamycin (50 µg/mL) for a period of 1 hour. Following incubation with antibiotic, cells were washed 3 times with PBS and lysed. Serial dilutions were made and plated for *Salmonella* enumeration. % invasion was calculated as the number of *Salmonella* from HeLa cells/input *Salmonella*. Results in FIG. 15 show that HeLa cell invasion by *Salmonella enterica* serovar Typhimurium strain SL1344 is reduced by more than 50% in the presence of NBX0018-NBX0018-NBX0018 (NBX trimer). Control refers to uninfected HeLa cells treated with PBS throughout the experiment.

Example 11—V$_H$H Block *Salmonella* Activity Dependent on Production System In order to colonize and establish successful infections, *Salmonella* must adhere to eukaryotic cells lining the GI tract. One mechanism by which *Salmonella* does this is to use its Type-1 Fimbriae to bind to mannose sugars on the surface of the eukaryotic cells. Disruption of the interaction between Type-1 Fimbriae and surface-expressed mannose sugars will lead to decreases in *Salmonella* colonization. Yeast cells also make these sugars on their surface and if exposed to *Salmonella* with function Type-1 Fimbriae, the yeast cells will clump together. The presence or absence of yeast clumping can be used as an in vitro proxy to determine if a V$_H$H is blocking Type-1 Fimbriae function. V$_H$Hs that are recombinantly produced in yeast (*Pichia pastoris*) rather than the bacterium *Escherichia coli* will be glycosylated with many sugars including mannose. This mannose glycosylation on the V$_H$H can add a function to the V$_H$H and block Type-1 Fimbriae function.

*Salmonella enterica* serovar Typhimurium strain SL1344 was grown for 96 hours in 5 mL of LB media at 37° C. without shaking. 0.45 mL of bacterial culture was pelleted by centrifugation and the supernatant was removed. The bacteria were resuspended in 0.45 mL of PBS to remove trace amounts of media. The bacterial culture was pelleted again by centrifugation and the supernatant was removed. The bacteria were resuspended in 0.045 mL of PBS, PBS containing 1 mg/ml NBX, or PBS containing 100 mM mannose (positive control for Type-1 Fimbriae inhibition). Bacteria were incubated for 1 hour at room temperature. *Saccharomyces cerevisiae* yeast cells were resuspended in PBS at an OD$_{600}$=10 and 5 µl was added to the bacteria. Mixtures were incubated at 4° C. for 20 hours. 10 µl of each mixture were placed in chamber microscope slides and visualized at 400× magnification. For each microscope slide, 20-30 random fields of view are observed and 3-5 representative images are photographed. If no yeast clumps are observed to this point, an additional 20-30 fields of view are observed to confirm lack of clumps.

Results in FIG. 16 show *Salmonella enterica* serovar Typhimurium strain SL1344 clumps *Saccharomyces cerevisiae* during PBS treatment (16A) or treatment with NBX0018 recombinantly produced in *Escherichia coli* (16D). In the presence of *Salmonella enterica* serovar Typhimurium strain SL1344 lacking the Type-1 Fimbriae (FimA mutant strain), *Saccharomyces cerevisiae* cells remain unclumped (16B). In the presence of *Salmonella enterica* serovar Typhimurium strain SL1344 with intact Type-1 Fimbriae and excess soluble mannose (16C) or NBX0018 recombinantly produced in *Pichia pastoris* (16E), *Saccharomyces cerevisiae* cells remain unclumped, indicating that the interaction between Type-1 Fimbriae and mannose sugars on the surface of the *Saccharomyces cerevisiae* cells has been blocked.

Example 12—Additional V$_H$H from Phage Display

M13KO7 phage carrying individual NBX genes were rescued from 1 mL cultures of *Escherichia coli* strain TG-1 upon superinfection with 10$^9$ plaque forming units of M13KO7 helper phage. Phage were separated from bacteria by centrifugation and stored at −20° C. until needed. ELISA plate wells were coated overnight at 4° C. with either 100 µl of PBS (negative control) or 100 µl of 5 µg/ml antigen. Wells were blocked for 2 hours at 37+ C. with 200 µl of PBS+ 0.05% (volume/volume) Tween-20+5% (weight/volume) Skim Milk Powder. 100 µl of phage preparations were added to wells for 1 hour at 37° C. Wells were washed four times with 300 µl of PBS+0.05% (volume/volume) Tween-20. 100 µl of anti-M13 IgG-horse radish peroxidase diluted 1 in 5000 in PBS was added for 1 hour at room temperature. Wells were washed four times with 300 µl of PBS+0.05% (volume/volume) Tween-20. 100 µl of 1 mg/ml 2,2'-azino-bis(3-ethylbenzothiazoline-6-sulphonic acid)+0.03% (volume/volume) hydrogen peroxide in sodium citrate-phosphate buffer pH 5.0 was added to wells for 15 minutes at room temperature. 100 µl of sodium dodecyl sulfate was added to wells. Absorbance at 405 nm was measured for each well. Data for additional V$_H$Hs specific for these targets is shown in FIG. 17-FIG. 22. CDR sequences are shown in Table. 2. Example 13—Stability of V$_H$Hs in GI Tract Fluid Background: The GI tract contains proteases (proteins that degrade other proteins) and, in some compartments, is acidic. NBXs identified as useful in in vitro studies should be able to survive the GI tract conditions in order to be useful in vivo. We have developed an ex vivo model using the contents of chicken GI tract organs to mimic in vivo conditions and determine survival of V$_H$H under these conditions.

Detailed Protocol: The GI tract was removed from a chicken and segmented by organ. The contents are collected from the organs, diluted 1:2 in water, centrifuged to pellet solids, and the supernatant is collected. NBXs are added to gut fluid samples or normal saline (untreated) at a final concentration of 0.625 µg/µL. The samples are incubated at 42° C. for a time equivalent to the natural transit time of material through the organ. In the case of the gizzard, provided as an example below, the incubation lasted for 30 minutes. Reactions are stopped on ice with the addition of sodium dodecyl sulfate loading dye, immediately vortexed, and boiled at 95° C. Samples are separated by size using sodium dodecyl sulfate-polyacrylamide gel electrophoresis (SDS-PAGE) and gels are stained with Coomassie R-250.

Figure 23:
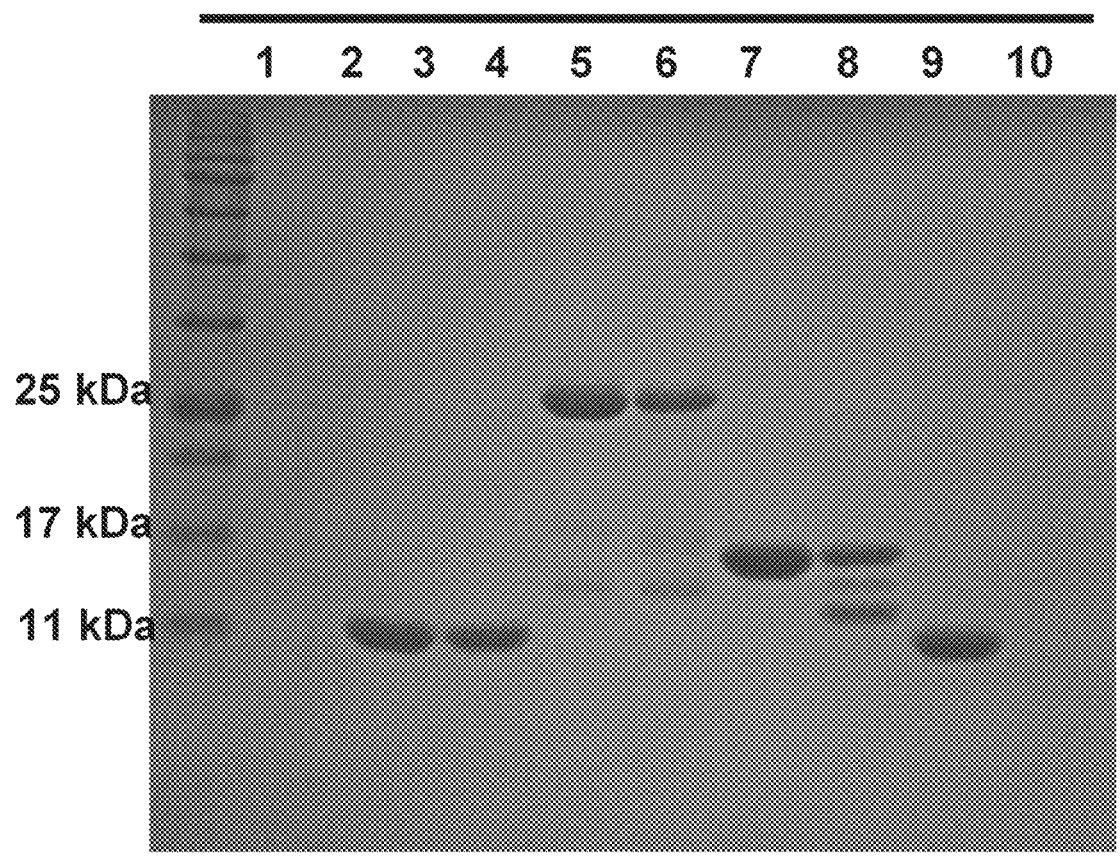
FIG. 23 shows stability of $V_HH$s in chicken GI fluids.

FIG. 23 shows that NBX0018 monomer and NBX0018-NBX0018 concatemer survive the ex vivo gizzard fluids better than NBX0015 or NBX0005. Lane 1 is a molecular weight marker and representative molecular weights are listed to the left of the gel. Lane 2 is the gizzard extract alone which indicates that there are very few background bands in the gizzard extract and that all bands in subsequent lanes are due to the presence of added NBXs. NBX0018 survives the gizzard extract well (lane 4) compared to the untreated control (lane 3). Similarly, the NBX0018-NBX0018 concatemer is also stable in the gizzard extract (lane 6) compared to the untreated control (lane 5). Some NBX0015 is degraded in the gizzard extract (lane 8) compared to the untreated control (lane 7). NBX0005 is completely degraded in the gizzard extract (lane 10) compared to the untreated control (lane 9).

Example 14—V$_H$Hs Can Be Detected Intact Throughout the GI Tract of a Chicken after Oral Administration 3 mg of NBX0018 was orally administered to a day-old chick. 30 minutes later, the GI tract was removed from the chicken and segmented by organ. The contents of the organs were collected and 10 µL of organ fluid was separated by size using SDS-PAGE. The material in the gel was transferred to nitrocellulose membranes and visualized by Western Blotting using an anti-His antibody.

Figure 24:
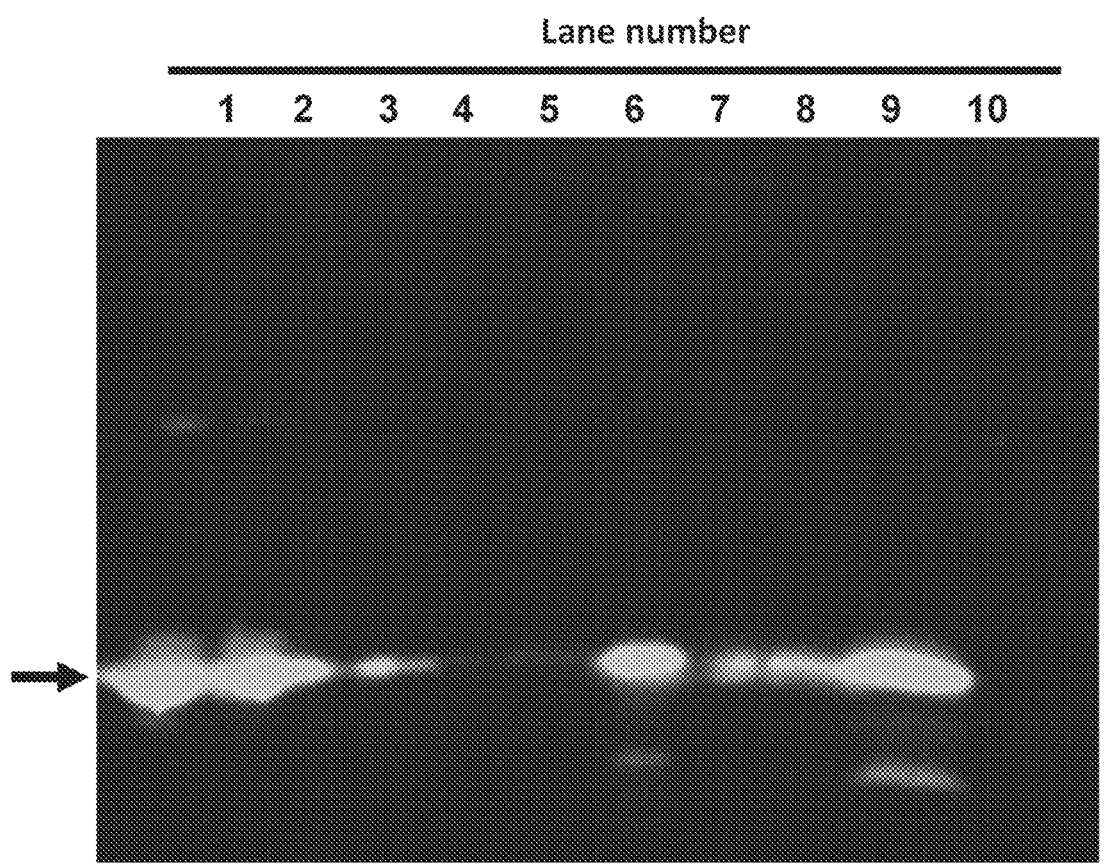
FIG. 24 shows presence of $V_HH$s in GI tract of a chicken after oral administration.

FIG. 24 shows that NBX0018 can be detected intact in chicken GI tract. Lanes 1 and 2 are both loaded with purified NBX0018 (marked with an arrow) to show the size of the intact protein. There is intact NBX0018 in the crop (lane 3), proventriculus (lane 4), gizzard (lane 5), duodenum (lane 6), jejunum (lane 7), ileum (lane 8), caecum (lane 9). Degradation products (bands running below the main band) are seen in the duodenum, jejunum, ileum, and caecum. Only the large intestine (lane 10) does not contain intact NBX0018.

Example 15—V$_H$Hs Are Non-Toxic to Chickens after Administration

Detailed Protocol: NBX0018, NBX0018-NBX0018 concatemer or PBS (negative control) was orally administered four times over a 3-day period to 7-day old chicks. Final body weights and spleen weights (as a % of body weights) were determined for each animal.

Figure 25A:
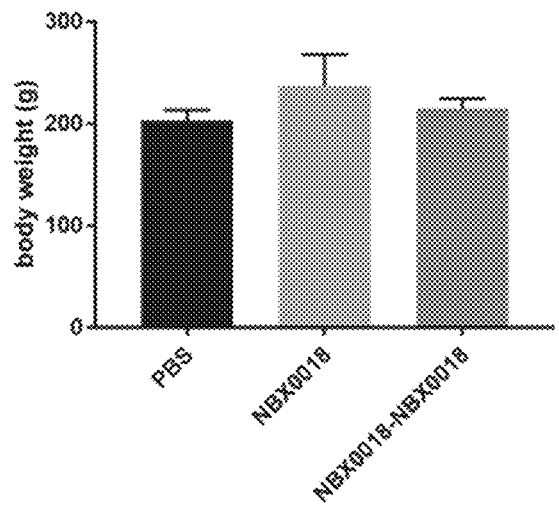
FIG. 25A and FIG. 25B show that $V_HH$ are non-toxic to Chicken and have no impact on bodyweight (A) or spleen weight (B).
Figure 25B:
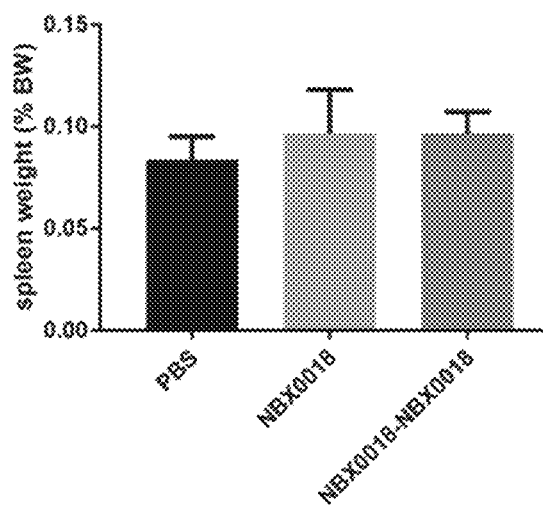

FIG. 25 shows that there were no statistically significant differences in (25A) body weights or (25B) spleen weights as a percentage of body weight (BW) in chickens treated with PBS (negative control), NBX0018, or NBX0018-NBX0018 concatemer. This indicates that there is no significant toxicity induced by NBXs in the chickens. Data represent the means of three (PBS) or five (NBX0018 and NBX0018-NBX0018) chickens per group and error bars represent the standard deviations. In addition, no GI lesions, organ damage, or abnormal behaviours were noted for any of the treatments.

Example 16—Crude V$_H$H Purification from Periplasmic Extracts and Activity in Bacterial Motility Assay NBX genes are cloned into the phagemid pRL144 and transformed into *E. coli* TG-1 cells as part of the phage display portion of antibody discovery. For NBX of interest, crude periplasmic extracts containing the NBX were prepared as follows. Bacteria are grown in 2×TY, 100 µg/ml ampicillin, and 0.1% (wt/vol) glucose for 3 hours at 37° C. 1 mM IPTG is added to induce protein production and the bacteria are incubated overnight at 30° C. Bacteria cells were pelleted by centrifugation and the supernatants were discarded. Cell pellets were frozen at −20° C. overnight. Pellets were thawed at room temperature for 15 minutes, resuspended in 500 µL of PBS, and rotated at 700 RPM for 30 minutes at room temperature to release the periplasmic contents. Remaining bacterial spheroplasts were pelleted and the NBX-containing supernatants were collected for in vitro testing. The live imaging motility assay protocol from example 4 was used to test the activity of crude periplasmic extracts. Results are shown in Table 7.

TABLE 7

| NBX Construct | Minimum Periplasmic Extract Concentration Required for 50% Motility Inhibition |
| --- | --- |
| NBX0202 | >66.7% |
| NBX0204 | 6.67% |
| NBX0205 | 6.67% |

Minimum periplasmic extract concentrations containing NBXs required to inhibit *Salmonella enterica* serovar *Enteritidis* strain LK5 motility by >50%. The concentration reported for NBX0202 was the highest concentrations tested and had no impact on bacterial motility.

Example 17—Purification of NBXs from *E. coli*

TEV protease-cleavable, 6×His-thioredoxin-NBX fusion proteins are expressed in the cytoplasm of *E. coli* grown in autoinducing media (Formedium) for 24 hours at 30° C. Bacteria are collected by centrifugation, resuspended in buffer A (10 mM HEPES, pH 7.5, 500 mM NaCl, 20 mM Imidazole) and lysed using homogenization. Insoluble material is removed by centrifugation and the remaining soluble fraction is applied to a HisTrap column (GE Biosciences) pre-equilibrated with buffer A. The protein is eluted from the column using an FPLC with a linear gradient between buffer A and buffer B (10 mM HEPES, pH 7.5, 500 mM NaCl, 500 mM Imidazole). The eluted protein is dialyzed overnight in the presence of TEV protease to buffer C (10 mM HEPES, pH 7.5, 500 mM NaCl). The dialyzed protein is applied to a HisTrap column (GE Biosciences) pre-equilibrated with buffer C. 6×His-tagged TEV and 6×His-tagged thioredoxin are bound to the column and highly purified NBX is collected in the flowthrough. NBX proteins are dialyzed overnight to PBS and concentrated to ~10 mg/ml.

Example 18—Purification of NBXs from *Pichia pastoris*

*Pichia pastoris* strain GS115 with constructs for the expression and secretion of 6×His-tagged NBX were grown for 5 days at 30° C. with daily induction of 0.5% (vol/vol) methanol. Yeast cells were removed by centrifugation and the NBX-containing supernatant was spiked with 10 mM imidazole. The supernatant was applied to a HisTrap column (GE Biosciences) pre-equilibrated with buffer A (10 mM HEPES, pH 7.5, 500 mM NaCl). The protein was eluted from the column using an FPLC with a linear gradient between buffer A and buffer B (10 mM HEPES, pH 7.5, 500 mM NaCl, 500 mM Imidazole). NBX proteins were dialyzed overnight to PBS and concentrated to ~1.5 mg/ml.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Antigen Sequences and Selected $V_HH$ Multimer Sequences:

```
Salmonella Typhimurium
SEQ ID NO: 274 FimA:
>sp|P37921|FIMA1_SALTY Type-1 fimbrial protein, A chain OS = Salmonella
typhimurium (strain LT2/SGSC1412/ATCC 700720) GN = fimA PE = 1 SV = 2
MKHKLMTSTIASLMFVAGAAVAADPTPVSVSGGTIHFEGKLVNAACAVSTKSADQTVTLG

QYRTASFTAIGNTTAQVPFSIVLNDCDPKVAANAAVAFSGQADNTNPNLLAVSSADNSTT

ATGVGIEILDNTSSPLKPDGATFSAKQSLVEGTNTLRFTARYKATAAATTPGQANADATF

IMKYE

SEQ ID NO: 275 FliC:
>sp|P06179|FLIC_SALTY Flagellin OS = Salmonella typhimurium (strain LT2/
SGSC1412/ATCC 700720) GN = fliC PE = 1 SV = 4
MAQVINTNSLSLLTQNNLNKSQSALGTAIERLSSGLRINSAKDDAAGQATANRFTANIKG

LTQASRNANDGISIAQTTEGALNEINNNLQRVRELAVQSANSTNSQSDLDSIQAEITQRL

NEIDRVSGQTQFNGVKVLAQDNTLTIQVGANDGETIDIDLKQINSQTLGLDTLNVQQKYK

VSDTAATVIGYADTTIALDNSTFKASATGLGGIDQKIDGDLKFDDITGKYYAKVIVIGGT

GKDGYYEVSVDKTNGEVTLAGGATSPLTGGLPATATEDVKNVQVANADLTEAKAALTAAG

VTGTASVVKMSYTDNNGKTIDGGLAVKVGDDYYSATQNKDGSISINTTKYTADDGTSKTA

LNKLGGADGKIEVVSIGGKTYAASKAEGHNFKAQPDLAEAAATTTENPLQKIDAALAQVD

TLRSDLGAVQNRFNSAITNLGNTVNNLTSARSRIEDSDYATEVSNMSRAQILQQAGTSVL

AQANQVPQNVLSLLR

SEQ ID NO: 276 PrgI:
>sp|P41784|PRGI_SALTY Protein PrgI OS = Salmonella typhimurium (strain
LT2/SGSC1412/ATCC 700720) GN = prgI PE = 1 SV = 1
MATPWSGYLDDVSAKFDTGVDNLQTQVTEALDKLAAKPSDPALLAAYQSKLSEYNLYRNA

QSNTVKVFKDIDAAIIQNFR
```

*Salmonella Enteritidis*:
SEQ ID NO: 277 FimA:
>tr|Q53483|Q53483_SALEN FimA OS = *Salmonella enteritidis* GN = fimA
PE = 4 SV = 1
MKHKLMTSTIASLMFVAGAAVAADPTPVSVSGGTIHFEGKLVNAACAVSTKSADQTVTLG

QYRTASFTAIGNTTAQVPFSIVLNDCDPKVAATAAVAFSGQADNTNPNLLAVSSADNSTT

ATGVGIEILDNTSSPLKPDGATFSAKQALVEGTNTLRFTARYKATATATTPGQANADATF

IMKYE

SEQ ID NO: 278 FliC:
>sp|Q06972|FLIC_SALEN Flagellin OS = *Salmonella enteritidis* GN = fliC
PE = 3 SV = 2
MAQVINTNSLSLLTQNNLNKSQSSLSSAIERLSSGLRINSAKDDAAGQATANRFTSNIKG

LTQASRNANDGISIAQTTEGALNEINNNLQRVRELSVQATNGTNSDSDLKSIQDEIQQRL

EEIDRVSNQTQFNGVKVLSQDNQMKIQVGANDGETITIDLQKIDVKSLGLDGFNVNGPKE

ATVGDLKSSFKNVTGYDTYAAGADKYRVDINSGAVVTDAAAPDKVYVNAANGQLTTDDAE

NNTAVDLEKTTKSTAGTAEAKAIAGAIKGGKEGDTFDYKGVTFTIDTKTGDDGNGKVSTT

INGEKVTLTVADIATGATDVNAATLQSSKNVYTSVVNGQFTFDDKTKNESAKLSDLEANN

AVKGESKITVNGAEYTANATGDKITLAGKTMFIDKTASGVSTLINEDAAAAKKSTANPLA

SIDSALSKVDAVRSSLGAIQNREDSAITNLGNIVINLNSARSRIEDADYATEVSNMSKAQ

ILQQAGTSVLAQANQVPQNVLSLLR

SEQ ID NO: 279 PrgI:
>tr|A0A0H3T8G7|A0A0H3T8G_SALEN PrgI protein OS = *Salmonella enteritidis*
GN = AC092_14050 PE = 4 SV = 1
MATPWSGYLDDVSAKFDTGVDNLQTQVTEALDKLAAKPSDPALLAAYQSKLSEYNLYRNA
QSNTVKVFKDIDAAIIQNFR
SEQ ID NO: 460 SipD Amino Acid Sequence (PubMed Locus WP_000932249)
MLNIQNYSASPHPGIVAERPQTPSASEHVETAVVPSTTEHRGTDIISLSQAATKIQQAQQTLQSTPPISEENN

DERTLARQQLTSSLNALAKSGVSLSAEQNENLRSAFSAPTSALFSASPMAQPRTTISDAEIWDMVSQNISAIG

DSYLGVYENVVAVYTDFYQAFSDILSKMGGWLLPGKDGNIVKLDVTSLKNDLNSLVNKYNQINSNTVLFPAQS

GSGVKVATEAEARQWLSELNLPNSCLKSYGSGYVVTVDLTPLQKMVQDIDGLGAPGKDSKLEMDNAKYQAWQS

GFKAQEENMKTTLQTLTQKYSNANSLYDNLVKVLSSTISSSLETAKSFLQG

SEQ ID NO: 461 PrgI-SipD Amino Acid Sequence:
ATPWSGYLDDVSAKFDTGVDNLQTQVTEALDKLAAKPSDPALLAAYQSKLSEYNLYRNAQSNTVKVFKDIDAA

IIQNFRGGSGGTTISDAEIWDMVSQNISAIGDSYLGVYENVVAVYTDFYQAFSDILSKMGGWLLPGKDGNTVK

LDVTSLKNDLNSLVNKYNQINSNTVLFPAQSGSGVKVATEAEARQWLSELNLPNSCLKSYGSGYVVTVDLTPL

QKMVQDIDGLGAPGKDSKLEMDNAKYQAWQSGFKAQEENMKTTLQTLTQKYSNANSLYDNLVKVLSSTISSSL

ETAKSFLQG

SEQ ID NO: 462 NBX0018-NBX0018
QVKLEESGGGLVQPGGSLEVSCAASGIIFSPNAMGWYRQAPGEQRELVATITSFGIINYADSVKDRFTISRDN

AKNTVYLQMTSLKPEDTAVYYCNAKTFDGTRWHDYWGQGTQVTVSSGGGGSGGGGSGGGGSQVKLEESGGGLV

QPGGSLEVSCAASGIIFSPNAMGWYRQAPGEQRELVATITSFGIINYADSVKDRFTISRDNAKNTVYLQMTSL

KPEDTAVYYCNAKTFDGTRWHDYWGQGTQVTVSS

SEQ ID NO: 463 NBX0018-NBX0018-NBX0018
QVKLEESGGGLVQPGGSLEVSCAASGIIFSPNAMGWYRQAPGEQRELVATITSFGIINYADSVKDRFTISRDN

AKNTVYLQMTSLKPEDTAVYYCNAKTFDGTRWHDYWGQGTQVTVSSGGGGSGGGGSGGGGSQVKLEESGGGLV

QPGGSLEVSCAASGIIFSPNAMGWYRQAPGEQRELVATITSFGIINYADSVKDRFTISRDNAKNTVYLQMTSL

KPEDTAVYYCNAKTFDGTRWHDYWGQGTQVTVSSGGGGSGGGGSGGGGSQVKLEESGGGLVQPGGSLEVSCAA

SGIIFSPNAMGWYRQAPGEQRELVATITSFGIINYADSVKDRFTISRDNAKNTVYLQMTSLKPEDTAVYYCNA

KTFDGTRWHDYWGQGTQVTVSS

SEQ ID NO: 464 NBX0005-NBX0005
QVQLVESGGGLVQPGGSLTLSCIVSGRSVSINPMYWYRQGPGKQRELVVSLLPSGRTHDAHFAKGRFIISRDN

AKNTVYLQMNSLKPEDTAVYYCNTADFWGQGTQVTVSSGGGGSGGGGSGGGGSQVQLVESGGGLVQPGGSLTL

SCIVSGRSVSINPMYWYRQGPGKQRELVVSLLPSGRTHDAHFAKGRFIISRDNAKNTVYLQMNSLKPEDTAVY

YCNTADFWGQGTQVTVSS

SEQ ID NO: 465 NBX0015-NBX0015
QVQLVESGGGLVQAGDSLRLSCTASGRTFSNNAMGWFRQAPGKQRELVAAISRAGNTNYADSMKGRVTISGDN

AKNTVYLQMNSLKPEDTAVYYCKASSGSSVYIGVGSWGQGTQVTVSSGGGGSGGGGSGGGGSQVQLVESGGGL

VQAGDSLRLSCTASGRTFSNNAMGWFRQAPGKQRELVAAISRAGNTNYADSMKGRVTISGDNAKNTVYLQMNS

LKPEDTAVYYCKASSGSSVYIGVGSWGQGTQVTVSS

SEQ ID NO: 466 NBX0018-E9 Immunity Protein
MQVKLEESGGGLVQPGGSLEVSCAASGIIFSPNAMGWYRQAPGEQRELVATITSFGIINYADSVKDRFTISRD

NAKNTVYLQMTSLKPEDTAVYYCNAKTFDGTRWHDYWGQGTQVIVSSELKHSISDYTEAEFLQLVTTICNADT

SSEEELVKLVTHFEEMTEHPSGSDLIYYPKEGDDDSPSGIVNTVKQWRAANGKSGFKQG

SEQ ID NO: 467 NBX0018-Colicin E9
MQVKLEESGGGLVQPGGSLEVSCAASGIIFSPNAMGWYRQAPGEQRELVATITSFGIINYADSVKDRFTISRD

NAKNTVYLQMTSLKPEDTAVYYCNAKTFDGTRWHDYWGQGTQVIVSSESKRNKPGKATGKGKPVGDKWLDDAG

KDSGAPIPDRIADKLRDKEFKSFDDFRKAVWEEVSKDPELSKNLNPCNKSSVSKGYSPFTPKNQQVGGRKVYE

LHADKPISQGGEVYDMDNIRVTTPKRHIDIHRGK

SEQ ID NO: 468 NBX0018-GCN4 PIL
QVKLEESGGGLVQPGGSLEVSCAASGIIFSPNAMGWYRQAPGEQRELVATITSFGIINYADSVKDRFTISRDN

AKNTVYLQMTSLKPEDTAVYYCNAKTFDGTRWHDYWGQGTQVIVSSGGGGSGGGSRMKQLEDKIEELLSKIYHL

ENEIARLKKLIGER

SEQ ID NO: 469 NBX0018-GCN4 PII
QVKLEESGGGLVQPGGSLEVSCAASGIIFSPNAMGWYRQAPGEQRELVATITSFGIINYADSVKDRFTISRDN

AKNTVYLQMTSLKPEDTAVYYCNAKTFDGTRWHDYWGQGTQVTVSSGGGGSGGGSRMKQIEDKIEEILSKIYHI

ENEIARIKKLIGER

SEQ ID NO: 470 NBX0018-GCN4 PLI
QVKLEESGGGLVQPGGSLEVSCAASGIIFSPNAMGWYRQAPGEQRELVATITSFGIINYADSVKDRFTISRDN

AKNTVYLQMTSLKPEDTAVYYCNAKTFDGTRWHDYWGQGTQVTVSSGGGGSGGGSRMKQIEDKLEEILSKLYHI

ENELARIKKLLG

SEQ ID NO: 471 NBX0018-Fos
QVKLEESGGGLVQPGGSLEVSCAASGIIFSPNAMGWYRQAPGEQRELVATITSFGIINYADSVKDRFTISRDN

AKNTVYLQMTSLKPEDTAVYYCNAKTFDGTRWHDYWGQGTQVTVSSGGGGGGGGGLTDTLQAETDQLEDEKS

ALQTEIANLLKEKEKLEFILAA

SEQ ID NO: 472 NBX0018-Jun
QVKLEESGGGLVQPGGSLEVSCAASGIIFSPNAMGWYRQAPGEQRELVATITSFGIINYADSVKDRFTISRDN

AKNTVYLQMTSLKPEDTAVYYCNAKTFDGTRWHDYWGQGTQVIVSSGGGGGGGGGGRIARLEEKVKILKAQNS

ELASTANMLREQVAQLKQKVMN

SEQ ID NO: 473 NBX0018-Kv1.2 T1 Domain
QVKLEESGGGLVQPGGSLEVSCAASGIIFSPNAMGWYRQAPGEQRELVATITSFGIINYADSVKDRFTISRDN

AKNTVYLQMTSLKPEDTAVYYCNAKTFDGTRWHDYWGQGTQVTVSSGGGGSERVVINISGLRFETQLKTLAQF

PETLLGDPKKRMRYFDPLRNEYFFDRNRPSFDAILYYYQSGGRLRRPVNVPLDIFSEEIRFYELG

-continued

```
SEQ ID NO: 474 NBX0018-CsgC
QVKLEESGGGLVQPGGSLEVSCAASGIIFSPNAMGWYRQAPGEQRELVATITSFGIINYADSVKDRFTISRDN

AKNTVYLQMTSLKPEDTAVYYCNAKTFDGTRWHDYWGQGTQVTVSSGGGGSGGGGSGGGGSGGGGSGGGGSAL

SNQITFITTQQGDIYTVIPQVTLNEPCVCQVQILSVRDGVGGQSHTQQKQTLSLPANQPIELSRLSVNISSED

SVKIIVTVSDGQSLHLSQQWPPSAQ

SEQ ID NO: 475 NBX0018
QVKLEESGGGLVQPGGSLEVSCAASGIIFSPNAMGWYRQAPGEQRELVATITSFGIINYADSVKDRFTISRDN

AKNTVYLQMTSLKPEDTAVYYCNAKTFDGTRWHDYWGQGTQVTV

SEQ ID NO: 476 NBX0005
QVQLVESGGGLVQPGGSLTLSCIVSGRSVSINPMYWYRQGPGKQRELVVSLLPSGRTHDAHFAKGRFIISRDN

AKNTVYLQMNSLKPEDTAVYYCNTADFWGQGTQVTV

SEQ ID NO: 477 NBX0015
QVQLVESGGGLVQAGDSLRLSCTASGRTFSNNAMGWFRQAPGKQRELVAAISRAGNTNYADSMKGRVTISGDN

AKNTVYLQMNSLKPEDTAVYYCKASSGSSVYIGVGSWGQGTQVTV
```

Selected Full $V_HH$ Sequences:

| SEQ ID | Clone | Amino acid sequence |
| --- | --- | --- |
| 478 | >NBX0005 | QVQLVESGGGLVQPGGSLTLSCIVSGRSVSINPMYWYRQGPGKQRE<br>LVVSLLPSGRTHDAHFAKGRFIISRDNAKNTVYLQMNSLKPEDTAV<br>YYCNTADFWGQGTQVTVSS |
| 479 | >NBX0015 | QVQLVESGGGLVQAGDSLRLSCTASGRTFSNNAMGWFRQAPGKQRE<br>LVAAISRAGNTNYADSMKGRVTISGDNAKNTVYLQMNSLKPEDTAV<br>YYCKASSGSSVYIGVGSWGQGTQVTVSS |
| 480 | >NBX0018 | QVKLEESGGGLVQPGGSLEVSCAASGIIFSPNAMGWYRQAPGEQRE<br>LVATITSFGIINYADSVKDRFTISRDNAKNTVYLQMTSLKPEDTAV<br>YYCNAKTFDGTRWHDYWGQGTQVTVSS |
| 481 | >NBX0019 | QVKLEESGGGLVQPGGSLEVSCAASGIIFSPNAMGWYRQAPGEQRE<br>LVATITSFGIINYADSVKDRFTISRDNAKNTVYLQMTSLKPEDTAV<br>YYCNAKAFDGTRWHDYWGQGTQVIVSS |
| 482 | >NBX0024 | QVKLEESGGGLVQAGGSLRLSCAVSGSIFSTNVMGWFRQAPGKQRG<br>FVAHITSGGNIDYADSVNGRFTMSRDNAKNIVYLQMNSLKPEDTAV<br>YYCAAQTLGSSYYDAWGQGTQVTVSS |
| 483 | >NBX0027 | QVQLVESGGGLVQAGGSLRLSCAASGRTFSSYAMGWFRQAPGKERE<br>FVASINWSGGRIYYADSVKGRFTISRDNAKNTVYLQMNSLKPEDTA<br>VYYCNADYDNSGSYYYQKGNYEYDYWGQGTQVTVSS |
| 484 | >NBX0200 | QVQLQESGGGLVQAGGSLRLSCAASGRTSSSAYTAWFRQAPGNERE<br>FVASISWSGTTTYYADPVKGRFTISRDNAKNTVYLQMNSLKPDDTA<br>VYYCAADRRSTIGSPRQQYAYWGQGTQVTVSS |
| 485 | >NBX0201 | QVQLQESGGGLVQAGGSLRLSCAASTRTSSSSYTAWFRQAPGNERE<br>FVASISYSGTTTYYADPVKGRFTISRDSAKNTVYLQMNSLKPDDTA<br>VYYCAADRRSTIGSPRQQYAYWGQGTQVTVSS |
| 486 | >NBX0202 | QVQLQESGGGLVQAGGSLRLSCAASGRTSSSAYTAWFRQAPGNERE<br>FVASISWSGTTTYHAHPVKGRFTIFRDNAKNIVYLQMNSLKPDDTG<br>VYYCAADRRSTIGTPREQYAYWGQGTQVTVSS |
| 487 | >NBX0204 | QVQLQESGGGLVQAGGSLRLSCAASGSTLSNYAVEWYRQAPGNQRE<br>YVARISSGGSTNYADSVKGRFTISRDNAKNTVYLQMNSLKPEDTAV<br>YYCHTYDFQGWGLRSDYWGQGTQVTVSS |
| 488 | >NBX0205 | QVQLQESGGRLVQAGGSLRLSCAASGRTFSSLAMGWFRQAPGKERE<br>FVAAISRSGDYTYFSDSVKGRFAISRDNAKDTVSLQMNNLKPDDTA<br>VYTCAATKIVTPWTSTYYYTKAYEWDYWGQGTQVTVSS |
| 489 | >NBX0104 | QVQLVESGGGLVQPGGSLRLSCAASGVAFNSRIMGWYRQAPGKQRE<br>LVALITSGGSTNYADSVKGRFTISRNNAKKTVYLQMNSLKPEDTAV<br>YYCNIRNYWGQGTQVTVSS |

-continued

| SEQ ID | Clone | Amino acid sequence |
|---|---|---|
| 490 | >NBX0105 | QVQLVESGGGLVQAGGSLRLSCAASGRTFNTYYMGWFRQAPGKERE FVSAIRWSDGGTWYADSMKGRFTISRDNAKNTGYLQMNSLKPEDTA IYYCNANVYDGNRWRTYWGQGTQVTVSS |
| 491 | >NBX0108 | QVKLEESGGGLVRAGGSLTLSCGASRGTFRTYSMGWFRQAPGKERE FVAAITWNGKYTYYGDSVQGRFTISKDNAKNTVSLQMNRLNPEDTA VYYCAANPIPTAQPPGIMAARSYVHWGQGTQVTVSS |
| 492 | >NBX0203 | QVQLQQSGGGLVQAGGSLRLSCAASGRTSPSSYTAWFRQAPGNERE FVASISWSGTTTYYADPVKGRFTISRDNAKNTVYLQMNSLKPDDTA VYYCAADRRSTIGSPRQQYAYWGQGTQVTVSS |
| 493 | >NBX0206 | QVQLQESGGRLVQAGGSLRLSCAASGRTFSSLAMGWFRQAPGKERE FVAAITRSGDYTYFSDSVKGRFAISRDNAKDTVSLQMNNLKPDDTA VYTCAATKIVTPWTSTYYYTKAYEWDYWGQGTQVTVSS |
| 494 | >NBX0207 | QVQLQESGGGLVQAGKSLRLSCAASTAILSIDSMGWNRQAVGNQRE LVAVIARGGSTKYADSVKGRFTITRDISKNTIYLQMNSLKPEDTGV YYCAADPGGASPLSWGQGTQVTVSL |
| 495 | >NBX0208 | QVQLQESGGGMVQAGGSLRLACTASGDISTIDVMGWNRQAPGKHRE LVAIIARGGTIKYADSVKGRFTISRDNTKNTVTVYLQMNNVNAEDT AVYYCAVDTGSPRLTWGQGTQVTVSS |
| 496 | >NBX0209 | QVQLQESGGGLVQAGGSLRLSCAASGFTFSSSIMAWYRQAPGKQRE AIASIPSFGSAVYADSVKDRFTISRDNNKNMVYLQMNSLKPEDTAV YYCNTRLYWGQGTQVTVSS |
| 497 | >NBX0210 | QVQLQESGGGLVQAGGSLRLACTASGDISSISVMGWNRQAPGKQQR ELVAAIASGGSVKYADSVKGRFTISRDNIKNIVYLQMNSVNAEDTA VYYCAVDTGSPRLTWGQGTQVTVSS |
| 498 | >NBX0211 | QVQLQESGGGLVQAGGSLRLSCAASGFTFSTNILAWYRQAPGKQRE AIASITPFGSAVYANSVKDRFTISRDNNKNMVYLQMNSLKPEDTAV YSCNTQLYWGQGTQVTVST |
| 499 | >NBX0212 | QVQLQESGGGLVQAGGSLRLSCAASTSILSINAMGWNREAPGNRRE MVAIIAPGGTTNYADSVKGRFTITRDISKNTIYLQMNNLKPEDTGV YYCAADPGGQSPLSWGQGTQVTVSL |
| 500 | >NBX0213 | QVQLQESGGGSVQAGGSLRLSCAASGSISSITAMGWNRQAPGNQRE LVAVIARGGMIKYDDSVKGRFTISRDIAKNTVFLQMDSLKPEDTGV YYCAVDNGDPRLHWGQGIQVTVSS |
| 501 | >NBX0214 | QVQLQESGGGLVQAGGSLRLSCAASGSISSITAMGWNRQAPGNQQR DLVAVIARGGMTKYADSVQGRFTISRDIAKNTVYLQMNSLKPEDTG VYYCALDNGDPRLHWGQGIQVTVSS |
| 502 | >NBX0215 | QVQLQESGGGLVQAGGSLRLSCAASGFTFSSAIMAWYRQAPGKQRE AIASIPSFGSAVYADSVKDRFTISRDNNKNMVYLQMDSLKPEDTAV YYCNTRLYWGQGTQVTVST |
| 503 | >NBX0216 | QVQLQESGGGLVQAGGSLRLSCAASTSILSIDAMGWNRQAPGNQRR DLVAVIARGGSTQYADSVKGRFTITRDISKNTIYLQMNSLKPEYTG VYYCAADPGGASGLSWGQGTQVTVSL |
| 504 | >NBX0217 | QVQLQESGGGLVQAGGSLRLSCAASGSISSITAMGWNRQAPGNQQR DLVAVIARGGMTKYADSVQGRFTISRDIANNTVYLQMNSLKPEDTG VYYCALYNGDPRLHWGQGIQVTVSS |
| 505 | >NBX0218 | QVQLQESGGGLVQAGGSLSLSCTASGSAFSGDAMGWYRRAPGKQRE FVAGISSGAITNYMDSVKGRFTISRDNAKNTVYLQMTKLKPEDTAV YYCNRIQAVLRGNSGWGQGTQVTVSS |
| 506 | >NBX0219 | QVQLQESGGGLVQPGGSLSLSCTASGSAFSGGDAMGWYRRAPGKQR EFVAGISSGGIANYMDSVKGRFTISRDNAKKAVYLQMTSLKPEDTA LYYCNSITAVLRGNSGWGQGTQVTVSS |
| 507 | >NBX0220 | QVQLQESGGGLVQAGGSLTLSCTASGSAFSGDAMGWYRRAPGKERE FVAGISSGGIPNYMGSVQGRFTISRDNAKNTVYLQMRRLKPEDTAV YYCNSISAVLRGNGVWGQGTQVTVSS |
| 508 | >NBX0221 | QVQLQESGGGLVQAGGSLRLSCAASGLTFNNYAMGWFRQAPGKERE FVATISRDGTNTRYADSVKGRFTISRDNAKNTVDLQMNSLKPEDTA VYYCGVGRGTGYAYTAINEYDYSKWGQGTQVTVSS |

-continued

| SEQ ID | Clone | Amino acid sequence |
|---|---|---|
| 509 | >NBX0222 | QVQLQESGGGLVQAGGSLRLSCAASGIDSSFYVMAWYRQAPGKQRE LVASLGTPDSATYADFVKGRFIISRDNAKSTVYLQMNSLKPEDTAV YYCYGLYRQVYWGQGTQVTVSS |
| 510 | >NBX0223 | QVQLQESGGGLVQAGGSLRLSCVASGIDSSFYVMAWYRQAPGKQRE LVASISSADSPRYEDFVKGRFTISRDNGKNTVYLQMNSLKPEDTAV YYCYGLYRQVHWGQGTQVTVSS |
| 511 | >NBX0224 | QVQLQQSGGGLVQAGGSLRLSCAASGLTFSSYAMGWFRQAPGKERE FIVAIGWSGGSTYYADSVKGRFTISRDNAKNTVYLHMNSLKPEDTA VYYCAARRTTAWGKGTDYWGQGTQVTVSS |
| 512 | >NBX0225 | QVQLQESGGGLVQAGGSLRLSCAASESIFSRNAMGWYRQAPGKERD LVAPGKERELVAGIGSDGSTNYAESVKGRFTISRDNAKNTVYLQMN SLKPEDTAVYYCRVVLATSPYNYWGQGTQVTVSS |
| 513 | >NBX0226 | QVQLQESGGGLVQAGGSLRLSCAASGITSSLYVMAWYRQAPGKQRE LVAHINSGDSPRYADFVQGRFTISRDNGKNTVYLQMNSLKPEDTAV YYCYGLYRQVHWGQGTQVTVSS |
| 514 | >NBX0227 | QVQLQESGGGLVQAGGSLRLACAASGLTFNNYAMGWFRQAPGKERE FVATISRDGTSTRYADSVKGRFTISRDNAKNTVNLQMNRLKPEDTA VYYCGVGRSGYAYSAINEYDYSSWGQGTQVTVSS |
| 515 | >NBX0228 | QVQLQESGGGLVQAGGSLRLSCAASGIDSSFYVMAWYRQAPGQQRE LVASISMTSADSPRYADFVKGRFTISRDNAKSTVYLQMNSLKPEDT AVYYCYGLYRQVHWGQGTQVTVSS |
| 516 | >NBX0229 | QVQLQESGGGLVQAGGSLRLSCAASGSGILFRISAMGWYRQAPGKE RDLVAGISSGGSTNYADSVKGRFTISRDNAKNTVYLQMNSLKPEDT AVYYCNIVGRIDSWGQGTQVIVSS |
| 517 | >NBX0230 | QVQLQESGGGSVQAGGSLRLSCAASARTLSNYAMGWFRQAPGKERE FVATISRSGGSIHYADSVKGRFTISRDNAKNTVNLQMNSLKVEDTA VYYCGRARGTGYAYTALNQYDYDWGQGTQVTVSS |
| 518 | >NBX0231 | QVQLQESGGGLVQAGGSLTLSCITSGSAFSGDAMGWYRRAPGQERE FVAGISSGGITNYMNFVKGRFTISRDNAKNTVYLQMTSLKPEDTAV YYCNSIKAVLRGNSGWGQGTQVTVSS |
| 519 | >NBX0232 | QVQLQESGGGLVQAGGSLRLSCAASGLTFHNYAMGWFRQAPGKERE FVATISRDGTNTHYADSVKGRFTISRDNAKNTVDLQMNSLKPEDTA VYYCGVGRSGYAYTAINEYDSKWGQGTQVTVSS |
| 520 | >NBX0233 | QVQLQESGGGLVQAGGSLSLCTASGSAFSGDAMGWYRRAPGKQRD FVAGISSGHITNYMDSVKGRFTISRDNAKNTVYLQMTKLKPEDTAV YYCNSITAVLRGNSGWGQGTQVTVSS |
| 521 | >NBX0234 | QVQLQESGGGLVQAGGSLRLSCAASGRTFSTYAMGWFRQAPGKERE FVATISRSGDNIYYADSVKGRFTISRDNAKNTVSLQMNSLKVEDTA VYYCGRARGTGYAHTALNQYDYDWGQGTQVTVSS |
| 522 | >NBX0235 | QVQLQESGGGLVQAGGSLSLSCRVSGSAFSGDAMGWYRRAPGKQRE FVAGISSGGIENYMDSVKGRFTISRDNAKNTVYLRMSSLKPEDTAV YYCNLIKAVLRGNSGWGQGTQVTVSS |
| 523 | >NBX0236 | QVQLQESGGGLVQAGGSLRLSCAASGLTFNNYAMGWFRQAPGKERE FVATISRDGTNTRYADSVKGRFTISRDNAKNTVNLQMNSLKPEDTA VYYCGVGRGTGYAYTAIREHDYSSWGQGTQVTVSS |
| 524 | >NBX0237 | QVQLQESGGGLVQAGGSLSLSCTASGSAFSGDAMGWYRRAPGKQRE FVAGISSGGITNYMNSVKGRFTISRDNAKNTVYLHMTGVKPADTAV YYCNSITAVLRGNSGWGPGTQVIVSS |
| 525 | >NBX0238 | QVQLQESGGGLVQPGGSLTLSCTASGSAFSGDAMGWYRRAPGKQRE FVAGISSGGIANYMDSTEGRFTISRDDAKNTVYLQMTGVKPADTAV YYCNTIKAVLRGNAGWGQGTQVTVSS |
| 526 | >NBX0239 | QVQLQESGGGLVQAGGSLSLSCTASGSAFSGDAMGWYRRAPGKQRE FVAGISSGAITNYMDSVKGRFTISRDNAKNMVYLQMTKLKPEDTAV YYCNSITAVLRGNSGWGQGTQVTVSS |
| 527 | >NBX0240 | QVQLQESGGGLVQAGGSLSLSCTASGSAFSGDAMGWYRRAPGKQRE FVAGISSGGITNYMDSVKGRFTISRDNAKNTVYLQMTSLKPEDTAV YYCNIISAVLRGNGGWGQGTQVTVSS |

-continued

| SEQ ID | Clone | Amino acid sequence |
|---|---|---|
| 528 | >NBX0241 | QVQLQQSGGGLVQAGGSLSLSCTASISGFSGDAMGWYRRAPGKQRE<br>FVAGISSGGITNYMDSVKGRFTISRDNAKNTVYLQMTNLKPEDTAV<br>YYCNTITGVLRGNSGWGQGTQVTVSS |
| 529 | >NBX0242 | QVQLQESGGGLVQAGGSLRLSCAGSGIISSAYVMAWYRQRPGKQRE<br>LVASITSGDSPRYEDFVKGRFTISRDNAKSTVYLQMNSLKPEDTAV<br>YYCYGLYRQVYWGQGTQVTVSS |
| 530 | >NBX0243 | QVQLQQSGGGLVQAGGSLKLSCAASGIAFSTYGMNWFRQTPGKQRE<br>YVAYITGNGDDNVAQSMEGRFTISRDNAKNTGYLQMNSLKPEDTGV<br>YYCNIGMYWGQGTQVTVSS |
| 531 | >NBX0244 | QVQLQESGGGLVQAGGSLSLSCTASGSAFSGDAMGWYRRAPGKQRE<br>FVAGISSGGITNYMGFVKGRFTISRDNAKNTVYLQMTSLKPEDTAV<br>YYCNSISAVLRGNSGWGQGTQVTVSA |
| 532 | >NBX0245 | QVQLQESGGGLVQAGGSLSLSCTASGSAFSGDAMGWYRRAPGKQRD<br>FVAGISSGGITNYMDSVKGRFTISRDNAKNTVYLQMTSLKPEDTAV<br>YYCNSISAVLRGNGGWGQGTQVTVSS |
| 533 | >NBX0246 | QVQLQESGGGLVQPGGSLSLSCTASGSAFSGDAMGWYRRAPGKQRE<br>FVAGISSGGITNYMDSVKDRFTISRDNAKNTLYLQMTNLKPEDTAV<br>YYCNSITAVLRGNSDWGQGTQVTVSS |
| 534 | >NBX0247 | QVQLQESGGGLVQAGGSLSLSCTTSGSAFSGDAMGWYRRAPGKQRE<br>FVAGISSGGIPNYMGFVRGRFTISRDNTKNTVYLQMTSLKPDDTAV<br>YYCNIIKTVLRGNAVWGQGTQVTVSS |
| 535 | >NBX0248 | QVQLQESGGGLVQAGGSLSLSCTASGSAFSGGDAMGWYRRAPGKQR<br>EFVAGISSGGITNYMDFVKGRFTISRDNAKNTVYLQMTSLKPEDTA<br>VYYCNSITAVLRGNSGWGQGTQVTVSS |
| 536 | >NBX0249 | QVQLQESGGGLVQAGGSLRLSCVASGITFSSDAMGWYRQAPGKQRE<br>FVAGISSGDITNYPDSVKGRFAISRDNAKNTVYLQMNSLKPEDTAV<br>YYCNTITRLLYGMDYWGKGTLVTVSS |
| 537 | >NBX0250 | QVQLQESGGGLVQPGGSLRLSCAASGFTLDGYAIGWFRQAPGKERE<br>WVSCIIYRDGSPAYADSVWGRFTISRDNAKNNVYLEMNSLKPEDTA<br>VYYCAARPGGACSRYPSNYDTWGQGTQVTASS |
| 538 | >NBX0001 | QVKLEESGGGLVQAGGSLRLSCAASGSIFSINAMGWYRQAPGKQRE<br>LVAAITTGGNTANTAYADSVKGRFTISRDKAKNTVYLQMNSLKPED<br>TAVYYCAARGLSYEYDYWGQGTQVTVSS |
| 539 | >NBX0002 | QVQLVESGGGLVQAGGSLRLSCAASGSIFSINAMGWYRQAPGKQRE<br>LVAAITITSGRGGNTAYADSVKGRFTISRDNAKNTVYLQMNTLKPE<br>DTAVYYCAARGAMTYEYDYWGQGTQVTVSS |
| 540 | >NBX0004 | QVQLVESGGGLVQAGGSLRLSCAASGIIFSPNAMGWYRQAPGKQRE<br>LVSTITSFGIINYADSVKDTISRDNAKNTVYLQMTSLKPEDTAVYY<br>CNAKTFDGTRWRDYWGQGAQVTVSS |
| 541 | >NBX0006 | QVKLEESGGGLVQAGGSLRLSCAASGNIFSINAMGWYRQAPGKQRE<br>LVAAITTGGSYGNTNYADSVKGRFTISRDNAKNTVYLQMNSLKPED<br>TAVYYCAARGSQTYEYDYWGQGTQVTVSS |
| 542 | >NBX0007 | QVKLEESGGGLVQPGGSLTLSCAASGRIFSIYDMGWFRQAPGKERE<br>LVSAITWGNGNTAYGDSVKGRFSISRDFAKNTVYLQIDSLKAEDTA<br>VYYCPARIVNGGSWDYWGQGTQVTVSS |
| 543 | >NBX0008 | QVKLEESGGGLVQPGGSLTLSCAASGRIFSIYDMGWFRQAPGKERE<br>LVSAITWGNGNTAYGDSVKGRFSISRDFAKNTVYLQIDSLKAEDTA<br>VYYCPARIVNGGSWDYWGQGTQVTVSS |
| 544 | >NBX0009 | QVKLEESGGGLVQAGGSLRLSCAASGRMFSSYDMGWFRQAPGKERD<br>IVAAITKNGRTTSYANSVKGRFTISRDNTKSTVYLQIHSLKPEDTA<br>VYYCAGRRSNADNWDYWGQGTQVTVSS |
| 545 | >NBX0010 | QVKLEESGGGLVQAGGSLRLSCAVSGSIFSINAVGWYRQAPGKQRE<br>LVAAIGTGGSSSGNTAYADSVKGRFTISNDAAKNTVYLQMNSLKPD<br>DTAVYYCAARGTISYEYDYWGQGTQVTVSS |
| 546 | >NBX0011 | QVQLVESGGGLVQAGGSLTLSCIVSGISVNINPMYWYRPGPGNQRE<br>LVVSLLPTGITHDAHFIKGRFIISKDDAKNTVYLLMNSLKPEDTAV<br>YYCNTADFWGQGTQVTVSS |

-continued

| SEQ ID | Clone | Amino acid sequence |
| --- | --- | --- |
| 547 | >NBX0012 | QVKLEESGGGLVQAGGSLRLSCAASGSTFSINAMGWFRQAPGKQRE LVAAISRAGSTNTADSVKGRFTISRDNAKNTVYLQMNSLKPEDTAV YYCKASSGSSVYIGFGSWGQGTQVTVSS |
| 548 | >NBX0013 | QVQLVESESGLVLAGGSLTLTRFCSVSSVSINPMYWYRQGPGKQRE LVLILLSMARAQNAHFPNGQFLISIYEDDNTMYLQLSIQKPEDADV YDCNTTDFWGQGTQVTVSS |
| 549 | >NBX0014 | QVKLEESGGGLVQAGGSLRLSCAASGRTFSRLAMGWFRQAPGKERE FVVAISWSGGNTNYADSVKGRFTISRDNAKNTVYLQMNSLNAEDTA VYYCAAPERSGSYAYTPSRLNEYAYWGQGTQVTVSS |
| 550 | >NBX0016 | QVQLVESGGGLVQAGGSLRLSCAASGRIFSSYDMGWFRQAPGKERE LVAAIRWGNGNTAYGDSVKGRFSISRDFAKNTVYLHIDSLKAEDTA VYYCAARGLAYEYEYWGQGTQVTVSS |
| 551 | >NBX0017 | QVQLVESGGGLVQAGGSLRLSCAASGRIFSSYDMGWFRQAPGKERE LVAAIRWGNGNTAYGDSVKGRFSISRDFAKNTVYLHIDSLKAEDTA VYYCAARIVNGGSWDYWGQGTQVTVSS |
| 552 | >NBX0020 | QVQLVESGGGSVQPAGSLRLSCAVSGIIFSPNALGWYRPAPGKERE LVASIISGGRSDYADSVKDRFTIARDNPKNTVTLQMNSLKPEDTAI YYCNANVYDGNRWRTYWGQGTQVTVSS |
| 553 | >NBX0021 | QVKLEESGGGLVQAGGSLRLSCAASGRTFRSYTMGWFRQAPGLERE IIAAISWSAGSTRYADSMSDRFTISRDNAKNTVYLGMDSLKPEDTA VYYCAAGTKYSDTIITWGSWGQGTQVTVSS |
| 554 | >NBX0022 | QVQLVESGGGLVQPGGSLRLSCAVSGSTVTISTVGWYRQAPGNQRV LVASISSDSTTNYAHSVKGTISRHNAENPVSRLQMNSLKPEDTAVY YCNVVGTYWTGADWRPFDTWGRGTQVIVSS |
| 555 | >NBX0023 | QVKLEESGGGLVQAGGSLRLSCAASGRSFSSYNMGWFRQAPGKERE FVAAITWSGNTYYADSVKGTISRDNAKNTVYLQMNSLKPEDTAVYF CKVRAEDTDYWGRGTQVTVSS |
| 556 | >NBX0025 | QVKLEESGGGLVQPGGSLRLSCAASGFTFSMYGMTWVRQAPGKGLE WVSAINSGGARTSYADSVKGRFTISRDNAKNTLYLQMNSLKPEDTA VYYCAKASLPWFDGSSPDYWGQGTQVTVSS |
| 557 | >NBX0026 | QVKLEESGGGLVQAGGSLRLSCAASGLTFSSYGMGWFRQGPGKERE SVAAIKMSGDTYYTDSVKGRFTISRDNAKNTVYLQMDSLKPEDTAV YFCAAARVRTPGWGPQKSYDYWGQGTQVTVSS |
| 558 | >NBX0028 | QVKLEESGGGLVQAGGSLRLSCAASGRTFGSLHMGWFRQAPGKERE FVSAISAAGGVTDYADSAKGRFTISRDNAKNTVYLQMNSLKPEDTA VYYCAAVKYWGRRQRADEYDYWGQGTQVTVSS |
| 559 | >NBX0029 | QVRLEKSGGGLVQPGGSLTLSCTASGSISSIKAMGWYRQAPGKQRE LAALWRMYSGTAYGDSVKGRSNLSVNHTNNTAYLQMNSLRPEDTAV YWCYLEIPESRGAFWGHGTQVTVSS |
| 560 | >NBX0030 | QVQLVESGGGLVQAGGSLRLSCAASGRTFSRDAMGWFRQAPGKERE FVATINWNGRSTYYTESVKGRFTISRDNAKNTVYLQMNSLKPEDTA VYYCAAGEWGIRPYNYDYWGQGTQVTVSS |
| 561 | >NBX0031 | QVQLVESGGGLVQAGGSLRLSCAASGRTFSSYAMGWFRQAPGKERE FVASINWSGGRIYYADSVKGRFTISRDNAKNTVYLQMNSLKPEDTA VYYCNTDYDNSGSYYYQKGNYEYDYWGQGTQVTVSS |
| 562 | >NBX0032 | QVQLVESGGGLVQPGSLKVSCAASGIIFSPNAMGWYRQAPGKQRD LVATITSSGIINYADSVKGTISRDNAKNTVYLQMTSLKPEDTAVYY CNAKAFDGTRWYDYWGQGTQVTVSS |
| 563 | >NBX0033 | QVKLEESGGGLVQAGGSLRLSCAASGRTFSSYVMGWFREAPGKERR FVASISWSGGSSSYADSVKGTISRDYAENMVYLQMNSLKPEDTATY YCAARTALGGTYDYWGQGTQVTVSS |
| 564 | >NBX0034 | QVQLAESGVGLVEPAGSLKFSCAASGIIFNPNAMGWHRQAPENQRE LVATITSFGIINYADSVKDSISRDHDTNAVYLQMTNLRPDDPAVYY CNAITFYGTRWLDYWGQGTQVTVSS |
| 565 | >NBX0035 | QVQLVESGGGLVQPGGSLRLSCAVSGIIFSPNALGWYRQAPGKERE LVASIISGGRSDYADSVKDTIARDNPKNTVTLQMNSLKPEDTAIYY CNADVYDGNRWRTYWGQGTQVTVSS |

-continued

| SEQ ID | Clone | Amino acid sequence |
|---|---|---|
| 566 | >NBX0036 | QVKLEESGGGLVQPGGSLKVSCAASGIIFSPNAMGWYRQAPGKQRE LVATITSFGIINYADSVKDTISRDNAKNTVYLQMTSLKPEDTAVFY CFAKTFDGTRWCDYWGQGTQVTVSS |
| 567 | >NBX0037 | QVQLVESGAGLVQPGGSLRLSCAVSGIIFSPNALGWYRQAPGKERE LVASIISGGRSDYADSVKDTIARDNPKNAVTLQMNSLKPEDTAIYY CNAIVYDGNRWRTYWGQGTQVTVSS |
| 568 | >NBX0038 | QVKLEESGEGLVQAGGSLRLSCAASGRTFSSYAMAWFRQAPGKERE FVARIRWTRSSTVYADSVKGTISGDNAKNTMYLQMNSLKPEDTAVY YCAADRYYRTDIYRASSYEYWGQGTQVTVSS |
| 569 | >NBX0039 | QVKLEESGGGLVQAGGSLRLSCVVSGRPFINYNMGWFRQAPGKEHE FVAAISWSGDSTYYEDSVKGTVSRDNAKNTVYLQMNNLKPEDTAVY YCAADNQHDIPLRPGGWQGTQVTVSS |
| 570 | >NBX0040 | QVQLVESGGGLVEAGGSLTLSCAASGLAFNTKTMAWFRQAPDKERA VVATITWGTINTSYADSVKGRFTISRDNAKNMVYLRMDSLKPEDTD VYYCESEALLETTPSRRPYEYNYWGPGTQVTVSS |
| 571 | >NBX0041 | QVKLEESGGGLVQAGGSLRLSCAASGRIFGSLHMGWFRQAPGKERE FVSPITAAGGVTDYDSSNEGIHSVLHKQRQEHVSSPMNSLKPDTHG RLLLCRTLGCSYYERADEYNYWGQGTQVTVSS |
| 572 | >NBX0100 | QVKLEESGGGLVQAGGSLRLSCAVSGSIFSTNLMGWYRQAPGKQRG FVAHITSGGNTDYLDSVKGRFTISRDNAKNTVYLQMNSLKPEDTAV YYCAAQTLGSSYYDAWGQGTQVTVSS |

Exemplary Framework regions for use with the CDRs of tables 1 or 2

| Seq ID | FR1 | Seq ID | FR2 | Seq ID | FR3 | Seq ID | FR4 |
|---|---|---|---|---|---|---|---|
| 573. | QVQLVESGGGLVQPGGSLTLSCIVS | 614. | YWYRQGPGKQRELVVS | 670. | HDAHFAKGRFIISRDNAKNTVYLQMNSLKPEDTAVYYC | 753. | WGQGTQVTVSS |
| 574. | QVQLVESGGGLVQAGDSLRLSCTAS | 615. | GWFRQAPGKQRELVAA | 671. | NYADSMKGRVTISGDNAKNTVYLQMNSLKPEDTAVYYC | 754. | WGQGTQVTVSL |
| 575. | QVKLEESGGGLVQPGGSLEVSCAAS | 616. | GWYRQAPGEQRELVAT | 672. | NYADSVKDRFTISRDNAKNTVYLQMTSLKPEDTAVYYC | 755. | WGQGTQVTVST |
| 576. | QVKLEESGGGLVQAGGSLRLSCAVS | 617. | GWFRQAPGKQRGFVAH | 673. | DYADSVNGRFTMSRDNAKNTVYLQMNSLKPEDTAVYYC | 756. | WGQGIQVTVSS |
| 577. | QVQLVESGGGLVQAGGSLRLSCAAS | 618. | GWFRQAPGKEREFVAS | 674. | YYADSVKGRFTISRDNAKNTVYLQMNSLKPEDTAVYYC | 757. | WGPGTQVTVSS |
| 578. | QVQLVESGGGLVQPGGSLRLSCAAS | 619. | AWFRQAPGNEREFVAS | 675. | YYADPVKGRFTISRDNAKNTVYLQMNSLKPDDTAVYYC | 758. | WGQGTQVTVSA |
| 579. | QVKLEESGGGLVRAGGSLTLSCGAS | 620. | EWYRQAPGNQREYVAR | 676. | YYADPVKGRFTISRDSAKNTVYLQMNSLKPDDTAVYYC | 759. | WGKGTLVTVSS |
| 580. | QVQLQQSGGGLVQAGGSLRLSCAAS | 621. | GWFRQAPGKEREFVAA | 677. | YHAHPVKGRFTIFRDNAKNTVYLQMNSLKPDDTGVYYC | 760. | WGQGTQVTASS |

Exemplary Framework regions for use with the CDRs of tables 1 or 2

| Seq ID | FR1 | Seq ID | FR2 | Seq ID | FR3 | Seq ID | FR4 |
|---|---|---|---|---|---|---|---|
| 581. | QVQLQESGGRLVQAGGSLRLSCAAS | 622. | GWYRQAPGKQRELVAL | 678. | NYADSVKGRFTISRDNAKNTVYLQMNSLKPEDTAVYYC | 761. | WGQGAQVTVSS |
| 582. | QVQLQESGGGLVQAGKSLRLSCAAS | 623. | GWFRQAPGKEREFVSA | 679. | YFSDSVKGRFAISRDNAKDTVSLQMNNLKPDDTAVYTC | 762. | WGRGTQVTVSS |
| 583. | QVQLQESGGGMVQAGGSLRLACTAS | 624. | GWNRQAVGNQRELVAV | 680. | NYADSVKGRFTISRNNAKKTVYLQMNSLKPEDTAVYYC | 763. | WGHGTQVTVSS |
| 584. | QVQLQESGGGLVQAGGSLRLSCAAS | 625. | GWNRQAPGKHRELVAI | 681. | WYADSMKGRFTISRDNAKNTGYLQMNSLKPEDTAIYYC | 764. | WQGTQVTVSS |
| 585. | QVQLQESGGGLVQAGGSLRLACTAS | 626. | AWYRQAPGKQREAIAS | 682. | YYGDSVQGRFTISKDNAKNTVSLQMNRLNPEDTAVYYC | | |
| 586. | QVQLQESGGGSVQAGGSLRLSCAAS | 627. | GWNRQAPGKQQRELVAA | 683. | KYADSVKGRFTITRDISKNTIYLQMNSLKPEDTGVYYC | | |
| 587. | QVQLQESGGGLVQAGGSLSLSCTAS | 628. | GWNREAPGNRREMVAI | 684. | KYADSVKGRFTISRDNTKNTVTVYLQMNNVNAEDTAVYYC | | |
| 588. | QVQLQESGGGLVQPGGSLSLSCTAS | 629. | GWNRQAPGNQRELVAV | 685. | KYADSVKGRFTISRDNTKNTVYLQMNSVNAEDTAVYYC | | |
| 589. | QVQLQESGGGLVQAGGSLTLSCTAS | 630. | GWNRQAPGNQQRDLVAV | 686. | VYANSVKDRFTISRDNNKNMVYLQMNSLKPEDTAVYSC | | |
| 590. | QVQLQESGGGLVQAGGSLTLSCITS | 631. | GWNRQAPGNQRRDLVAV | 687. | NYADSVKGRFTITRDISKNTIYLQMNNLKPEDTGVYYC | | |
| 591. | QVQLQESGGGLVQAGGSLSLSCRVS | 632. | GWYRRAPGKQREFVAG | 688. | KYDDSVKGRFTISRDIAKNTVFLQMDSLKPEDTGVYYC | | |
| 592. | QVQLQESGGGLVQPGGSLTLSCTAS | 633. | GWYRRAPGKEREFVAG | 689. | KYADSVQGRFTISRDIAKNTVYLQMNSLKPEDTGVYYC | | |
| 593. | QVQLQQSGGGLVQAGGSLSLSCTAS | 634. | GWFRQAPGKEREFVAT | 690. | VYADSVKDRFTISRDNNKNMVYLQMDSLKPEDTAVYYC | | |
| 594. | QVQLQESGGGLVQAGGSLRLSCAGS | 635. | AWYRQAPGKQRELVAS | 691. | QYADSVKGRFTITRDISKNTIYLQMNSLKPEYTGVYYC | | |
| 595. | QVQLQQSGGGLVQAGGSLKLSCAAS | 636. | GWFRQAPGKEREFIVAI | 692. | KYADSVQGRFTISRDIANNTVYLQMNSLKPEDTGVYYC | | |

-continued

| \multicolumn{8}{c}{Exemplary Framework regions for use with the CDRs of tables 1 or 2} |
| Seq ID | FR1 | Seq ID | FR2 | Seq ID | FR3 | Seq ID | FR4 |
|---|---|---|---|---|---|---|---|
| 596. | QVQLQESGGGLVQAGGSLSLSCITS | 637. | GWYRQAPGKERDLVAP | 693. | NYMDSVKGRFTISRDNAKNTVYLQMTKLKPEDTAVYYC | | |
| 597. | QVQLQESGGGLVQAGGSLRLSCVAS | 638. | AWYRQAPGKQRELVAH | 694. | NYMDSVKGRFTISRDNAKKAVYLQMTSLKPEDTALYYC | | |
| 598. | QVQLQESGGGLVQPGGSLRLSCAAS | 639. | AWYRQAPGQQRELVAS | 695. | NYMGSVQGRFTISRDNAKNTVYLQMRRLKPEDTAVYYC | | |
| 599. | QVKLEESGGGLVQAGGSLRLSCAAS | 640. | GWYRQAPGKERDLVAG | 696. | RYADSVKGRFTISRDNAKNTVDLQMNSLKPEDTAVYYC | | |
| 600. | QVKLEESGGGLVQPGGSLTLSCAAS | 641. | GWYRRAPGQEREFVAG | 697. | TYADFVKGRFIISRDNAKSTVYLQMNSLKPEDTAVYYC | | |
| 601. | QVKLEESGEGLVQAGGSLRLSCAAS | 642. | GWYRRAPGKQRDFVAG | 698. | RYEDFVKGRFTISRDNGKNTVYLQMNSLKPEDTAVYYC | | |
| 602. | QVQLVESGGGLVQAGGSLTLSCIVS | 643. | AWYRQRPGKQRELVAS | 699. | YYADSVKGRFTISRDNAKNTVYLHMNSLKPEDTAVYYC | | |
| 603. | QVQLVESESGLVLAGGSLTLTRFCS | 644. | NWFRQTPGKQREYVAY | 700. | NYAESVKGRFTISRDNAKNTVYLQMNSLKPEDTAVYYC | | |
| 604. | QVQLVESGGGSVQPAGSLRLSCAVS | 645. | GWFRQAPGKEREWVSC | 701. | RYADFVQGRFTISRDNGKNTVYLQMNSLKPEDTAVYYC | | |
| 605. | QVQLVESGGGLVQPGGSLRLSCAVS | 646. | GWYRQAPGKQRELVAA | 702. | RYADSVKGRFTISRDNAKNTVNLQMNRLKPEDTAVYYC | | |
| 606. | QVKLEESGGGLVQPGGSLRLSCAAS | 647. | GWYRQAPGKQRELVST | 703. | RYADFVKGRFTISRDNAKSTVYLQMNSLKPEDTAVYYC | | |
| 607. | QVRLEKSGGGLVQPGGSLTLSCTAS | 648. | GWFRQAPGKERELVSA | 704. | HYADSVKGRFTISRDNAKNTVNLQMNSLKVEDTAVYYC | | |
| 608. | QVQLVESGGGLVQPGGSLKVSCAAS | 649. | GWFRQAPGKERELVAA | 705. | NYMNFVKGRFTISRDNAKNTVYLQMTSLKPEDTAVYYC | | |
| 609. | QVQLAESGVGLVEPAGSLKFSCAAS | 650. | GWFRQAPGKERDIVAA | 706. | HYADSVKGRFTISRDNAKNTVDLQMNSLKPEDTAVYYC | | |
| 610. | QVKLEESGGGLVQPGGSLKVSCAAS | 651. | YWYRPGPGNQRELVVS | 707. | YYADSVKGRFTISRDNAKNTVSLQMNSLKVEDTAVYYC | | |

Exemplary Framework regions for use with the CDRs of tables 1 or 2

| Seq ID | FR1 | Seq ID | FR2 | Seq ID | FR3 | Seq ID | FR4 |
|---|---|---|---|---|---|---|---|
| 611. | QVQLVESGAGLVQPGGSLRLSCAVS | 652. | YWYRQGPGKQRELVLI | 708. | NYMDSVKGRFTISRDNAKNTVYLRMSSLKPEDTAVYYC | | |
| 612. | QVKLEESGGGLVQAGGSLRLSCVVS | 653. | GWFRQAPGKEREFVVA | 709. | RYADSVKGRFTISRDNAKNTVNLQMNSLKPEDTAVYYC | | |
| 613. | QVQLVESGGGLVEAGGSLTLSCAAS | 654. | GWYRPAPGKERELVAS | 710. | NYMNSVKGRFTISRDNAKNTVYLHMTGVKPADTAVYYC | | |
| | | 655. | GWFRQAPGLEREIIAA | 711. | NYMDSTEGRFTISRDDAKNTVYLQMTGVKPADTAVYYC | | |
| | | 656. | GWYRQAPGNQRVLVAS | 712. | NYMDSVKGRFTISRDNAKNMVYLQMTKLKPEDTAVYYC | | |
| | | 657. | TWVRQAPGKGLEWVSA | 713. | NYMDSVKGRFTISRDNAKNTVYLQMTSLKPEDTAVYYC | | |
| | | 658. | GWFRQGPGKERESVAA | 714. | NYMDSVKGRFTISRDNAKNTVYLQMTNLKPEDTAVYYC | | |
| | | 659. | GWYRQAPGKQRELAAL | 715. | RYEDFVKGRFTISRDNAKSTVYLQMNSLKPEDTAVYYC | | |
| | | 660. | GWYRQAPGKQRDLVAT | 716. | NVAQSMEGRFTISRDNAKNTGYLQMNSLKPEDTGVYYC | | |
| | | 661. | GWFREAPGKERRFVAS | 717. | NYMGFVKGRFTISRDNAKNTVYLQMTSLKPEDTAVYYC | | |
| | | 662. | GWHRQAPENQRELVAT | 718. | NYMDSVKDRFTISRDNAKNTLYLQMTNLKPEDTAVYYC | | |
| | | 663. | GWYRQAPGKERELVAS | 719. | NYMGFVRGRFTISRDNTKNTVYLQMTSLKPDDTAVYYC | | |
| | | 664. | GWYRQAPGKQRELVAT | 720. | NYMDFVKGRFTISRDNAKNTVYLQMTSLKPEDTAVYYC | | |
| | | 665. | AWFRQAPGKEREFVAR | 721. | NYPDSVKGRFAISRDNAKNTVYLQMNSLKPEDTAVYYC | | |
| | | 666. | GWFRQAPGKEHEFVAA | 722. | AYADSVWGRFTISRDNAKNNVYLEMNSLKPEDTAVYYC | | |
| | | 667. | AWFRQAPDKERAVVAT | 723. | AYADSVKGRFTISRDKAKNTVYLQMNSLKPEDTAVYYC | | |
| | | 668. | GWFRQAPGKEREFVSP | 724. | AYADSVKGRFTISRDNAKNTVYLQMNTLKPEDTAVYYC | | |
| | | 669. | GWYRQAPGKQRGFVAH | 725. | NYADSVKDTISRDNAKNTVYLQMTSLKPEDTAVYYC | | |

| Exemplary Framework regions for use with the CDRs of tables 1 or 2 | | | |
|---|---|---|---|
| Seq ID FR1 | Seq ID FR2 | Seq ID FR3 | Seq ID FR4 |
| | | 726. AYGDSVKGRFSISR DFAKNTVYLQIDSL KAEDTAVYYC | |
| | | 727. SYANSVKGRFTISR DNTKSTVYLQIHSL KPEDTAVYYC | |
| | | 728. AYADSVKGRFTISN DAAKNTVYLQMNS LKPDDTAVYYC | |
| | | 729. HDAHFTKGRFIISK DDAKNTVYLLMNS LKPEDTAVYYC | |
| | | 730. NTADSVKGRFTISR DNAKNTVYLQMNS LKPEDTAVYYC | |
| | | 731. QNAHFPNGQFLISI YEDDNTMYLQLSIQ KPEDADVYDC | |
| | | 732. NYADSVKGRFTISR DNAKNTVYLQMNS LNAEDTAVYYC | |
| | | 733. AYGDSVKGRFSISR DFAKNTVYLHIDSL KAEDTAVYYC | |
| | | 734. DYADSVKDRFTIAR DNPKNTVTLQMNS LKPEDTAIYYC | |
| | | 735. RYADSMSDRFTISR DNAKNTVYLGMDS LKPEDTAVYYC | |
| | | 736. NYAHSVKGTISRHN AENPVSRLQMNSL KPEDTAVYYC | |
| | | 737. YYADSVKGTISRDN AKNTVYLQMNSLK PEDTAVYFC | |
| | | 738. SYADSVKGRFTISR DNAKNTLYLQMNS LKPEDTAVYYC | |
| | | 739. YYTDSVKGRFTISR DNAKNTVYLQMDS LKPEDTAVYFC | |
| | | 740. DYADSAKGRFTISR DNAKNTVYLQMNS LKPEDTAVYYC | |
| | | 741. AYGDSVKGRSNLSV NHTNNTAYLQMN SLRPEDTAVYWC | |
| | | 742. YYTESVKGRFTISRD NAKNTVYLQMNSL KPEDTAVYYC | |
| | | 743. NYADSVKGTISRDN AKNTVYLQMTSLK PEDTAVYYC | |

Exemplary Framework regions for use with the CDRs of tables 1 or 2

| Seq ID FR1 | Seq ID FR2 | Seq ID FR3 | Seq ID FR4 |
|---|---|---|---|
| | | 744. SYADSVKGTISRDY AENMVYLQMNSL KPEDTATYYC | |
| | | 745. NYADSVKDSISRDH DTNAVYLQMTNLR PDDPAVYYC | |
| | | 746. DYADSVKDTIARDN PKNTVTLQMNSLK PEDTAIYYC | |
| | | 747. NYADSVKDTISRDN AKNTVYLQMTSLK PEDTAVFYC | |
| | | 748. DYADSVKDTIARDN PKNAVTLQMNSLK PEDTAIYYC | |
| | | 749. VYADSVKGTISGDN AKNTMYLQMNSLK PEDTAVYYC | |
| | | 750. YYEDSVKGTVSRDN AKNTVYLQMNNLK PEDTAVYYC | |
| | | 751. SYADSVKGRFTISR DNAKNMVYLRMD SLKPEDTDVYYC | |
| | | 752. DYLDSVKGRFTISR DNAKNTVYLQMNS LKPEDTAVYYC | |

What is claimed is:

1. A polypeptide comprising a variable region fragment of a heavy chain antibody ($V_HH$), wherein the $V_HH$ specifically binds *Salmonella enterica*, wherein the $V_HH$ comprises an amino acid sequence as set forth in SEQ ID NOs: 530.

2. The polypeptide of claim 1, wherein the polypeptide comprises more than one $V_HH$, the $V_HHs$ being covalently coupled to one another by a linker, the linker comprising one or more amino acids.

3. The polypeptide of claim 1, wherein the $V_HH$ specifically binds a *Salmonella enterica* virulence factor, wherein the virulence factor is involved in one or more of bacterial motility, adhesion, invasion, and biofilm formation.

4. The polypeptide of claim 3, wherein the virulence factor comprises a flagellum, FliC, PrgI, FimA, or SipD.

5. The polypeptide of claim 1, wherein the polypeptide that specifically binds the *Salmonella enterica* virulence factor specifically binds a virulence factor of any of the *Salmonella enterica* serotypes: *Typhimurium*; *Enteritidis*; Newport; Heidelberg; *Gallinarum*; Hadar; Javiana; *Infantis*; Montevideo; Muenchen; Braenderup; Saintpaul; Thompson; Agona, Litchfield; Anatum; Berta; Mbandaka; Oranienburg; Poona; Uganda; *Senftenberg*; Weltevreden; I 4,[5], 12:i:-; I 13,23:b:-; or any combination thereof.

6. The polypeptide of claim 1, wherein the $V_HH$ reduces *Salmonella enterica* bacterial motility compared to a negative control antibody by at least 40%.

7. The polypeptide of claim 4, wherein the $V_HH$ reduces biofilm formation by at least 10%.

8. A composition comprising the polypeptide of claim 1 and an animal feed.

9. A composition comprising the polypeptide of claim 1 and a pharmaceutically acceptable vehicle, carrier, excipient, or diluent.

* * * * *